US011034682B2

(12) United States Patent
KC et al.

(10) Patent No.: US 11,034,682 B2
(45) Date of Patent: Jun. 15, 2021

(54) GAMMA-DIKETONES AS WNT/β-CATENIN SIGNALING PATHWAY ACTIVATORS

(71) Applicant: Samumed, LLC, San Diego, CA (US)

(72) Inventors: Sunil Kumar KC, San Diego, CA (US); David Mark Wallace, San Diego, CA (US); John Hood, San Diego, CA (US); Charlene F. Barroga, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 16/577,592

(22) Filed: Sep. 20, 2019

(65) Prior Publication Data
US 2020/0223834 A1 Jul. 16, 2020

Related U.S. Application Data

(62) Division of application No. 15/918,086, filed on Mar. 12, 2018, now Pat. No. 10,457,672, which is a division of application No. 15/356,903, filed on Nov. 21, 2016, now Pat. No. 9,951,053, which is a division of application No. 14/187,063, filed on Feb. 21, 2014, now Pat. No. 9,533,976.

(60) Provisional application No. 61/768,033, filed on Feb. 22, 2013.

(51) Int. Cl.
C07D 411/06 (2006.01)
C07D 213/50 (2006.01)
C07D 317/46 (2006.01)
C07D 319/16 (2006.01)
C07D 327/06 (2006.01)
C07D 339/08 (2006.01)
C07D 401/06 (2006.01)
C07D 405/06 (2006.01)
C07D 409/06 (2006.01)
C07D 263/56 (2006.01)
C07D 311/58 (2006.01)
C07D 317/54 (2006.01)
C07D 319/18 (2006.01)
C07D 231/56 (2006.01)
C07D 333/54 (2006.01)
C07D 235/06 (2006.01)
C07D 407/06 (2006.01)
C07D 413/06 (2006.01)
C07D 307/80 (2006.01)
A61P 25/00 (2006.01)

(52) U.S. Cl.
CPC ............ C07D 411/06 (2013.01); A61P 25/00 (2018.01); C07D 213/50 (2013.01); C07D 231/56 (2013.01); C07D 235/06 (2013.01); C07D 263/56 (2013.01); C07D 307/80 (2013.01); C07D 311/58 (2013.01); C07D 317/46 (2013.01); C07D 317/54 (2013.01); C07D 319/16 (2013.01); C07D 319/18 (2013.01); C07D 327/06 (2013.01); C07D 333/54 (2013.01); C07D 339/08 (2013.01); C07D 401/06 (2013.01); C07D 405/06 (2013.01); C07D 407/06 (2013.01); C07D 409/06 (2013.01); C07D 413/06 (2013.01)

(58) Field of Classification Search
CPC .............................. C07D 411/06; A61P 25/00
See application file for complete search history.

(56) References Cited

U.S. PATENT DOCUMENTS

| 3,040,054 A | 6/1962 | Bodanszky et al. |
| 3,855,675 A | 12/1974 | Denzel et al. |
| 4,014,889 A | 3/1977 | Stetter et al. |
| 4,032,526 A | 6/1977 | Cross et al. |
| 4,164,559 A | 8/1979 | Miyata et al. |
| 4,284,629 A | 8/1981 | Grohe et al. |
| 4,474,752 A | 10/1984 | Haslam et al. |
| 4,537,617 A | 8/1985 | Plath et al. |

(Continued)

FOREIGN PATENT DOCUMENTS

| CN | 1382688 | 12/2002 |
| CN | 1440391 | 9/2003 |

(Continued)

OTHER PUBLICATIONS

Cole et al (2008): STN International, HCAPLUS database (Columbus, Ohio), Accession No. 2008: 151652.*
Cherkasov et al (2011): STN International, HCAPLUS database (Columbus, Ohio), Accession No. 2011: 1619070.*
Yang et al., "Mixed-valence tetra- and hexanuclear manganese complexes from the flexibility of pyridine-containing beta-diketone ligands," Inorganic Chemistry, 2008, 47(6):1925-1939.

(Continued)

Primary Examiner — Golam M Shameem
(74) Attorney, Agent, or Firm — Fish & Richardson P.C.

(57) ABSTRACT

The present disclosure provides γ-diketones or analogs thereof, that activate Wnt/β-catenin signaling and thus treat or prevent diseases related to signal transduction, such as osteoporosis and osteoarthropathy; osteogenesis imperfecta, bone defects, bone fractures, periodontal disease, otosclerosis, wound healing, craniofacial defects, oncolytic bone disease, traumatic brain injuries or spine injuries, brain atrophy/neurological disorders related to the differentiation and development of the central nervous system, including Parkinson's disease, strokes, ischemic cerebral disease, epilepsy, Alzheimer's disease, depression, bipolar disorder, schizophrenia; otic disorders like cochlear hair cell loss; eye diseases such as age related macular degeneration, diabetic macular edema or retinitis pigmentosa and diseases related to differentiation and growth of stem cell, such as hair loss, hematopoiesis related diseases and tissue regeneration related diseases.

10 Claims, No Drawings

(56) References Cited

U.S. PATENT DOCUMENTS

| | | |
|---|---|---|
| 4,761,471 A | 8/1988 | Urist |
| 5,068,393 A | 11/1991 | Maignan et al. |
| 5,194,619 A | 3/1993 | Reuschling et al. |
| 5,252,191 A | 10/1993 | Pauli et al. |
| 5,420,273 A | 5/1995 | Klaus et al. |
| 5,585,118 A | 12/1996 | Stoll |
| 5,977,108 A | 11/1999 | Kikuchi et al. |
| 6,020,488 A | 2/2000 | Wuonola et al. |
| 6,120,484 A | 9/2000 | Silverstein |
| 6,310,049 B1 | 10/2001 | Wada et al. |
| 6,346,260 B1 | 2/2002 | Hölzl et al. |
| 6,377,849 B1 | 4/2002 | Lenarz et al. |
| 6,440,102 B1 | 8/2002 | Arenberg et al. |
| 6,620,804 B2 | 9/2003 | Chang et al. |
| 6,624,184 B1 | 9/2003 | Gu et al. |
| 6,648,873 B2 | 11/2003 | Arenberg et al. |
| 6,911,211 B2 | 6/2005 | Eini et al. |
| 6,960,591 B2 | 11/2005 | Hirano et al. |
| 7,012,075 B2 | 3/2006 | Prasit et al. |
| 7,041,837 B2 | 5/2006 | Lohray et al. |
| 7,053,111 B2 | 5/2006 | Gu et al. |
| 7,060,720 B2 | 6/2006 | Gu et al. |
| 7,205,324 B2 | 4/2007 | Gu et al. |
| 7,524,975 B2 | 4/2009 | Mae et al. |
| 7,709,519 B2 | 5/2010 | Hirano et al. |
| 7,960,562 B2 | 6/2011 | Hirano et al. |
| 8,088,369 B2 | 1/2012 | Izawa et al. |
| 8,124,760 B2 | 2/2012 | Haga et al. |
| 8,410,109 B2 | 4/2013 | Wong et al. |
| 8,609,717 B2 | 12/2013 | KC et al. |
| 8,629,176 B1 | 1/2014 | KC et al. |
| 8,741,357 B2 | 6/2014 | Linter et al. |
| 8,921,413 B2 | 12/2014 | KC et al. |
| 9,303,010 B2 | 4/2016 | KC et al. |
| 9,493,437 B2 | 11/2016 | KC et al. |
| 9,533,976 B2 | 1/2017 | KC et al. |
| 9,795,550 B2 | 10/2017 | Hood et al. |
| 9,884,053 B2 | 2/2018 | KC et al. |
| 10,314,832 B2 | 6/2019 | KC et al. |
| 10,434,052 B2 * | 10/2019 | Hood .................. A61Q 19/007 |
| 10,457,672 B2 * | 10/2019 | KC ...................... C07D 263/56 |
| 2003/0028015 A1 | 2/2003 | Chang et al. |
| 2003/0087922 A1 | 5/2003 | Bethiel et al. |
| 2004/0224003 A1 | 11/2004 | Schultz |
| 2004/0266732 A1 | 12/2004 | Galvez et al. |
| 2005/0054578 A1 | 3/2005 | Sandberg et al. |
| 2005/0267110 A1 | 12/2005 | Hirano et al. |
| 2005/0282707 A1 | 12/2005 | Almsick et al. |
| 2006/0134155 A1 | 6/2006 | Laurence et al. |
| 2006/0142358 A1 | 6/2006 | Autier et al. |
| 2006/0264897 A1 | 11/2006 | Lobl |
| 2006/0276536 A1 | 12/2006 | Vander Jagt et al. |
| 2007/0021606 A1 | 1/2007 | Egle et al. |
| 2007/0060644 A1 | 3/2007 | Vander Jagt et al. |
| 2007/0185152 A1 | 8/2007 | Yamashita et al. |
| 2007/0238733 A1 | 10/2007 | Joshi et al. |
| 2008/0139585 A1 | 6/2008 | Rathinavelu et al. |
| 2008/0146555 A1 | 6/2008 | Caligiuri et al. |
| 2008/0262205 A1 | 10/2008 | ter Harr et al. |
| 2009/0232754 A1 | 9/2009 | Meyer et al. |
| 2010/0152493 A1 | 6/2010 | Shibata et al. |
| 2010/0204245 A1 | 8/2010 | Malamas et al. |
| 2010/0204246 A1 | 8/2010 | Davies et al. |
| 2010/0210036 A1 | 8/2010 | Arnold et al. |
| 2012/0046320 A1 | 2/2012 | KC et al. |
| 2013/0079643 A1 | 3/2013 | Korichi et al. |
| 2013/0171274 A1 | 7/2013 | Son et al. |
| 2013/0172291 A1 | 7/2013 | Peter et al. |
| 2014/0005228 A1 | 1/2014 | KC et al. |
| 2014/0080902 A1 | 3/2014 | KC et al. |
| 2014/0179642 A1 | 6/2014 | Santhanam et al. |
| 2014/0243349 A1 | 8/2014 | KC et al. |
| 2015/0299157 A1 | 10/2015 | KC et al. |
| 2015/0299174 A1 | 10/2015 | KC et al. |
| 2017/0246154 A1 | 8/2017 | KC et al. |
| 2017/0260176 A1 | 9/2017 | KC et al. |
| 2018/0193244 A1 | 7/2018 | Hood et al. |

FOREIGN PATENT DOCUMENTS

| | | |
|---|---|---|
| CN | 1558758 | 12/2004 |
| CN | 103153053 | 2/2015 |
| EA | 201000673 | 4/2011 |
| EA | 201000718 | 6/2011 |
| EA | 201101244 | 4/2012 |
| EP | 0230110 | 7/1987 |
| EP | 0290442 | 11/1988 |
| EP | 0322033 | 6/1989 |
| EP | 0360701 | 3/1990 |
| EP | 0365089 | 4/1990 |
| EP | 0500005 | 8/1992 |
| EP | 0557089 | 8/1993 |
| EP | 0738705 | 10/1996 |
| EP | 0885869 | 12/1998 |
| EP | 1067195 | 1/2001 |
| EP | 2740741 | 9/2017 |
| JP | H05-170764 | 7/1993 |
| JP | 2001503381 | 3/2001 |
| JP | 2008106011 | 5/2008 |
| JP | 2008222606 | 9/2008 |
| JP | 2009-179619 | 8/2009 |
| JP | 2010195768 | 9/2010 |
| RU | 2003/128076 | 4/2005 |
| WO | WO1987005297 | 9/1987 |
| WO | WO1988003805 | 6/1988 |
| WO | WO1990011366 | 10/1990 |
| WO | WO1993022259 | 11/1993 |
| WO | WO1996021665 | 7/1996 |
| WO | WO1996032938 | 10/1996 |
| WO | WO1996040668 | 12/1996 |
| WO | WO9746225 | 12/1997 |
| WO | WO2000026197 | 5/2000 |
| WO | WO2001000578 | 1/2001 |
| WO | WO2001004100 | 1/2001 |
| WO | WO2001019822 | 3/2001 |
| WO | WO2001027116 | 4/2001 |
| WO | WO2001049291 | 7/2001 |
| WO | WO2001053268 | 7/2001 |
| WO | WO2001077090 | 10/2001 |
| WO | WO2002043675 | 6/2002 |
| WO | WO02085897 | 10/2002 |
| WO | WO2003009841 | 2/2003 |
| WO | WO2003016266 | 2/2003 |
| WO | WO2003037316 | 5/2003 |
| WO | WO2003/048109 | 6/2003 |
| WO | WO2004016592 | 2/2004 |
| WO | WO2005009997 | 2/2005 |
| WO | WO2005108347 | 11/2005 |
| WO | WO2006017896 | 1/2006 |
| WO | WO2006002119 | 2/2006 |
| WO | WO2006077851 | 7/2006 |
| WO | WO2007003389 | 1/2007 |
| WO | WO2007051314 | 5/2007 |
| WO | WO2007059108 | 5/2007 |
| WO | WO2007103584 | 9/2007 |
| WO | WO2008001921 | 1/2008 |
| WO | WO2008020625 | 2/2008 |
| WO | WO2008118626 | 10/2008 |
| WO | WO2008156345 | 12/2008 |
| WO | WO2009071997 | 6/2009 |
| WO | WO2009129267 | 10/2009 |
| WO | WO2009136889 | 11/2009 |
| WO | WO2010054126 | 5/2010 |
| WO | WO2010/075551 | 7/2010 |
| WO | WO2010075551 | 7/2010 |
| WO | WO2011009826 | 1/2011 |
| WO | WO2012024404 | 2/2012 |
| WO | WO2012106343 | 8/2012 |
| WO | WO2013113722 | 8/2013 |
| WO | WO2013169724 | 11/2013 |
| WO | WO2014128207 | 8/2014 |

(56) References Cited

FOREIGN PATENT DOCUMENTS

| WO | WO2014128591 | 8/2014 |
|---|---|---|
| WO | WO2014130869 | 8/2014 |
| WO | WO2014130879 | 8/2014 |

OTHER PUBLICATIONS

Adam et al., "The Importance of Spin Polarization in Electronic Substituent Effects of the Zero-Field EPR D Parameter in 1,3-Dialylcyclopentane-1,3-diyl Triplet Diradicals," *J. Am. Chem. Soc.*, 121(46): 10820-10827, Nov. 6, 1999.
Agathocleous et al., "A directional Wnt/β-catenin-Sox2-proneural pathway regulates the transition from proliferation to differentiation in the *Xenopus* retina," *Development* 2009, 136(19), 3289-3299.
Akiri et al., "Wnt pathway aberrations including autocrine Wnt activation occur at high frequency in human non-small-cell lung carcinoma," *Oncogene* 2009, 28(21): 2163-2172.
Amit et al., "Axin-mediated CKI phosphorylation of β-catenin at Ser 45: a molecular switch for the Wnt pathway," Genes & Development 2002, 16(9): 1066-1076.
Baron and Rawadi, "Minireview: Targeting the Wnt/-Catenin Pathway to Regulate Bone Formation in the Adult Skeleton," *Endocrinology* Jun. 2007, 148(6): 2635-2643.
Belgodere et al., "Studies in isomeric pyridylisoxazoles," *Heterocycles*, 20(3): 501-504, 1983.
Benati et al., "Thermal reactions of aryl azides with trans-1,2-dibenzoyl- and trans-1,2-diacetyl-ethylene. Reactivity of 4,5-dibenzoyl- and 4,5-diacetyl-l-aryltriazoles" *J. Chem. Soc.*, Perkin Trans. 1, No. 12 (1989), pp. 2235-2243.
Bhattacharyya and Dayal, "Age-related cochlear hair cell loss in the chinchilla," *Ann Otol Rhinol Laryngol.*, 94(1 Pt 1):75-80, Jan.-Feb. 1985.
Bienz and Clevers, "Linking colorectal cancer to Wnt signaling," *Cell*, 103(2):311-320, Oct. 13, 2000.
Biftu et al., "Syntheses of lignans from 2,3-diaroylbutanes," J Chem Soc Perkin 1: Organic and Bio-Organic Chemistry (1972-1999), (1978), vol. 19, pp. 1147-1150.
Bodine et al., "A small molecule inhibitor of the Wnt antagonist secreted frizzled-related protein-1 stimulates bone formation," *Bone* 2009, 44(6): 1063-1068.
Bogdan Allemann et al., "Antioxidants used in skin care formulations," Skin Therapy Lett., 13(7):5-9, Sep. 2008.
Boger et al., "Non-Amide-Based Combinatorial Libraries Derived from N-Boc-Iminodiacetic Acid: Solution-Phase Synthesis of Piperazinone Libraries with Activity Against LEF-1/β-Catenin-Mediated Transcription," *Helvetica Chimica Acta*, 83(8): 1825-1845, Aug. 9, 2000.
Bruchhausen and Lingner, [A Synthesis of DL-Asarinin and DL-Sesamin] "Eine Synthese von DL-Asarinin and DL-Sesamin," *Archiv Der Pharmazie*, 290:1-16, Jan. 1957 [English translation included], 38 pages.
Bylund et al., "Vertebrate neurogenesis is counteracted by Sox1-3 activity," *Nature Neuroscience* 2003, 6(11): 1162-1168.
Cairo et al., "Hepatic stem-like phenotype and interplay of Wnt/beta-catenin and Myc signaling in aggressive childhood liver cancer." *Cancer Cell* Dec. 2008, 14(6): 471-484.
Chai et al., "Wnt signaling induces proliferation of sensory precursors in the postnatal mouse cochlea," *Proc Natl Acad Sci U S A.*, 109(21):8167-72, Epub May 4, 2012.
Chemical Abstracts 154:83772 of Wang et al, Natural Product Communications (2009), 4(11), pp. 1571-1574. [Abstract].
Chen and Alman, "Wnt Pathway, an Essential Role in Bone Regeneration," 2009, *Journal of Cellular Biochemistry* 106:353-362.
Chilosi et al., "Aberrant Wnt/beta-catenin pathway activation in idiopathic pulmonary fibrosis," *Am J Pathol.*, 162(5):1495-1502, May 2003.
Chou and Talalay, "Quantitative analysis of dose-effect relationships: the combined effects of multiple drugs or enzyme inhibitors," *Adv Enzyme Regul.*, 22:27-55, 1984.

Clarke, A. R. "Wnt signaling in the mouse intestine," *Oncogene* 2006, 25(57): 7512-7521.
Cointet et al., "Synthèse et propriètès pharmacologiques des acètoacètyl-3 indoles et leurs dèrivès," [Synthesis and pharmacological properties of 3-acetoacetylindoles and their derivatives] *European Journal of Medicinal Chemistry*, 11(5):471-479, 1976 [English machine translation].
Constable et al., "Platinamacrocycles containing 2, 5-thiophenediyl and poly (2, 5-thiophenediyl)-linked azaaromatic ligands. New structural paradigms for metallosupramolecular chemistry," *Polyhedron* 25(8): 1844-1863, 2006.
Corr, "Wnt-β-catenin signaling in the pathogenesis of osteoarthritis" Nature Clinical Practice, Oct. 2008, 4(10): 550-556.
Denayer et al., "Canonical Wnt signaling controls proliferation of retinal stem/progenitor cells in postembryonic Xenopus eyes," *Stem Cells* 2008, 26(8): 2063-2074.
Dulińska-Molak et al., "Age-related changes in the mechanical properties of human fibroblasts and its prospective reversal after anti-wrinkle tripeptide treatment," International journal of peptide research and therapeutics, 20(1): 77-85, 2014.
Extended European Search Report for Application No. 14753569.4, dated Jun. 8, 2016, 6 pages.
Extended European Search Report for Application No. 15833863.2, dated Mar. 12, 2018, 5 pages.
Extended European Search Report for Application No. 17193280.9, dated Mar. 6, 2018, 6 pages.
Farwick et al., "An ECM-derived Tetrapeptide to Counterbalance ECM Degeneration," Cosmetics & Toiletries, 124: 51-54, 2009.
Fernández-Martos et al., "Differential expression of Wnts after spinal cord contusion injury in adult rats," *PLoS One*, 6(11):e27000, 12 pages, Epub Nov. 2011.
Fischer et al., "Direct and non-direct measurement techniques for analysis of skin surface topography," Skin Pharmacol Appl Skin Physiol., 12(1-2):1-11, Jan.-Apr. 1999.
Ford et al., "Anti-irritants: Myth or reality? an overview," Exogenous Dermatology., 3(3):154-160, 2004.
Gerbino, *Remington: The Science and Practice of Pharmacy*, 21st Edition. Philadelphia, PA: Lippincott Williams & Wilkins, 2005.
Glass et al., "Canonical Wnt Signaling in Differentiated Osteoblasts Controls Osteoclast Differentiation," *Developmental Cell* 2005, 8(5): 751-764.
González et al., "The latest on skin photoprotection," Clin Dermatol., 26(6):614-626, Nov.-Dec. 2008.
Graham et al., "SOX2 Functions to Maintain Neural Progenitor Identity," *Neuron* 2003, 39(5): 749-765.
Greene and Wuts, "The role of protective groups in organic synthesis," *Protective Groups in Organic Synthesis*, 4th Ed., John Wiley & Sons, 15 pages, 2007.
Harris, "Cellular diversification in the vertebrate retina," *Current Opinion in Genetics & Development* 1997, 7(5): 651-658.
Hollis and Zou, "Expression of the Wnt signaling system in central nervous system axon guidance and regeneration," *Front Mol Neurosci.*, 5:5, 5 pages, Feb. 2012.
Hollis and Zou, "Reinduced Wnt signaling limits regenerative potential of sensory axons in the spinal cord following conditioning lesion," *Proc Natl Acad Sci U S A.*, 109(36):14663-14668, Aug. 2012.
Huntzicker et al., "Controlling Hair Follicle Signaling Pathways through Polyubiquitination," *Investigative Dermatology* 2008, 128(5): 1081-1087.
Inestrosa and Arenas, "Emerging roles of Wnts in the adult nervous system" *Nature Reviews* 2010, 11:77-86.
International Preliminary Report on Patentability for International App. No. PCT/US2015/046120, dated Mar. 2, 2017, 27 pages.
International Preliminary Report on Patentability for PCT/US2011/48086, dated Feb. 28, 2013, 6 pages.
International Preliminary Report on Patentability for PCT/US2014/017794, dated Aug. 25, 2015, 7 pages.
International Search Report and Written Opinion for PCT/US2011/48086 dated Jan. 5, 2012, 7 pages.
International Search Report and Written Opinion for PCT/US2014/017794, dated May 9, 2014, 15 pages.

(56) References Cited

OTHER PUBLICATIONS

International Search Report and Written Opinion for PCT/US2015/046120, dated Jan. 12, 2016, 35 pages.
Invitation to Pay for International App. No. PCT/US2015/046120, dated Nov. 4, 2015, 2 pages.
Jaenisch and Young, "Stem cells, the molecular circuitry of pluripotency and nuclear reprogramming," Cell, 132(4):567-582, Feb. 22, 2008.
Japanese Office Action in Japanese Application No. 2015-559015, dated Jan. 17, 2018, 11 pages.
Jiang et al., "Pluripotency of mesenchymal stem cells derived from adult marrow," Nature 2002, 418 (6893): 41-49.
Jończyk et al., "Reactions of carbanions from 2-(dialkylamino)-arylacetonitriles with acetylene—simple syntheses of 1,3-dienamines and 1,4-diketones¹," Tetrahedron, vol. 46, No. 3 (1990), pp. 1025-1038.
Kale et al., "Synthesis and characterization of some important indazolyl derivatives," Journal of Heterocyclic Chemistry, 44(2): 289-301, Mar.-Apr. 2007.
Kazimierz et al, "Condensation of phenylglyoxals with 3-Acetylpyridine," Acta Poloniae Pharmaceutica, Jan. 1, 1981, 38(1):33-39.
Kel'in and Kulinkovich, "A New Simple Synthesis of Aryl-Substituted 1,4-Diketones," Synthesis 1996, pp. 330-332.
Kim et al., "Anti-wrinkle and anti-inflammatory effects of active garlic components and the inhibition of MMPs via NF-κB signaling," PLoS One., 8(9):e73877, Sep. 16, 2013.
Kim et al., "The mechanism of retinol-induced irritation and its application to anti-irritant development," Toxicol Lett., 146(1):65-73, Dec. 15, 2003.
Klopp et al., "Effect of four treatment variants on the functional and cosmetic state of mature scars," J Wound Care., 9(7):319-324, Jul. 2000.
Koenekoo et al., "Novel RPGR mutations with distinct retinitis pigmentosa phenotypes in French-Canadian families," Am J Ophthalmol., 136(4):678-687, Oct. 2003.
Kubo et al., "Wnt2b controls retinal cell differentiation at the ciliary marginal zone," Development, 130(3):587-598, Feb. 2003.
Kubo et al., "Wnt2b inhibits differentiation of retinal progenitor cells in the absence of Notch activity by downregulating the expression of proneural genes," Development, 132(12):2759-2770, Epub May 18, 2005.
Lee et al., "Canonical Wnt signaling through Lef1 is required for hypothalamic neurogenesis," Development 2006, 133(22): 4451-4461.
Li et al., "Ring-opening of tertiary cyclopropanols derived from β-diketones," Tetrahedron, 62(33):7762-7771, Aug. 14, 2006.
Lie et al., "Wnt signalling regulates adult hippocampal neurogenesis," Nature 2005, 437(7063): 1370-1375.
Lindsley et al., "Canonical Wnt signaling is required for development of embryonic stem cell-derived mesoderm," Development, 2006, 133(19): 3787-3796.
Livesey and Cepko, "Vertebrate Neural Cell-Fate Determination: Lessons from the Retina," Nature Reviews Neuroscience 2001, 2: 109-118.
Logan and Nusse, "The Wnt signaling pathway in development and disease," Annu Rev Cell Dev Biol., 20:781-810, 2004.
Lopes L M X et al: "Further lignoids from Virola Sebifera," Jan. 1, 1984 (Jan. 1, 1984), Phytochemistry, Pergamon Press, Gb pp. 2647-2652, XP02662136.
Mao et al., "Low-Density Lipoprotein Receptor-Related Protein-5 Binds to Axin and Regulates the Canonical Wnt Signaling Pathway," Molecular Cell 2001, 7(4): 801-809.
Maramaldi et al., "Anti-inflammaging and antiglycation activity of a novel botanical ingredient from African biodiversity (Centevita™)," Clin Cosmet Investig Dermatol., 7:1-9, Dec. 12, 2013.
Marson et al., "Wnt signaling promotes reprogramming of somatic cells to pluripotency," Cell Stem Cell, 3(2): 132-135, Aug. 7, 2008.
Marvin et al., "Inhibition of Wnt activity induces heart formation from posterior mesoderm," Genes & Development 2001, 15(3): 316-327.

McCormick et al., "Comparative ototoxicity of netilmicin, gentamicin, and tobramycin in cats," Toxicol Appl Pharmacol., 77(3):479-489, Mar. 15, 1985.
McCrea et al., "A homolog of the armadillo protein in Drosophila (plakoglobin) associated with E-cadherin," Science, 1991, 254(5036): 1359-1361.
Merrill, "Develop-WNTs in Somatic Cell Reprogramming," Cell Stem Cell 2008, 3(5): 465-466.
Michaelidis and Lie, "Wnt signaling and neural stem cells: caught in the Wnt web," Cell Tissue Res., 331(1):193-210, Epub Sep. 9, 2007.
Mitani et al., "Prevention of the photodamage in the hairless mouse dorsal skin by kojic acid as an iron chelator," Eur J Pharmacol., 411(1-2):169-174, Jan. 5, 2001.
Moon et al., "The Promise and Perils of Wnt Signaling Through β-Catenin," Science 2002, 296(5573): 1644-1646.
More et al., "Synthesis antioxidant and antimicrobial activities of some 7-methoxy-3methyl benzofuran incorporated chromon-4-ones," Indian Journal of Heterocyclic Chemistry, 16(4): 379-382, Apr.-Jun. 2007.
Morin, "Beta-catenin signaling and cancer," BioEssays, Dec. 1999, 21(12): 1021-1030.
Morrison, Sean J. "Neuronal potential and lineage determination by neural stem cells," Current Opinion in Cell Biology, 2001, 13: 666-672.
Morvan et al., "Deletion of a single allele of the Dkk1 gene leads to an increase in bone formation and bone mass ," Journal of Bone and Mineral Research, 2009, 21(6): 934-945.
Naito et al., "Developmental stage-specific biphasic roles of Wnt/β-catenin signaling in cardiomyogenesis and hematopoiesis," Proc Natl Acad Sci USA. 2006, 103(52): 19812-19817.
Nevar et al., "One Step Preparation of 1,4-Diketones from Methyl Ketones and α-Bromomethyl Ketones in the Presence of $ZnCl_2$ • t-BuOH • $Et_2NR$ as a Condensation Agent" Synthesis, No. 9 (2000), pp. 1259-1262.
Nishiyama and Kobayashi, "Synthesis of 1,4-Diketones: Reaction of α-Bromo Ketones with Tetrakis (dimethylamino)ethylene (TDAE)," Tetrahedron Letters, vol. 47, (2006) pp. 5565-5567.
Nuriev et al., "Synthetic pathways to a family of pyridine-containing azoles-promising ligands for coordination chemistry," Arkivoc 4: 208-224, 2005.
Okano et al., "Improvement of wrinkles by an all-trans-retinoic acid derivative, D-δ-tocopheryl retinoate," Journal of Dermatological Science Supplement, 2(1): S65-S74.
Okita et al., "Generation of germline-competent induced pluripotent stem cells," Nature (2007), 448(7151): 313-317.
Osakada et al., "Wnt Signaling Promotes Regeneration in the Retina of Adult Mammals," Journal of Neuroscience (2007), 27(15): 4210-4219.
Parker et al., "Polymers for drug eluting stents," Curr Pharm Des., 16(36):3978-3988, 2010.
Passarotti et al., "Synthesis of some 5-azaflavones," Bollettino Chimico Farmaceuitico, 130(8):312-314, Sep. 1991.
Patani et al., "Bioisosterism: A rational approach in drug design," Chem. Rev. 96: 3147-3176, 1996.
Pelletier et al., "(1-(4-(Naphthalen-2-yl)pyrimidin-2-yl)piperidin-4-yl)methanamine: a wingless beta-catenin agonist that increases bone formation rate," Journal of Medicinal Chemistry, 2009, 52(22): 6962-6965.
Polakis, "Wnt signaling and cancer," Genes Dev., 2000, 14(15): 1837-1851.
Rajesh et al., "Synthesis and in vitro short term cytotoxic studies of some novel β-di ketones," Indian drugs, 40(1): 37-40, Jan. 2003.
Robinson et al., "Wnt/-Catenin Signaling Is a Normal Physiological Response to Mechanical Loading in Bone," The Journal of Biological Chemistry, Oct. 2006, 281(42): 31720-31728.
Rosa et al., "N-and C-Acylation in β-Enamino Ketones: Structural Effects on Regiocontrol," Synlett, No. 20 (2007), pp. 3165-3717.
Rosenberg Zand et al., "Flavonoids can block PSA production by breast and prostate cancer cell lines," Clinica Chimica Acta, 317:17-26, 2002.

(56) References Cited

OTHER PUBLICATIONS

Sakanaka et al., "Casein kinase IE in the Wnt pathway: Regulation of β-catenin function," *Proceedings of the National Academy of Sciences of the USA* 1999, 96(22): 12548-12552.
Sampath, et al., "Isolation of osteogenin, an extracellular matrix-associated, bone-inductive protein, by heparin affinity chromatography," *Proc. Natl. Acad. Sci.* USA 1987, 84(20): 7109-7113.
Santini et al., "New molecular targets in bone metastases" *Cancer Treatment Reviews*, 36S3 (2010) S6-S10.
Sauthier et al., "Carbonylative 1,4-addition of potassium aryltrifluoroborates to vinyl ketones," *New J. Chem.*, vol. 33 (2009), pp. 969-971.
Schneider et al., "Wnt antagonism initiates cardiogenesis in *Xenopus laevis*," *Genes & Development*, 2001, 15(3): 304-315.
Selic et al., "A Simple Stereoselective One-Pot Conversion of Compounds with a Dimethylaminomethylene Group into Enol Esters," *Synthetic Communications*, vol. 31, No. 11 (2001) pp. 1743-1752.
Selvamurugan and Aidhen, "N-Methoxy-N-methyl-3-bromopropionamide: a new three carbon homologating agent for the synthesis of unsymmetrical 1,4-diketones," *Tetrahedron* vol. 57, No. 28 (Jul. 2001) pp. 6065-6069.
Sheikh et al., "Synthesis of heterocyclic beta-diketones," *Indian Journal of Heterocyclic Chemistry*, 18(4): 333-336, Jan.-Mar. 2009.
Shi et al., "Identification of a novel signal for activation of Ti plasmid-encoded vir genes from rice (*Oryza sativa* L.)," *Chinese Science Bulletin*, 40(21): 1824-1828, Nov. 1995.
Shi et al., "Wnt-responsive Lgr5-expressing stem cells are hair cell progenitors in the cochlea," *J Neurosci.*, 32(28):9639-9648, Jul. 11, 2012.
Silkstone et al., "β-Catenin in the race to fracture repair: in it to Wnt," *Nature Clinical Practice*, Aug. 2008, 4(8): 413-419.
Slepecky et al., "Correlation of audiometric data with changes in cochlear hair cell stereocilia resulting from impulse noise trauma," *Acta Otolaryngol.*, 93(5-6):329-340, May-Jun. 1982.
Sorsak et al., "The synthesis of ethyl 2-[(2,2-dibenzoyl)ethenyl]amino-3-dimethyl-aminopropanoate and its application to the synthesis of fused 3-aminopyran-2-ones and 3-aminoazolo- and -aminopyridine-4(4H)-ones," *J. Heterocyclic Chem*, vol. 35, No. 6, pp. 1275-1279, 1998.
Sosnovskikh et al., "3-(Polyhaloacyl)chromones and Their Hetero Analogues: Synthesis and Reactions with Amines," *Synthesis*, No. 16 (2006) pp. 2707-2718.
Sosnovskikh et al., "Synthesis and some properties of 6-di(tri)fluoromethyl-and 5-di(tri)fluoroacetyl-3-methyl-1-phenylpyrano[2,3-c]pyrazol-4(1H)-ones," *Russian Chemical Bulletin*, vol. 54, No. 12 (2005), pp. 2846-2850.
Soufyane et al., "Synthesis of some fluorinatednitrogen heterocycles from (diethylaminomethylene)hexafluoroacetylacetone (DAMFA)," *Tetrahedron Letters*, vol. 34, No. 48 (Nov. 1993), pp. 7737-7740.
Sperling, L. C.; "Hair anatomy for the clinician," *J. Amer. Acad. Dermatology* 1991, 25(1, Part 1): 1-17.
Suh et al., "Axonal regeneration effects of Wnt3a-secreting fibroblast transplantation in spinal cord-injured rats," *Acta Neurochir* (Wien), 153(5):1003-1010, Epub Jan. 2011.
Tamura et al., "Role of the Wnt signaling pathway in bone and tooth," *Frontiers in Bioscience*, Jun. 2010, E2, 1405-1413.
Tashiro, et al., "A Synthetic Peptide Containing the IKVAV Sequence from the A Chain of Laminin Mediates Cell Attachment, Migration, and Neurite Outgrowth," *The Journal of Biological Chemistry* 1989, 264(27): 16174-16182.
Tencer, et al., "The effect of local controlled release of sodium fluoride on the stimulation of bone growth," *Journal of Biomedical Materials Research* 1989, 23(6): 571-589.
Trivedi et al., "Investigational anabolic therapies for osteoporosis" *Expert Opin. Investig. Drugs*, 2010, 19(8): 995-1005.
Tsukahara et al., "Inhibition of ultraviolet-B-induced wrinkle formation by an elastase-inhibiting herbal extract: implication for the mechanism underlying elastase-associated wrinkles," Int J Dermatol., 45(4):460-468, Apr. 2006.
Van Raay et al., "Frizzled 5 signaling governs the neural potential of progenitors in the developing Xenopus retina," *Neuron* 2005, 46(1): 23-36.
Van Uitert et al., "Coordination compounds. II. The dissociation constants of beta-diketones in water-dioxane solutions," Journal of the American Chemical Society, 75:455-457, Jan. 20, 1953.
Voituriez et al., "Preparation of a Storable Zinc Carbenoid Species and Its Application in Cyclopropanation, Chain Extension, and [2,3]-Sigmatropic Rearrangement Reactions," *J. Org. Chem*, vol. 75, No. 4 (2010), pp. 1244-1250.
Wagner et al., "The Therapeutic Potential of the Wnt Signaling Pathway in Bone Disorders" *Current Molecular Pharmacology*, 2011, 4:14-25.
Wang et al, "Evaluation of the influence of compound structure on stacked-dimer formation in the DNA minor groove," Biochemistry, 40(8): 2511-2521, Feb. 2001.
Wang et al., "Caspase inhibitors, but not c-Jun NH2-terminal kinase inhibitor treatment, prevent cisplatm-induced hearing loss," *Cancer Res.*, 64(24):9217-9224, Dec. 15, 2004.
Wang et al., "Two new lignans from the fruits of Schisandra sphenanthera," *Nat Prod Commun.*, 4(11):1571-1574, Nov. 2009.
Wernig et al., "Neurons derived from reprogrammed fibroblasts functionally integrate into the fetal brain and improve symptoms of rats with Parkinson's disease," *Proc. Natl. Acad. Sci. USA* 2008, 105(15): 5856-5861.
Wong et al., "Effects of forced expression of an NH2-terminal truncated beta-Catenin on mouse intestinal epithelial homeostasis," *J Cell Biol.*, 141(3):765-777, May 4, 1998.
Wong et al., "Selection of multipotent stem cells during morphogenesis of small intestinal crypts of Lieberkuhn is perturbed by stimulation of Lef-1/beta-catenin signaling," *J Biol Chem.*, 277(18):15843-50. Epub Feb. 19, 2002.
Wu and Farrelly, "Regulatory perspectives of Type II prodrug development and time-dependent toxicity management: nonclinical Pharm/Tox analysis and the role of comparative toxicology," *Toxicology*, 236(1-2):1-6, Epub Apr. 2007.
Wu Anxin et al: "An Expeditious Synthetic Route to Furolignans having Two Different Aryl Groups+," J. of Chem. Res.—Synopses, No. 3, Jan. 1, 1998 (Jan. 1, 1997), pp. 136-137, XP055276538.
Xue et al., "Zinc-mediated chain extension reaction of 1,3-diketones to 1,4-diketones and diastereoselective synthesis of trans-1,2-disubstituted cyclopropanols," *Journal of Organic Chemistry* 2006, 71(1): 215-218.
Yamaguchi et al., "Histone deacetylase 1 regulates retinal neurogenesis in zebrafish by suppressing Wnt and Notch signaling pathways," *Development*, 132(13):3027-3043, Jul. 2005.
Yasuda et al., "Cross-coupling reaction of alpha-chloroketones and organotin enolates catalyzed by zinc halides for synthesis of gamma-diketones," *J Am Chem Soc.*, vol. 124, No. 25 (Jun. 2002), pp. 7440-7447.
Yavropoulou and Yovos, "The role of the wnt signaling pathway in osteoblast commitment and differentiation" *Hormones*, 2007, 6(4):279-294.
Yoon et al., "Anti-wrinkle effect of bone morphogenetic protein receptor 1a-extracellular domain (BMPR1a-ECD)," BMB Rep., 46(9):465-470, Sep. 2013.
Yoshimura et al., "Discovery of novel and potent retinoic acid receptor alpha agonists: syntheses and evaluation of benzofuranyl-pyrrole and benzothiophenyl-pyrrole derivatives," *J Med Chem.*, 43(15):2929-2937, Jul. 27, 2000.
Zaragosi et al., Effects of GSK3 inhibitors on in vitro expansion and differentiation of human adipose-derived stem cells into adipocytes. BMC Cell Biology 2008, 9(11), pp. 1-9, Published Feb. 13, 2006, Abstract; p. 2.
Zhang et al., "Role of the conserved aspartate and phenylalanine residues in prokaryotic and mitochondrial elongation factor Ts in guanine nucleotide exchange," *FEBS Lett.*, 391(3):330-332, Aug. 12, 1996.

(56) References Cited

OTHER PUBLICATIONS

Zhu and Zhang, "Synthesis and reaction of β,β-di(trifluoroacetyl) ethylenederivatives, $(CF_3CO)_2C=CR_1R_2$," *Journal of Fluorine Chemistry*, vol. 74, No. 2 (1995), pp. 167-170.

* cited by examiner

GAMMA-DIKETONES AS WNT/β-CATENIN SIGNALING PATHWAY ACTIVATORS

CROSS-REFERENCE TO RELATED APPLICATIONS

This application is a continuation application of U.S. application Ser. No. 15/918,086, filed on Mar. 12, 2018, which is a divisional application of U.S. application Ser. No. 15/356,903, filed Nov. 21, 2016, which is a divisional application of U.S. application Ser. No. 14/187,063, filed Feb. 21, 2014, and claims the benefit of U.S. Provisional Application No. 61/768,033, filed Feb. 22, 2013, each of which is incorporated herein by reference in its entirety.

BACKGROUND

Technical Field

This disclosure relates to activators of one or more proteins in the Wnt pathway, including activators of one or more Wnt proteins, and compositions comprising the same. More particularly, it concerns the use of a γ-diketones or salts or analogs thereof, in the treatment of osteoporosis and osteoarthropathy; osteogenesis imperfecta; bone defects; bone fractures; periodontal disease; otosclerosis; wound healing; craniofacial defects; oncolytic bone disease; traumatic brain or spine injuries; brain atrophy/neurological disorders related to the differentiation and development of the central nervous system, including Parkinson's disease, strokes, ischemic cerebral disease, epilepsy, Alzheimer's disease, depression, bipolar disorder, and schizophrenia; otic disorders like cochlear hair cell loss; eye diseases such as age related macular degeneration, diabetic macular edema or retinitis pigmentosa; and diseases related to differentiation and growth of stem cell, such as hair loss, hematopoiesis related diseases and tissue regeneration related diseases.

Background

The Wnt/β-catenin signaling pathway is involved in many biological processes. For example, aberrant activation of the Wnt/β-catenin pathway has led to several phenotypes, including the development of a variety of human cancers, and diseases leading to abnormal development and functioning of stem cells [*Oncogene* (2009), 28(21), 2163-2172; *Cancer Cell* (2008), 14(6), 471-484; *American Journal of Pathology* (2003), 162(5), 1495-1502]. Chronic activation of the Wnt/β-catenin signaling pathway has been implicated in the development of a variety of human malignancies, including high bone mass syndrome, sclerosteosis, colorectal carcinomas, hepatocellular carcinomas (HCCs), ovarian, uterine, pancreatic carcinomas, and melanomas [*BioEssays* (1999) 21(12), 1021-1030; *Cell* (2000), 103(2), 311-320; *Genes Dev.* (2000), 14(15), 1837-1851]. Since the Wnt/β-catenin pathway is involved in a number of growth and development processes, mutation of the proteins involved in the Wnt/β-catenin signal transduction system has also been linked to other human diseases such as abnormalities in development, hair follicle morphogenesis, stem cell differentiation, bone formation, and cell proliferation.

SUMMARY

The present disclosure relates to methods for increasing cell or tissue regeneration in a vertebrate patient. The disclosure relates to methods for increasing the activity of embryonic and/or adult stem cells, progenitor cells, mesenchymal progenitor/stem cells and/or differentiated cells in vivo in a vertebrate patient. The disclosure further relates to methods for increasing cell or tissue regeneration in a vertebrate patient by administering to a vertebrate patient in need thereof a compound according to Formula I, II, III, IIIa, IIIb, and/or IV, and increasing a stem cell, progenitor cell, and/or differentiated cell population in the vertebrate patient as compared to the stem cell, progenitor cell, and/or differentiated cell population in the vertebrate patient before treatment. Increasing the stem cell, progenitor cell, or differentiated cell population in the vertebrate patient can be a result of one or more of cell proliferation, cell homing, decreased apoptosis, self-renewal, and increased cell survival.

In one embodiment, the cell or tissue regeneration can occur in tissues including but not limited to, bone, chondrocytes/cartilage, muscle, skeletal muscle, cardiac muscle, pancreatic cells, endothelial cells, vascular endothelial cells, adipose cells, liver, skin, connective tissue, hematopoietic stem cells, neonatal cells, umbilical cord blood cells, fetal liver cells, adult cells, bone marrow cells, peripheral blood cells, erythroid cells, granulocyte cells, macrophage cells, granulocyte-macrophage cells, B cells, T cells, multipotent mixed lineage colony types, embryonic stem cells, mesenchymal progenitor/stem cells, mesodermal progenitor/stem cells, neural progenitor/stem cells, or nerve cells. The vertebrate can be mammalian, avian, reptilian, amphibian, osteichthyes, or chondrichthyes.

In one embodiment, the present disclosure provides a composition for preventing or decreasing the loss of hair and/or for stimulating or increasing hair growth or regrowth in a patient, wherein the composition comprises a compound according to Formula I, II, III, IIIa, IIIb, and/or IV.

In one embodiment, the present disclosure provides a composition for preventing cochlear hair cell loss in a patient, wherein the composition comprises a compound according to Formula I, II, III, IIIa, IIIb, and/or IV.

One embodiment of the present disclosure provides a pharmaceutical composition for the treatment of a neurodegenerative disease in a patient.

For example, the neurological disorder can be Alzheimer's disease, schizophrenia or schizo-affective disorder, bipolar disorder or unipolar disorder, depression, substance abuse, neurodegenerative disease, autism or autism spectrum disorder, or a disorder resulting from neural damage such as spinal injuries or brain injuries. The neurodegenerative disease may be, for instance, amyotrophic lateral sclerosis (Lou Gehrig's disease) or Parkinson's disease. In some embodiments, the disclosure provides methods for treating a brain injury resulting from a traumatic injury or stroke.

In some embodiments, the neurological disorder is an eye disease such as age related macular degeneration, diabetic macular edema or retinitis pigmentosa.

In one embodiment, the disclosure relates to methods for (i) reducing loss of bone mass or bone density, (ii) increasing bone mass or bone density, (iii) maintaining bone mass or bone density and/or (iv) reducing loss of calcium from bone in a patient, the method comprising: administering to the patient a therapeutically effective amount of a compound according to Formula I, II, III, IIIa, IIIb, and/or IV. As used in this disclosure, the term "bone mass" and "bone density" are used interchangeably.

In one embodiment, the disclosure relates to methods for regulating osteoblast activity or osteoclast activity comprising the use of a compound according to Formula I, II, III, IIIa, IIIb, and/or IV. Osteoblast activity can be regulated by regulating the proliferation or function of osteoblasts. The function of osteoblasts and/or osteoclasts can be regulated directly or indirectly.

In one embodiment, the method is for the treatment of a bone condition or a bone defect. For example, the bone condition being treated can include frailty, an osteoporotic fracture, a bone defect, childhood idiopathic bone loss, alveolar bone loss, mandibular bone loss, bone fracture, osteotomy, bone loss associated with periodontitis, or prosthetic ingrowth. In some embodiments, the bone condition being treated is Paget's disease. In another embodiment, the bone condition being treated is oncolytic bone disease.

In another embodiment, the disclosure relates to methods for promoting healing of bone fractures, bone defects, craniofacial defects, otosclerosis or osteogenesis imperfecta comprising: administering to a patient in need thereof a therapeutically effective amount of a compound according to Formula I, II, III, IIIa, IIIb, and/or IV.

In another embodiment, the disclosure relates to methods for bone tissue engineering comprising the use of a compound according to Formula I, II, III, IIIa, IIIb, and/or IV. In one embodiment, the cells used for bone tissue engineering are contacted with an effective amount of a compound according to Formula I, II, III, IIIa, IIIb, and/or IV.

In another embodiment, the disclosure relates to the use of a compound according to Formula I, II, III, IIIa, IIIb, and/or IV as a medicament for healing bone fractures or repairing bone defects in a mammal.

In one embodiment, the bone condition being treated is osteoporosis. For example, the osteoporosis being treated can be selected from the group consisting of: glucocorticoid-induced osteoporosis, hyperthyroidism-induced osteoporosis, immobilization-induced osteoporosis, heparin-induced osteoporosis, and immunosuppressive-induced osteoporosis.

In one embodiment, a compound according to Formula I, II, III, IIIa, IIIb, and/or IV is administered conjointly with an agent that increases bone mass or prevents the loss of bone mass. In one embodiment, the agent that increases bone mass is a growth factor, a mineral, a vitamin, a hormone, a prostaglandin, an inhibitor of 15-lipoxygenase, a bone morphogenic protein or another member of the TGF-beta superfamily which increases bone formation, an ACE inhibitor, a Hedgehog protein, examethasone, calcitonin, or an active fragment thereof. In one embodiment, the agent that prevents the loss of bone mass is progestin, estrogen, an estrogen/progestin combinations, estrone, estriol, 17α- or 17β-ethynyl estradiol, SB242784, polyphosphonates, bisphosphonates, or an active fragment thereof.

In one embodiment of the disclosure, a compound according to Formula I, II, III, IIIa, IIIb, and/or IV, is administered to a patient in need thereof to enhance proliferation of intestinal epithelium, for the treatment, or as a therapeutic adjunct in the treatment, of diseases that compromise the intestinal epithelia, including inflammatory bowel diseases, mucositis (oral and gastrointestinal) and Celiac disease.

In another embodiment, the disclosure relates to methods for organ tissue engineering comprising the use of a compound according to Formula I, II, III, IIIa, IIIb, and/or IV. In one embodiment the cells used for organ tissue engineering are contacted with an effective amount of a compound according to Formula I, II, III, IIIa, IIIb, and/or IV.

Some embodiments disclosed herein include a Wnt/β-catenin signaling pathway activator containing a γ-diketone core. Other embodiments disclosed herein include pharmaceutical compositions and methods of treatment using one or more of the compounds provided herein.

One embodiment of a Wnt/β-catenin signaling pathway activator disclosed herein includes compounds of Formula I:

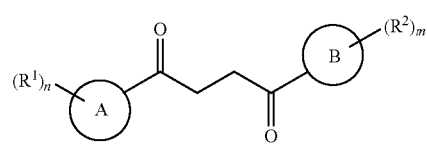

or a pharmaceutically acceptable salt thereof.

In some embodiments of Formula I:
Ring A is a 7-12 membered heteroaryl, with the proviso that a carbon atom on the ring is attached to the carbonyl carbon;

Ring B is selected from the group consisting of phenyl and a 5-6 membered heteroaryl, with the proviso that a carbon atom on the ring is attached to the carbonyl carbon;

$R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN;

$R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN;

each $R^3$ is independently selected from the group consisting of H, unsubstituted —$C_{1-6}$ alkyl, —$C_{1-3}$ haloalkyl, and $CF_3$;

each $R^{3b}$ is independently selected from the group consisting of H and unsubstituted —$C_{1-3}$ alkyl;

each n is an integer of 1 to 10; and
each m is an integer of 1 to 5.

Another embodiment of a Wnt/β-catenin signaling pathway activator disclosed herein includes compounds of Formula II:

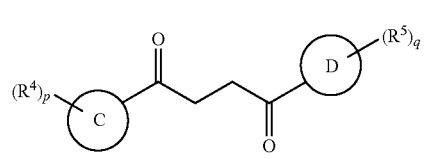

or a pharmaceutically acceptable salt thereof.

In some embodiments of Formula II:
Ring C is a 5-6 membered heteroaryl, with the proviso that a carbon atom on the ring is attached to the carbonyl carbon;

Ring D is selected from the group consisting of phenyl and a 5-6 membered heteroaryl, with the proviso that a carbon atom on the ring is attached to the carbonyl carbon;

$R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN;

$R^5$ is a substituent attached to Ring D and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN;

each $R^6$ is independently selected from the group consisting of H, unsubstituted —$C_{1-6}$ alkyl, —$C_{1-3}$ haloalkyl, and $CF_3$;

each $R^{6b}$ is independently selected from the group consisting of H and unsubstituted —$C_{1-3}$ alkyl;

each q is an integer of 1 to 4; and each p is an integer of 1 to 5.

Another embodiment of a Wnt/β-catenin signaling pathway activator disclosed herein includes compounds of Formula III:

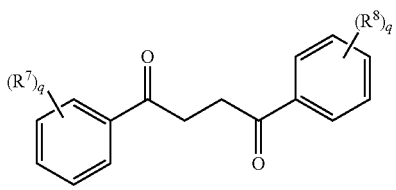

or a pharmaceutically acceptable salt thereof.

In some embodiments of Formula III:

$R^7$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, $CF_3$, and CN;

$R^8$ is a substituent attached to the phenyl ring and is independently selected at each occurrence from the group consisting of H, unsubstituted —$C_{1-6}$ alkyl, —$CH_2OH$, —$CH_2N(R^{9a})_2$, —$C_{1-3}$ haloalkyl, halide, —$OR^9$, $CF_3$, and CN;

each $R^9$ is independently selected from the group consisting of H, unsubstituted —$C_{1-6}$ alkyl, —$C_{1-3}$ haloalkyl and $CF_3$;

each $R^{9a}$ is independently selected from the group consisting of H and unsubstituted —$C_{1-3}$ alkyl; and each q is an integer of 1 to 5.

Another embodiment of a Wnt/β-catenin signaling pathway activator disclosed herein includes compounds of Formula IIIa:

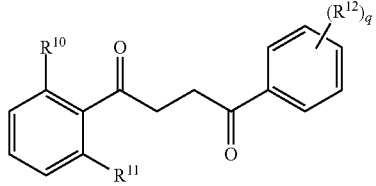

or a pharmaceutically acceptable salt thereof.

In some embodiments of Formula IIIa:

$R^{10}$ is selected from the group consisting of H, unsubstituted —$C_{1-6}$ alkyl, —$C_{1-3}$ haloalkyl, halide, —$OR^{13}$, $CF_3$, and CN;

$R^{11}$ is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, $CF_3$, and CN;

$R^{12}$ is a substituent attached to the phenyl ring and is independently selected at each occurrence from the group consisting of H, unsubstituted —$C_{1-6}$ alkyl, —$CH_2OH$, —$CH_2N(R^{13b})_2$, —$C_{1-3}$ haloalkyl, halide, —$OR^{13}$, $CF_3$, and CN;

each $R^{13}$ is independently selected from the group consisting of unsubstituted —$C_{1-6}$ alkyl, —$C_{1-3}$ haloalkyl, and $CF_3$;

each $R^{13b}$ is independently selected from the group consisting of H and unsubstituted —$C_{1-3}$ alkyl; and each q is an integer of 1 to 5.

Another embodiment of a Wnt/β-catenin signaling pathway activator disclosed herein includes compounds of Formula IIIb:

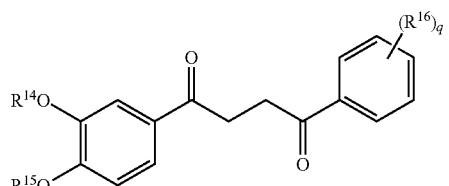

or a pharmaceutically acceptable salt thereof.

In some embodiments of Formula IIIb:

$R^{14}$ is selected from the group consisting of unsubstituted —$C_{1-6}$ alkyl, —$C_{1-3}$ haloalkyl, and $CF_3$;

$R^{15}$ is selected from the group consisting of unsubstituted —$C_{1-6}$ alkyl, —$C_{1-3}$ haloalkyl, and $CF_3$;

$R^{16}$ is a substituent attached to the phenyl ring and is independently selected at each occurrence from the group consisting of H, unsubstituted —$C_{1-6}$ alkyl, $CH_2OH$, —$CH_2N(R^{17b})_2$, —$C_{1-3}$ haloalkyl, halide, —$OR^{17}$, $CF_3$, and CN;

each $R^{17}$ is independently selected from the group consisting of unsubstituted —$C_{1-6}$ alkyl, —$C_{1-3}$ haloalkyl, and $CF_3$;

each $R^{17b}$ is independently selected from the group consisting of H and unsubstituted —$C_{1-3}$ alkyl; and each q is an integer of 1 to 5.

Another embodiment of a Wnt/β-catenin signaling pathway activator disclosed herein includes compounds of Formula IV:

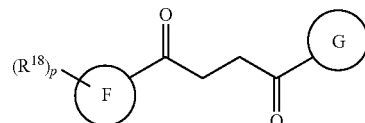

or a pharmaceutically acceptable salt thereof.

In some embodiments of Formula IV:

Ring F is

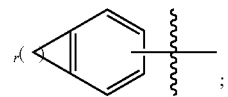

Ring G is selected from the group consisting of

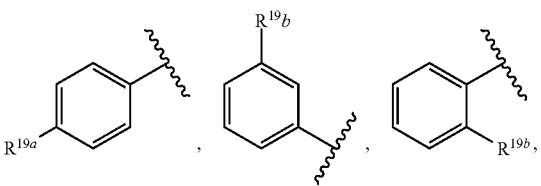

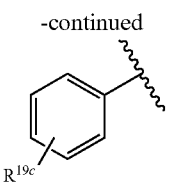

and a 5-6 membered heteroaryl $R^{19d}$, with the proviso that a carbon atom on the ring is attached to the carbonyl carbon;

each $R^{18}$ is a substituent attached to Ring F and is independently selected at each occurrence from the group consisting of H, —$C_{1-3}$ haloalkyl, halide, —$OR^{20}$, $CF_3$, and CN;

$R^{19a}$ is a substituent attached to the para position of phenyl and is selected from the group consisting of H, unsubstituted —$C_{2-6}$ alkyl, —$CH_2OH$, —$CH_2N(R^{21})_2$, —$C_{1-3}$ haloalkyl, F, Br, I, —$OR^{20}$, $CF_3$, and CN;

$R^{19b}$ is a substituent attached to the meta or ortho position of phenyl and is selected from the group consisting of H, unsubstituted —$C_{2-6}$ alkyl, —$CH_2OH$, —$CH_2N(R^{21})_2$, —$C_{1-3}$ haloalkyl, halide, —$OR^{20}$, $CF_3$, and CN;

$R^{19c}$ is 2-5 substituents, each attached to the phenyl and are independently selected at each occurrence from the group consisting of H, —$CH_2OH$, —$CH_2N(R^{21})_2$, —$C_{1-3}$ haloalkyl, halide, —$OR^{20}$, $CF_3$, and CN;

$R^{19d}$ is 1-4 substituents, each attached to the heteroaryl ring and is independently selected at each occurrence from the group consisting of H, —$CH_2OH$, —$CH_2N(R^{21})_2$, —$C_{1-3}$ haloalkyl, halide, —$OR^{20}$, $CF_3$, and CN;

each $R^{20}$ is independently selected from the group consisting of H, unsubstituted —$C_{3-6}$ alkyl, —$C_{1-3}$ haloalkyl, and $CF_3$;

each $R^{21}$ is independently selected from the group consisting of H and unsubstituted —$C_{1-3}$ alkyl;

p is an integer of 1 to 13; and r is an integer of 1 to 5.

Some embodiments include stereoisomers of a compound of Formula I, II, III, IIIa, and/or IIIb.

Some embodiments include prodrugs of a compound of Formula I, II, III, IIIa, and/or IIIb. For example, prodrugs of a compound of Formula I, II, III, IIIa, and/or IIIb can be prodrug polymer conjugates for delayed release or extended release.

Also provided herein are pharmaceutical compositions comprising a compound of Formula I, II, III, IIIa, and/or IIIb and a pharmaceutically acceptable carrier, diluent, or excipient.

Some embodiments of the present disclosure include methods to prepare compounds of Formula I, II, III, IIIa, and/or IIIb.

It is to be understood that both the foregoing general description and the following detailed description are exemplary and explanatory only and are not restrictive of the invention, as claimed.

DETAILED DESCRIPTION

Provided herein are γ-diketones capable of activating the Wnt/β-catenin signaling pathway. The Wnt/β-catenin signaling pathway has been found to play a role in the differentiation and development of nerve cells for the central nervous system, bone formation, hair follicle development and regeneration, and stimulation of stem cell growth, maintenance and differentiation.

The present disclosure relates to methods for increasing cell or tissue regeneration in a vertebrate patient. The disclosure relates to methods for increasing the activity of embryonic and/or adult stem cells, progenitor cells, mesenchymal progenitor/stem cells, or differentiated cells in vivo in a vertebrate patient. The disclosure further relates to methods for increasing cell or tissue regeneration by administering a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV to a vertebrate patient in need thereof, and increasing a stem cell, progenitor cell population, or differentiated cell in the vertebrate patient compared to the stem cell or progenitor cell, or differentiated cell population in the vertebrate patient before treatment. In some embodiments, a method for increasing stem cell or progenitor cell population can be used to repair or replace damaged tissue in a vertebrate patient, wherein the cell or tissue regeneration occurs in bone, chondrocytes/cartilage, muscle, skeletal muscle, cardiac muscle, pancreatic cells, endothelial cells, vascular endothelial cells, adipose cells, liver, skin, connective tissue, hematopoietic stem cells, neonatal cells, umbilical cord blood cells, fetal liver cells, adult cells, bone marrow cells, peripheral blood cells, erythroid cells, granulocyte cells, macrophage cells, granulocyte-macrophage cells, B cells, T cells, multipotent mixed lineage colony types, embryonic stem cells, mesenchymal progenitor/stem cells, mesodermal progenitor/stem cells, neural progenitor/stem cells, or nerve cells.

Hair Growth

Compositions comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to promote hair growth.

"Promoting hair growth" refers to maintaining, inducing, stimulating, accelerating, or revitalizing the growth of hair.

The methods of the present disclosure can be useful in the treatment of alopecia in mammals, and as such may be used to promote, increase, or assist in the growth of hair. Patients may be male or female. The term alopecia refers to both the complete absence of hair in skin which typically exhibits hair growth, as well as to a loss or diminution in the amount of hair. Multiple types and causes of alopecia are recognized in humans, including male pattern baldness, chemotherapy induced hair loss, congenital alopecia, and alopecia areata. The treatment of alopecia can include the treatment of skin with a total absence of hair growth as well as the treatment of skin having reduced or patchy hair growth. Successful treatment results in an increased number of hairs.

Patients to be treated according to the disclosure include human patients as well as other mammalian patients, such as dogs, cats, mice, rats, goats, llamas, minks, seals, beavers, ermines, and sheep. Patients can be treated for hair loss or to enhance the growth of hair, for example to increase wool or pelt production.

"Treating alopecia" refers to (i) preventing alopecia in an animal which may be predisposed to alopecia, (ii) inhibiting, retarding or reducing alopecia, (iii) promoting hair growth, and/or (iv) prolonging the anagen phase of the hair cycle.

A method for promoting hair growth in accordance with the present disclosure can include applying an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmacologically acceptable salt thereof, to the skin of mammals. For example, the compound can be applied to a human scalp.

Cochlear Hair Cell Loss

Compositions comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to promote regeneration of lost or damaged sensory hair cells.

"Promoting the regeneration of sensory hair cells" refers to maintaining, inducing, stimulating, accelerating, or revitalizing the growth of sensory hair cells.

The methods of the present disclosure are useful in the treatment of presbycusis in mammals, and as such may be used to promote, increase, or assist in the growth of cochlea hair cells. Mammalian cochlear hair cells come in two anatomically and functionally distinct types: the outer and inner hair cells. Patients may be male or female. Presbycusis can be caused by the slow loss of hearing that occurs as a result of ageing, after repeated exposure to loud noises, or as a symptom of certain medical conditions or medications. Multiple types and causes of presbycusis are recognized in humans, including, for example, arteriosclerosis (may diminish vascularity of the cochlea, thereby reducing its oxygen supply), diabetes mellitus (may cause vasculitis and endothelial proliferation in the blood vessels of the cochlea, thereby reducing its blood supply), poor diet (increased intake of saturated fat may accelerate atherosclerotic changes), stress, heart disease, diabetes blood vessel complications, high blood pressure, smoking (postulated to accentuate atherosclerotic changes in blood vessels), and viral or bacterial infections. Drugs, medications, substances, or toxins that can cause presbycusis as a symptom include, for example, aminoglycosides (gentamycin, streptomycin, etc.) and other antibiotics (macrolides and vancomycin), antineoplastic agents (platinum-based compounds cisplatin and carboplatin), salicylates (aspirin), quinine, and loop diuretics (ethacrynic acid, furosemide, bumetanide, etc.).

The term treating presbycusis refers to both the treatment of patients with total hearing loss as well as partial hearing loss. Successful treatment results in an improvement in a patient's hearing.

A method for promoting the regeneration of sensory hair cells in accordance with the present disclosure can include applying an effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmacologically acceptable salt thereof, in the ear of mammals. For example, the compound may be applied to the inner ear, or via intratympanic injection to the round window membrane or vicinity of the round window membrane.

Neurological Disorder

Compounds according to the present disclosure can modulate the cellular fate of neural stem cells and promote the differentiation of these neural precursors to functional neurons and glial cells.

Compositions comprising one or more compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to treat neurodegenerative diseases.

Non-limiting examples of neurodegenerative diseases include Alzheimer's disease, schizophrenia or schizo-affective disorder, bipolar disorder or unipolar disorder, depression, substance abuse, neurodegenerative disease, autism or autism spectrum disorder, or a disorder resulting from neural damage such as spinal injuries or brain injuries. The neurodegenerative disease may be, for instance, amyotrophic lateral sclerosis (Lou Gehrig's disease) or Parkinson's disease.

Other non-limiting examples of neurodegenerative diseases include eye diseases including, but not limited to, wet age-related macular degeneration, dry age-related macular degeneration, geographic atrophy, diabetic retinopathy, diabetic macular edema, retinal detachment, retinal degeneration, retinal vein occlusion, retinopathy of prematurity, retinitis pigmentosa, retinopathies, Leber congenital amaurosis and glaucoma.

The disclosure also provides methods for treating brain injury resulting from a traumatic injury or stroke.

Another aspect of the disclosure is a method for enhancing neural progenitor proliferation and differentiation by contacting a neural progenitor cell with a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV in an effective amount to enhance neural progenitor proliferation and differentiation.

In one aspect the disclosure provides a method for enhancing nerve generation, by contacting a nerve with a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV in an effective amount to enhance nerve generation.

In another aspect, the present disclosure provides a method for treating a neurodegenerative disease in a patient requiring such treatment, which comprises administering an effective amount of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof.

The compounds according to the present disclosure may be administered alone or in combination with another active agent. In one embodiment, a compound provided herein can be co-administered with an acetylcholinesterase inhibitor (e.g. Aricept) for Alzheimer's disease or L-DOPA for Parkinson disease.

Bone Formation

Compositions comprising one or more compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be used to treat, prevent or alleviate bone conditions. The present disclosure provides methods for (i) reducing loss of bone mass, (ii) increasing bone mass, (iii) maintaining bone mass, and/or (iv) reducing loss of calcium from bone, comprising: administering to a patient in need thereof a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV. The method could be used for treating, preventing, or delaying a bone condition. The disclosure further provides a method for promoting the healing of bone fractures or bone defects comprising: administering to a patient a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV. Any of the above mentioned methods can involve the conjoint administration of an agent that increases bone mass or prevents the loss of bone mass.

The disclosure also provides for the use of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV as a medicament for treating, preventing or delaying a bone condition.

As used herein, the term "bone condition" includes any condition where it is desirable to increase bone mass or bone density and/or prevent the loss of bone mass or bone density. A bone condition includes any condition that increases osteoclast number, increases osteoclast activity, increases bone resorption, increases marrow fibrosis, or alters the calcium content of bone.

Non-limiting examples of bone conditions include metabolic bone conditions such as renal osteodystrophy, primary forms of osteoporosis (e.g., postmenopausal and senile osteoporosis), and secondary forms of osteoporosis that develop as a result of an underlying disease state. For example, osteoporosis can develop in patients that have endocrine disorders such as hyperparathyroidism, hypo- and hyperthyroidism, hypogonadism, hypercalcemia due to malignancy, pituitary tumors, type I diabetes, or Addison's disease. Neoplasias such as multiple myeloma and carcinomatosis also can lead to development of osteoporosis. In addition, gastrointestinal problems such as malnutrition, malabsorption, hepatic insufficiency, and vitamin C or D deficiencies, and chronic administration of drugs such as anticoagulants, chemotherapeutics, corticosteroids, anticonvulsants, and alcohol can lead to development of osteoporosis.

Non-limiting examples of bone conditions also include osteonecrosis, osteoarthritis, rheumatoid arthritis, Paget's disease, osteogenesis imperfecta, chronic hyperparathyroidism, hyperthyroidism, Gorham-Stout disease, McCune-Albright syndrome, and alveolar ridge bone loss.

Bone conditions can also include, without limitation, conditions resulting in bone loss, for example, cancers and tumors (such as osteosarcoma and multiple myeloma), renal disease (including acute renal failure, chronic renal failure, renal bone dystrophy and renal reperfusion injury), kidney disease, and premature ovarian failure.

Endocrine disorders, vitamin deficiencies and viral infections also can lead to the development of bone conditions that can be treated as described herein. An example of a bone condition caused by a nutritional disorder is osteomalacia, a nutritional disorder caused by a deficiency of vitamin D and calcium. It is referred to as "rickets" in children, and "osteomalacia" in adults. It is marked by a softening of the bones (due to impaired mineralization, with excess accumulation of osteoid), pain, tenderness, muscle wasting and weakness, anorexia, and overall weight loss. It can result from malnutrition, repeated pregnancies and lactation (exhausting or depleting vitamin D and calcium stores), and vitamin D resistance.

Bone conditions include conditions resulting from the treatment of a patient with drugs, for example the osteopenia resulting from the treatment with Cyclosporin A or FK506.

Bone conditions also include bone fractures, bone trauma, conditions associated with post-traumatic bone surgery, post-prosthetic joint surgery, post-plastic bone surgery, post-dental surgery, bone chemotherapy, post-dental surgery, and bone radiotherapy. Fractures include all types of microscopic and macroscopic fractures. Examples of fractures includes avulsion fracture, comminuted fracture, transverse fracture, oblique fracture, spiral fracture, segmental fracture, displaced fracture, impacted fracture, greenstick fracture, torus fracture, fatigue fracture, intra-articular fracture (epiphyseal fracture), closed fracture (simple fracture), open fracture (compound fracture), and occult fracture.

Other non-limiting examples of bone conditions include bone deformation, spinal deformation, prosthesis loosening, bone dysplasia, scoliosis, periodontal disease and defects, tooth repair, and fibrous osteitis.

The disclosure also provides a method for treating a patient with a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, wherein the patient is in need of bone repair following surgery, such as cranio-maxillofacial repair following tumor removal, surgical bone reconstruction following traumatic injury, repair of hereditary or other physical abnormalities, and promotion of bone healing in plastic surgery.

The disclosure also provides a method for treating a patient with a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, wherein the patient is in need of bone repair after receiving an implant (including joint replacements and dental implants), prosthesis or a bone graft.

The disclosure also provides a method for treating a patient with a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, wherein the patient: a) is in need of increased bone density or bone healing; b) has undergone or is presently undergoing corticosteroid therapy, dialysis, chemotherapy for postmenopausal bone loss, radiation therapy for cancer, or hormone replacement therapy; c) is immobilized or subjected to extended bed rest due to bone injury; d) suffers from alcoholism, diabetes, hyperprolactinemia, anorexia nervosa, primary and secondary amenorrhea, or oophorectomy; e) suffers from renal failure; f) is 50 years or older; or g) is a female.

The disclosure also provides a method for treating a patient with a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, wherein the patient is affected by a disease selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, bone spurs, cartilage or ligament degeneration due to hydroxyapatite crystal deposition, and chondrocalcinosis.

The disclosure also provides a method for treating a patient with a therapeutically effective amount of a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV conjointly with an agent that increases bone mass or prevents the loss of bone mass. In one embodiment, the agent that increases bone mass is a growth factor, a mineral, a vitamin, a hormone, a prostaglandin, an inhibitor of 15-lipoxygenase, a bone morphogenic protein or another member of the TGF-beta superfamily which increases bone formation, an ACE inhibitor, a Hedgehog protein, examethasone, calcitonin, or an active fragment thereof. In one embodiment, the agent that prevents the loss of bone mass is progestin, estrogen, an estrogen/progestin combinations, estrone, estriol, 17α- or 17β-ethynyl estradiol, SB242784, polyphosphonates, bisphosphonates, or an active fragment thereof.

Intestinal Diseases

Compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can also administered for the treatment of gastrointestinal inflammation. "Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils.

"Chronic gastrointestinal inflammation" refers to inflammation of the mucosal of the gastrointestinal tract that is characterized by a relatively longer period of onset, is long-lasting (e. g., from several days, weeks, months, or years and up to the life of the patient), and is associated with infiltration or influx of mononuclear cells and can be further associated with periods of spontaneous remission and spontaneous occurrence. Thus, patients with chronic gastrointestinal inflammation may be expected to require a long period of supervision, observation, or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis induced by environmental insults (e. g., gastrointestinal inflammation (e. g., colitis) caused by or associated with (e. g., as a side effect) a therapeutic regimen, such as administration of chemotherapy, radiation therapy, and the like), colitis in conditions such as chronic granulomatous disease, celiac disease, celiac sprue (a heritable disease in which the intestinal lining is inflamed in response to the ingestion of a protein known as gluten), food allergies, gastritis, infectious gastritis or enterocolitis (e. g., *Helicobacter pylori*-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel diseases include, but are not limited to, Crohn's disease and ulcerative colitis. Reference to IBD throughout the specification is used throughout the specification as an example of the gastrointestinal inflammatory conditions provided herein, and is not meant to be limiting.

Compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be administered to a patient prior to onset of more severe symptoms (e.g., prior to onset of an acute inflammatory attack), or after onset of acute or chronic symptoms (e.g., after onset of an acute inflammatory attack). As such, the agents can be administered at any time, and may be administered at any interval. In one embodiment, a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can be administered about 8 hours, about 12 hours, about 24 hours, about 2 days, about 4 days, about 8 days, about 16 days, about 30 days or 1 month, about 2 months, about 4 months, about 8 months, or about 1 year after the initial onset of gastrointestinal inflammation-associated symptoms and/or after diagnosis of gastrointestinal inflammation in the patient.

When multiple doses are administered, subsequent doses can be administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose. In one embodiment, does are administered at intervals ranging from at least every two weeks to every four weeks (e.g., monthly intervals) in order to maintain the maximal desired therapeutic effect (e.g., to provide for maintenance of relief from IBD-associated symptoms).

Compounds according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV can also be administered for the treatment of mucositis. "Mucositis" as used herein refers to inflammatory and/or ulcerative lesions anywhere along the gastrointestinal (GI) tract. Infectious disease, immune deficiency, and medications can be causative. One of the major causes of mucositis is high-dose cancer therapy. In some embodiments, the mucositis is alimentary tract mucositis or oral mucositis. Alimentary tract mucositis refers to the expression of mucosal injury across the continuum of oral and gastrointestinal mucosa, from the mouth to the anus. Oral mucositis refers to the particular inflammation and ulceration that occurs in the mouth. Oral mucositis is a common and often debilitating complication of cancer treatment.

Regenerative Medicine

According to the present disclosure, pluripotent stem cells (PS cells) are capable of differentiating into any cell type of the body and retain the property of self-renewal, thereby providing a potentially unlimited source of new healthy tissue. In this regard, PS cells have attracted a great deal of attention due to their potential use for tissue and cell based therapies. PS cell derivation originally depended on the viral expression of the four transcription factors i.e. Oct4, Sox2, Klf4 and c-Myc. However, recent efforts to avoid genetic manipulation with the ultimate goal of clinical applications have led researchers to further define the signaling pathways involved in cell reprogramming with the aim of replacing ectopic gene expression with proteins or small molecules. Wnt/3-catenin signaling in particular has been highlighted as one of the key pathways in this process.

Somatic cells as referred to in the present disclosure refer to cells that have reached differentiation into cells that compose various organs of the body. In some embodiments, two or more somatic cells may be used in the methods described herein. For example, a combination of an epithelial cell line and mesenchymal cells, a combination of endothelial cells and mesenchymal cells, or a combination of epithelial cells and mesenchymal cells can be used.

There are no particular limitations on organs capable of being formed by the somatic cells provided herein. Non-limiting examples include various organs such as hair follicle, lung, kidney, liver, pancreas, spleen, heart, gallbladder, small intestine, colon, large intestine, joint, bone, tooth, blood vessel, lymph duct, cornea, cartilage, olfactory organ, or auditory organ.

Various mammals can be used without limitation as the origin of the cells provided herein depending on the ultimate intended purpose of the cells. For example, mammals include chimpanzees, other primates, domestic animals such as dogs or cats, farm animals such as cows, pigs, horses, sheep or goats, laboratory animals such as rabbits, rats, mice or guinea pigs. In some embodiments, the mammals are nude mice, SCID mice, or nude rats. In addition, combinations of cells can include homogeneous combinations or heterogeneous combinations. In some embodiments, the combination is a homogeneous combination. In some embodiments, culturing somatic cells of one or more types of differentiated somatic cells as described above can be combine with one or more Wnt/β-catenin signaling pathway activators according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. Alkyl groups can be saturated or unsaturated (e.g., containing —C═C— or —C≡C— subunits), at one or several positions. Typically, alkyl groups will comprise 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. Typically, carbocyclyl groups will comprise 3 to 10 carbon atoms, for example, 3 to 6 carbon atoms.

As used herein, "lower alkyl" means a subset of alkyl having 1 to 3 carbon atoms, which is linear or branched. Examples of lower alkyls include methyl, ethyl, n-propyl and isopropyl. Likewise, radicals using the terminology "lower" refer to radicals having 1 to about 3 carbons in the alkyl portion of the radical.

As used herein, "aryl" means an aromatic ring system containing a single-ring (e.g., phenyl) or multiple condensed rings (e.g., naphthyl or anthryl) with only carbon atoms present in the ring backbone. Aryl groups can either be unsubstituted or substituted with one or more substituents. In some embodiments, the aryl is phenyl.

As used herein, "arylalkyl" means an aryl-alkyl-group in which the aryl and alkyl moieties are as previously described. Preferred arylalkyl groups contain a $C_1$-4alkyl moiety. Exemplary arylalkyl groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, 2,3-dihydrobenzo[b][1,4]oxathiine, and others.

As used herein, "heteroarylalkyl" means a heteroaryl-alkyl-group in which the heteroaryl and alkyl moieties are as previously described. Preferred heteroarylalkyl groups contain a $C_{1-4}$ alkyl moiety. Exemplary heteroarylalkyl groups include pyridylmethyl.

As used herein, "acyl" means an H—CO— or alkyl-CO—, carbocyclyl-CO—, aryl-CO—, heteroaryl-CO—, or heterocyclyl-CO— group wherein the alkyl, carbocyclyl, aryl or heterocyclyl group is as herein described. In some embodiments, acyls contain a lower alkyl. Exemplary alkyl acyl groups include formyl, acetyl, propanoyl, 2-methylpropanoyl, t-butylacetyl, butanoyl, and palmitoyl.

As used herein, "alkoxycarbonyl" means an alkyl-O—CO— group in which the alkyl group is as described herein. Exemplary alkoxycarbonyl groups include methoxy- and ethoxycarbonyl.

As used herein, "alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy, s-butoxy, t-butoxy, pentoxy, hexoxy and heptoxy, and also the linear or branched positional isomers thereof.

As used herein, "halo", "halide" or "halogen" is a chloro, bromo, fluoro, or iodo atom radical. In some embodiments, a halo is a chloro, bromo or fluoro. For example, a halo can be fluoro.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one up to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, an alkyl, a halide, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an arylalkyl, a heteroarylalkyl, an aryl, or heteroaryl moiety.

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, for example, as described in WO 87/05297.

"Solvate" refers to the compound formed by the interaction of a solvent and a Wnt pathway activator as provided herein or a salt thereof. Suitable solvates are pharmaceutically acceptable solvates including hydrates.

The term "patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

The term "mammal" is used in its usual biological sense. Thus, it specifically includes humans, cattle, horses, monkeys, dogs, cats, mouse, rat, a cow, sheep, pig, goat, and non-human primate but also includes many other species.

The term "vertebrate" is used in its usual biological sense. Thus, it specifically includes the classes' agnatha (jawless fishes), chondrichthyes (cartilaginous fishes), osteichthyes (bony fishes), amphibia (amphibians), reptilia (reptiles), aves (birds) and mammalia (mammals).

By "therapeutically effective amount" or "pharmaceutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV in combination with one or more other agents that are effective to treat Wnt related diseases and/or conditions. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and can include curing a disease. "Curing" means that the symptoms of a disease are eliminated. However, certain long-term or permanent effects of the disease may exist even after a cure is obtained (such as extensive tissue damage).

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder, and/or reducing the severity of symptoms that will or are expected to develop.

The expression "compound-eluting" shall be understood to refer to any and all mechanisms, e.g., diffusion, migration, permeation, and/or desorption by which the compound(s) incorporated in the compound-eluting material or coating pass therefrom over time into the surrounding body tissue.

The expression "controlled release" encompasses many types of controlled release, including, for example, immediate release, pulsatile release, slow release, sustained release, and delayed release, to achieve a desired compound delivery profile.

The expression "compound-eluting material" and/or "compound-eluting coating" and/or "controlled release material" shall be understood herein to mean any natural, synthetic, or semi-synthetic material into which one or more compounds can be incorporated and from which incorporated compound(s) are capable of eluting over time. Materials for the delivery of a compound include a wide range of polymers and small-molecule matrices. For many compound-polymer systems, the release of the compound is dominated by the diffusion of the compound through a polymer matrix. Polymer materials for compound delivery coatings may be durable or degradable [see, e.g., *Current Pharmaceutical Design* (2010), 16(36), 3978-3988]. Durable polymers are used in devices such as Cordis Cypher, Boston Scientific Taxus, Boston Scientific Promus, Abbott Xience, and Medtronic Resolute stents. Durable polymers can allow for longer delivery times and the underlying matrix does not change over time. Degradable polymer coatings are used in devices such as OrbusNeich Combo stent. These materials enable control over the release of a compound by both diffusion (similar to durable systems) and degradation of the polymer, which can change the polymer Tg, coating thickness, and encapsulation of the compound over time. Some devices utilize both durable and biodegradable coatings, such as a stent coated on the inner and outer lumen for two different compound delivery mechanisms in a single device. In some embodiments, water insoluble/hydrophobic compounds may be coated directly onto the device with or without one or more additives [U.S. Pat. Appl. Publ. (2004), US20040224003 & PCT Int. Appl. (2013), WO/2013/169724].

The following abbreviations have the indicated meanings:

AD=Alzheimer's disease
APC=adenomatous polyposis coli
L-DOPA=L-3,4-dihydroxyphenylalanine
Lef=lymphoid enhancing factor
MMTV=mouse mammary tumor virus
SCID=severe combined immunodeficiency
TCF=T-cell factor
TGF=transforming growth factor
Wnt=wingless-type MMTV integration site family member Compounds The compounds and compositions described herein are capable of activating the Wnt/β-catenin signaling pathway. The Wnt/β-catenin signaling pathway has been found to play a role in the differentiation and development of nerve cells for the central nervous system, bone formation, hair follicle development and regeneration, and stimulation of stem cell growth, maintenance, and differentiation.

Some embodiments of the present disclosure include compounds of Formula (I):

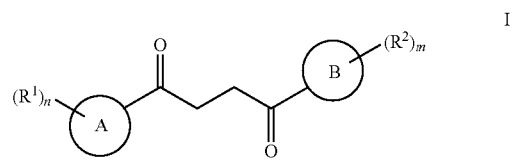

or salts, pharmaceutically acceptable salts, or prodrugs thereof.

In some embodiments of Formula I, Ring A is a 7-12 membered heteroaryl, wherein a carbon atom on the ring is attached to the carbonyl carbon.

In some embodiments of Formula I, Ring B is selected from the group consisting of phenyl and a 5-6 membered heteroaryl, with the proviso that a carbon atom on the ring is attached to the carbonyl carbon.

In some embodiments of Formula I, $R^1$ is a substituent attached to Ring A and is independently selected at each occurrence from the group consisting of H, unsubstituted $C_{1-6}$ alkyl, $C_{1-3}$ haloalkyl, halide, $-OR^3$, $CF_3$, and CN.

In some embodiments of Formula I, $R^2$ is a substituent attached to Ring B and is independently selected at each occurrence from the group consisting of H, unsubstituted $C_{1-6}$ alkyl, $-CH_2OH$, $-CH_2N(R^{3b})_2$, $C_{1-3}$ haloalkyl, halide, $-OR^3$, $CF_3$, and CN.

In some embodiments of Formula I, each $R^3$ is independently selected from the group consisting of H, unsubstituted $C_{1-6}$ alkyl, $C_{1-3}$ haloalkyl, and $CF_3$.

In some embodiments of Formula I, each $R^{3b}$ is independently selected from the group consisting of H and unsubstituted $C_{1-3}$ alkyl.

In some embodiments of Formula I, each n is an integer of 1 to 10.

In some embodiments of Formula I, each m is an integer of 1 to 5.

In some embodiments of Formula I, there is the proviso that a compound of Formula I is not a compound selected from the group consisting of:

with the proviso that the compound of Formula I is not a compound selected from the group consisting of:

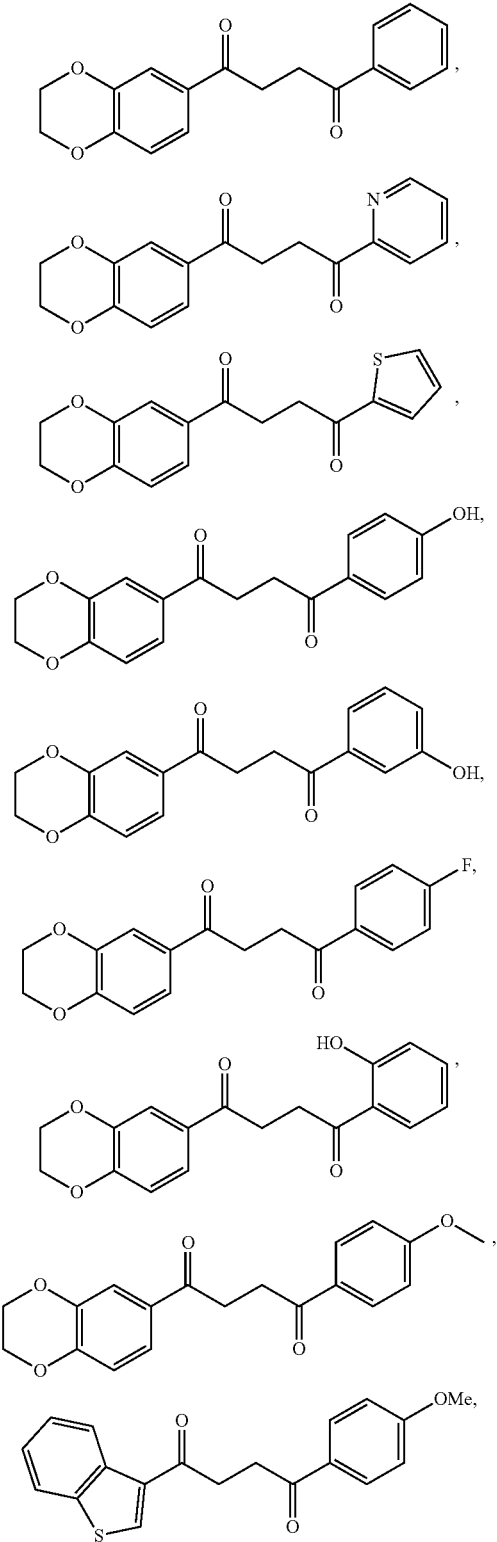

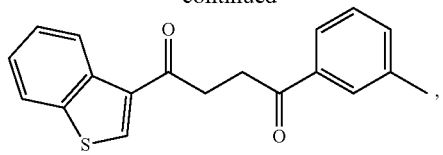
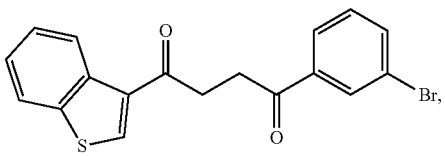
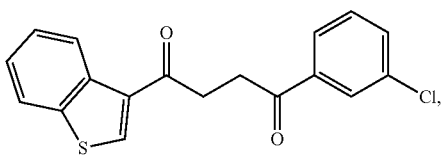
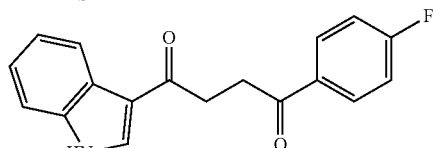
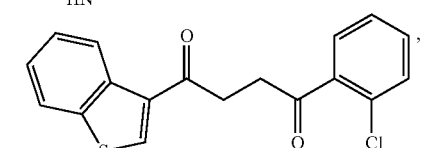
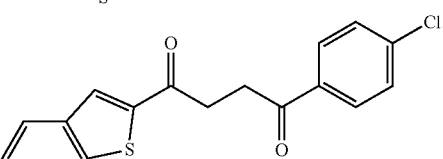
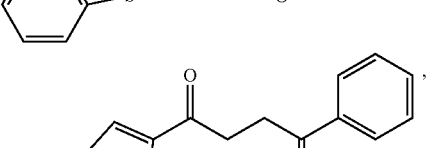
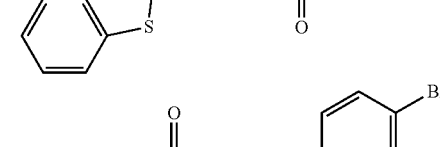
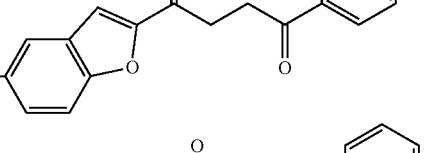
and
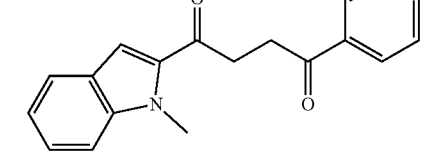

In some embodiments of Formula I, Ring A is a 9-membered bicyclic heteroaryl ring containing 1-3 heteroatoms selected from the group consisting of N, O, and S.

In some embodiments of Formula I, Ring A is a 10-membered bicyclic heteroaryl ring containing 1-3 heteroatoms selected from the group consisting of N, O, and S.

In some embodiments of Formula I, Ia, Ib, Ic, Id, Ie, If, Ig, Ih, and/or Ii, $R^1$ is selected from the group consisting of H, F, Cl, Me, OMe, OH, $CF_3$, and CN.

In some embodiments of Formula I, Ia, Ib, Ic, Id, Ie, If, Ig, Ih, and/or Ii, $R^1$ is H.

In some embodiments of Formula I, Ia, Ib, Ic, Id, Ie, If, Ig, Ih, and/or Ii, $R^1$ is a halide.

In some embodiments of Formula I, Ia, Ib, Ic, Id, Ie, If, Ig, Ih, and/or Ii, $R^1$ is F.

In some embodiments of Formula I, Ia, Ib, Ic, Id, Ie, If, Ig, Ih, and/or Ii, $R^1$ is Cl.

In some embodiments of Formula I, Ia, Ib, Ic, Id, Ie, If, Ig, Ih, and/or Ii, $R^1$ is Me.

In some embodiments of Formula I, Ia, Ib, Ic, Id, Ie, If, Ig, Ih, and/or Ii, $R^1$ is OH.

In some embodiments of Formula I, Ia, Ib, Ic, Id, Ie, If, Ig, Ih, and/or Ii, $R^1$ is OMe.

In some embodiments of Formula I, Ia, Ib, Ic, Id, Ie, If, Ig, Ih, and/or Ii, $R^1$ is $CF_3$.

In some embodiments of Formula I, Ia, Ib, Ic, Id, Ie, If, Ig, Ih, and/or Ii, $R^1$ is CN.

In some embodiments of Formula I, Ia, Ib, Ic, Id, Ie, If, Ig, Ih, and/or Ii, n is an integer from 1-8.

In some embodiments of Formula I, Ia, Ib, Ic, Id, Ie, If, Ig, Ih, and/or Ii, n is an integer from 1-6.

In some embodiments of Formula I, Ia, Ib, Ic, Id, Ie, If, Ig, Ih, and/or Ii, n is an integer from 1-4.

In some embodiments of Formula I, Ia, Ib, Ic, Id, Ie, If, Ig, Ih, and/or Ii, n is an integer from 1-2.

In some embodiments of Formula I, Ia, Ib, Ic, Id, Ie, If, Ig, Ih, and/or Ii, $R^1$ is F; and n is 1.

In some embodiments of Formula I, Ia, Ib, Ic, Id, Ie, If, Ig, Ih, and/or Ii, $R^1$ is F; and n is an integer from 1-2.

In some embodiments of Formula I, Ia, Ib, Ic, Id, Ie, If, Ig, Ih, and/or Ii, $R^1$ is F; and n is an integer from 3-4.

In some embodiments of Formula I, Ia, Ib, Ic, Id, Ie, If, Ig, Ih, and/or Ii, $R^1$ is OH; and n is an integer from 1-2.

In some embodiments of Formula I, Ia, Ib, Ic, Id, Ie, If, Ig, Ih, and/or Ii, $R^1$ is OMe; and n is an integer from 1-2.

In some embodiments of Formula I, Ia, Ib, Ic, Id, Ie, If, Ig, Ih, and/or Ii, $R^1$ is —$C_{1-2}$ alkyl.

In some embodiments of Formula I, Ia, Ib, Ic, Id, Ie, If, Ig, Ih, and/or Ii, $R^1$ is —$C_{1-3}$ alkyl.

In some embodiments of Formula I, Ia, Ib, Ic, Id, Ie, If, Ig, Ih, and/or Ii, $R^1$ is —$C_{1-4}$ alkyl.

In some embodiments of Formula I, Ia, Ib, Ic, Id, Ie, If, Ig, Ih, and/or Ii, $R^1$ is —$C_{1-5}$ alkyl.

In some embodiments of Formula I, Ia, Ib, Ic, Id, Ie, If, Ig, Ih, and/or Ii, $R^1$ is —$C_{1-6}$ alkyl.

In some embodiments of Formula I, Ia, Ib, Ic, Id, Ie, If, Ig, Ih, and/or Ii, $R^1$ is —$C_{2-6}$ alkyl.

In some embodiments of Formula I, Ia, Ib, Ic, Id, Ie, If, Ig, Ih, and/or Ii, $R^1$ is —$C_{3-6}$ alkyl.

In some embodiments of Formula I, Ia, Ib, Ic, Id, Ie, If, Ig, Ih, and/or Ii, $R^1$ is —$C_{4-6}$ alkyl.

In some embodiments, each $R^1$ is the same.

In some embodiments of Formula I, Ring A is selected from the group consisting of:

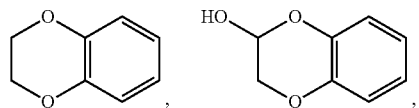

-continued

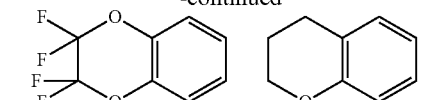
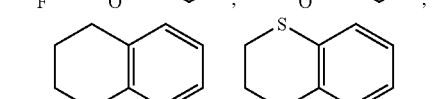
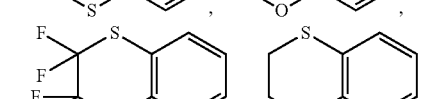
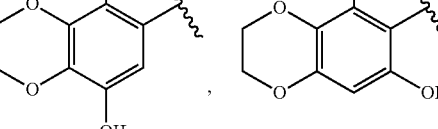
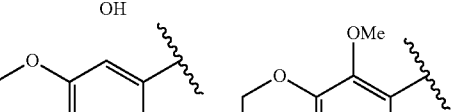
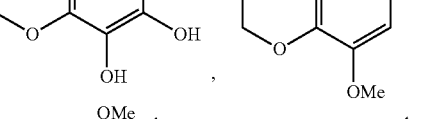
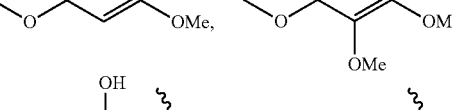
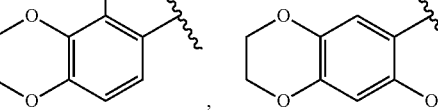
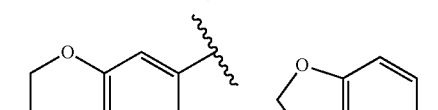
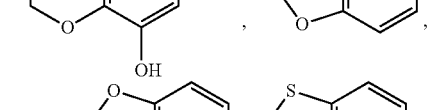
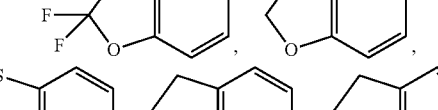
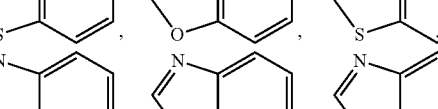
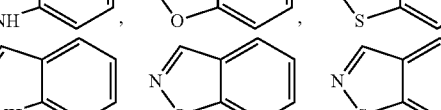
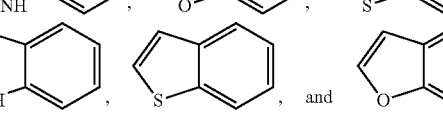

wherein, unless otherwise designated, the carbonyl carbon of Formula I can form a bond with any unsubstituted carbon on Ring A.

In some embodiments of Formula I, Ring A is selected from the group consisting of:

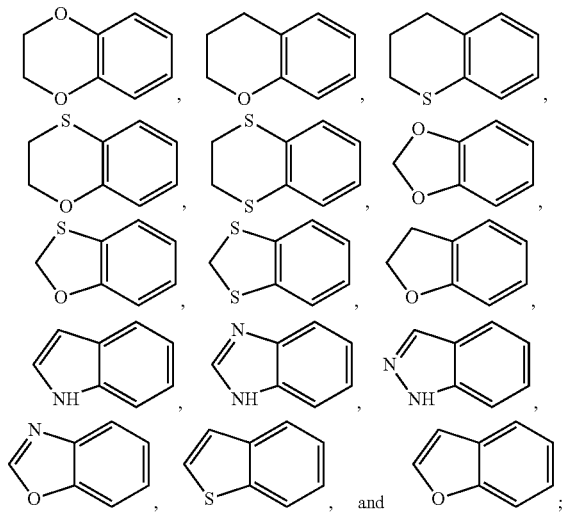

wherein the carbonyl carbon of Formula I can form a bond with any unsubstituted carbon on Ring A.

In some embodiments of Formula I, Ring A is selected from the group consisting of:

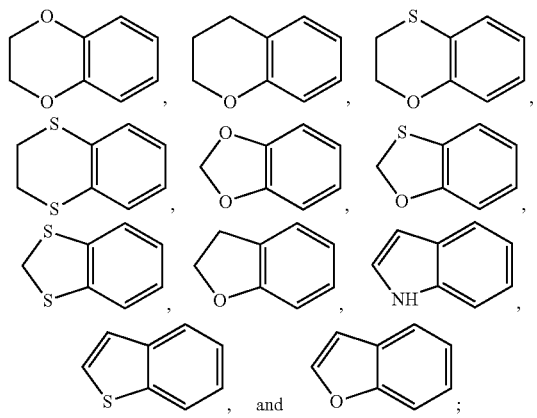

wherein the carbonyl carbon of Formula I can form a bond with any unsubstituted carbon on the Ring A.

In some embodiments of Formula I, Ring A is selected from the group consisting of:

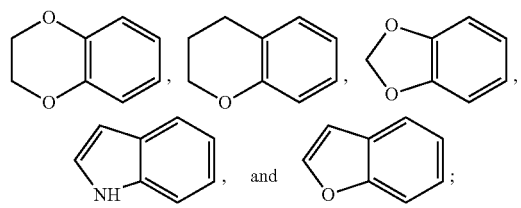

wherein the carbonyl carbon of Formula I can form a bond with any unsubstituted carbon on the Ring A.

In some embodiments of Formula I, Ring A is selected from the group consisting of

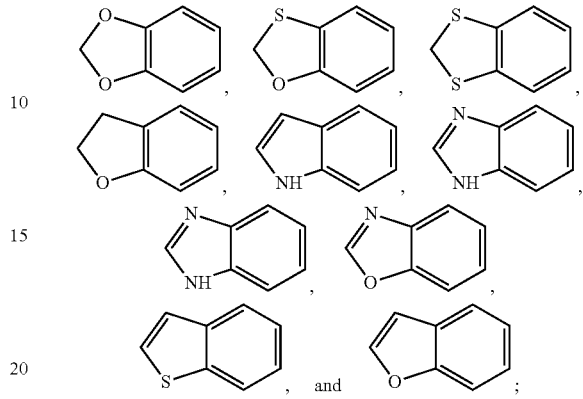

wherein the carbonyl carbon of Formula I can form a bond with any unsubstituted carbon on the Ring A.

In some embodiments of Formula I, Ring A is selected from the group consisting of

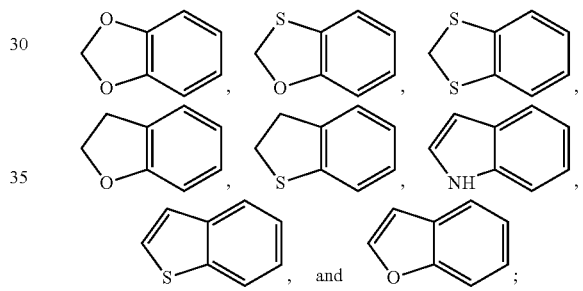

wherein the carbonyl carbon of Formula I can form a bond with any unsubstituted carbon on the Ring A.

In some embodiments of Formula I, Ring A is selected from the group consisting of

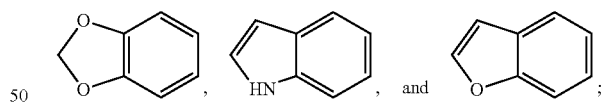

wherein the carbonyl carbon of Formula I can form a bond with any unsubstituted carbon on the Ring A.

In some embodiments of Formula I, Ring A is selected from the group consisting of

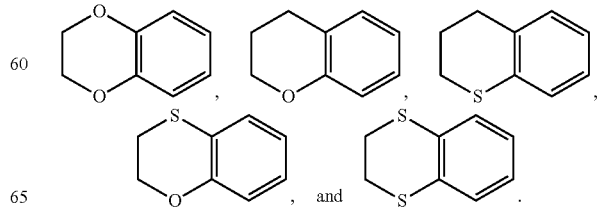

In some embodiments of Formula I, Ia, Ib, Ic, Id, Ie, If, Ig, Ih, and/or Ii, $R^1$ is independently selected at each occurrence from the group consisting of H, F, Cl, Me, OMe, OH, $CF_3$; and CN, and n is 1 or 2.

In some embodiments, Ring A is selected from the group consisting of

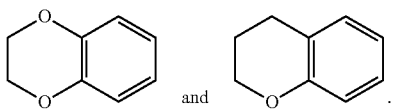 [SMILES: c1ccc2c(c1)OCCO2 ; c1ccc2c(c1)CCCO2]

In some embodiments of Formula I, Ib, Ic, Ie, If, Ih, and/or Ii, Ring B is phenyl.

In some embodiments of Formula I, Ib, Ic, Ie, If, Ih, and/or Ii, Ring B is a 5-membered heteroaryl containing 1-3 heteroatoms selected from the group consisting of N, O, and S.

In some embodiments of Formula I, Ib, Ic, Ie, If, Ih, and/or Ii, Ring B is a 6-membered heteroaryl containing 1-2 nitrogen atoms.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2OH$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2N(R^{3b})_2$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2NH_2$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2NHMe$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2NMe_2$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2NHEt$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2N(Me)(Et)$.

In some embodiments of Formula I, Ia, Ib, Ic, Id, Ie, If, Ig, Ih, and/or Ii, $R^2$, $R^{2a}$, $R^{2b}$, $R^{2c}$, $R^{2d}$, $R^{2e}$, $R^{2f}$, and/or $R^{2g}$ is $-CH_2NEt_2$.

In some embodiments of Formula I, Ib, Ic, Ie, If, Ih, and/or Ii, $R^2$ is independently selected at each occurrence from the group consisting of H, F, Cl, Me, OMe, OH, $CF_3$, and CN.

In some embodiments of Formula I, Ib, Ic, Ie, If, Ih, and/or Ii, $R^2$ is H.

In some embodiments of Formula I, Ib, Ic, Ie, If, Ih, and/or Ii, $R^2$ is a halide.

In some embodiments of Formula I, Ib, Ic, Ie, If, Ih, and/or Ii, $R^2$ is F.

In some embodiments of Formula I, Ib, Ic, Ie, If, Ih, and/or Ii, $R^2$ is Cl.

In some embodiments of Formula I, Ib, Ic, Ie, If, Ih, and/or Ii, $R^2$ is Me.

In some embodiments of Formula I, Ib, Ic, Ie, If, Ih, and/or Ii, $R^2$ is OH.

In some embodiments of Formula I, Ib, Ic, Ie, If, Ih, and/or Ii, $R^2$ is OMe.

In some embodiments of Formula I, Ib, Ic, Ie, If, Ih, and/or Ii, $R^2$ is $CF_3$.

In some embodiments of Formula I, Ib, Ic, Ie, If, Ih, and/or Ii, $R^2$ is CN.

In some embodiments of Formula I, Ib, Ic, Ie, If, Ih, and/or Ii, m is an integer from 1-4.

In some embodiments of Formula I, Ib, Ic, Ie, If, Ih, and/or Ii, m is an integer from 1-2.

In some embodiments of Formula I, Ib, Ic, Ie, If, Ih, and/or Ii, m is 1.

In some embodiments of Formula I, Ib, Ic, Ie, If, Ih, and/or Ii, m is 2.

In some embodiments of Formula I, Ib, Ic, Ie, If, Ih, and/or Ii, $R^2$ is F; and m is 1.

In some embodiments of Formula I, Ib, Ic, Ie, If, Ih, and/or Ii, $R^2$ is F; and m is 2.

In some embodiments of Formula I, Ib, Ic, Ie, If, Ih, and/or Ii, $R^2$ is Me; and m is 1.

In some embodiments of Formula I, Ib, Ic, Ie, If, Ih, and/or Ii, $R^2$ is Me; and m is 2.

In some embodiments of Formula I, Ib, Ic, Ie, If, Ih, and/or Ii, $R^2$ is $CF_3$; and m is 1.

In some embodiments of Formula I, Ib, Ic, Ie, If, Ih, and/or Ii, $R^2$ is $CF_3$; and m is 2.

In some embodiments of Formula I, Ib, Ic, Ie, If, Ih, and/or Ii, $R^2$ is OMe; and m is 1.

In some embodiments of Formula I, Ib, Ic, Ie, If, Ih, and/or Ii, $R^2$ is OMe; and m is 2.

In some embodiments of Formula I, Ib, Ic, Ie, If, Ih, and/or Ii, $R^2$ is F and Me' and m is 2.

In some embodiments of Formula I, Ib, Ic, Ie, If, Ih, and/or Ii, $R^2$ is F and $CF_3$; and m is 2.

In some embodiments of Formula I, Ib, Ic, Ie, If, Ih, and/or Ii, $R^2$ is F and OMe; and m is 2.

In some embodiments of Formula I, Ib, Ic, Ie, If, Ih, and/or Ii, $R^2$ is CN; and m is 1.

In some embodiments of Formula I, Ib, Ic, Ie, If, Ih, and/or Ii, $R^2$ is CN; and m is 2.

In some embodiments of Formula I, Ib, Ic, Ie, If, Ih, and/or Ii, $R^2$ is F and CN; and m is 2.

In some embodiments of Formula I, Ib, Ic, Ie, If, Ih, and/or Ii, $R^2$ is $-C_{1-2}$ alkyl.

In some embodiments of Formula I, Ib, Ic, Ie, If, Ih, and/or Ii, $R^2$ is $-C_{1-3}$ alkyl.

In some embodiments of Formula I, Ib, Ic, Ie, If, Ih, and/or Ii, $R^2$ is $-C_{1-4}$ alkyl.

In some embodiments of Formula I, Ib, Ic, Ie, If, Ih, and/or Ii, $R^2$ is $-C_{1-5}$ alkyl.

In some embodiments of Formula I, Ib, Ic, Ie, If, Ih, and/or Ii, $R^2$ is $-C_{1-6}$ alkyl.

In some embodiments of Formula I, Ib, Ic, Ie, If, Ih, and/or Ii, $R^2$ is $-C_{2-6}$ alkyl.

In some embodiments of Formula I, Ib, Ic, Ie, If, Ih, and/or Ii, $R^2$ is $-C_{3-6}$ alkyl.

In some embodiments of Formula I, Ib, Ic, Ie, If, Ih, and/or Ii, $R^2$ is $-C_{4-6}$ alkyl.

In some embodiments of Formula I, Ia, Ib, Ic, Id, Ie, If, Ig, Ih, and/or Ii, $R^3$ is $-C_{1-2}$ alkyl.

In some embodiments of Formula I, Ia, Ib, Ic, Id, Ie, If, Ig, Ih, and/or Ii, $R^3$ is $-C_{1-3}$ alkyl.

In some embodiments of Formula I, Ia, Ib, Ic, Id, Ie, If, Ig, Ih, and/or Ii, $R^3$ is $-C_{1-4}$ alkyl.

In some embodiments of Formula I, Ia, Ib, Ic, Id, Ie, If, Ig, Ih, and/or Ii, $R^3$ is $-C_{1-5}$ alkyl.

In some embodiments of Formula I, Ia, Ib, Ic, Id, Ie, If, Ig, Ih, and/or Ii, $R^3$ is $-C_{1-6}$ alkyl.

In some embodiments of Formula I, Ia, Ib, Ic, Id, Ie, If, Ig, Ih, and/or Ii, $R^3$ and/or $R^{3a}$ is $-C_{2-6}$ alkyl.

In some embodiments of Formula I, Ia, Ib, Ic, Id, Ie, If, Ig, Ih, and/or Ii, $R^3$ and/or $R^{3a}$ is —$C_{3-6}$ alkyl.

In some embodiments of Formula I, Ia, Ib, Ic, Id, Ie, If, Ig, Ih, and/or Ii, $R^3$ and/or $R^{3a}$ is —$C_{4-6}$ alkyl.

In some embodiments of Formula I, Ia, Ib, Ic, Id, Ie, If, Ig, Ih, and/or Ii, $R^3$ and/or $R^{3a}$ is —$C_{2-5}$ alkyl.

In some embodiments of Formula I, Ia, Ib, Ic, Id, Ie, If, Ig, Ih, and/or Ii, $R^3$ and/or $R^{3a}$ is —$C_{3-4}$ alkyl.

In some embodiments of Formula I, Ib, Ic, Ie, If, Ih, and/or Ii, Ring B is a phenyl or 6-membered heteroaryl; $R^2$ is selected from the group consisting of F, Cl, Me, OMe, OH, $CF_3$, and CN; m is 1; and $R^2$ is attached to an ortho carbon of the 6-membered ring.

In some embodiments of Formula I, Ib, Ic, Ie, If, Ih, and/or Ii, Ring B is a phenyl; $R^2$ is selected from the group consisting of F, Cl, Me, OMe, OH, $CF_3$; and CN; m is 1; and $R^2$ is attached to an ortho position of the phenyl ring.

In some embodiments of Formula I, Ib, Ic, Ie, If, Ih, and/or Ii, Ring B is a pyridine; $R^2$ is selected from the group consisting of F, Cl, Me, OMe, OH, $CF_3$, and CN; m is 1; and $R^2$ is attached to an ortho carbon of the pyridine ring.

In some embodiments of Formula I, Ib, Ic, Ie, If, Ih, and/or Ii,

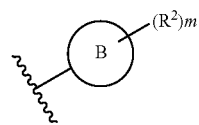

is selected from the group consisting of:

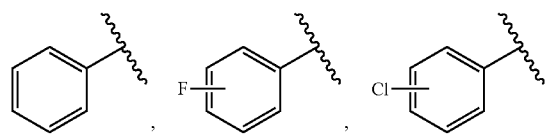

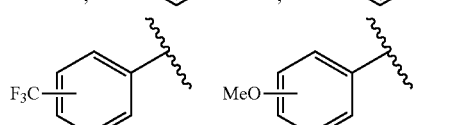

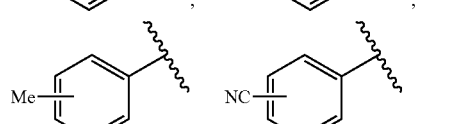

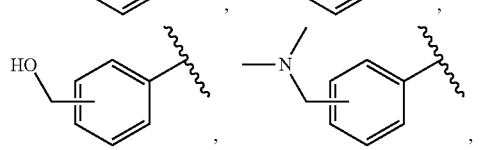

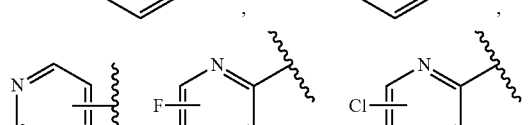

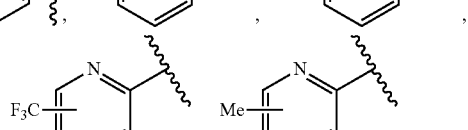

-continued

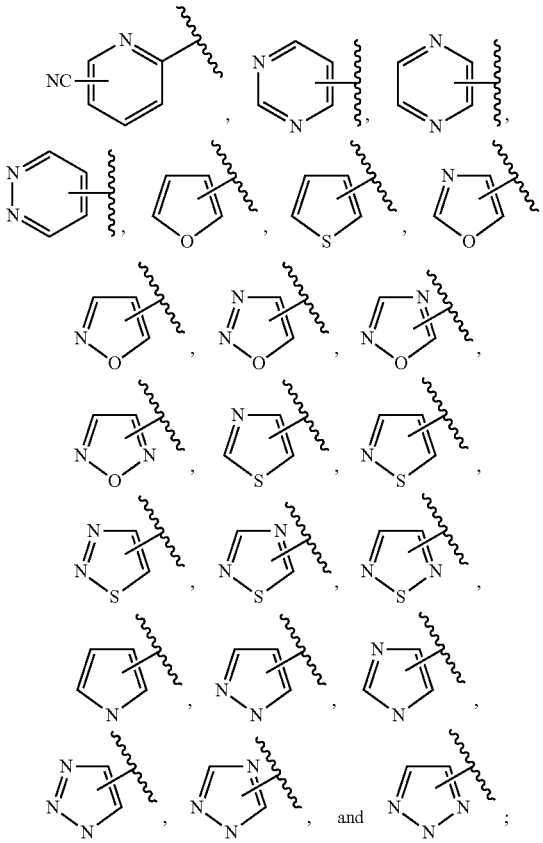

wherein the carbonyl carbon of Formula I, Ib, Ic, Ie, If, Ih, and/or Ii, can form a bond with any unsubstituted carbon on the Ring B.

In some embodiments of Formula I, Ib, Ic, Ie, If, Ih, and/or Ii,

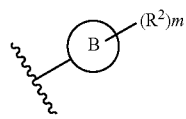

is selected from the group consisting of:

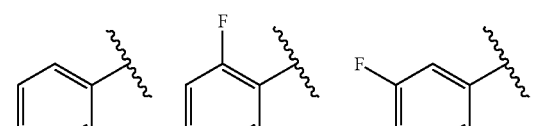

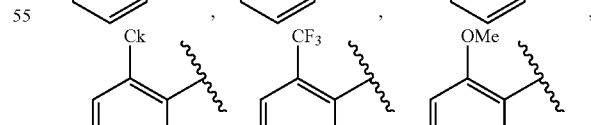

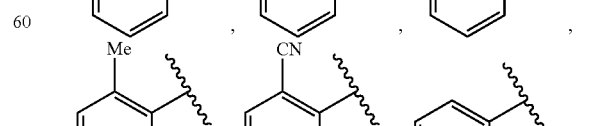

-continued

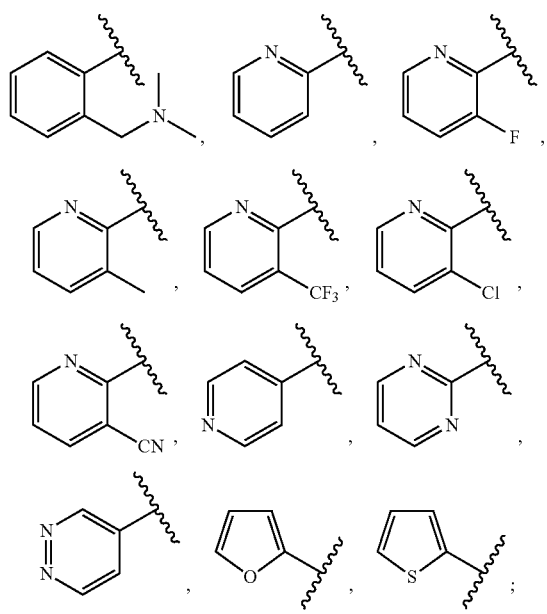

wherein the carbonyl carbon of Formula I, Ib, Ic, Ie, If, Ih, and/or Ii, can form a bond with any unsubstituted carbon on the Ring B.

In some embodiments of Formula I, Ib, Ic, Ie, If, Ih, and/or Ii,

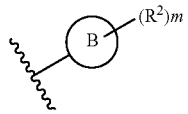

is selected from the group consisting of:

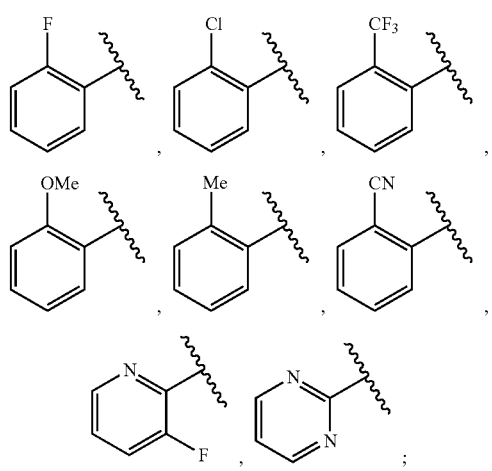

wherein the carbonyl carbon of Formula I, Ib, Ic, Ie, If, Ih, and/or Ii, can form a bond with any unsubstituted carbon on the Ring B.

In some embodiments of Formula I, Ib, Ic, Ie, If, Ih, and/or Ii,

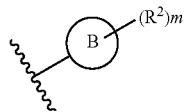

is selected from the group consisting of

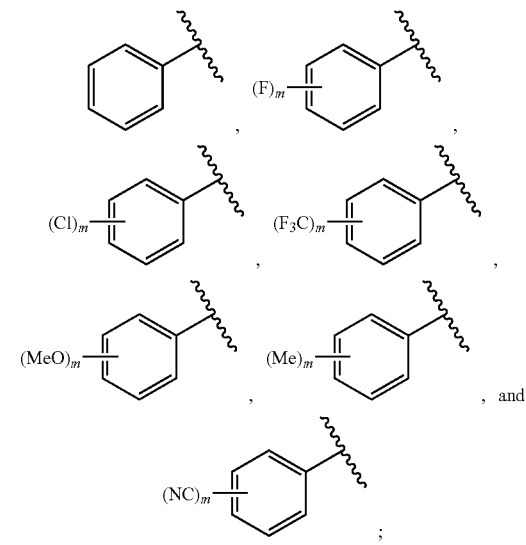

and m is 1 or 2.

In some embodiments of Formula I, Ib, Ic, Ie, If, Ih, and/or Ii,

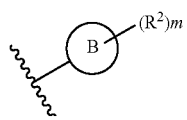

is selected from the group consisting of

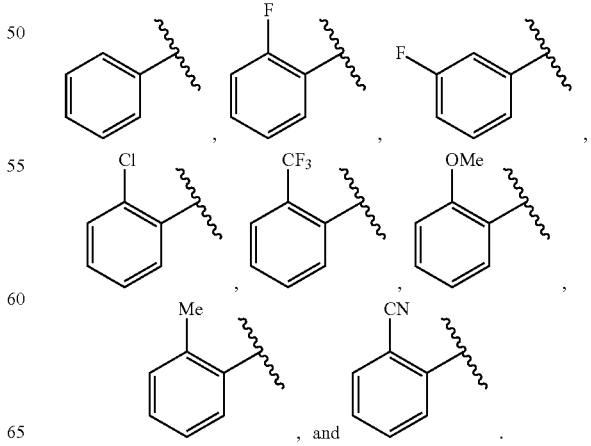

In some embodiments of Formula I, Ib, Ic, Ie, If, Ih, and/or Ii,

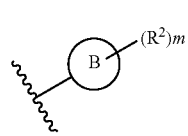

is selected from the group consisting of

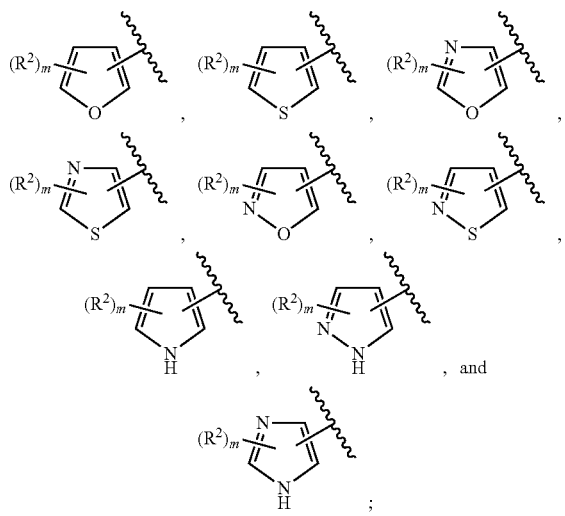

and m is 1 or 2.

In some embodiments of Formula I, Ib, Ic, Ie, If, Ih, and/or Ii,

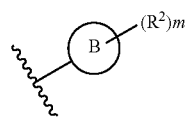

is selected from the group consisting of

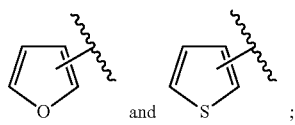

and $R^2$ is H

In some embodiments of Formula I, Ib, Ic, Ie, If, Ih, and/or Ii,

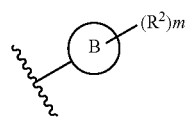

is selected from the group consisting of

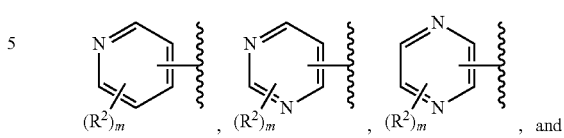

and m is 1 or 2.

In some embodiments of Formula I, Ib, Ic, Ie, If, Ih, and/or Ii,

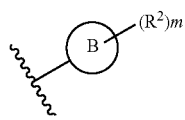

is selected from the group consisting of

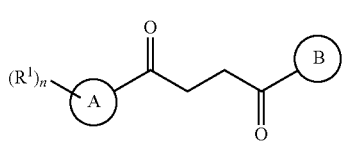

and $R^2$ is H.

Some additional embodiments of Formula I include compounds of Formula (Ia):

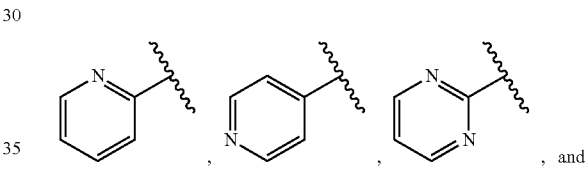

Ia or salts, pharmaceutically acceptable salts, or prodrugs thereof.

In some embodiments of Formula Ia, Ring A is

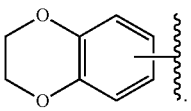

In some embodiments of Formula Ia, Ring B is selected from the group consisting of

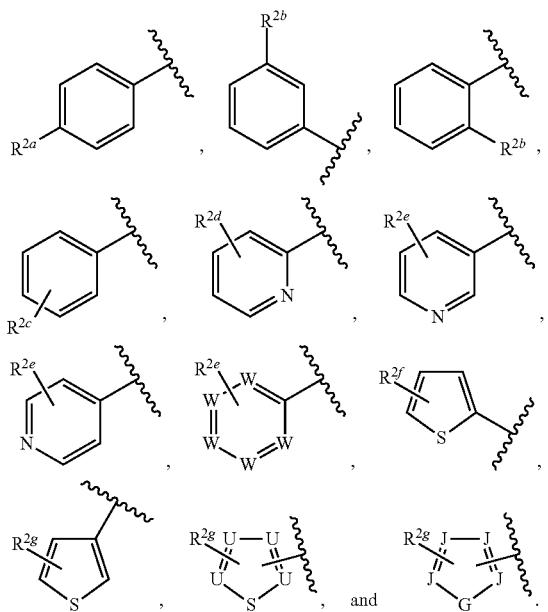

In some embodiments of Formula Ia, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ia, $R^{2a}$ is a substituent attached to the para position of phenyl and selected from the group consisting of unsubstituted —$C_{1-6}$ alkyl, —$CH_2OH$, —$CH_2N(R^{3b})_2$, —$C_{1-3}$ haloalkyl, Cl, Br, I, —$OR^{3a}$, $CF_3$, and CN.

In some embodiments of Formula Ia, $R^{2b}$ is a substituent attached to the meta or ortho position of phenyl and selected from the group consisting of unsubstituted —$C_{1-6}$ alkyl, —$CH_2OH$, —$CH_2N(R^{3b})_2$, —$C_{1-3}$ haloalkyl, halide, —$OR^{3a}$, $CF_3$, and CN.

In some embodiments of Formula Ia, $R^{2c}$ is 2-5 substituents, each attached to the phenyl and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ia, $R^{2d}$ is 1-4 substituents, each attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ia, $R^{2e}$ is 1-4 substituents, each attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ia, $R^{2f}$ is 1-3 substituents, each attached to the heteroaryl ring and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ia, $R^{2g}$ is 1-3 substituents, each attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ia, each $R^3$ is independently selected from the group consisting of H, unsubstituted —$C_{1-6}$ alkyl, —$C_{1-3}$ haloalkyl, and $CF_3$.

In some embodiments of Formula Ia, each $R^{3a}$ is independently selected from the group consisting of unsubstituted —$C_{2-6}$ alkyl, —$C_{1-3}$ haloalkyl, and $CF_3$.

In some embodiments of Formula Ia, each $R^{3b}$ is independently selected from the group consisting of H and unsubstituted —$C_{1-3}$ alkyl.

In some embodiments of Formula Ia, each W is N or C.

In some embodiments of Formula Ia, at least two W must be N.

In some embodiments of Formula Ia, each U is N or C.

In some embodiments of Formula Ia, at least one U must be N and at least one U must be C.

In some embodiments of Formula Ia, G is NH or O.

In some embodiments of Formula Ia, each J is N or C.

In some embodiments of Formula Ia, at least one J must be C.

In some embodiments of Formula Ia, n is an integer of 1 to 7.

In some embodiments of Formula Ia, Ring A is selected from the group consisting of

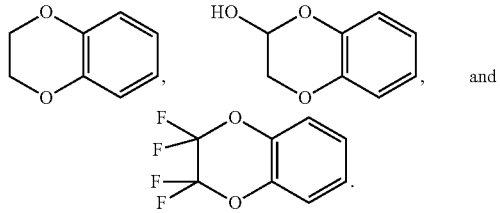

In some embodiments of Formula Ia, Ring B is selected from the group consisting of

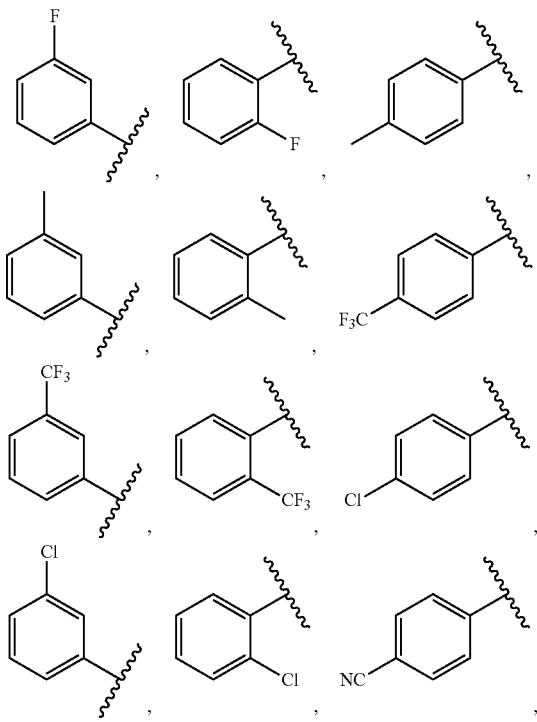

-continued
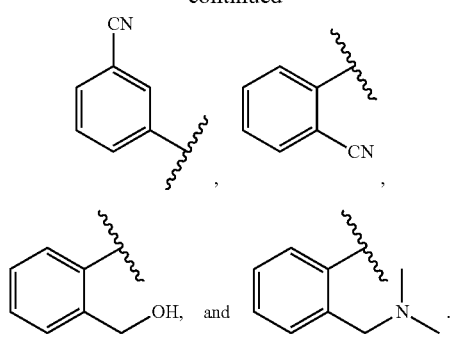
In some embodiments of Formula Ia, Ring B is selected from the group consisting of
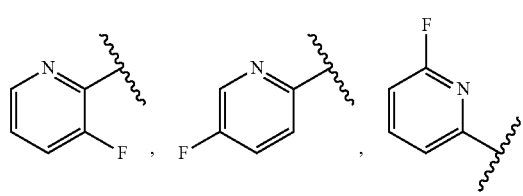
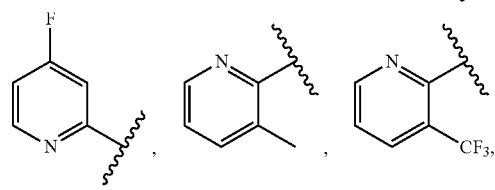
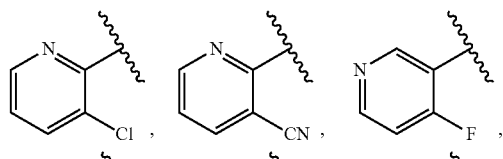
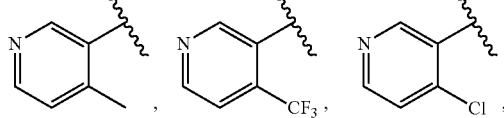
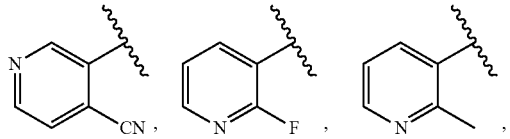
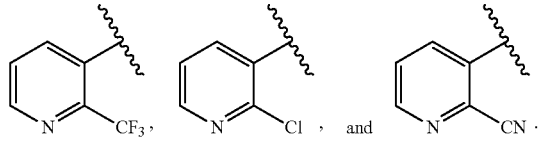
In some embodiments of Formula Ia, Ring B is selected from the group consisting of
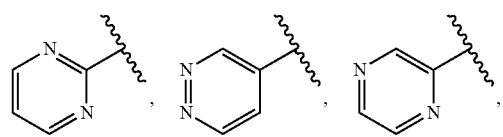
-continued
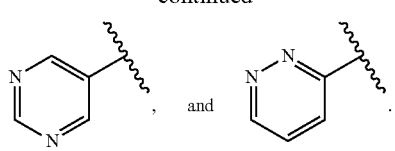
In some embodiments of Formula Ia, Ring B is selected from the group consisting of
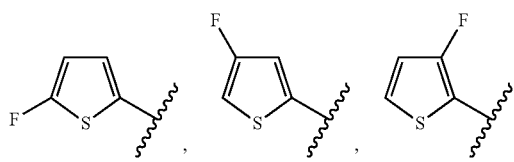
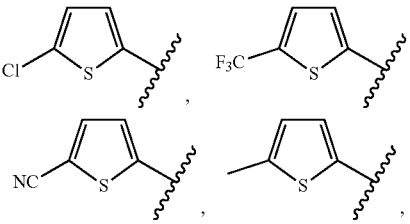
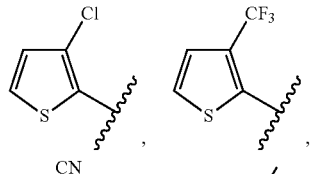
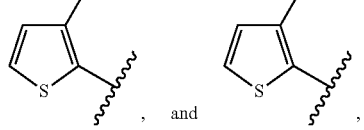
In some embodiments of Formula Ia, Ring B is selected from the group consisting of
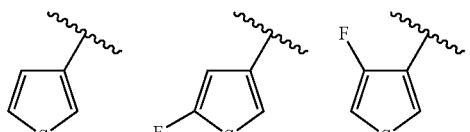
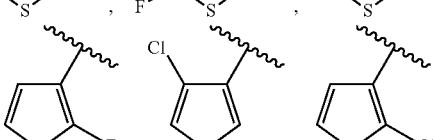
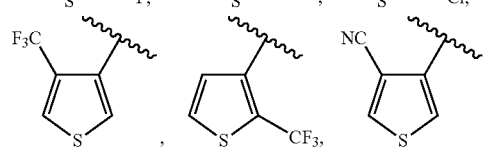
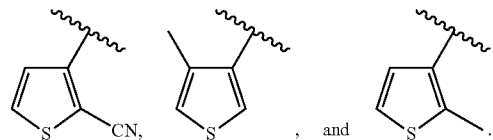

In some embodiments of Formula Ia, Ring B is selecting from the group consisting of

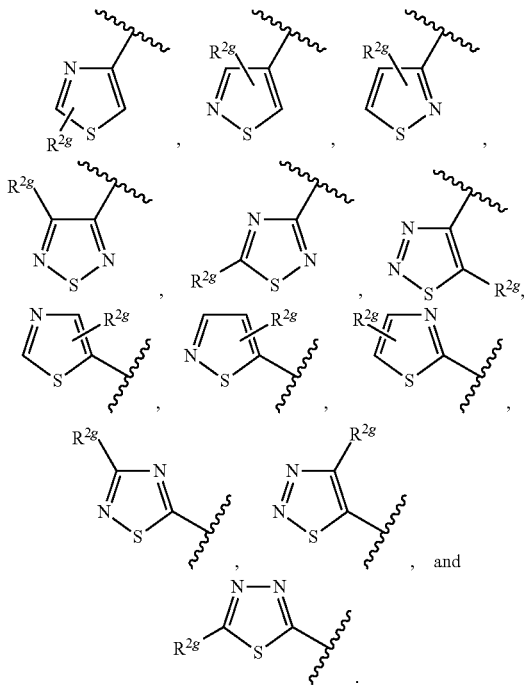

In some embodiments of Formula Ia, Ring B is selected from the group consisting of

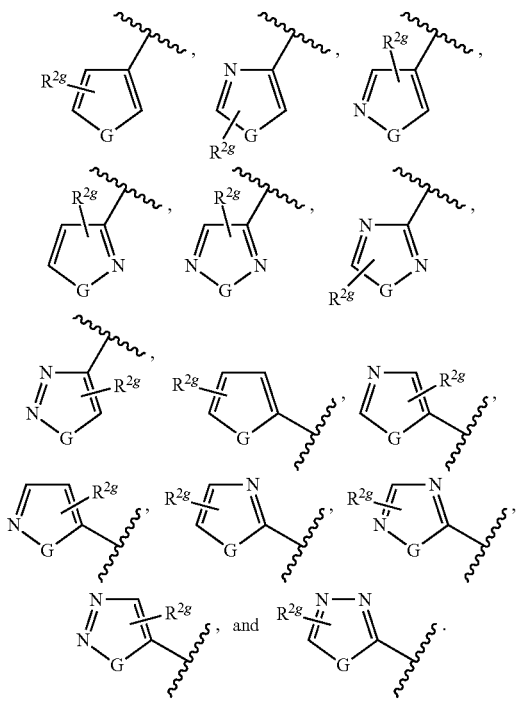

In some embodiments of Formula Ia and/or Id, $R^{2a}$ is Cl.

In some embodiments of Formula Ia, Id, and/or Ig, $R^{2a}$ is Me.

In some embodiments of Formula Ia, Id, and/or Ig, $R^{2a}$ is $CF_3$.

In some embodiments of Formula Ia, Id, and/or Ig, $R^{2a}$ is CN.

In some embodiments of Formula Ia, Id, and/or Ig, $R^{2a}$ is 1 substituent and is Me.

In some embodiments of Formula Ia, Id, and/or Ig, $R^{2a}$ is 2 substituents and both are Me.

In some embodiments of Formula Ia, Id, and/or Ig, $R^{2a}$ is 1 substituent and is $CF_3$.

In some embodiments of Formula Ia, Id, and/or Ig, $R^{2a}$ is 2 substituents and both are $CF_3$.

In some embodiments of Formula Ia, Id, and/or Ig, $R^{2a}$ is 1 substituent and is CN.

In some embodiments of Formula Ia, Id, and/or Ig, $R^{2a}$ is 2 substituents and both are CN.

In some embodiments of Formula Ia, Id, and/or Ig, $R^{2a}$ is —$C_{1-2}$ alkyl.

In some embodiments of Formula Ia, Id, and/or Ig, $R^{2a}$ is —$C_{1-3}$ alkyl.

In some embodiments of Formula Ia, Id, and/or Ig, $R^{2a}$ is —$C_{1-4}$ alkyl.

In some embodiments of Formula Ia, Id, and/or Ig, $R^{2a}$ is —$C_{1-5}$ alkyl.

In some embodiments of Formula Ia, Id, and/or Ig, $R^{2a}$ is —$C_{1-6}$ alkyl.

In some embodiments of Formula Ia, Id, and/or Ig, $R^{2a}$ is —$C_{2-6}$ alkyl.

In some embodiments of Formula Ia, Id, and/or Ig, $R^{2a}$ is —$C_{3-6}$ alkyl.

In some embodiments of Formula Ia, Id, and/or Ig, $R^{2a}$ is —$C_{4-6}$ alkyl.

In some embodiments of Formula Ia, Id, and/or Ig, $R^{2a}$ is —$C_{2-5}$ alkyl.

In some embodiments of Formula Ia, Id, and/or Ig, $R^{2a}$ is —$C_{3-4}$ alkyl.

In some embodiments of Formula Ia and/or Ig, $R^{2b}$ is a halide.

In some embodiments of Formula Ia, Id, and/or Ig, $R^{2b}$ is F.

In some embodiments of Formula Ia and/or Ig, $R^{2b}$ is Cl.

In some embodiments of Formula Ia, $R^{2b}$ is Me.

In some embodiments of Formula Id and/or Ig, $R^{2b}$ is OH.

In some embodiments of Formula Id and/or Ig, $R^{2b}$ is OMe.

In some embodiments of Formula Ia, Id, and/or Ig, $R^{2b}$ is $CF_3$.

In some embodiments of Formula Ia, Id, and/or Ig, $R^{2b}$ is CN.

In some embodiments of Formula Ia, Id, and/or Ig, $R^{2b}$ is 1 substituent and is F.

In some embodiments of Formula Ia, Id, and/or Ig, $R^{2b}$ is 2 substituents and both are F.

In some embodiments of Formula Ia, $R^{2b}$ is 1 substituent and is Me.

In some embodiments of Formula Ia, $R^{2b}$ is 2 substituents and both are Me.

In some embodiments of Formula Ia, Id, and/or Ig, $R^{2b}$ is 1 substituent and is $CF_3$.

In some embodiments of Formula Ia, Id, and/or Ig, $R^{2b}$ is 2 substituents and both are $CF_3$.

In some embodiments of Formula Id and/or Ig, $R^{2b}$ is 1 substituent and is OMe.

In some embodiments of Formula Id and/or Ig, $R^{2b}$ is 2 substituents and both are OMe.

In some embodiments of Formula Ia, $R^{2b}$ is 2 substituents and are F and Me.

In some embodiments of Formula Ia, Id, and/or Ig, $R^{2b}$ is 2 substituents and are F and $CF_3$.

In some embodiments of Formula Id and/or Ig, $R^{2b}$ is 2 substituents and are F and OMe.

In some embodiments of Formula Ia, Id, and/or Ig, $R^{2b}$ is 1 substituent and is CN.

In some embodiments of Formula Ia, Id, and/or Ig, $R^{2b}$ is 2 substituents and both are CN.

In some embodiments of Formula Ia, Id, and/or Ig, $R^{2b}$ is 2 substituents and are F and CN.

In some embodiments of Formula Ia, $R^{2b}$ is —$C_{1-2}$ alkyl.

In some embodiments of Formula Ia, $R^{2b}$ is —$C_{1-3}$ alkyl.

In some embodiments of Formula Ia, $R^{2b}$ is —$C_{1-4}$ alkyl.

In some embodiments of Formula Ia, $R^{2b}$ is —$C_{1-5}$ alkyl.

In some embodiments of Formula Ia, $R^{2b}$ is —$C_{1-6}$ alkyl.

In some embodiments of Formula Ia, Id, and/or Ig, $R^{2b}$ is —$C_{2-6}$ alkyl.

In some embodiments of Formula Ia, Id, and/or Ig, $R^{2b}$ is —$C_{3-6}$ alkyl.

In some embodiments of Formula Ia, Id, and/or Ig, $R^{2b}$ is —$C_{4-6}$ alkyl.

In some embodiments of Formula Ia, Id, and/or Ig, $R^{2b}$ is —$C_{2-5}$ alkyl.

In some embodiments of Formula Ia, Id, and/or Ig, $R^{2b}$ is —$C_{3-4}$ alkyl.

In some embodiments of Formula Ia and/or Ig, $R^{2c}$ is a halide.

In some embodiments of Formula Ia, Id, and/or Ig, $R^{2c}$ is F.

In some embodiments of Formula Ia and/or Ig, $R^{2c}$ is Cl.

In some embodiments of Formula Ia, Id, and/or Ig, $R^{2c}$ is Me.

In some embodiments of Formula Ia, Id, and/or Ig, $R^{2c}$ is OH.

In some embodiments of Formula Ia, Id, and/or Ig, $R^{2c}$ is OMe.

In some embodiments of Formula Ia, Id, and/or Ig, $R^{2c}$ is $CF_3$.

In some embodiments of Formula Ia, Id, and/or Ig, $R^{2c}$ is CN.

In some embodiments of Formula Ia, Id, and/or Ig, $R^{2c}$ is 1 substituent and is F.

In some embodiments of Formula Ia, Id, and/or Ig, $R^{2c}$ is 2 substituents and both are F.

In some embodiments of Formula Ia, Id, and/or Ig, $R^{2c}$ is 1 substituent and is Me.

In some embodiments of Formula Ia, Id, and/or Ig, $R^{2c}$ is 2 substituents and both are Me.

In some embodiments of Formula Ia, Id, and/or Ig, $R^{2c}$ is 1 substituent and is $CF_3$.

In some embodiments of Formula Ia, Id, and/or Ig, $R^{2c}$ is 2 substituents and both are $CF_3$.

In some embodiments of Formula Ia, Id, and/or Ig, $R^{2c}$ is 1 substituent and is OMe.

In some embodiments of Formula Ia, Id, and/or Ig, $R^{2c}$ is 2 substituents and both are OMe.

In some embodiments of Formula Ia, Id, and/or Ig, $R^{2c}$ is 2 substituents and are F and Me.

In some embodiments of Formula Ia, Id, and/or Ig, $R^{2c}$ is 2 substituents and are F and $CF_3$.

In some embodiments of Formula Ia, Id, and/or Ig, $R^{2c}$ is 2 substituents and are F and OMe.

In some embodiments of Formula Ia, Id, and/or Ig, $R^{2c}$ is 1 substituent and is CN.

In some embodiments of Formula Ia, Id, and/or Ig, $R^{2c}$ is 2 substituents and both are CN.

In some embodiments of Formula Ia, Id, and/or Ig, $R^{2c}$ is 2 substituents and are F and CN.

In some embodiments of Formula Ia, Id, and/or Ig, $R^{2c}$ is —$C_{1-2}$ alkyl.

In some embodiments of Formula Ia, Id, and/or Ig, $R^{2c}$ is —$C_{1-3}$ alkyl.

In some embodiments of Formula Ia, Id, and/or Ig, $R^{2c}$ is —$C_{1-4}$ alkyl.

In some embodiments of Formula Ia, Id, and/or Ig, $R^{2c}$ is —$C_{1-5}$ alkyl.

In some embodiments of Formula Ia, Id, and/or Ig, $R^{2c}$ is —$C_{1-6}$ alkyl.

In some embodiments of Formula Ia, Id, and/or Ig, $R^{2c}$ is —$C_{2-6}$ alkyl.

In some embodiments of Formula Ia, Id, and/or Ig, $R^{2c}$ is —$C_{3-6}$ alkyl.

In some embodiments of Formula Ia, Id, and/or Ig, $R^{2c}$ is —$C_{4-6}$ alkyl.

In some embodiments of Formula Ia, Id, and/or Ig, $R^{2c}$ is —$C_{2-5}$ alkyl.

In some embodiments of Formula Ia, Id, and/or Ig, $R^{2c}$ is —$C_{3-4}$ alkyl.

In some embodiments of Formula Ia and/or Ig, $R^{2d}$ is a halide.

In some embodiments of Formula Ia, Id, and/or Ig, $R^{2d}$ is F.

In some embodiments of Formula Ia, Id, and/or Ig, $R^{2d}$ is Cl.

In some embodiments of Formula Ia, Id, and/or Ig, $R^{2d}$ is Me.

In some embodiments of Formula Ia, Id, and/or Ig, $R^{2d}$ is OH.

In some embodiments of Formula Ia, Id, and/or Ig, $R^{2d}$ is OMe.

In some embodiments of Formula Ia, Id, and/or Ig, $R^{2d}$ is $CF_3$.

In some embodiments of Formula Ia, Id, and/or Ig, $R^{2d}$ is CN.

In some embodiments of Formula Ia, Id, and/or Ig, $R^{2d}$ is 1 substituent and is F.

In some embodiments of Formula Ia, Id, and/or Ig, $R^{2d}$ is 2 substituents and both are F.

In some embodiments of Formula Ia, Id, and/or Ig, $R^{2d}$ is 1 substituent and is Me.

In some embodiments of Formula Ia, Id, and/or Ig, $R^{2d}$ is 2 substituents and both are Me.

In some embodiments of Formula Ia, Id, and/or Ig, $R^{2d}$ is 1 substituent and is $CF_3$.

In some embodiments of Formula Ia, Id, and/or Ig, $R^{2d}$ is 2 substituents and both are $CF_3$.

In some embodiments of Formula Ia, Id, and/or Ig, $R^{2d}$ is 1 substituent and is OMe.

In some embodiments of Formula Ia, Id, and/or Ig, $R^{2d}$ is 2 substituents and both are OMe.

In some embodiments of Formula Ia, Id, and/or Ig, $R^{2d}$ is 2 substituents and are F and Me.

In some embodiments of Formula Ia, Id, and/or Ig, $R^{2d}$ is 2 substituents and are F and $CF_3$.

In some embodiments of Formula Ia, Id, and/or Ig, $R^{2d}$ is 2 substituents and are F and OMe.

In some embodiments of Formula Ia, Id, and/or Ig, $R^{2d}$ is 1 substituent and is CN.

In some embodiments of Formula Ia, Id, and/or Ig, $R^{2d}$ is 2 substituents and both are CN.

In some embodiments of Formula Ia, Id, and/or Ig, $R^{2d}$ is 2 substituents and are F and CN.

In some embodiments of Formula Ia, Id, and/or Ig, $R^{2d}$ is —$C_{1-2}$ alkyl.
In some embodiments of Formula Ia, Id, and/or Ig, $R^{2d}$ is —$C_{1-3}$ alkyl.
In some embodiments of Formula Ia, Id, and/or Ig, $R^{2d}$ is —$C_{1-4}$ alkyl.
In some embodiments of Formula Ia, Id, and/or Ig, $R^{2d}$ is —$C_{1-5}$ alkyl.
In some embodiments of Formula Ia, Id, and/or Ig, $R^{2d}$ is —$C_{1-6}$ alkyl.
In some embodiments of Formula Ia, Id, and/or Ig, $R^{2d}$ is —$C_{2-6}$ alkyl.
In some embodiments of Formula Ia, Id, and/or Ig, $R^{2d}$ is —$C_{3-6}$ alkyl.
In some embodiments of Formula Ia, Id, and/or Ig, $R^{2d}$ is —$C_{4-6}$ alkyl.
In some embodiments of Formula Ia, Id, and/or Ig, $R^{2d}$ is —$C_{2-5}$ alkyl.
In some embodiments of Formula Ia, Id, and/or Ig, $R^{2d}$ is —$C_{3-4}$ alkyl.
In some embodiments of Formula Ia and/or Id, $R^{2e}$ is H.
In some embodiments of Formula Ia and/or Id, $R^{2e}$ is a halide.
In some embodiments of Formula Ia and/or Id, $R^{2e}$ is F.
In some embodiments of Formula Ia and/or Id, $R^{2e}$ is Cl.
In some embodiments of Formula Ia and/or Id, $R^{2e}$ is Me.
In some embodiments of Formula Ia and/or Id, $R^{2e}$ is OH.
In some embodiments of Formula Ia and/or Id, $R^{2e}$ is OMe.
In some embodiments of Formula Ia and/or Id, $R^{2e}$ is $CF_3$.
In some embodiments of Formula Ia and/or Id, $R^{2e}$ is CN.
In some embodiments of Formula Ia and/or Id, $R^{2e}$ is 1 substituent and is F.
In some embodiments of Formula Ia and/or Id, $R^{2e}$ is 2 substituents and both are F.
In some embodiments of Formula Ia and/or Id, $R^{2e}$ is 1 substituent and is Me.
In some embodiments of Formula Ia and/or Id, $R^{2e}$ is 2 substituents and both are Me.
In some embodiments of Formula Ia and/or Id, $R^{2e}$ is 1 substituent and is $CF_3$.
In some embodiments of Formula Ia and/or Id, $R^{2e}$ is 2 substituents and both are $CF_3$.
In some embodiments of Formula Ia and/or Id, $R^{2e}$ is 1 substituent and is OMe.
In some embodiments of Formula Ia and/or Id, $R^{2e}$ is 2 substituents and both are OMe.
In some embodiments of Formula Ia and/or Id, $R^{2e}$ is 2 substituents and are F and Me.
In some embodiments of Formula Ia and/or Id, $R^{2e}$ is 2 substituents and are F and $CF_3$.
In some embodiments of Formula Ia and/or Id, $R^{2e}$ is 2 substituents and are F and OMe.
In some embodiments of Formula Ia and/or Id, $R^{2e}$ is 1 substituent and is CN.
In some embodiments of Formula Ia and/or Id, $R^{2e}$ is 2 substituents and both are CN.
In some embodiments of Formula Ia and/or Id, $R^{2e}$ is 2 substituents and are F and CN.
In some embodiments of Formula Ia and/or Id, $R^{2e}$ is —$C_{1-2}$ alkyl.
In some embodiments of Formula Ia and/or Id, $R^{2e}$ is —$C_{1-3}$ alkyl.
In some embodiments of Formula Ia and/or Id, $R^{2e}$ is —$C_{1-4}$ alkyl.
In some embodiments of Formula Ia and/or Id, $R^{2e}$ is —$C_{1-5}$ alkyl.
In some embodiments of Formula Ia and/or Id, $R^{2e}$ is —$C_{1-6}$ alkyl.
In some embodiments of Formula Ia and/or Id, $R^{2e}$ is —$C_{2-6}$ alkyl.
In some embodiments of Formula Ia and/or Id, $R^{2e}$ is —$C_{3-6}$ alkyl.
In some embodiments of Formula Ia and/or Id, $R^{2e}$ is —$C_{4-6}$ alkyl.
In some embodiments of Formula Ia and/or Id, $R^{2e}$ is —$C_{2-5}$ alkyl.
In some embodiments of Formula Ia and/or Id, $R^{2e}$ is —$C_{3-4}$ alkyl.
In some embodiments of Formula Ia, $R^{2f}$ is a halide.
In some embodiments of Formula Ia, $R^{2f}$ is F.
In some embodiments of Formula Ia, $R^{2f}$ is Cl.
In some embodiments of Formula Ia, $R^{2f}$ is Me.
In some embodiments of Formula Ia, $R^{2f}$ is OH.
In some embodiments of Formula Ia, $R^{2f}$ is OMe.
In some embodiments of Formula Ia, $R^{2f}$ is $CF_3$.
In some embodiments of Formula Ia, $R^{2f}$ is CN.
In some embodiments of Formula Ia, $R^{2f}$ is 1 substituent and is F.
In some embodiments of Formula Ia, $R^{2f}$ is 2 substituents and both are F.
In some embodiments of Formula Ia, $R^{2f}$ is 1 substituent and is Me.
In some embodiments of Formula Ia, $R^{2f}$ is 2 substituents and both are Me.
In some embodiments of Formula Ia, $R^{2f}$ is 1 substituent and is $CF_3$.
In some embodiments of Formula Ia, $R^{2f}$ is 2 substituents and both are $CF_3$.
In some embodiments of Formula Ia, $R^{2f}$ is 1 substituent and is OMe.
In some embodiments of Formula Ia, $R^{2f}$ is 2 substituents and both are OMe.
In some embodiments of Formula Ia, $R^{2f}$ is 2 substituents and are F and Me.
In some embodiments of Formula Ia, $R^{2f}$ is 2 substituents and are F and $CF_3$.
In some embodiments of Formula Ia, $R^{2f}$ is 2 substituents and are F and OMe.
In some embodiments of Formula Ia, $R^{2f}$ is 1 substituent and is CN.
In some embodiments of Formula Ia, $R^{2f}$ is 2 substituents and both are CN.
In some embodiments of Formula Ia, $R^{2f}$ is 2 substituents and are F and CN.
In some embodiments of Formula Ia, $R^{2f}$ is —$C_{1-2}$ alkyl.
In some embodiments of Formula Ia, $R^{2f}$ is —$C_{1-3}$ alkyl.
In some embodiments of Formula Ia, $R^{2f}$ is —$C_{1-4}$ alkyl.
In some embodiments of Formula Ia, $R^{2f}$ is —$C_{1-5}$ alkyl.
In some embodiments of Formula Ia, $R^{2f}$ is —$C_{1-6}$ alkyl.
In some embodiments of Formula Ia, $R^{2f}$ is —$C_{2-6}$ alkyl.
In some embodiments of Formula Ia, $R^{2f}$ is —$C_{3-6}$ alkyl.
In some embodiments of Formula Ia, $R^{2f}$ is —$C_{4-6}$ alkyl.
In some embodiments of Formula Ia, $R^{2f}$ is —$C_{2-5}$ alkyl.
In some embodiments of Formula Ia, $R^{2f}$ is —$C_{3-4}$ alkyl.
In some embodiments of Formula Ia, $R^{2g}$ is H.
In some embodiments of Formula Ia, $R^{2g}$ is a halide.
In some embodiments of Formula Ia, $R^{2g}$ is F.
In some embodiments of Formula Ia, $R^{2g}$ is Cl.
In some embodiments of Formula Ia, $R^{2g}$ is Me.
In some embodiments of Formula Ia, $R^{2g}$ is OH.
In some embodiments of Formula Ia, $R^{2g}$ is OMe.
In some embodiments of Formula Ia, $R^{2g}$ is $CF_3$.
In some embodiments of Formula Ia, $R^{2g}$ is CN.

In some embodiments of Formula Ia, $R^{2g}$ is 1 substituent and is F.
In some embodiments of Formula Ia, $R^{2g}$ is 2 substituents and both are F.
In some embodiments of Formula Ia, $R^{2g}$ is 1 substituent and is Me.
In some embodiments of Formula Ia, $R^{2g}$ is 2 substituents and both are Me.
In some embodiments of Formula Ia, $R^{2g}$ is 1 substituent and is $CF_3$.
In some embodiments of Formula Ia, $R^{2g}$ is 2 substituents and both are $CF_3$.
In some embodiments of Formula Ia, $R^{2g}$ is 1 substituent and is OMe.
In some embodiments of Formula Ia, $R^{2g}$ is 2 substituents and both are OMe.
In some embodiments of Formula Ia, $R^{2g}$ is 2 substituents and are F and Me.
In some embodiments of Formula Ia, $R^{2g}$ is 2 substituents and are F and $CF_3$.
In some embodiments of Formula Ia, $R^{2g}$ is 2 substituents and are F and OMe.
In some embodiments of Formula Ia, $R^{2g}$ is 1 substituent and is CN.
In some embodiments of Formula Ia, $R^{2g}$ is 2 substituents and both are CN.
In some embodiments of Formula Ia, $R^{2g}$ is 2 substituents and are F and CN.
In some embodiments of Formula Ia, $R^{2g}$ is —$C_{1-2}$ alkyl.
In some embodiments of Formula Ia, $R^{2g}$ is —$C_{1-3}$ alkyl.
In some embodiments of Formula Ia, $R^{2g}$ is —$C_{1-4}$ alkyl.
In some embodiments of Formula Ia, $R^{2g}$ is —$C_{1-5}$ alkyl.
In some embodiments of Formula Ia, $R^{2g}$ is —$C_{1-6}$ alkyl.
In some embodiments of Formula Ia, $R^{2g}$ is —$C_{2-6}$ alkyl.
In some embodiments of Formula Ia, $R^{2g}$ is —$C_{3-6}$ alkyl.
In some embodiments of Formula Ia, $R^{2g}$ is —$C_{4-6}$ alkyl.
In some embodiments of Formula Ia, $R^{2g}$ is —$C_{2-5}$ alkyl.
In some embodiments of Formula Ia, $R^{2g}$ is —$C_{3-4}$ alkyl.

Some additional embodiments of Formula I include compounds of Formula (Ib):

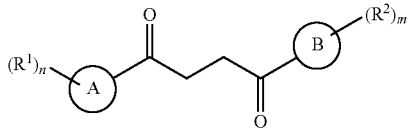

or salts, pharmaceutically acceptable salts, or prodrugs thereof.

In some embodiments of Formula Ib, Ring A is

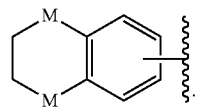

In some embodiments of Formula Ib, Ring B is selected from the group consisting of phenyl and a 5-6 membered heteroaryl, wherein a carbon atom on the ring is attached to the carbonyl carbon.

In some embodiments of Formula Ib, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ib, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ib, each $R^3$ is independently selected from the group consisting of H, unsubstituted —$C_{1-6}$ alkyl, —$C_{1-3}$ haloalkyl, and $CF_3$.

In some embodiments of Formula Ib, each $R^{3b}$ is independently selected from the group consisting of H and unsubstituted —$C_{1-3}$ alkyl.

In some embodiments of Formula Ib, each M is independently selected from the group consisting of N, C, S and O.

In some embodiments of Formula Ib, both M are not O.

In some embodiments of Formula Ib, both M are not C.

In some embodiments of Formula Ib, m is an integer of 1 to 5.

In some embodiments of Formula Ib, n is an integer of 1 to 10.

In some embodiments of Formula Ib, Ring A is selected from the group consisting of

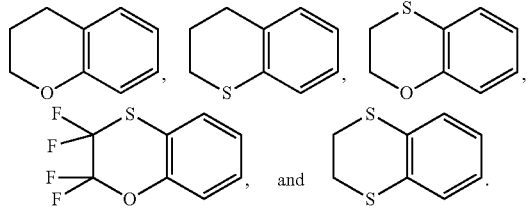

Some additional embodiments of Formula I include compounds of Formula (Ic):

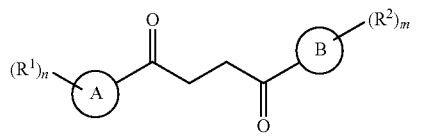

or salts, pharmaceutically acceptable salts, or prodrugs thereof.

In some embodiments of Formula Ic, Ring A is

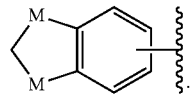

In some embodiments of Formula Ic, Ring B is selected from the group consisting of phenyl and a 5-6 membered heteroaryl, wherein a carbon atom on the ring is attached to the carbonyl carbon.

In some embodiments of Formula Ic, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ic, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ic, each $R^3$ is independently selected from the group consisting of H, unsubstituted —$C_{1-6}$ alkyl, —$C_{1-3}$ haloalkyl, and $CF_3$.

In some embodiments of Formula Ic, each $R^{3b}$ is independently selected from the group consisting of H and unsubstituted —$C_{1-3}$ alkyl.

In some embodiments of Formula Ic, each M is independently selected from the group consisting of N, C, S and O.

In some embodiments of Formula Ic, if one M is C, the other M is selected from the group consisting of N, S, and O.

In some embodiments of Formula Ic, m is an integer of 1 to 5.

In some embodiments of Formula Ic, n is an integer of 1 to 10.

In some embodiments of Formula Ic, Ring A is selected from the group consisting of

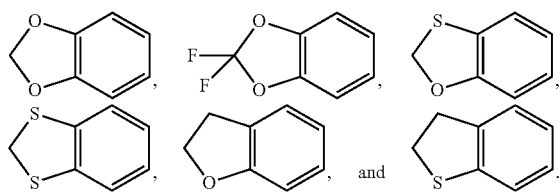

Some additional embodiments of Formula I include compounds of Formula (Id):

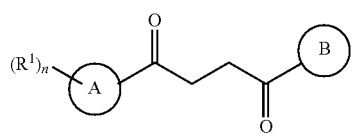

or salts, pharmaceutically acceptable salts, or prodrugs thereof.

In some embodiments of Formula Id, Ring A is

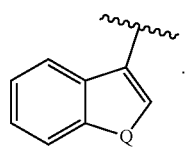

In some embodiments of Formula Id, Ring B is selected from the group consisting of

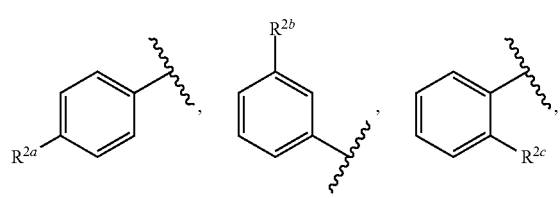

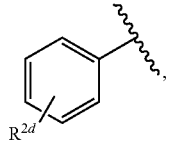

and a 5-6 membered heteroaryl $R^{2e}$, wherein a carbon atom on the ring is attached to the carbonyl carbon.

In some embodiments of Formula Id, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Id, $R^{2a}$ is a substituent attached to the para position of phenyl and selected from the group consisting of H, unsubstituted —$C_{1-6}$ alkyl, —$CH_2OH$, —$CH_2N(R^{3b})_2$, —$C_{1-3}$ haloalkyl, Cl, Br, I, —$OR^{3a}$, $CF_3$, and CN.

In some embodiments of Formula Id, $R^{2b}$ is a substituent attached to the meta position of phenyl and selected from the group consisting of H, unsubstituted —$C_{2-6}$ alkyl, —$CH_2OH$, —$CH_2N(R^{3b})_2$, —$C_{1-3}$ haloalkyl, F, I, —$OR^3$, $CF_3$, and CN.

In some embodiments of Formula Id, $R^{2c}$ is a substituent attached to the ortho position of phenyl and selected from the group consisting of H, unsubstituted —$C_{1-6}$ alkyl, —$CH_2OH$, —$CH_2N(R^{3b})_2$, —$C_{1-3}$ haloalkyl, F, Br, I, —$OR^3$, $CF_3$, and CN.

In some embodiments of Formula Id, $R^{2d}$ is 2-5 substituents, each attached to the phenyl and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Id, $R^{2e}$ is 1-3 substituents, each attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Id, each $R^3$ is independently selected from the group consisting of H, unsubstituted —$C_{1-6}$ alkyl, —$C_{1-3}$ haloalkyl, and $CF_3$.

In some embodiments of Formula Id, each $R^{3a}$ is independently selected from the group consisting of H, unsubstituted —$C_{2-6}$ alkyl, —$C_{1-3}$ haloalkyl, and $CF_3$;

In some embodiments of Formula Id, each $R^{3b}$ is independently selected from the group consisting of H and unsubstituted —$C_{1-3}$ alkyl.

In some embodiments of Formula Id, Q is S or NH.

In some embodiments of Formula Id, n is an integer of 1 to 5.

In some embodiments of Formula Id, Ring A is selected from the group consisting of

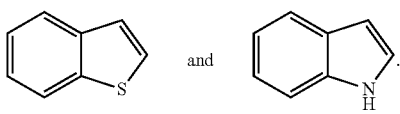 [SMILES: c1ccc2sccc2c1 ; c1ccc2[nH]ccc2c1]

In some embodiments of Formula Id, $R^{2a}$ is H.
In some embodiments of Formula Id, $R^{2b}$ is H.
In some embodiments of Formula Id, $R^{2c}$ is H.
In some embodiments of Formula Id, $R^{2d}$ is H.

Some additional embodiments of Formula I include compounds of Formula (Ie):

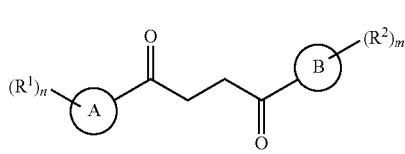

or salts, pharmaceutically acceptable salts, or prodrugs thereof.

In some embodiments of Formula Ie, Ring A is

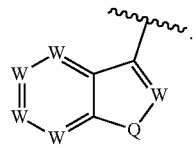

In some embodiments of Formula Ie, Ring B is selected from the group consisting of phenyl and a 5-6 membered heteroaryl, wherein a carbon atom on the ring is attached to the carbonyl carbon.

In some embodiments of Formula Ie, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ie, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ie, each $R^3$ is independently selected from the group consisting of H, unsubstituted —$C_{1-6}$ alkyl, —$C_{1-3}$ haloalkyl, and $CF_3$.

In some embodiments of Formula Ie, each $R^{3b}$ is independently selected from the group consisting of H and unsubstituted —$C_{1-3}$ alkyl.

In some embodiments of Formula Ie, each W is N or C.

In some embodiments of Formula Ie, at least one W must be N.

In some embodiments of Formula Ie, Q is S or NH.

In some embodiments of Formula Ie, m is an integer of 1 to 5.

In some embodiments of Formula Ie, n is an integer of 1 to 4.

In some embodiments of Formula Ie, Ring A is selected from the group consisting of

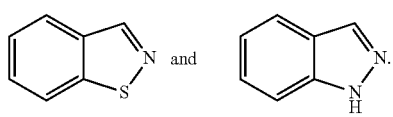 [SMILES: c1ccc2sncc2c1 ; "and" ; c1ccc2[nH]ncc2c1]

Some additional embodiments of Formula I include compounds of Formula (If):

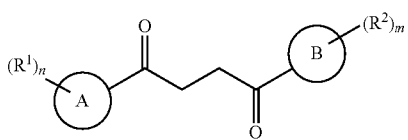

or salts, pharmaceutically acceptable salts, or prodrugs thereof.

In some embodiments of Formula If, Ring A is

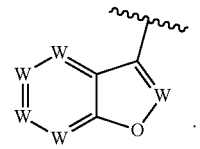

In some embodiments of Formula If, Ring B is selected from the group consisting of phenyl and a 5-6 membered heteroaryl, wherein a carbon atom on the ring is attached to the carbonyl carbon.

In some embodiments of Formula If, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula If, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula If, each $R^3$ is independently selected from the group consisting of H, unsubstituted —$C_{1-6}$ alkyl, —$C_{1-3}$ haloalkyl, and $CF_3$.

In some embodiments of Formula If, each $R^{3b}$ is independently selected from the group consisting of H and unsubstituted —$C_{1-3}$ alkyl.

In some embodiments of Formula If, each W is N or C.

In some embodiments of Formula If, m is an integer of 1 to 5.

In some embodiments of Formula If, n is an integer of 1 to 5.

In some embodiments of Formula If, Ring A is selected from the group consisting of

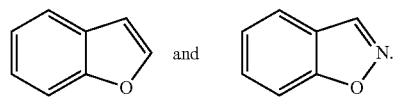 [SMILES: c1ccc2occc2c1 ; "and" ; c1ccc2oncc2c1]

Some additional embodiments of Formula I include compounds of Formula (Ig):

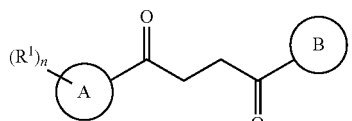

or salts, pharmaceutically acceptable salts, or prodrugs thereof.

In some embodiments of Formula Ig, Ring A is

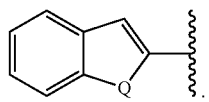

In some embodiments of Formula Ig, Ring B is selected from the group consisting of

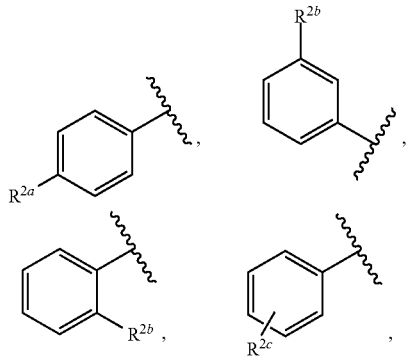

and a 5-6 membered heteroaryl $R^{2d}$, wherein a carbon atom on the ring is attached to the carbonyl carbon.

In some embodiments of Formula Ig, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ig, $R^{2a}$ is a substituent attached to the para position of phenyl and is selected from the group consisting of unsubstituted —$C_{1-6}$ alkyl, —$CH_2OH$, —$CH_2N(R^{3b})_2$, —$C_{1-3}$ haloalkyl, F, I, —$OR^3$, $CF_3$, and CN.

In some embodiments of Formula Ig, $R^{2b}$ is a substituent attached to the meta or ortho position of phenyl and is selected from the group consisting of unsubstituted —$C_{2-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ig, $R^{2c}$ is 2-5 substituents, each attached to the phenyl and are independently selected at each occurrence from the group consisting of unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ig, $R^{2d}$ is 1-3 substituents, each attached to the heteroaryl ring and are independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ig, each $R^3$ is independently selected from the group consisting of H, unsubstituted —$C_{1-6}$ alkyl, —$C_{1-3}$ haloalkyl, and $CF_3$.

In some embodiments of Formula Ig, each $R^{3b}$ is independently selected from the group consisting of H and unsubstituted —$C_{1-3}$ alkyl.

In some embodiments of Formula Ig, Q is independently selected from the group consisting of O, S, and NH.

In some embodiments of Formula Ig, n is an integer of 1 to 5.

In some embodiments of Formula Ig, Ring A is selected from the group consisting of

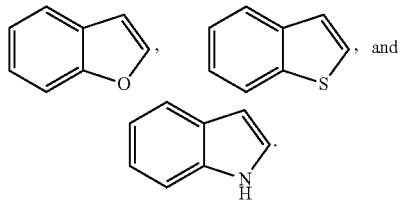

In some embodiments of Formula Ig, $R^{2a}$ is F.
In some embodiments of Formula Ig, $R^{2a}$ is OH.
In some embodiments of Formula Ig, $R^{2a}$ is OMe.
In some embodiments of Formula Ig, $R^{2a}$ is 1 substituent and is F.
In some embodiments of Formula Ig, $R^{2a}$ is 2 substituents and both are F.
In some embodiments of Formula Ig, $R^{2a}$ is 1 substituent and is OMe.
In some embodiments of Formula Ig, $R^{2a}$ is 2 substituents and both are OMe.
In some embodiments of Formula Ig, $R^{2a}$ is 2 substituents and are F and Me.
In some embodiments of Formula Ig, $R^{2a}$ is 2 substituents and are F and $CF_3$.
In some embodiments of Formula Ig, $R^{2a}$ is 2 substituents and are F and OMe.
In some embodiments of Formula Ig, $R^{2a}$ is 2 substituents and are F and CN.

Some additional embodiments of Formula I include compounds of Formula (Ih):

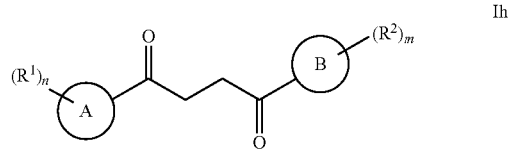

or salts, pharmaceutically acceptable salts, or prodrugs thereof.

In some embodiments of Formula Ih, Ring A is

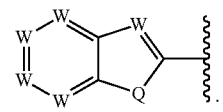

In some embodiments of Formula Ih, Ring B is selected from the group consisting of phenyl and a 5-6 membered heteroaryl, wherein a carbon atom on the ring is attached to the carbonyl carbon.

In some embodiments of Formula Ih, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ih, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ih, each $R^3$ is independently selected from the group consisting of H, unsubstituted —$C_{1-6}$ alkyl, —$C_{1-3}$ haloalkyl, and $CF_3$.

In some embodiments of Formula Ih, each $R^{3b}$ is independently selected from the group consisting of H and unsubstituted —$C_{1-3}$ alkyl.

In some embodiments of Formula Ih, each W is N or C.

In some embodiments of Formula Ih, at least one W must be N.

In some embodiments of Formula Ih, Q is independently selected from the group consisting of O, S, and NH.

In some embodiments of Formula Ih, m is an integer of 1 to 5.

In some embodiments of Formula Ih, n is an integer of 1 to 4.

In some embodiments of Formula Ih, Ring A is selected from the group consisting of

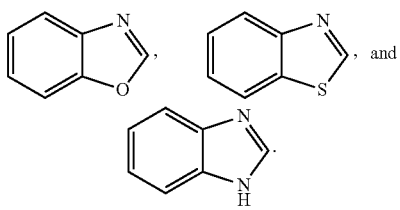

Some additional embodiments of Formula I include compounds of Formula (Ii):

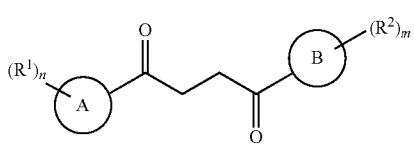

or salts, pharmaceutically acceptable salts, or prodrugs thereof.

In some embodiments of Formula Ii, Ring A is

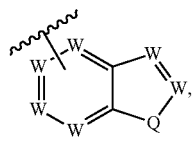

wherein a carbon atom on the ring is attached to the carbonyl carbon.

In some embodiments of Formula Ii, Ring B is selected from the group consisting of phenyl and a 5-6 membered heteroaryl, wherein a carbon atom on the ring is attached to the carbonyl carbon.

In some embodiments of Formula Ii, each $R^1$ is a substituent attached to Ring A and is independently selected at each occurrence from the group consisting of H, unsubstituted —$C_{1-6}$ alkyl, —$C_{1-3}$ haloalkyl, halide, —$OR^3$, $CF_3$, and CN.

In some embodiments of Formula Ii, each $R^2$ is a substituent attached to Ring B and is independently selected at each occurrence from the group consisting of H, unsubstituted —$C_{1-6}$ alkyl, —$CH_2OH$, —$CH_2N(R^{3b})_2$, —$C_{1-3}$ haloalkyl, halide, —$OR^3$, $CF_3$, and CN.

In some embodiments of Formula Ii, each $R^3$ is independently selected from the group consisting of H, unsubstituted —$C_{1-6}$ alkyl, —$C_{1-3}$ haloalkyl, and $CF_3$.

In some embodiments of Formula Ii, each $R^{3b}$ is independently selected from the group consisting of H and unsubstituted —$C_{1-3}$ alkyl.

In some embodiments of Formula Ii, each W is N or C.

In some embodiments of Formula Ii, at least one W is C.

In some embodiments of Formula Ii, Q is independently selected from the group consisting of O, S, and N.

In some embodiments of Formula Ii, m is an integer of 1 to 5.

In some embodiments of Formula Ii, n is an integer of 1 to 7.

In some embodiments of Formula Ii, Ring A is selected from the group consisting of

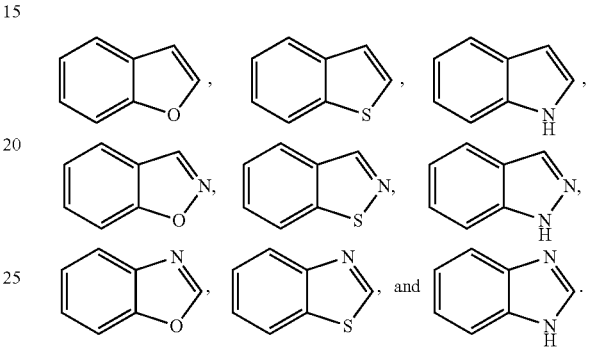

Some embodiments of the present disclosure include compounds of Formula (II):

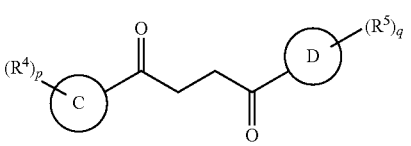

or salts, pharmaceutically acceptable salts, or prodrugs thereof.

In some embodiments of Formula II, Ring C is a 5-6 membered heteroaryl, wherein a carbon atom on the ring is attached to the carbonyl carbon.

In some embodiments of Formula II, Ring D is selected from the group consisting of phenyl and a 5-6 membered heteroaryl, wherein a carbon atom on the ring is attached to the carbonyl carbon.

In some embodiments of Formula II, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula II, each $R^5$ is a substituent attached to Ring D and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula II, each $R^6$ is independently selected from the group consisting of H, unsubstituted —$C_{1-6}$ alkyl, —$C_{1-3}$ haloalkyl, and $CF_3$.

In some embodiments of Formula II, each $R^{6b}$ is independently selected from the group consisting of H and unsubstituted —$C_{1-3}$ alkyl.

In some embodiments of Formula II, each q is an integer of 1 to 4.

In some embodiments of Formula II, each p is an integer of 1 to 5.
In some embodiments of Formula II, there is the proviso that a compound of Formula II is not a compound selected from the group consisting of:
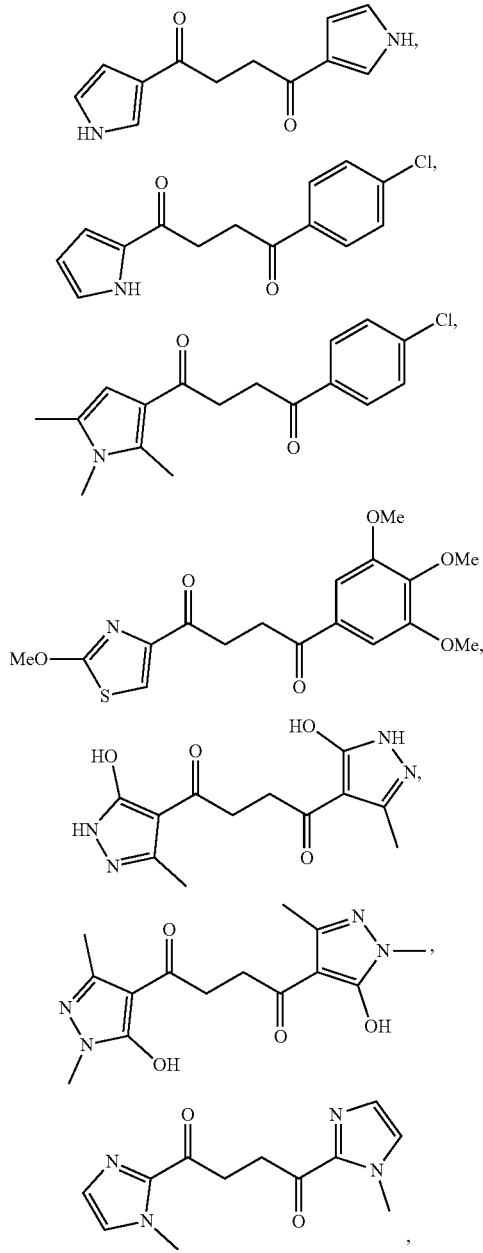
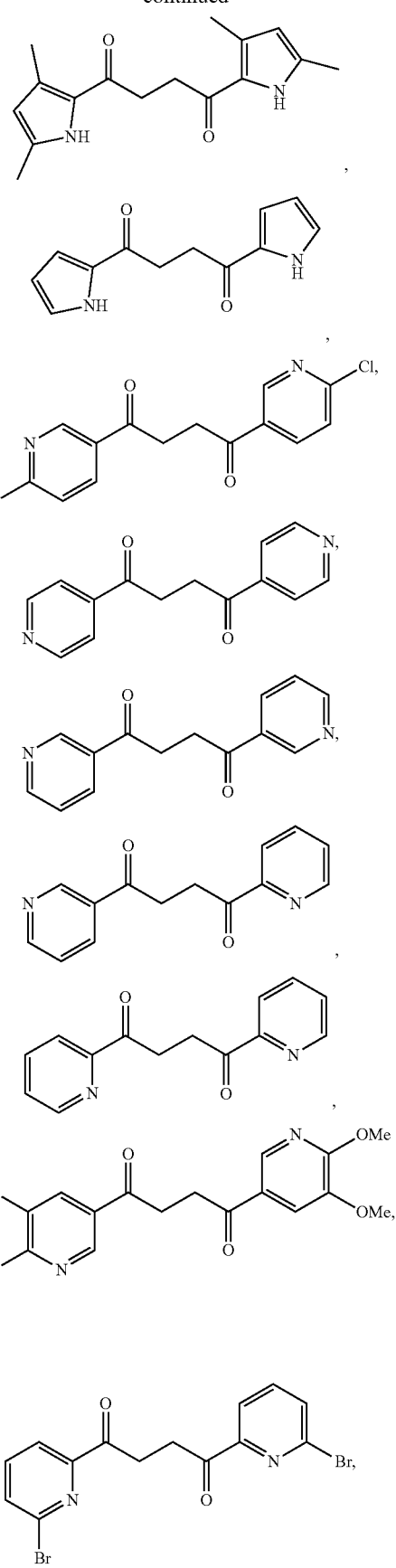

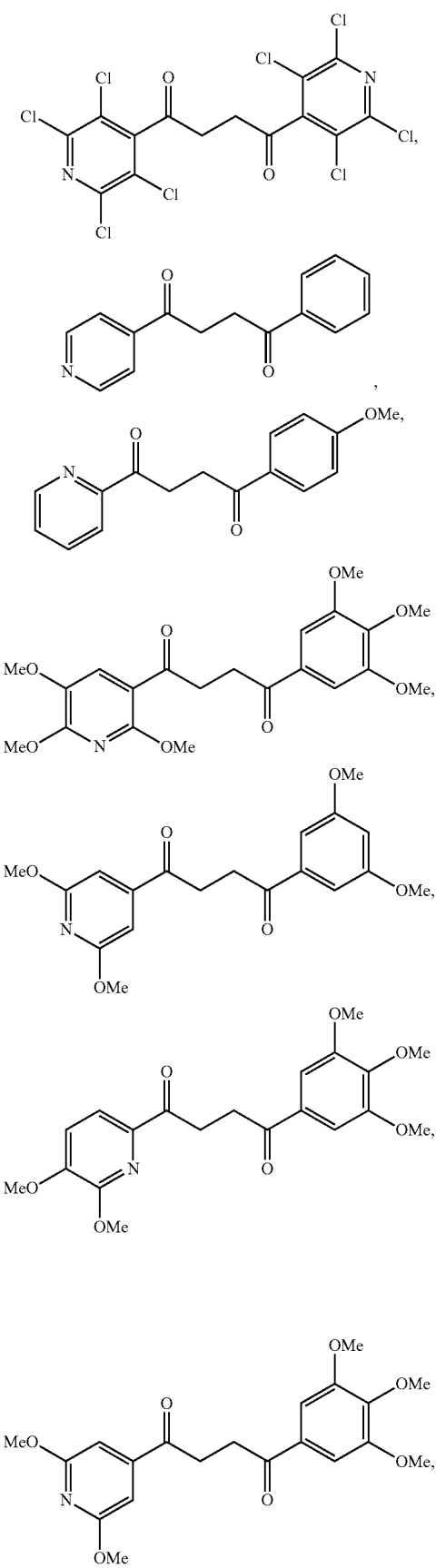
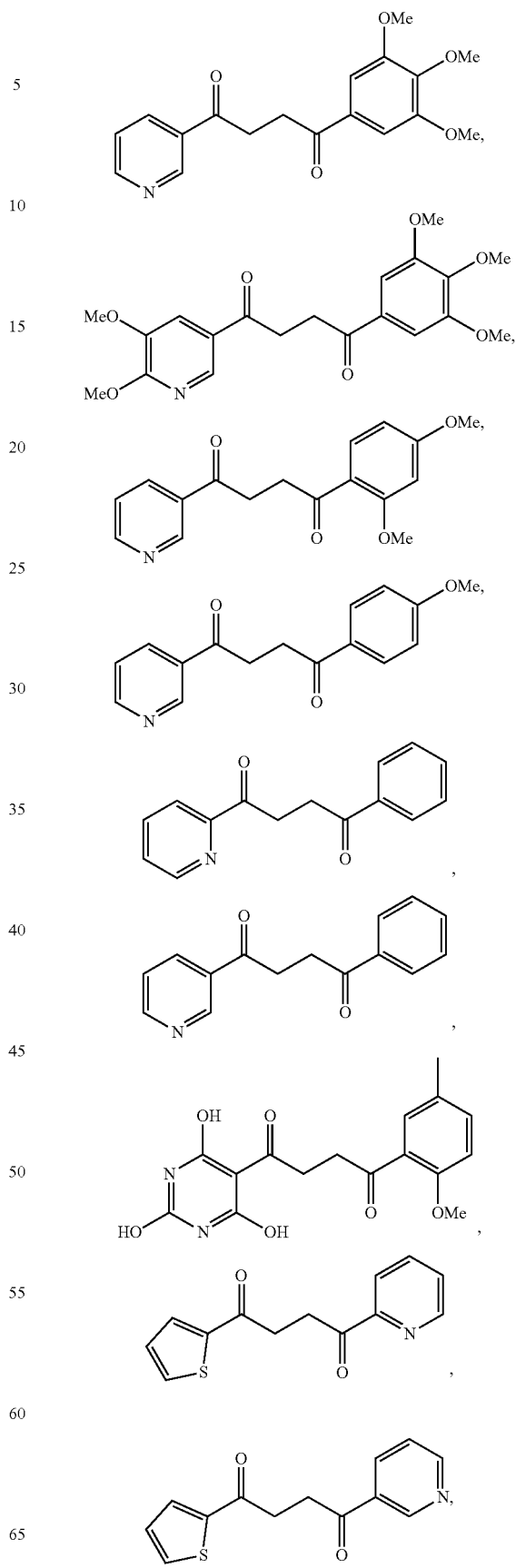

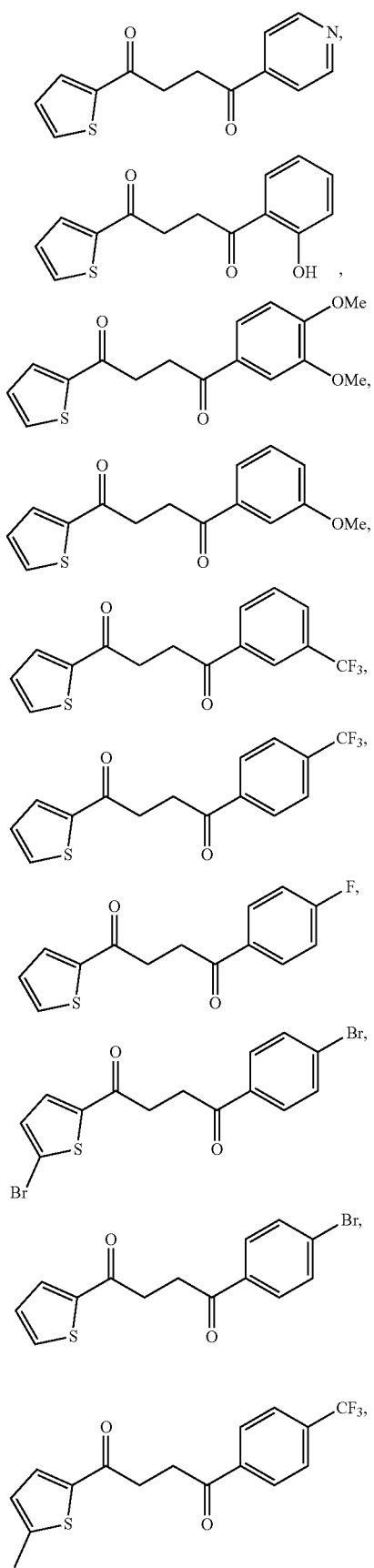
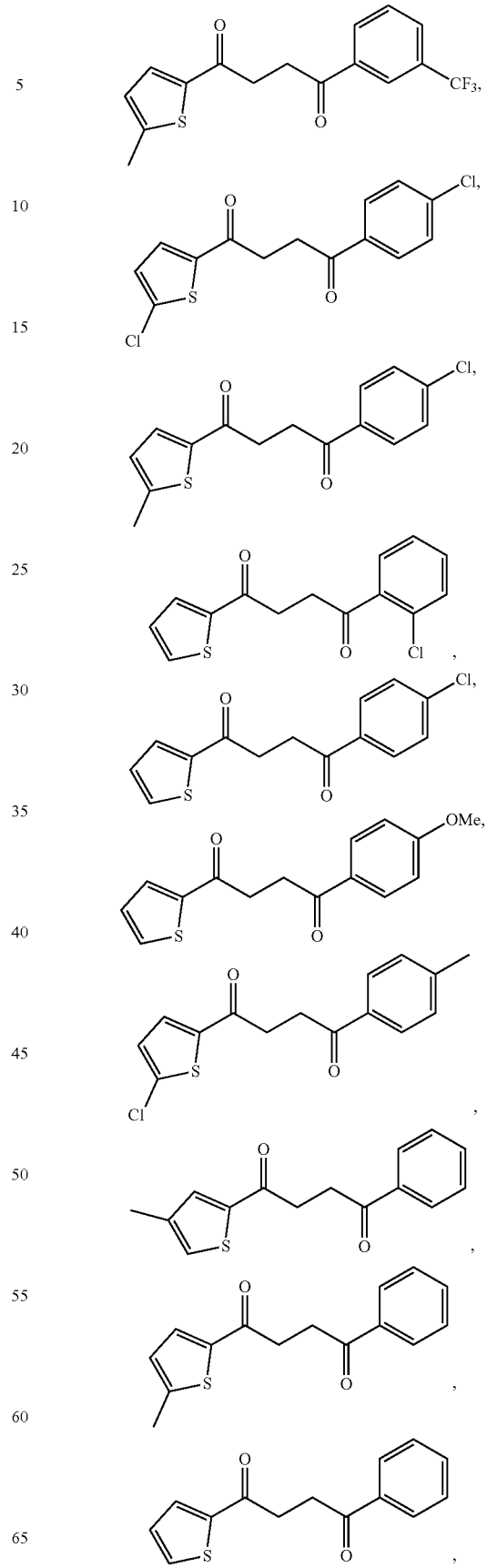

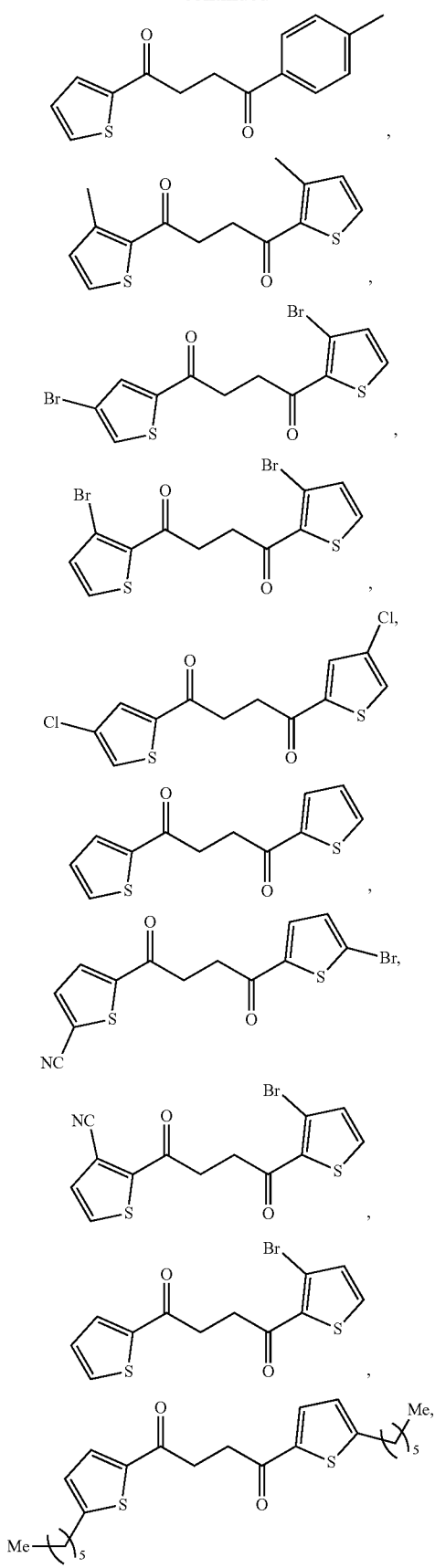
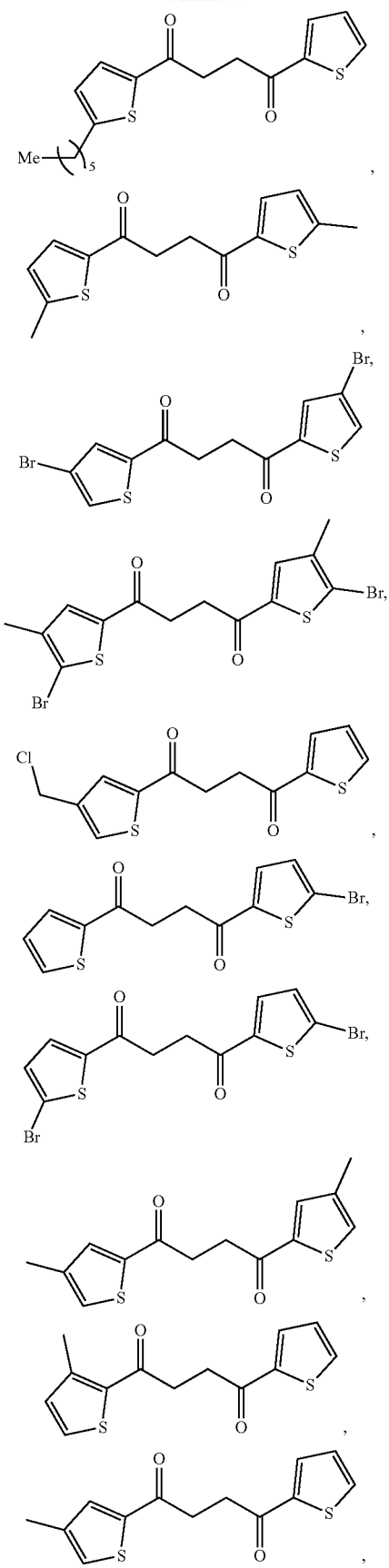

-continued
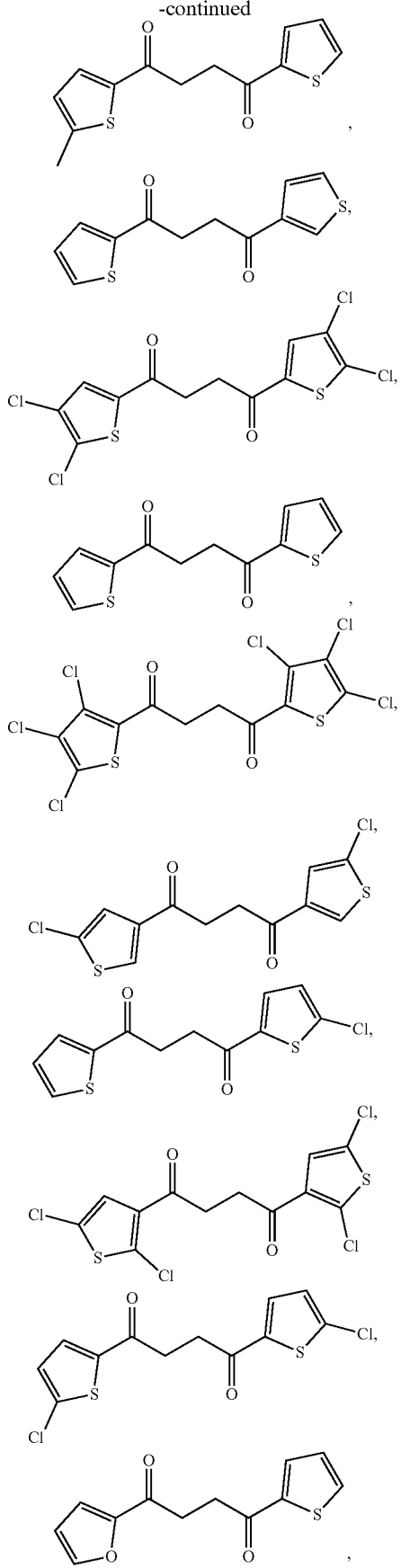
-continued
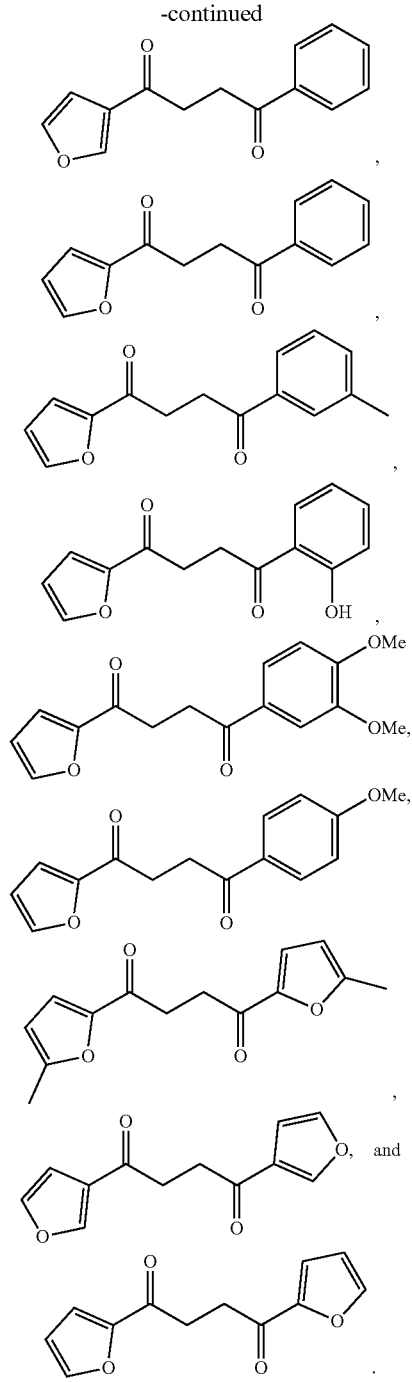
In some embodiments of Formula II, Ring C is a 5-membered heteroaryl ring containing 1-3 heteroatoms selected from the group consisting of N, O, and S.
In some embodiments of Formula II,
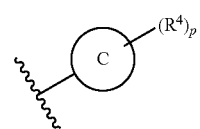

is selected from the group consisting of

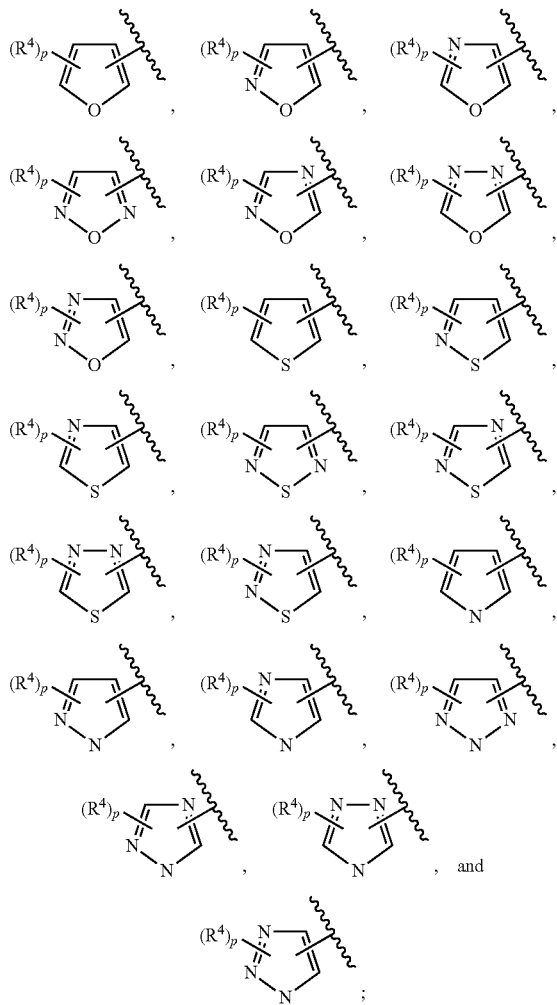

and p is 1 or 2.

In some embodiments of Formula II,

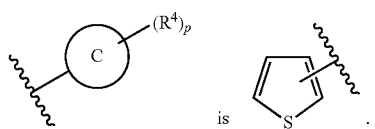

In some embodiments of Formula II, Ring C is a 6-membered heteroaryl ring containing 1-2 nitrogens.

In some embodiments of Formula II,

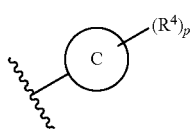

is selected from the group consisting of

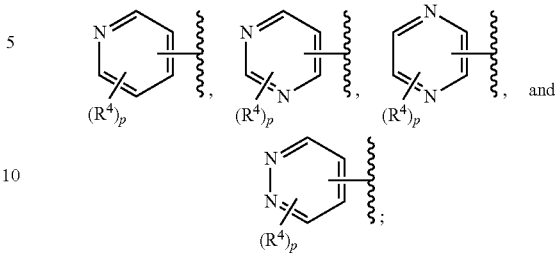

and p is 1 or 2.

In some embodiments of Formula II,

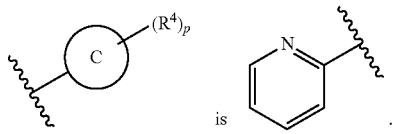

In some embodiments of Formula II, each $R^4$ is independently selected from the group consisting of H, F, Cl, Me, OMe, OH, $CF_3$ and CN.

In some embodiments of Formula II, IIa, IIc, IId, IIe, and/or IIf, each $R^4$ is independently selected from the group consisting of H, F, Cl, Me, OMe, OH, $CF_3$ and CN; and p is 1 or 2.

In some embodiments of Formula II, IIa, IIb, IIc, IId, IIe, and/or IIf, $R^4$ is H.

In some embodiments of Formula II, IIa, IIb, IIc, IId, IIe, and/or IIf, $R^4$ is a halide.

In some embodiments of Formula II, IIa, IIb, IIc, IId, IIe, and/or IIf, $R^4$ is F.

In some embodiments of Formula II, IIa, IIb, IIc, IId, IIe, and/or IIf, $R^4$ is Cl.

In some embodiments of Formula II, IIa, IIb, IIc, IId, IIe, and/or IIf, $R^4$ is Me.

In some embodiments of Formula II, IIa, IIc, IId, IIe, and/or IIf, $R^4$ is OH.

In some embodiments of Formula II, IIa, IIb, IIc, IId, IIe, and/or IIf, $R^4$ is OMe.

In some embodiments of Formula II, IIa, IIb, IIc, IId, IIe, and/or IIf, $R^4$ is $CF_3$.

In some embodiments of Formula II, IIa, IIb, IIc, IId, IIe, and/or IIf, $R^4$ is CN.

In some embodiments of Formula II, IIa, IIb, IIc, IId, IIe, and/or IIf, p is an integer from 1-3.

In some embodiments of Formula II, IIa, IIb, IIc, IId, IIe, and/or IIf, p is an integer from 1-2.

In some embodiments of Formula II, IIa, IIb, IIc, IId, IIe, and/or IIf, p is 2.

In some embodiments of Formula II, IIa, IIb, IIc, IId, IIe, and/or IIf, p is 1.

In some embodiments of Formula II, IIa, IIb, IIc, IId, IIe, and/or IIf, $R^4$ is F; and p is 1.

In some embodiments of Formula II, IIa, IIb, IIc, IId, IIe, and/or IIf, $R^4$ is F; and p is 2.

In some embodiments of Formula II, IIa, IIc, IId, IIe, and/or IIf, $R^4$ is OH; and p is 1.

In some embodiments of Formula II, IIa, IIb, IIc, IId, IIe, and/or IIf, $R^4$ is OMe; and p is an integer from 1-2.

In some embodiments of Formula II, IIa, IIb, IIc, IId, IIe, and/or IIf, $R^4$ is —$C_{1-2}$ alkyl.

In some embodiments of Formula II, IIa, IIb, IIc, IId, IIe, and/or IIf, $R^4$ is —$C_{1-3}$ alkyl.

In some embodiments of Formula II, IIa, IIb, IIc, IId, IIe, and/or IIf, $R^4$ is —$C_{1-4}$ alkyl.

In some embodiments of Formula II, IIa, IIb, IIc, IId, IIe, and/or IIf, $R^4$ is —$C_{1-5}$ alkyl.

In some embodiments of Formula II, IIa, IIb, IIc, IId, IIe, and/or IIf, $R^4$ is —$C_{1-6}$ alkyl.

In some embodiments of Formula II, IIa, IIb, IIc, IId, IIe, and/or IIf, $R^4$ is —$C_{2-6}$ alkyl.

In some embodiments of Formula II, IIa, IIb, IIc, IId, IIe, and/or IIf, $R^4$ is —$C_{3-6}$ alkyl.

In some embodiments of Formula II, IIa, IIb, IIc, IId, IIe, and/or IIf, $R^4$ is —$C_{4-6}$ alkyl.

In some embodiments of Formula II, IIa, IIb, IIc, IId, IIe, and/or IIf, $R^4$ is —$C_{2-5}$ alkyl.

In some embodiments of Formula II, IIa, IIb, IIc, IId, IIe, and/or IIf, $R^4$ is —$C_{3-5}$ alkyl.

In some embodiments of Formula II, Ring C is selected from the group consisting of:

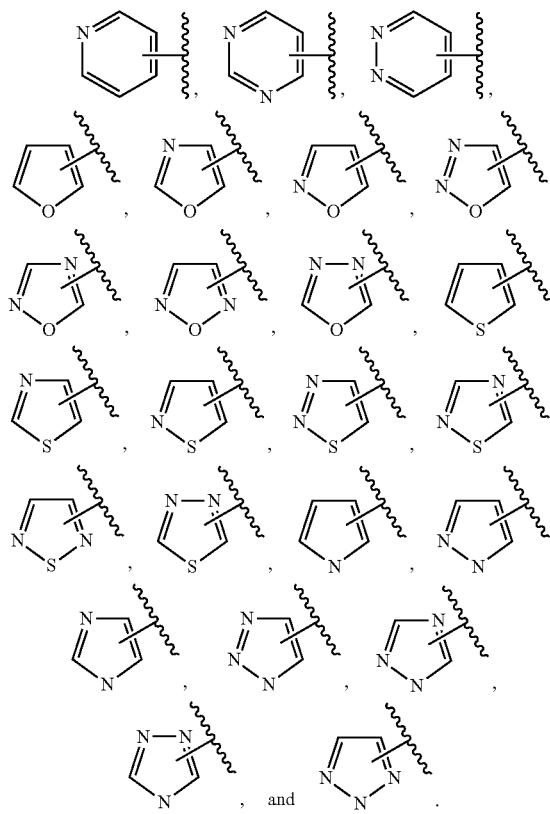

In some embodiments of Formula II and/or IIb, Ring D is phenyl.

In some embodiments of Formula II and/or IIb,

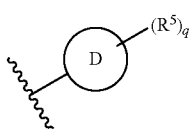

is selected from the group consisting of

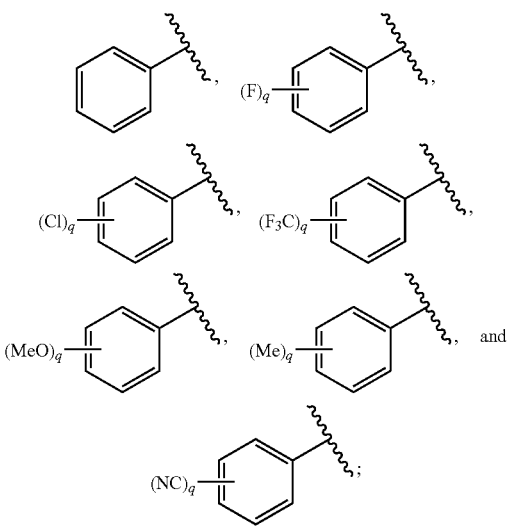

and; and q is 1 or 2.

In some embodiments of Formula II and/or IIb,

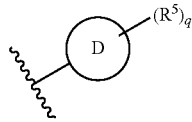

is selected from the group consisting of

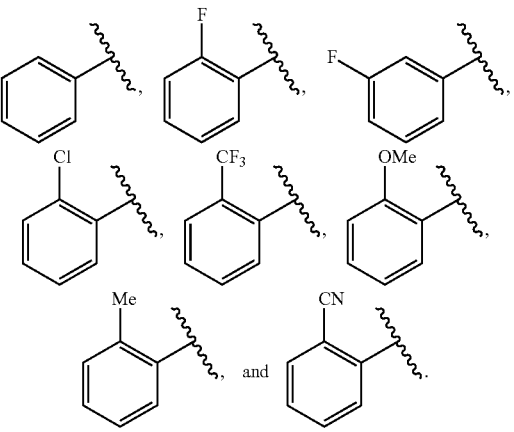

In some embodiments of Formula II and/or IIb, Ring D is a 5-membered heteroaryl containing 1-3 heteroatoms selected from the group consisting of N, O, and S.

In some embodiments of Formula II and/or IIb,

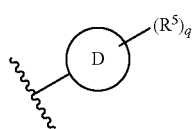

is selected from the group consisting of

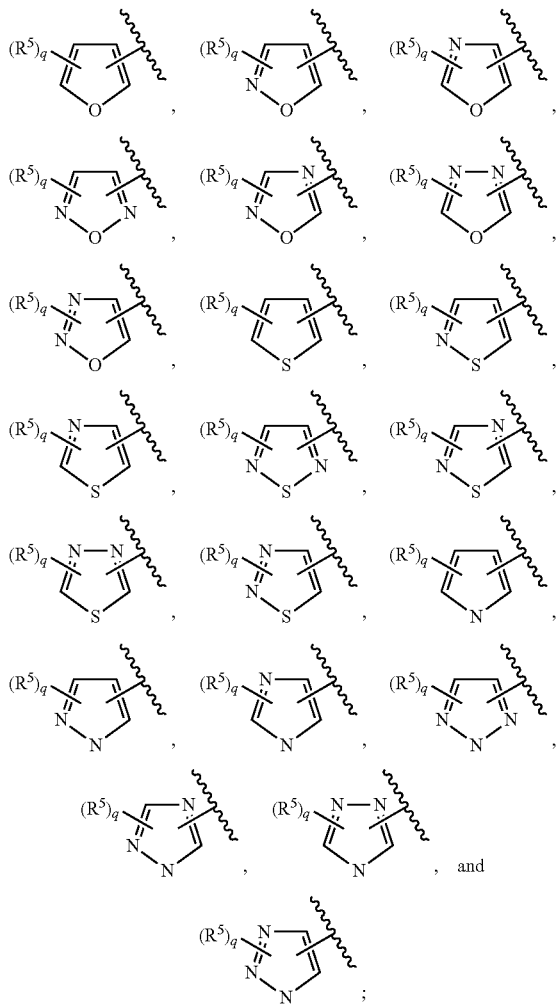

and q is 1 or 2.

In some embodiments of Formula II and/or IIb,

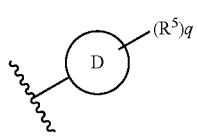

is selected from the group consisting of

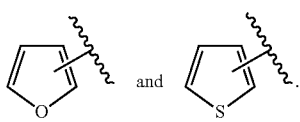

In some embodiments of Formula II and/or IIb, Ring D is a 6-membered heteroaryl containing 1-2 nitrogen atoms.

In some embodiments of Formula II and/or IIb,

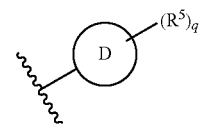

is selected from the group consisting of

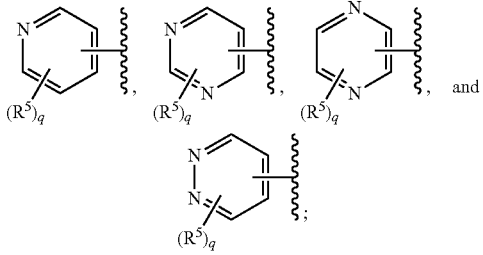

and q is 1 or 2.

In some embodiments of Formula II and/or IIb,

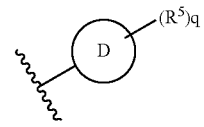

is selected from the group consisting of

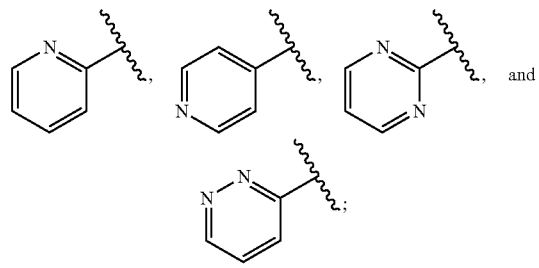

and $R^5$ is H.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$OH.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}R^{5h}$, and/or $R^{5i}$ is —CH$_2$N($R^{3b}$)$_2$.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$NH$_2$.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$NHMe.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$NMe$_2$.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$NHEt.

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$N(Me)(Et).

In some embodiments of Formula II, IIa, IIb, IIc, IId, IIe, and/or IIf, $R^5$, $R^{5a}$, $R^{5b}$, $R^{5c}$, $R^{5d}$, $R^{5e}$, $R^{5f}$, $R^{5g}$, $R^{5h}$, and/or $R^{5i}$ is —CH$_2$NEt$_2$.

In some embodiments of Formula II and/or IIb, each $R^5$ is independently selected from the group consisting of H, F, Cl, Me, OMe, OH, CF$_3$, and CN.

In some embodiments of Formula II and/or IIb, $R^5$ is H.

In some embodiments of Formula II and/or IIb, $R^5$ is a halide.

In some embodiments of Formula II and/or IIb, $R^5$ is F.

In some embodiments of Formula II and/or IIb, $R^5$ is Cl.

In some embodiments of Formula II and/or IIb, $R^5$ is Me.

In some embodiments of Formula II and/or IIb, $R^5$ is OH.

In some embodiments of Formula II and/or IIb, $R^5$ is OMe.

In some embodiments of Formula II and/or IIb, $R^5$ is CF$_3$.

In some embodiments of Formula II and/or IIb, $R^5$ is CN.

In some embodiments of Formula II and/or IIb, q is an integer from 1-4.

In some embodiments of Formula II and/or IIb, q is an integer from 1-2.

In some embodiments of Formula II and/or IIb, q is 1.

In some embodiments of Formula II and/or IIb, q is 2.

In some embodiments of Formula II and/or IIb, $R^5$ is F; and q is 1.

In some embodiments of Formula II and/or IIb, $R^5$ is F; and q is 2.

In some embodiments of Formula II and/or IIb, $R^5$ is Me; and q is 1.

In some embodiments of Formula II and/or IIb, $R^5$ is Me; and q is 2.

In some embodiments of Formula II and/or IIb, $R^5$ is CF$_3$; and q is 1.

In some embodiments of Formula II and/or IIb, $R^5$ is CF$_3$; and q is 2.

In some embodiments of Formula II and/or IIb, $R^5$ is OMe; and q is 1.

In some embodiments of Formula II and/or IIb, $R^5$ is OMe; and q is 2.

In some embodiments of Formula II and/or IIb, $R^5$ is F and Me; and q is 2.

In some embodiments of Formula II and/or IIb, $R^5$ is F and CF$_3$; and q is 2.

In some embodiments of Formula II and/or IIb, $R^5$ is F and OMe; and q is 2.

In some embodiments of Formula II and/or IIb, $R^5$ is CN; and q is 1.

In some embodiments of Formula II and/or IIb, $R^5$ is CN; and q is 2.

In some embodiments of Formula II and/or IIb, $R^5$ is F and CN; and q is 2.

In some embodiments of Formula II and/or IIb, $R^5$ is —C$_{1-2}$ alkyl.

In some embodiments of Formula II and/or IIb, $R^5$ is —C$_{1-3}$ alkyl.

In some embodiments of Formula II and/or IIb, $R^5$ is —C$_{1-4}$ alkyl.

In some embodiments of Formula II and/or IIb, $R^5$ is —C$_{1-5}$ alkyl.

In some embodiments of Formula II and/or IIb, $R^5$ is —C$_{1-6}$ alkyl.

In some embodiments of Formula II and/or IIb, $R^5$ is —C$_{2-6}$ alkyl.

In some embodiments of Formula II and/or IIb, $R^5$ is —C$_{3-6}$ alkyl.

In some embodiments of Formula II and/or IIb, $R^5$ is —C$_{4-6}$ alkyl.

In some embodiments of Formula II and/or IIb, $R^5$ is —C$_{2-5}$ alkyl.

In some embodiments of Formula II and/or IIb, $R^5$ is —C$_{3-5}$ alkyl.

In some embodiments of Formula II, IIa, IIb, IIc, IId, IIe, and/or IIf, $R^6$ is —C$_{1-2}$ alkyl.

In some embodiments of Formula II, IIa, IIb, IIc, IId, IIe, and/or IIf, $R^6$ is —C$_{1-3}$ alkyl.

In some embodiments of Formula II, IIa, IIb, IIc, IId, IIe, and/or IIf, $R^6$ is —C$_{1-4}$ alkyl.

In some embodiments of Formula II, IIa, IIb, IIc, IId, IIe, and/or IIf, $R^6$ is —C$_{1-5}$ alkyl.

In some embodiments of Formula II, IIa, IIb, IIc, IId, IIe, and/or IIf, $R^6$ is —C$_{1-6}$ alkyl.

In some embodiments of Formula II, IIa, IIb, IIc, IId, IIe, and/or IIf, $R^6$ is —C$_{2-6}$ alkyl.

In some embodiments of Formula II, IIa, IIb, IIc, IId, IIe, and/or IIf, $R^6$ is —C$_{3-6}$ alkyl.

In some embodiments of Formula II, IIa, IIb, IIc, IId, IIe, and/or IIf, $R^6$ is —C$_{4-6}$ alkyl.

In some embodiments of Formula II, IIa, IIb, IIc, IId, IIe, and/or IIf, $R^6$ is —C$_{2-5}$ alkyl.

In some embodiments of Formula II, IIa, IIb, IIc, IId, IIe, and/or IIf, $R^6$ is —C$_{3-5}$ alkyl.

In some embodiments of Formula II, Ring D is a phenyl or 6-membered heteroaryl; $R^5$ is selected from the group consisting of F, Cl, Me, OMe, OH, CF$_3$ and CN; q is 1; and $R^5$ is attached to an ortho carbon of the 6-membered ring.

In some embodiments of Formula II, Ring D is a phenyl, $R^5$ is selected from the group consisting of F, Cl, Me, OMe, OH, CF$_3$ and CN; q is 1; and $R^5$ is attached to an ortho position of the phenyl ring.

In some embodiments of Formula II, Ring D is a pyridine, $R^5$ is selected from the group consisting of F, Cl, Me, OMe, OH, CF$_3$ and CN; q is 1; and $R^5$ is attached to an ortho carbon of the pyridine ring.

In some embodiments of Formula II,

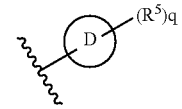

is selected from the group consisting of:

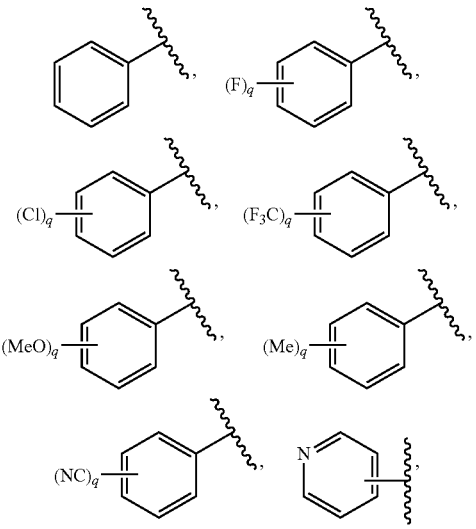

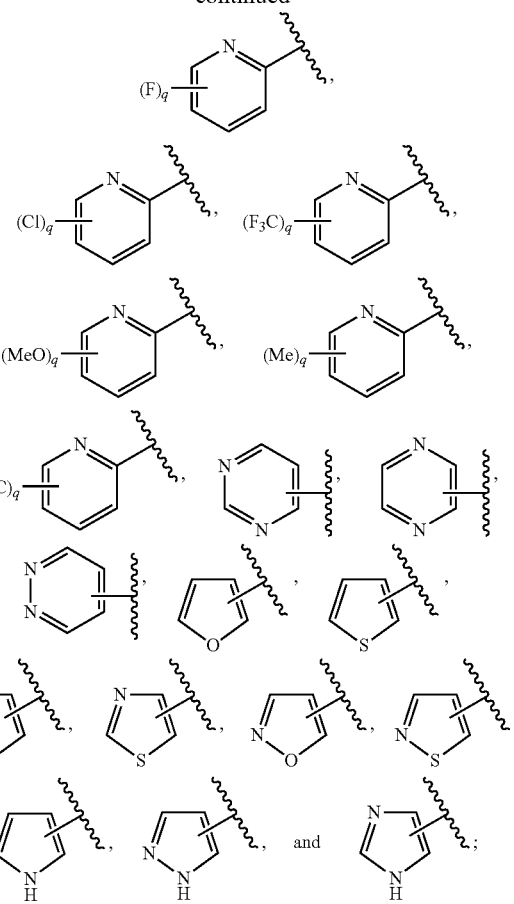
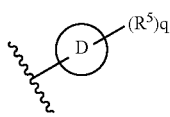

wherein the carbonyl carbon of Formula II can form a bond with any unsubstituted carbon on the Ring D.

In some embodiments of Formula II,

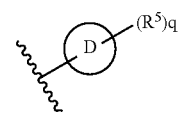

is selected from the group consisting of:

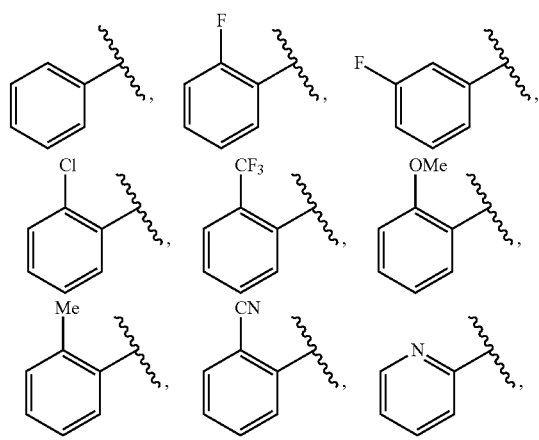

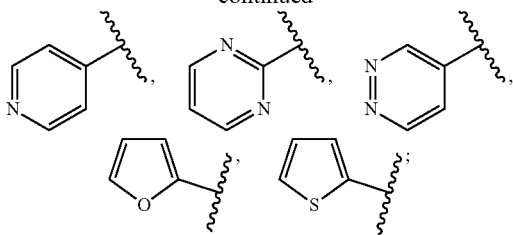

wherein the carbonyl carbon of Formula II can form a bond with any unsubstituted carbon on the Ring D.

In some embodiments of Formula II,

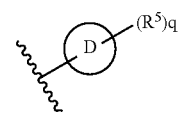

is selected from the group consisting of:

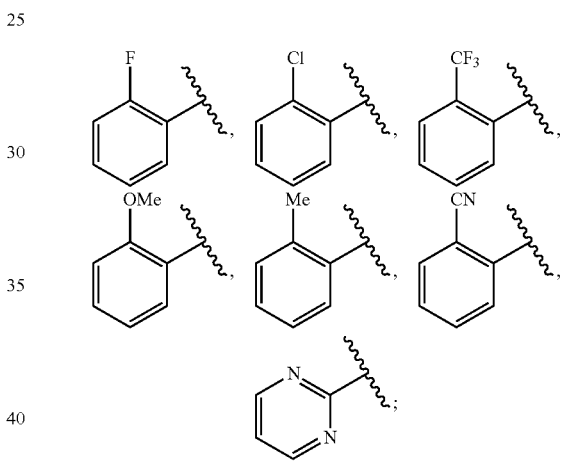

wherein the carbonyl carbon of Formula II can form a bond with any unsubstituted carbon on the Ring D.

Some additional embodiments of Formula II include compounds of Formula (IIa):

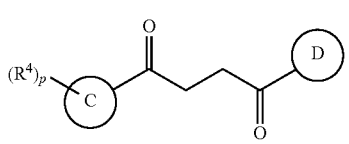

IIa or salts, pharmaceutically acceptable salts, or prodrugs thereof.

In some embodiments of Formula IIa, Ring C is

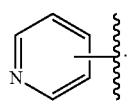

In some embodiments of Formula IIa, Ring D is selected from the group consisting of

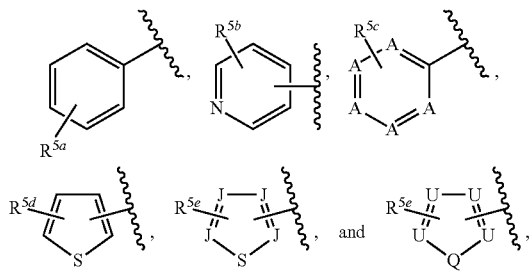

wherein a carbon atom on the ring is attached to the carbonyl carbon.

In some embodiments of Formula IIa, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula IIa, $R^{5a}$ is 1-5 substituents, each attached to Ring D and are independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^{6a}$, $CF_3$, and CN.

In some embodiments of Formula IIa, $R^{5b}$ is 1-4 substituents, each attached to Ring D and are independently selected at each occurrence from the group consisting of unsubstituted —$C_{1-6}$ alkyl, —$CH_2OH$, —$CH_2N(R^{6b})_2$, —$C_{1-3}$ haloalkyl, F, I, —$OR^{6a}$, $CF_3$, and CN.

In some embodiments of Formula IIa, $R^{5c}$ is 1-3 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIa, $R^{5d}$ is 1-2 substituents, each attached to Ring D and are independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIa, $R^{5e}$ is 1-3 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIa, each $R^6$ is independently selected from the group consisting of H, unsubstituted —$C_{1-6}$ alkyl, —$C_{1-3}$ haloalkyl, and $CF_3$.

In some embodiments of Formula IIa, each $R^{6a}$ is independently selected from the group consisting of H, unsubstituted —$C_{2-6}$ alkyl, —$C_{1-3}$ haloalkyl, and $CF_3$.

In some embodiments of Formula IIa, each $R^{6b}$ is independently selected from the group consisting of H and unsubstituted —$C_{1-3}$ alkyl.

In some embodiments of Formula IIa, each A is N or C.
In some embodiments of Formula IIa, at least two A must be N.
In some embodiments of Formula IIa, each J is N or C.
In some embodiments of Formula IIa, at least one J must be N and at least one J must be C.
In some embodiments of Formula IIa, each U is N or C.
In some embodiments of Formula IIa, at least one U must be C.
In some embodiments of Formula IIa, Q is O or N.
In some embodiments of Formula IIa, p is an integer of 1 to 4.

In some embodiments of Formula IIa, Ring D is selected from the group consisting of

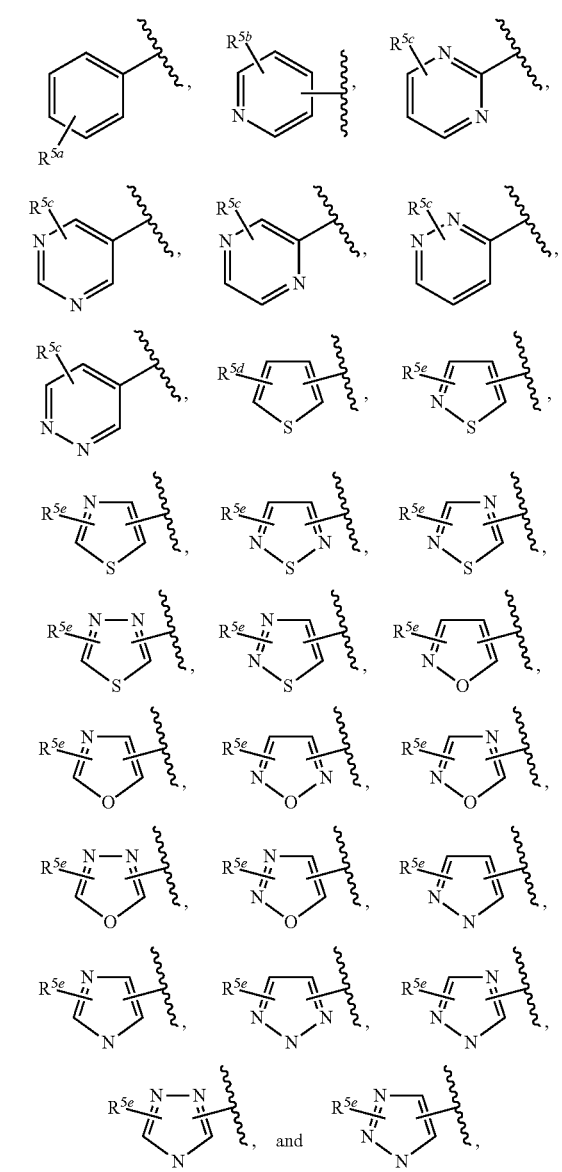

wherein a carbon atom on the ring is attached to the carbonyl carbon.

In some embodiments of Formula IIa, Ring D is selected from the group consisting of:

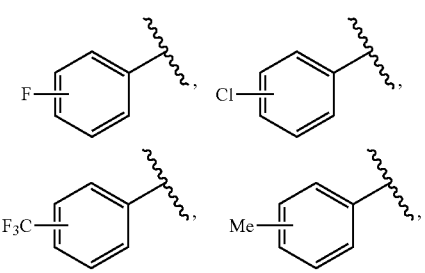

-continued

[Structures shown: NC-phenyl, pyrimidine, pyrazine, pyridazine, F-pyridine, Cl-pyridine, F₃C-pyridine, MeO-pyridine, Me-pyridine, NC-pyridine, furan, thiophene, oxazole, thiazole, isoxazole, isothiazole, pyrrole, pyrazole, and imidazole]

In some embodiments of Formula IIa, IId, IIe, and/or IIf, $R^{5a}$ is 1 substituent and is F.

In some embodiments of Formula IIa, IId, IIe, and/or IIf, $R^{5a}$ is 2 substituents and are both F.

In some embodiments of Formula IIa, IIe, and/or IIf, $R^{5a}$ is 1 substituent and is Me.

In some embodiments of Formula IIa, IIe, and/or IIf, $R^{5a}$ is 2 substituents and are both Me.

In some embodiments of Formula IIa, IId, Ie, and/or IIf, $R^{5a}$ is 1 substituent and is $CF_3$.

In some embodiments of Formula IIa, IId, IIe, and/or IIf, $R^{5a}$ is 2 substituents and are both $CF_3$.

In some embodiments of Formula IIa, IIe, and/or IIf, $R^{5a}$ is 2 substituents and are F and Me.

In some embodiments of Formula IIa, IId, IIe, and/or IIf, $R^{5a}$ is 2 substituents and are F and $CF_3$.

In some embodiments of Formula IIa, IIc, IId, IIe, and/or IIf, $R^{5a}$ is 1 substituent and is CN.

In some embodiments of Formula IIa, IIc, IId, IIe, and/or IIf, $R^{5a}$ is 2 substituents and are both CN.

In some embodiments of Formula IIa, IId, IIe, and/or IIf, $R^{5a}$ is 2 substituents and are F and CN.

In some embodiments of Formula IIa, IIe, and/or IIf, $R^{5a}$ is $—C_{1-2}$ alkyl.

In some embodiments of Formula IIa, IIe, and/or IIf, $R^{5a}$ is $—C_{1-3}$ alkyl.

In some embodiments of Formula IIa, IIe, and/or IIf, $R^{5a}$ is $—C_{1-4}$ alkyl.

In some embodiments of Formula IIa, IIe, and/or IIf, $R^{5a}$ is $—C_{1-5}$ alkyl.

In some embodiments of Formula IIa, IIe, and/or IIf, $R^{5a}$ is $—C_{1-6}$ alkyl.

In some embodiments of Formula IIa, IId, IIe, and/or IIf, $R^{5a}$ is $—C_{2-6}$ alkyl.

In some embodiments of Formula IIa, IId, IIe, and/or IIf, $R^{5a}$ is $—C_{3-6}$ alkyl.

In some embodiments of Formula IIa, IId, IIe, and/or IIf, $R^{5a}$ is $—C_{4-6}$ alkyl.

In some embodiments of Formula IIa, IId, IIe, and/or IIf, $R^{5a}$ is $—C_{2-5}$ alkyl.

In some embodiments of Formula IIa, IId, IIe, and/or IIf, $R^{5a}$ is $—C_{3-5}$ alkyl.

In some embodiments of Formula IIa, IIc, IId, IIe, and/or IIf, $R^{5b}$ is 1 substituent and is F.

In some embodiments of Formula IIa, IIc, IId, IIe, and/or IIf, $R^{5b}$ is 2 substituents and both are F.

In some embodiments of Formula IIa, IIc, IId, IIe, and/or IIf, $R^{5b}$ is 1 substituent and is Me.

In some embodiments of Formula IIa, IIc, IId, IIe, and/or IIf, $R^{5b}$ is 2 substituents and both are Me.

In some embodiments of Formula IIa, IId, IIe, and/or IIf, $R^{5b}$ is 1 substituent and is $CF_3$.

In some embodiments of Formula IIa, IId, IIe, and/or IIf, $R^{5b}$ is 2 substituents and both are $CF_3$.

In some embodiments of Formula IIa, IIc, IId, IIe, and/or IIf, $R^{5b}$ is 2 substituents and are F and Me.

In some embodiments of Formula IIa, IId, IIe, and/or IIf, $R^{5b}$ is 2 substituents and are F and $CF_3$.

In some embodiments of Formula IIa, IIc, IId, IIe, and/or IIf, $R^{5b}$ is 1 substituent and is CN.

In some embodiments of Formula IIa, IIc, IId, IIe, and/or IIf, $R^{5b}$ is 2 substituents and both are CN.

In some embodiments of Formula IIa, IIc, IId, IIe, and/or IIf, $R^{5b}$ is 2 substituents and are F and CN.

In some embodiments of Formula IIa, IIc, IId, IIe, and/or IIf, $R^{5b}$ is $—C_{1-2}$ alkyl.

In some embodiments of Formula IIa, IIc, IId, IIe, and/or IIf, $R^{5b}$ is $—C_{1-3}$ alkyl.

In some embodiments of Formula IIa, IIc, IId, IIe, and/or IIf, $R^{5b}$ is $—C_{1-4}$ alkyl.

In some embodiments of Formula IIa, IIc, IId, IIe, and/or IIf, $R^{5b}$ is $—C_{1-5}$ alkyl.

In some embodiments of Formula IIa, IIc, IId, IIe, and/or IIf, $R^{5b}$ is $—C_{1-6}$ alkyl.

In some embodiments of Formula IIa, IIc, IId, IIe, and/or IIf, $R^{5b}$ is $—C_{2-6}$ alkyl.

In some embodiments of Formula IIa, IIc, IId, IIe, and/or IIf, $R^{5b}$ is $—C_{3-6}$ alkyl.

In some embodiments of Formula IIa, IIc, IId, IIe, and/or IIf, $R^{5b}$ is $—C_{4-6}$ alkyl.

In some embodiments of Formula IIa, IIc, IId, IIe, and/or IIf, $R^{5b}$ is $—C_{2-5}$ alkyl.

In some embodiments of Formula IIa, IIc, IId, IIe, and/or IIf, $R^{5b}$ is $—C_{3-5}$ alkyl.

In some embodiments of Formula IIa and/or IIb, $R^{5c}$ is H.

In some embodiments of Formula IIa, IId, and/or IIe, $R^{5c}$ is a halide.

In some embodiments of Formula IIa, IIc, IId, and/or IIe, $R^{5c}$ is F.

In some embodiments of Formula IIa, IId, and/or IIe, $R^{5c}$ is Cl.

In some embodiments of Formula IIa and/or IIc, $R^{5c}$ is Me.

In some embodiments of Formula IIa, IId, and/or IIe, $R^{5c}$ is OH.

In some embodiments of Formula IIa, IId, and/or IIe, $R^{5c}$ is OMe.

In some embodiments of Formula IIa, IIc, IId, and/or IIe, $R^{5c}$ is $CF_3$.

In some embodiments of Formula IIa, IIc, IId, and/or IIe, $R^{5c}$ is CN.

In some embodiments of Formula IIa, IIc, IId, and/or IIe, $R^{5c}$ is 1 substituent and is F.

In some embodiments of Formula IIa, IIc, IId, and/or IIe, $R^{5c}$ is 2 substituents and are both F.

In some embodiments of Formula IIa and/or IIc, $R^{5c}$ is 1 substituent and is Me.

In some embodiments of Formula IIa and/or IIc, $R^{5c}$ is 2 substituents and are both Me.

In some embodiments of Formula IIa, IIc, IId, and/or IIe, $R^{5c}$ is 1 substituent and is $CF_3$.

In some embodiments of Formula IIa, IIc, IId, and/or IIe, $R^{5c}$ is 2 substituents and both are $CF_3$.

In some embodiments of Formula IIa, IId, and/or IIe, $R^{5c}$ is 1 substituent and is OMe.

In some embodiments of Formula IIa, IId, and/or IIe, $R^{5c}$ is 2 substituents and both are OMe.

In some embodiments of Formula IIa and/or IIc, $R^{5c}$ is 2 substituents and are F and Me.

In some embodiments of Formula IIa, IIc, IId, and/or IIe, $R^{5c}$ is 2 substituents and are F and $CF_3$.

In some embodiments of Formula IIa, IId, and/or IIe, $R^{5c}$ is 2 substituents and are F and OMe.

In some embodiments of Formula IIa, IIc, IId, and/or IIe, $R^{5c}$ is 1 substituent and is CN.

In some embodiments of Formula IIa, IIc, IId, and/or IIe, $R^{5c}$ is 2 substituents and both are CN.

In some embodiments of Formula IIa, IIc, IId, and/or IIe, $R^{5c}$ is 2 substituents and are F and CN.

In some embodiments of Formula IIa and/or IIc, $R^{5c}$ is —$C_{1-2}$ alkyl.

In some embodiments of Formula IIa and/or IIc, $R^{5c}$ is —$C_{1-3}$ alkyl.

In some embodiments of Formula IIa and/or IIc, $R^{5c}$ is —$C_{1-4}$ alkyl.

In some embodiments of Formula IIa and/or IIc, $R^{5c}$ is —$C_{1-5}$ alkyl.

In some embodiments of Formula IIa and/or IIc, $R^{5c}$ is —$C_{1-6}$ alkyl.

In some embodiments of Formula IIa, IIc, IId, and/or IIe, $R^{5c}$ is —$C_{2-6}$ alkyl.

In some embodiments of Formula IIa, IIc, IId, and/or IIe, $R^{5c}$ is —$C_{3-6}$ alkyl.

In some embodiments of Formula IIa, IIc, IId, and/or IIe, $R^{5c}$ is —$C_{4-6}$ alkyl.

In some embodiments of Formula IIa, IIc, IId, and/or IIe, $R^{5c}$ is —$C_{2-5}$ alkyl.

In some embodiments of Formula IIa, IIc, IId, and/or IIe, $R^{5c}$ is —$C_{3-5}$ alkyl.

In some embodiments of Formula IIa, IIc, IId, and/or IIe, $R^{5d}$ is a halide.

In some embodiments of Formula IIa, IIc, IId, and/or IIe, $R^{5d}$ is F.

In some embodiments of Formula IIa, IIc, IId, and/or IIe, $R^{5d}$ is Cl.

In some embodiments of Formula IIa, IIc, and/or IId, $R^{5d}$ is Me.

In some embodiments of Formula IIa, and/or IId, $R^{5d}$ is OH.

In some embodiments of Formula IIa, and/or IId, $R^{5d}$ is OMe.

In some embodiments of Formula IIa, IIc, IId, and/or IIe, $R^{5d}$ is $CF_3$.

In some embodiments of Formula IIa, IIc, IId, and/or IIe, $R^{5d}$ is CN.

In some embodiments of Formula IIa, IIc, IId, and/or IIe, $R^{5d}$ is 1 substituent and is F.

In some embodiments of Formula IIa, IIc, IId, and/or IIe, $R^{5d}$ is 2 substituents and both are F.

In some embodiments of Formula IIa, IIc, and/or IId, $R^{5d}$ is 1 substituent and is Me.

In some embodiments of Formula IIa, IIc, and/or IId, $R^{5d}$ is 2 substituents and both are Me.

In some embodiments of Formula IIa, IIc, IId, and/or IIe, $R^{5d}$ is 1 substituent and is $CF_3$.

In some embodiments of Formula IIa, IIc, IId, and/or IIe, $R^{5d}$ is 2 substituents and both are $CF_3$.

In some embodiments of Formula IIa and/or IId, $R^{5d}$ is 1 substituent and is OMe.

In some embodiments of Formula IIa and/or IId, $R^{5d}$ is 2 substituents and are both OMe.

In some embodiments of Formula IIa, IIc, and/or IId, $R^{5d}$ is 2 substituents and are F and Me.

In some embodiments of Formula IIa, IIc, IId, and/or IIe, $R^{5d}$ is 2 substituents and are F and $CF_3$.

In some embodiments of Formula IIa and/or IId, $R^{5d}$ is 2 substituents and are F and OMe.

In some embodiments of Formula IIa, IIc, IId, and/or IIe, $R^{5d}$ is 1 substituent and is CN.

In some embodiments of Formula IIa, IIc, IId, and/or IIe, $R^{5d}$ is 2 substituents and both are CN.

In some embodiments of Formula IIa, IIc, IId, and/or IIe, $R^{5d}$ is 2 substituents and are F and CN.

In some embodiments of Formula IIa, IIc, and/or IId, $R^{5d}$ is —$C_{1-2}$ alkyl.

In some embodiments of Formula IIa, IIc, and/or IId, $R^{5d}$ is —$C_{1-3}$ alkyl.

In some embodiments of Formula IIa, IIc, and/or IId, $R^{5d}$ is —$C_{1-4}$ alkyl.

In some embodiments of Formula IIa, IIc, and/or IId, $R^{5d}$ is —$C_{1-5}$ alkyl.

In some embodiments of Formula IIa, IIc, and/or IId, $R^{5d}$ is —$C_{1-6}$ alkyl.

In some embodiments of Formula IIa, IIc, IId, and/or IIe, $R^{5d}$ is —$C_{2-6}$ alkyl.

In some embodiments of Formula IIa, IIc, IId, and/or IIe, $R^{5d}$ is —$C_{3-6}$ alkyl.

In some embodiments of Formula IIa, IIc, IId, and/or IIe, $R^{5d}$ is —$C_{4-6}$ alkyl.

In some embodiments of Formula IIa, IIc, IId, and/or IIe, $R^{5d}$ is —$C_{2-5}$ alkyl.

In some embodiments of Formula IIa, IIc, IId, and/or IIe, $R^{5d}$ is —$C_{3-5}$ alkyl.

In some embodiments of Formula IIa and/or IId, $R^{5e}$ is H.

In some embodiments of Formula IIa and/or IId, $R^{5e}$ is a halide.

In some embodiments of Formula IIa, IIc, and/or IId, $R^{5e}$ is F.

In some embodiments of Formula IIa and/or IId, $R^{5e}$ is Cl.

In some embodiments of Formula IIa and/or IId, $R^{5e}$ is Me.

In some embodiments of Formula IIa, IIc, and/or IId, $R^{5e}$ is OH.

In some embodiments of Formula IIa, IIc, and/or IId, $R^{5e}$ is OMe.

In some embodiments of Formula IIa and/or IId, $R^{5e}$ is $CF_3$.

In some embodiments of Formula IIa, IIc, and/or IId, $R^{5e}$ is CN.

In some embodiments of Formula IIa, IIc, and/or IId, $R^{5e}$ is 1 substituent and is F.

In some embodiments of Formula IIa, IIc, and/or IId, $R^{5e}$ is 2 substituents and are both F.

In some embodiments of Formula IIa and/or IId, $R^{5e}$ is 1 substituent and is Me.

In some embodiments of Formula IIa and/or IId, $R^{5e}$ is 2 substituents and are both Me.

In some embodiments of Formula IIa and/or IId, $R^{5e}$ is 1 substituent and is $CF_3$.

In some embodiments of Formula IIa and/or IId, $R^{5e}$ is 2 substituents and are both $CF_3$.

In some embodiments of Formula IIa, IIc, and/or IId, $R^{5e}$ is 1 substituent and is OMe.

In some embodiments of Formula IIa, IIc, and/or IId, $R^{5e}$ is 2 substituents and are both OMe.

In some embodiments of Formula IIa, IIc, and/or IId, $R^{5e}$ is 2 substituents and are F and Me.

In some embodiments of Formula IIa, IIc, and/or IId, $R^{5e}$ is 2 substituents and are F and $CF_3$.

In some embodiments of Formula IIa, IIc, and/or IId, $R^{5e}$ is 2 substituents and are F and OMe.

In some embodiments of Formula IIa, IIc, and/or IId, $R^{5e}$ is 1 substituent and is CN.

In some embodiments of Formula IIa, IIc, and/or IId, $R^{5e}$ is 2 substituents and are both CN.

In some embodiments of Formula IIa, IIc, and/or IId, $R^{5e}$ is 2 substituents and are F and CN.

In some embodiments of Formula IIa and/or IId, $R^{5e}$ is —$C_{1-2}$ alkyl.

In some embodiments of Formula IIa and/or IId, $R^{5e}$ is —$C_{1-3}$ alkyl.

In some embodiments of Formula IIa and/or IId, $R^{5e}$ is —$C_{1-4}$ alkyl.

In some embodiments of Formula IIa and/or IId, $R^{5e}$ is —$C_{1-5}$ alkyl.

In some embodiments of Formula IIa and/or IId, $R^{5e}$ is —$C_{1-6}$ alkyl.

In some embodiments of Formula IIa and/or IId, $R^{5e}$ is —$C_{2-6}$ alkyl.

In some embodiments of Formula IIa, IIc, IId, and/or IIe, $R^{5e}$ is —$C_{3-6}$ alkyl.

In some embodiments of Formula IIa and/or IId, $R^{5e}$ is —$C_{4-6}$ alkyl.

In some embodiments of Formula IIa, IIc, and/or IId, $R^{5e}$ is —$C_{2-5}$ alkyl.

In some embodiments of Formula IIa, IIc, and/or IId, $R^{5e}$ is —$C_{3-5}$ alkyl.

Some additional embodiments of Formula II include compounds of Formula (IIb):

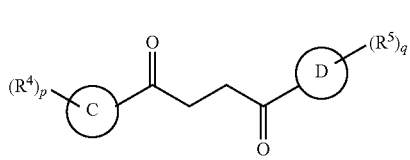

or salts, pharmaceutically acceptable salts, or prodrugs thereof.

In some embodiments of Formula IIb, Ring C is

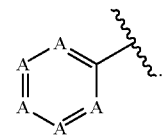

In some embodiments of Formula IIb, Ring D is selected from the group consisting of phenyl and a 5-6 membered heteroaryl, wherein a carbon atom on the ring is attached to the carbonyl carbon.

In some embodiments of Formula IIb, each $R^4$ is a substituent attached to Ring C and is independently selected at each occurrence from the group consisting of H, unsubstituted —$C_{1-6}$ alkyl, —$C_{1-3}$ haloalkyl, halide, —$OR^{6a}$, $CF_3$, and CN.

In some embodiments of Formula IIb, each $R^5$ is a substituent attached to Ring D and is independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIb, each $R^6$ is independently selected from the group consisting of H, unsubstituted —$C_{1-6}$ alkyl, —$C_{1-3}$ haloalkyl, and $CF_3$.

In some embodiments of Formula IIb, each $R^{6a}$ is independently selected from the group consisting of unsubstituted —$C_{1-6}$ alkyl, —$C_{1-3}$ haloalkyl, and $CF_3$.

In some embodiments of Formula IIb, each $R^{6b}$ is independently selected from the group consisting of H and unsubstituted —$C_{1-3}$ alkyl.

In some embodiments of Formula IIb, each A is N or C.

In some embodiments of Formula IIb, at least two A must be N.

In some embodiments of Formula IIb, p is an integer of 1 to 3.

In some embodiments of Formula IIb, q is an integer of 1 to 5.

In some embodiments of Formula IIb, Ring C is selected from the group consisting of

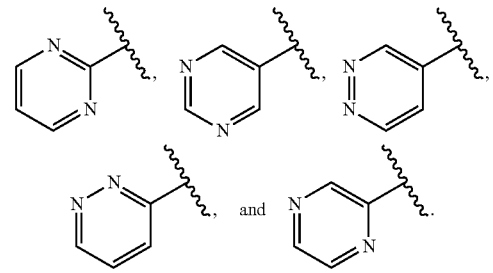

Some additional embodiments of Formula II include compounds of Formula (IIc):

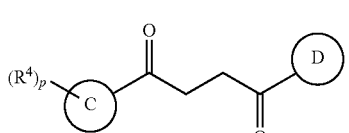

or salts, pharmaceutically acceptable salts, or prodrugs thereof.

In some embodiments of Formula IIc, Ring C is

In some embodiments of Formula IIc, Ring D is selected from the group consisting of

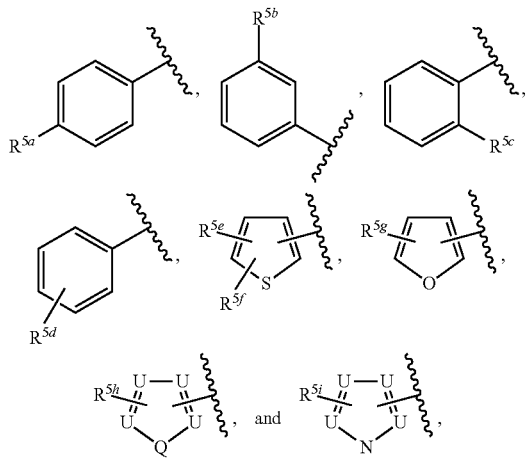

wherein a carbon atom on the ring is attached to the carbonyl carbon.

In some embodiments of Formula IIc, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula IIc, $R^{5a}$ is a substituent attached to the para position of phenyl and is selected from the group consisting of unsubstituted —$C_2$-6 alkyl, —$CH_2OH$, —$CH_2N(R^{6b})_2$, —$C_{2-3}$ haloalkyl, iodide, —$OR^{6a}$, and CN.

In some embodiments of Formula IIc, $R^{5b}$ is a substituent attached to the meta position of phenyl and is selected from the group consisting of unsubstituted —$C_{1-6}$ alkyl, —$CH_2OH$, —$CH_2N(R^{6b})_2$, —$C_{2-3}$ haloalkyl, halide, —$OR^{6a}$, and CN.

In some embodiments of Formula IIc, $R^{5c}$ is a substituent attached to the ortho position of phenyl and is selected from the group consisting of unsubstituted —$C_{1-6}$ alkyl, —$CH_2OH$, —$CH_2N(R^{6b})_2$, —$C_{1-3}$ haloalkyl, F, Br, I, —$OR^{6a}$, $CF_3$, and CN.

In some embodiments of Formula IIc, $R^{5d}$ is 2-5 substituents, each attached to the phenyl and are independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^{6a}$, $CF_3$, and CN.

In some embodiments of Formula IIc, $R^{5e}$ is 1 substituent attached to Ring D and selected from the group consisting of unsubstituted —$C_{2-5}$ alkyl, —$CH_2OH$, —$CH_2N(R^{6b})_2$, —$C_{1-3}$ haloalkyl, F, I, —$OR^6$, $CF_3$, and CN.

In some embodiments of Formula IIc, $R^{5f}$ is 1-2 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, F, Br, I, —$OR^6$, $CF_3$, and CN.

In some embodiments of Formula IIc, $R^{5g}$ is 1-3 substituents, each attached to Ring D and are independently selected at each occurrence from the group consisting of unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIc, $R^{5h}$ is 1-2 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIc, $R^{5i}$ is 1-4 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIc, each $R^6$ is independently selected from the group consisting of H, unsubstituted —$C_{1-6}$ alkyl, —$C_{1-3}$ haloalkyl, and $CF_3$.

In some embodiments of Formula IIc, each $R^{6a}$ is independently selected from the group consisting of unsubstituted —$C_{2-6}$ alkyl, —$C_{1-3}$ haloalkyl, and $CF_3$.

In some embodiments of Formula IIc, each $R^{6b}$ is independently selected from the group consisting of H and unsubstituted —$C_{1-3}$ alkyl.

In some embodiments of Formula IIc, each J is N or C.

In some embodiments of Formula IIc, at least one J must be C.

In some embodiments of Formula IIc, Q is S or O.

In some embodiments of Formula IIc, each U is N or C.

In some embodiments of Formula IIc, at least one U must be N and at least one U must be C.

In some embodiments of Formula IIc, p is an integer of 1 to 3.

In some embodiments of Formula IIc, Ring D is selected from the group consisting of

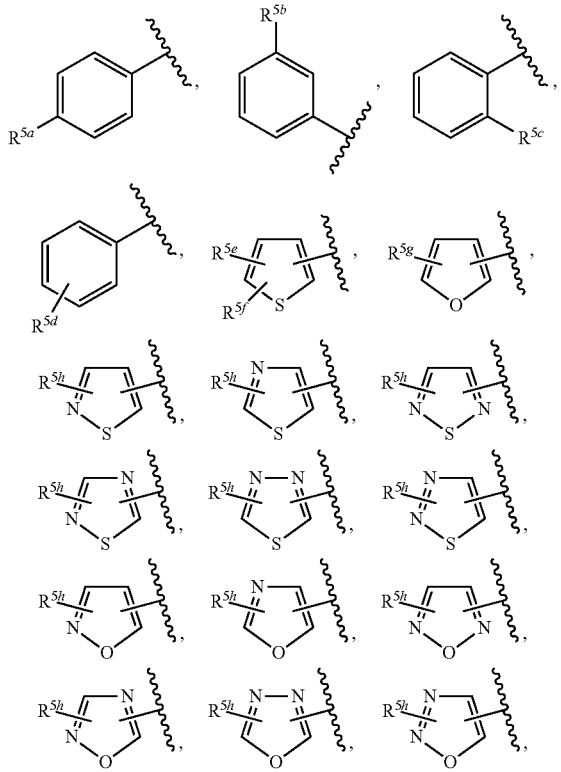

[Structures showing pyrazole/triazole rings with $R^{5i}$ substituents], and wherein a carbon atom on the ring is attached to the carbonyl carbon.

In some embodiments of Formula IIc, $R^{5f}$ is H.
In some embodiments of Formula IIc, $R^{5f}$ is a halide.
In some embodiments of Formula IIc, $R^{5f}$ is F.
In some embodiments of Formula IIc, $R^{5f}$ is Cl.
In some embodiments of Formula IIc, $R^{5f}$ is Me.
In some embodiments of Formula IIc, $R^{5f}$ is OH.
In some embodiments of Formula IIc, $R^{5f}$ is OMe.
In some embodiments of Formula IIc, $R^{5f}$ is $CF_3$.
In some embodiments of Formula IIc, $R^{5f}$ is CN.
In some embodiments of Formula IIc, $R^{5f}$ is 1 substituent and is F.
In some embodiments of Formula IIc, $R^{5f}$ is 2 substituents and are both F.
In some embodiments of Formula IIc, $R^{5f}$ is 1 substituent and is Me.
In some embodiments of Formula IIc, $R^{5f}$ is 2 substituents and are both Me.
In some embodiments of Formula IIc, $R^{5f}$ is 1 substituent and is $CF_3$.
In some embodiments of Formula IIc, $R^{5f}$ is 2 substituents and are both $CF_3$.
In some embodiments of Formula IIc, $R^{5f}$ is 1 substituent and is OMe.
In some embodiments of Formula IIc, $R^{5f}$ is 2 substituents and are both OMe.
In some embodiments of Formula IIc, $R^{5f}$ is 2 substituents and are F and Me.
In some embodiments of Formula IIc, $R^{5f}$ is 2 substituents and are F and $CF_3$.
In some embodiments of Formula IIc, $R^{5f}$ is 2 substituents and are F and OMe.
In some embodiments of Formula IIc, $R^{5f}$ is 1 substituent and is CN.
In some embodiments of Formula IIc, $R^{5f}$ is 2 substituents and are both CN.
In some embodiments of Formula IIc, $R^{5f}$ is 2 substituents and are F and CN.
In some embodiments of Formula IIc, $R^{5f}$ is —$C_{1-2}$ alkyl.
In some embodiments of Formula IIc, $R^{5f}$ is —$C_{1-3}$ alkyl.
In some embodiments of Formula IIc, $R^{5f}$ is —$C_{1-4}$ alkyl.
In some embodiments of Formula IIc, $R^{5f}$ is —$C_{1-5}$ alkyl.
In some embodiments of Formula IIc, $R^{5f}$ is —$C_{1-6}$ alkyl.
In some embodiments of Formula IIc, $R^{5f}$ is —$C_{2-6}$ alkyl.
In some embodiments of Formula IIc, $R^{5f}$ is —$C_{3-6}$ alkyl.
In some embodiments of Formula IIc, $R^{5f}$ is —$C_{4-6}$ alkyl.
In some embodiments of Formula IIc, $R^{5f}$ is —$C_{2-5}$ alkyl.
In some embodiments of Formula IIc, $R^{5f}$ is —$C_{3-5}$ alkyl.
In some embodiments of Formula IIc, $R^{5g}$ is a halide.
In some embodiments of Formula IIc, $R^{5g}$ is F.
In some embodiments of Formula IIc, $R^{5g}$ is Cl.
In some embodiments of Formula IIc, $R^{5g}$ is Me.
In some embodiments of Formula IIc, $R^{5g}$ is OH.
In some embodiments of Formula IIc, $R^{5g}$ is OMe.
In some embodiments of Formula IIc, $R^{5g}$ is $CF_3$.
In some embodiments of Formula IIc, $R^{5g}$ is CN.

In some embodiments of Formula IIc, $R^{5g}$ is 1 substituent and is F.
In some embodiments of Formula IIc, $R^{5g}$ is 2 substituents and are both F.
In some embodiments of Formula IIc, $R^{5g}$ is 1 substituent and is Me.
In some embodiments of Formula IIc, $R^{5g}$ is 2 substituents and are both Me.
In some embodiments of Formula IIc, $R^{5g}$ is 1 substituent and is $CF_3$.
In some embodiments of Formula IIc, $R^{5g}$ is 2 substituents and are both $CF_3$.
In some embodiments of Formula IIc, $R^{5g}$ is 1 substituent and is OMe.
In some embodiments of Formula IIc, $R^{5g}$ is 2 substituents and are both OMe.
In some embodiments of Formula IIc, $R^{5g}$ is 2 substituents and are F and Me.
In some embodiments of Formula IIc, $R^{5g}$ is 2 substituents and are F and $CF_3$.
In some embodiments of Formula IIc, $R^{5g}$ is 2 substituents and are F and OMe.
In some embodiments of Formula IIc, $R^{5g}$ is 1 substituent and is CN.
In some embodiments of Formula IIc, $R^{5g}$ is 2 substituents and are both CN.
In some embodiments of Formula IIc, $R^{5g}$ is 2 substituents and are F and CN.
In some embodiments of Formula IIc, $R^{5g}$ is —$C_{1-2}$ alkyl.
In some embodiments of Formula IIc, $R^{5g}$ is —$C_{1-3}$ alkyl.
In some embodiments of Formula IIc, $R^{5g}$ is —$C_{1-4}$ alkyl.
In some embodiments of Formula IIc, $R^{5g}$ is —$C_{1-5}$ alkyl.
In some embodiments of Formula IIc, $R^{5g}$ is —$C_{1-6}$ alkyl.
In some embodiments of Formula IIc, $R^{5g}$ is —$C_{2-6}$ alkyl.
In some embodiments of Formula IIc, $R^{5g}$ is —$C_{3-6}$ alkyl.
In some embodiments of Formula IIc, $R^{5g}$ is —$C_{4-6}$ alkyl.
In some embodiments of Formula IIc, $R^{5g}$ is —$C_{2-5}$ alkyl.
In some embodiments of Formula IIc, $R^{5g}$ is —$C_{3-5}$ alkyl.
In some embodiments of Formula IIc, $R^{5i}$ is H.
In some embodiments of Formula IIc, $R^{5i}$ is a halide.
In some embodiments of Formula IIc, $R^{5i}$ is F.
In some embodiments of Formula IIc, $R^{5i}$ is Cl.
In some embodiments of Formula IIc, $R^{5i}$ is Me.
In some embodiments of Formula IIc, $R^{5i}$ is OH.
In some embodiments of Formula IIc, $R^{5i}$ is OMe.
In some embodiments of Formula IIc, $R^{5i}$ is $CF_3$.
In some embodiments of Formula IIc, $R^{5i}$ is CN.
In some embodiments of Formula IIc, $R^{5i}$ is 1 substituent and is F.
In some embodiments of Formula IIc, $R^{5i}$ is 2 substituents and are both F.
In some embodiments of Formula IIc, $R^{5i}$ is 1 substituent and is Me.
In some embodiments of Formula IIc, $R^{5i}$ is 2 substituents and are both Me.
In some embodiments of Formula IIc, $R^{5i}$ is 1 substituent and is $CF_3$.
In some embodiments of Formula IIc, $R^{5i}$ is 2 substituents and are both $CF_3$.
In some embodiments of Formula IIc, $R^{5i}$ is 1 substituent and is OMe.
In some embodiments of Formula IIc, $R^{5i}$ is 2 substituents and are both OMe.
In some embodiments of Formula IIc, $R^{5i}$ is 2 substituents and are F and Me.

In some embodiments of Formula IIc, $R^{5i}$ is 2 substituents and are F and $CF_3$.

In some embodiments of Formula IIc, $R^{5i}$ is 2 substituents and are F and OMe.

In some embodiments of Formula IIc, $R^{5i}$ is 1 substituent and is CN.

In some embodiments of Formula IIc, $R^{5i}$ is 2 substituents and are both CN.

In some embodiments of Formula IIc, $R^{5i}$ is 2 substituents and are F and CN.

In some embodiments of Formula IIc, $R^{5i}$ is —$C_{1-2}$ alkyl.
In some embodiments of Formula IIc, $R^{5i}$ is —$C_{1-3}$ alkyl.
In some embodiments of Formula IIc, $R^{5i}$ is —$C_{1-4}$ alkyl.
In some embodiments of Formula IIc, $R^{5i}$ is —$C_{1-5}$ alkyl.
In some embodiments of Formula IIc, $R^{5i}$ is —$C_{1-6}$ alkyl.
In some embodiments of Formula IIc, $R^{5i}$ is —$C_{2-6}$ alkyl.
In some embodiments of Formula IIc, $R^{5i}$ is —$C_{3-6}$ alkyl.
In some embodiments of Formula IIc, $R^{5i}$ is —$C_{4-6}$ alkyl.
In some embodiments of Formula IIc, $R^{5i}$ is —$C_{2-5}$ alkyl.
In some embodiments of Formula IIc, $R^{5i}$ is —$C_{3-5}$ alkyl.

Some additional embodiments of Formula II include compounds of Formula (IId):

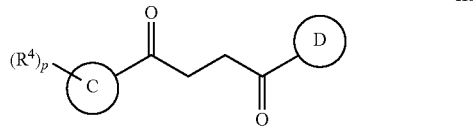

IId or salts, pharmaceutically acceptable salts, or prodrugs thereof.

In some embodiments of Formula IId, Ring C is

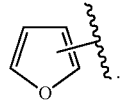

In some embodiments of Formula IId, Ring D is selected from the group consisting of

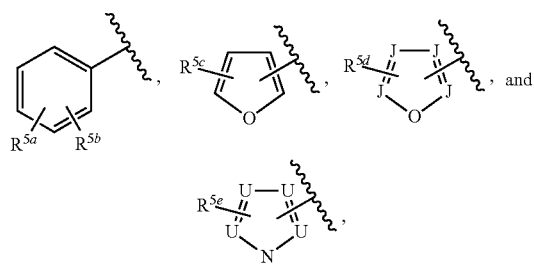

and wherein a carbon atom on the ring is attached to the carbonyl carbon.

In some embodiments of Formula IId, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula IId, $R^{5a}$ is 1 substituent attached to Ring D and selected from the group consisting of unsubstituted —$C_{2-6}$ alkyl, —$CH_2OH$, —$CH_2N(R^{6b})_2$, —$C_{1-3}$ haloalkyl, halide, —$OR^{6a}$, and CN.

In some embodiments of Formula IId, $R^{5b}$ is 1-4 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^{6a}$, $CF_3$, and CN.

In some embodiments of Formula IId, $R^{5c}$ is 1-3 substituents, each attached to Ring D and are independently selected at each occurrence from the group consisting of unsubstituted —$C_{2-5}$ alkyl, —$CH_2OH$, —$CH_2N(R^{6b})_2$, —$C_{1-3}$ haloalkyl, halide, —$OR^6$, $CF_3$, and CN.

In some embodiments of Formula IId, $R^{5d}$ is 1-2 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IId, $R^{5e}$ is 1-4 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IId, each $R^6$ is independently selected from the group consisting of H, unsubstituted —$C_{1-6}$ alkyl, —$C_{1-3}$ haloalkyl, and $CF_3$.

In some embodiments of Formula IId, each $R^{6a}$ is independently selected from the group consisting of unsubstituted —$C_{2-6}$ alkyl, —$C_{1-3}$ haloalkyl, and $CF_3$.

In some embodiments of Formula IId, each $R^{6b}$ is independently selected from the group consisting of H and unsubstituted —$C_{1-3}$ alkyl.

In some embodiments of Formula IId, each J is N or C.

In some embodiments of Formula IId, at least one J must be N and at least one J must be C.

In some embodiments of Formula IId, Q is S or O.

In some embodiments of Formula IId, each U is N or C.

In some embodiments of Formula IId, at least one U must be C.

In some embodiments of Formula IId, p is an integer of 1 to 3.

In some embodiments of Formula IId, Ring D is selected from the group consisting of

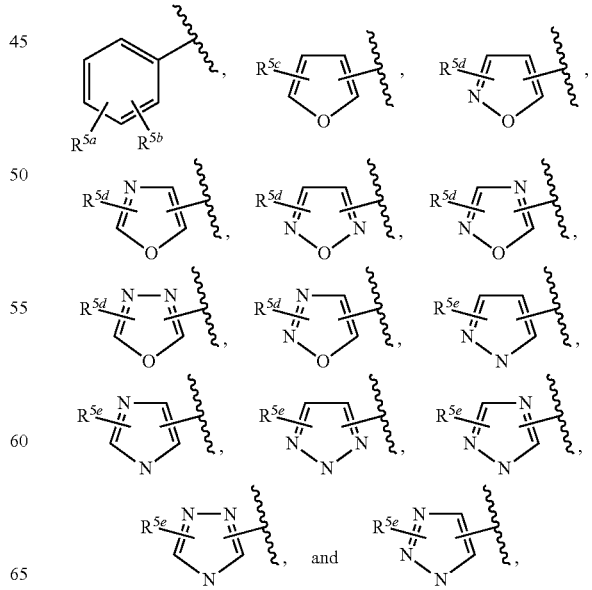

and wherein a carbon atom on the ring is attached to the carbonyl carbon.

In some embodiments of Formula IId, $R^{5b}$ is H.

In some embodiments of Formula IId and/or IIe, $R^{5d}$ is H.

Some additional embodiments of Formula II include compounds of Formula (IIe):

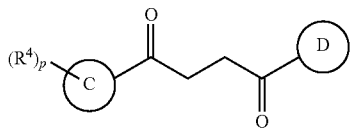

or salts, pharmaceutically acceptable salts, or prodrugs thereof.

In some embodiments of Formula IIe, Ring C is

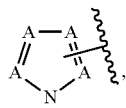

wherein a carbon atom on the ring is attached to the carbonyl carbon.

In some embodiments of Formula IIe, Ring D is selected from the group consisting of

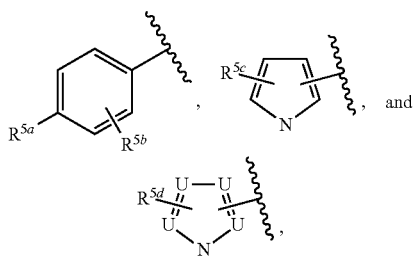

wherein a carbon atom on the ring is attached to the carbonyl carbon.

In some embodiments of Formula IIe, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula IIe, $R^{5a}$ is a substituent attached to the para position of phenyl and is selected from the group consisting of H, unsubstituted —$C_{1-6}$ alkyl, —$CH_2OH$, —$CH_2N(R^{6b})_2$, —$C_{1-3}$ haloalkyl, F, Br, I, —$OR^6$, $CF_3$, and CN.

In some embodiments of Formula IIe, $R^{5b}$ is 1-4 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIe, $R^{5c}$ is 1-4 substituents, each attached to Ring D and are independently selected at each occurrence from the group consisting of unsubstituted —$C_{2-5}$ alkyl, —$CH_2OH$, —$CH_2N(R^{6b})_2$, —$C_{1-3}$ haloalkyl, halide, —$OR^6$, $CF_3$, and CN.

In some embodiments of Formula IIe, $R^{5d}$ is 1-2 substituents, each attached to Ring D and are independently selected at each occurrence from the group consisting of H, unsubstituted —$C_{2-6}$ alkyl, —$CH_2OH$, —$CH_2N(R^{6b})_2$, —$C_{1-3}$ haloalkyl, halide, —$OR^{6a}$, $CF_3$, and CN.

In some embodiments of Formula IIe, each $R^6$ is independently selected from the group consisting of H, unsubstituted —$C_{1-6}$ alkyl, —$C_{1-3}$ haloalkyl, and $CF_3$.

In some embodiments of Formula IIe, each $R^{6a}$ is independently selected from the group consisting of unsubstituted —$C_{1-6}$ alkyl, —$C_{1-3}$ haloalkyl, and $CF_3$.

In some embodiments of Formula IIe, each $R^{6b}$ is independently selected from the group consisting of H and unsubstituted —$C_{1-3}$ alkyl.

In some embodiments of Formula IIe, each A is N or C.

In some embodiments of Formula IIe, at least one A must be C.

In some embodiments of Formula IIe, each U is N or C.

In some embodiments of Formula IIe, at least one U must be N and at least one U must be C.

In some embodiments of Formula IIe, p is an integer of 1 to 4.

In some embodiments of Formula IIe, Ring C is selected from the group consisting of

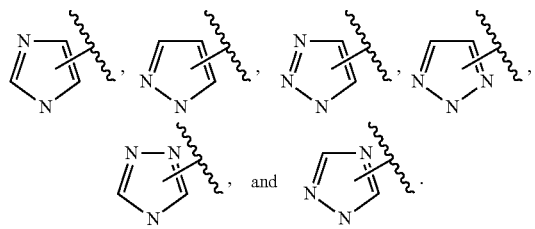

In some embodiments of Formula IIe, Ring D is selected from the group consisting of

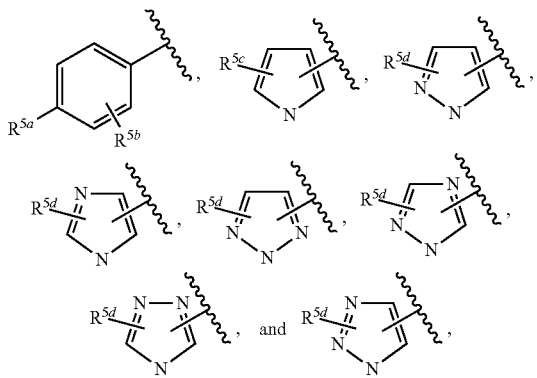

wherein a carbon atom on the ring is attached to the carbonyl carbon.

In some embodiments of Formula IIe, $R^{5a}$ is 1 substituent and is OMe.

In some embodiments of Formula IIe, $R^{5a}$ is 2 substituents and both are OMe.

In some embodiments of Formula IIe, $R^{5a}$ is 2 substituents and are F and OMe.

In some embodiments of Formula IIe and/or IIf, $R^{5b}$ is H.

In some embodiments of Formula IIe and/or IIf, $R^{5b}$ is 1 substituent and is OMe.

In some embodiments of Formula IIe and/or IIf, $R^{5b}$ is 2 substituents and both are OMe.

In some embodiments of Formula IIe and/or IIf, $R^{5b}$ is 2 substituents and are F and OMe.

Some additional embodiments of Formula II include compounds of Formula (IIf):

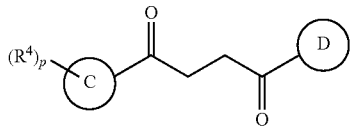

IIf or salts, pharmaceutically acceptable salts, or prodrugs thereof.

In some embodiments of Formula IIf, Ring C is

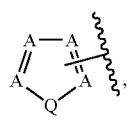

wherein a carbon atom on the ring is attached to the carbonyl carbon.

In some embodiments of Formula IIf, Ring D is selected from the group consisting of

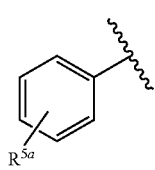

and a 5-membered heteroaryl $R^{5b}$, wherein a carbon atom on the ring is attached to the carbonyl carbon.

In some embodiments of Formula IIf, each $R^4$ is a substituent attached to Ring C and is independently selected at each occurrence from the group consisting of H, unsubstituted —$C_{1-6}$ alkyl, —$C_{1-3}$ haloalkyl, halide, —$OR^6$, $CF_3$, and CN.

In some embodiments of Formula IIf, $R^{5a}$ is 1-5 substituents, each attached to phenyl and selected from the group consisting of H, unsubstituted —$C_{1-6}$ alkyl, —$CH_2OH$, —$CH_2N(R^{6b})_2$, —$C_{1-3}$ haloalkyl, halide, —$OR^{6a}$, $CF_3$, and CN.

In some embodiments of Formula IIf, $R^{5b}$ is 1-4 substituents, each attached to Ring D and are independently selected at each occurrence from the group consisting of H, unsubstituted —$C_{1-6}$ alkyl, —$CH_2OH$, —$CH_2N(R^{6b})_2$, —$C_{1-3}$ haloalkyl, halide, —$OR^6$, $CF_3$, and CN.

In some embodiments of Formula IIf, each $R^6$ is independently selected from the group consisting of H, unsubstituted —$C_{1-6}$ alkyl, —$C_{1-3}$ haloalkyl, and $CF_3$.

In some embodiments of Formula IIf, each $R^{6a}$ is independently selected from the group consisting of unsubstituted —$C_{2-6}$ alkyl, —$C_{1-3}$ haloalkyl, and $CF_3$.

In some embodiments of Formula IIf, each $R^{6b}$ is independently selected from the group consisting of H and unsubstituted —$C_{1-3}$ alkyl.

In some embodiments of Formula IIf, each A is N or C.

In some embodiments of Formula IIf, at least one A must be N and at least one A must be C.

In some embodiments of Formula IIf, Q is S or O.

In some embodiments of Formula IIf, p is an integer of 1 to 4.

In some embodiments of Formula IIf, Ring C is selected from the group consisting of

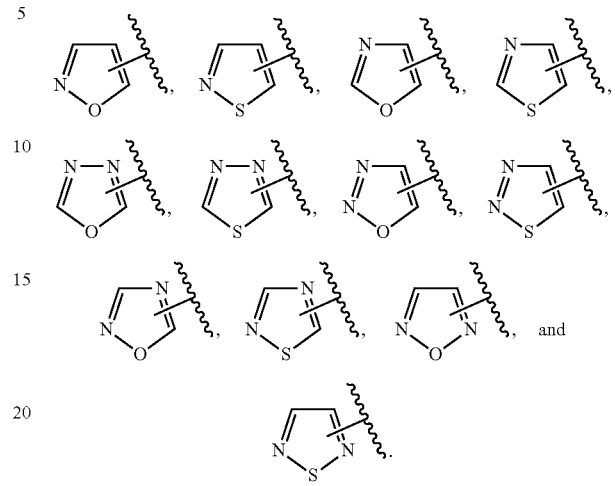

In some embodiments of Formula IIf, Ring D is selected from the group consisting of

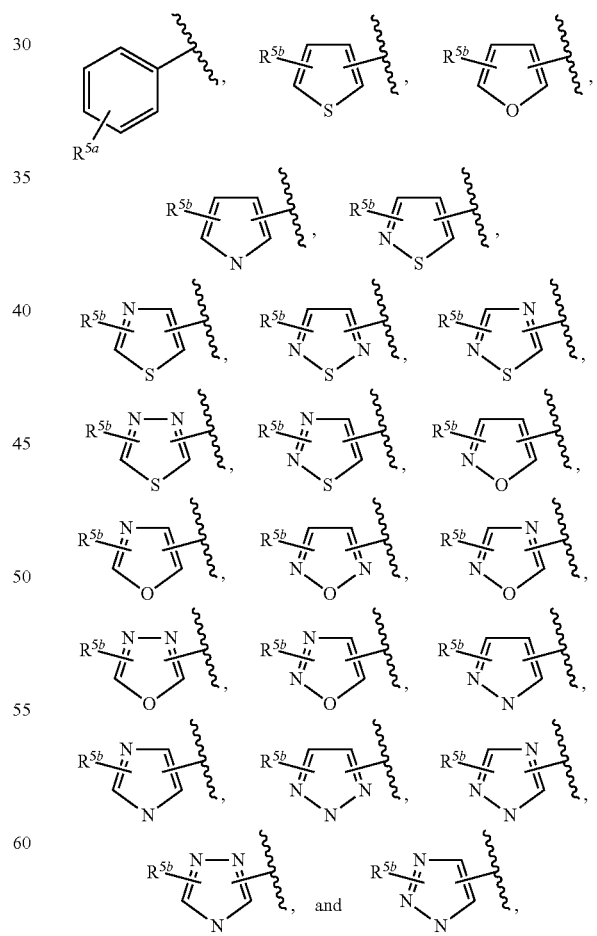

wherein a carbon atom on the ring is attached to the carbonyl carbon.

Some embodiments of the present disclosure include compounds of Formula (III):

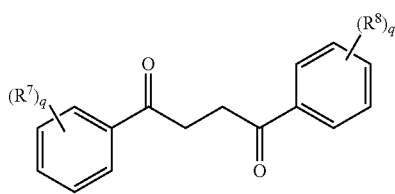

or salts, pharmaceutically acceptable salts or prodrugs thereof.

In some embodiments of Formula III, each $R^7$ is a substituent attached to the phenyl ring and is independently selected at each occurrence from the group consisting of unsubstituted —$C_{1-6}$ alkyl, —$CH_2OH$, —$CH_2N(R^{9a})_2$, —$C_{1-3}$ haloalkyl, halide, —$OR^9$, $CF_3$, and CN.

In some embodiments of Formula III, each $R^8$ is a substituent attached to the phenyl ring and is independently selected at each occurrence from the group consisting of H, unsubstituted —$C_{1-6}$ alkyl, —$CH_2OH$, —$CH_2N(R^{9a})_2$, —$C_{1-3}$ haloalkyl, halide, —$OR^9$, $CF_3$, and CN.

In some embodiments of Formula III, each $R^9$ is independently selected from the group consisting of H, unsubstituted —$C_{1-6}$ alkyl, —$C_{1-3}$ haloalkyl, and $CF_3$.

In some embodiments of Formula III, each $R^{9a}$ is independently selected from the group consisting of H and unsubstituted —$C_{1-3}$ alkyl.

In some embodiments of Formula III, each q is an integer of 1 to 5.

In some embodiments of Formula III, each $R^7$ is independently selected from the group consisting of F, Cl, Me, OMe, OH, $CF_3$ and CN.

In some embodiments of Formula III, $R^7$ is a halide.
In some embodiments of Formula III, $R^7$ is F.
In some embodiments of Formula III, $R^7$ is Cl.
In some embodiments of Formula III, $R^7$ is Me.
In some embodiments of Formula III, $R^7$ is OH.
In some embodiments of Formula III, $R^7$ is OMe.
In some embodiments of Formula III, $R^7$ is $CF_3$.
In some embodiments of Formula III, $R^7$ is CN.
In some embodiments of Formula III, q is an integer from 1-4.
In some embodiments of Formula III, q is an integer from 1-3.
In some embodiments of Formula III, q is an integer from 1-2.
In some embodiments of Formula III, q is 2.
In some embodiments of Formula III, q is 1.
In some embodiments of Formula III, $R^7$ is F; and q is 1.
In some embodiments of Formula III, $R^7$ is F; and q is 2.
In some embodiments of Formula III, $R^7$ is Me; and q is 1.
In some embodiments of Formula III, $R^7$ is Me; and q is 2.
In some embodiments of Formula III, $R^7$ is $CF_3$; and q is 1.
In some embodiments of Formula III, $R^7$ is $CF_3$; and q is 2.
In some embodiments of Formula III, $R^7$ is OMe; and q is 1.
In some embodiments of Formula III, $R^7$ is OMe; and q is 2.
In some embodiments of Formula III, $R^7$ is F and Me; and q is 2.
In some embodiments of Formula III, $R^7$ is F and $CF_3$; and q is 2.
In some embodiments of Formula III, $R^7$ is F and OMe; and q is 2.
In some embodiments of Formula III, $R^7$ is CN; and q is 1.
In some embodiments of Formula III, $R^7$ is CN; and q is 2.
In some embodiments of Formula III, $R^7$ is F and CN; and q is 2.
In some embodiments of Formula III, $R^7$ is —$C_{1-2}$ alkyl.
In some embodiments of Formula III, $R^7$ is —$C_{1-3}$ alkyl.
In some embodiments of Formula III, $R^7$ is —$C_{1-4}$ alkyl.
In some embodiments of Formula III, $R^7$ is —$C_{1-5}$ alkyl.
In some embodiments of Formula III, $R^7$ is —$C_{1-6}$ alkyl.
In some embodiments of Formula III, $R^7$ is —$C_{2-6}$ alkyl.
In some embodiments of Formula III, $R^7$ is —$C_{3-6}$ alkyl.
In some embodiments of Formula III, $R^7$ is —$C_{4-6}$ alkyl.
In some embodiments of Formula III, $R^7$ is —$C_{2-5}$ alkyl.
In some embodiments of Formula III, $R^7$ is —$C_{3-5}$ alkyl.
In some embodiments of Formula III, each $R^8$ is independently selected from the group consisting of H, F, Cl, Me, OMe, OH, $CF_3$ and CN.

In some embodiments of Formula III, $R^8$ is H.
In some embodiments of Formula III, $R^8$ is a halide.
In some embodiments of Formula III, $R^8$ is F.
In some embodiments of Formula III, $R^8$ is Cl.
In some embodiments of Formula III, $R^8$ is Me.
In some embodiments of Formula III, $R^8$ is OH.
In some embodiments of Formula III, $R^8$ is OMe.
In some embodiments of Formula III, $R^8$ is $CF_3$.
In some embodiments of Formula III, $R^8$ is CN.
In some embodiments of Formula III, q is an integer from 1-4.
In some embodiments of Formula III, q is an integer from 1-3.
In some embodiments of Formula III, q is an integer from 1-2.
In some embodiments of Formula III, q is 2.
In some embodiments of Formula III, q is 1.
In some embodiments of Formula III, $R^8$ is F; and q is 1.
In some embodiments of Formula III, $R^8$ is F; and q is 2.
In some embodiments of Formula III, $R^8$ is Me; and q is 1.
In some embodiments of Formula III, $R^8$ is Me; and q is 2.
In some embodiments of Formula III, $R^8$ is $CF_3$; and q is 1.
In some embodiments of Formula III, $R^8$ is $CF_3$; and q is 2.
In some embodiments of Formula III, $R^8$ is OMe; and q is 1.
In some embodiments of Formula III, $R^8$ is OMe; and q is 2.
In some embodiments of Formula III, $R^8$ is F and Me; and q is 2.
In some embodiments of Formula III, $R^8$ is F and $CF_3$; and q is 2.
In some embodiments of Formula III, $R^8$ is F and OMe; and q is 2.
In some embodiments of Formula III, $R^8$ is CN; and q is 1.
In some embodiments of Formula III, $R^8$ is CN; and q is 2.

In some embodiments of Formula III, $R^8$ is F and CN; and q is 2.

In some embodiments of Formula III, $R^8$ is $-C_{1-2}$ alkyl.
In some embodiments of Formula III, $R^8$ is $-C_{1-3}$ alkyl.
In some embodiments of Formula III, $R^8$ is $-C_{1-4}$ alkyl.
In some embodiments of Formula III, $R^8$ is $-C_{1-5}$ alkyl.
In some embodiments of Formula III, $R^8$ is $-C_{1-6}$ alkyl.
In some embodiments of Formula III, $R^8$ is $-C_{2-6}$ alkyl.
In some embodiments of Formula III, $R^8$ is $-C_{3-6}$ alkyl.
In some embodiments of Formula III, $R^8$ is $-C_{4-6}$ alkyl.
In some embodiments of Formula III, $R^8$ is $-C_{2-5}$ alkyl.
In some embodiments of Formula III, $R^8$ is $-C_{3-5}$ alkyl.
In some embodiments of Formula III, $R^9$ is $-C_{1-2}$ alkyl.
In some embodiments of Formula III, $R^9$ is $-C_{1-3}$ alkyl.
In some embodiments of Formula III, $R^9$ is $-C_{1-4}$ alkyl.
In some embodiments of Formula III, $R^9$ is $-C_{1-5}$ alkyl.
In some embodiments of Formula III, $R^9$ is $-C_{1-6}$ alkyl.
In some embodiments of Formula III, $R^9$ is $-C_{2-6}$ alkyl.
In some embodiments of Formula III, $R^9$ is $-C_{3-6}$ alkyl.
In some embodiments of Formula III, $R^9$ is $-C_{4-6}$ alkyl.
In some embodiments of Formula III, $R^9$ is $-C_{2-5}$ alkyl.
In some embodiments of Formula III, $R^9$ is $-C_{3-5}$ alkyl.

In some embodiments of Formula III, $R^7$ and/or $R^8$ is $-CH_2OH$.
In some embodiments of Formula III, $R^7$ and/or $R^8$ is $-CH_2N(R^{9a})_2$.
In some embodiments of Formula III, $R^7$ and/or $R^8$ is $-CH_2NH_2$.
In some embodiments of Formula III, $R^7$ and/or $R^8$ is $-CH_2NHMe$.
In some embodiments of Formula III, $R^7$ and/or $R^8$ is $-CH_2NMe_2$.
In some embodiments of Formula III, $R^7$ and/or $R^8$ is $-CH_2NHEt$.
In some embodiments of Formula III, $R^7$ and/or $R^8$ is $-CH_2N(Me)(Et)$.
In some embodiments of Formula III, $R^7$ and/or $R^8$ is $-CH_2NEt_2$.

Some additional embodiments of Formula III include compounds of Formula (IIIa):

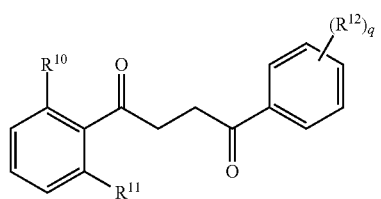

or salts, pharmaceutically acceptable salts, or prodrugs thereof.

In some embodiments of Formula IIIa, $R^{10}$ is selected from the group consisting of H, unsubstituted $-C_{1-6}$ alkyl, $-C_{1-3}$ haloalkyl, halide, $-OR^{13}$, $CF_3$, and CN.

In some embodiments of Formula IIIa, $R^{11}$ is selected from the group consisting of unsubstituted $-C_{1-6}$ alkyl, $-CH_2OH$, $-CH_2N(R^{13b})_2$, $-C_{1-3}$ haloalkyl, halide, $-OR^{13}$, $CF_3$, and CN.

In some embodiments of Formula IIIa, each $R^{12}$ is a substituent attached to the phenyl ring and is independently selected at each occurrence from the group consisting of H, unsubstituted $-C_{1-6}$ alkyl, $-CH_2OH$, $-CH_2N(R^{13b})_2$, $-C_{1-3}$ haloalkyl, halide, $-OR^{13}$, $CF_3$, and CN.

In some embodiments of Formula IIIa, each $R^{13}$ is independently selected from the group consisting of unsubstituted $-C_{1-6}$ alkyl, $-C_{1-3}$ haloalkyl, and $CF_3$.

In some embodiments of Formula IIIa, each $R^{13b}$ is independently selected from the group consisting of H and unsubstituted $-C_{1-3}$ alkyl.

In some embodiments of Formula IIIa, each q is an integer of 1 to 5.

In some embodiments of Formula IIIa, there is the proviso that a compound Formula IIIa is not a compound selected from the group consisting of:

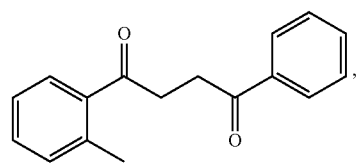

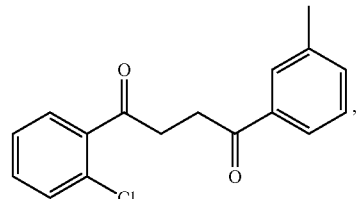

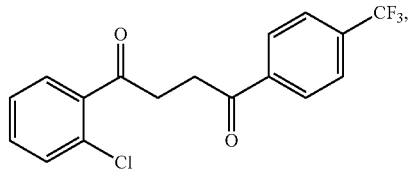

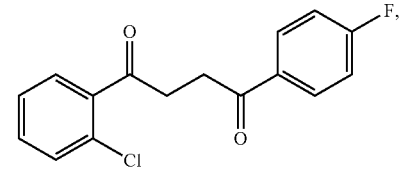

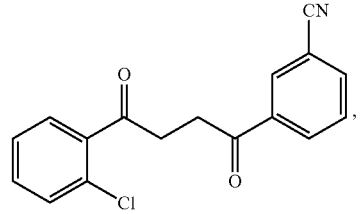

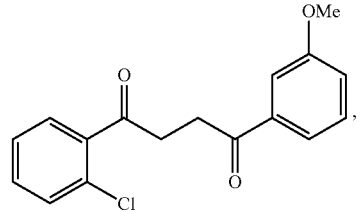

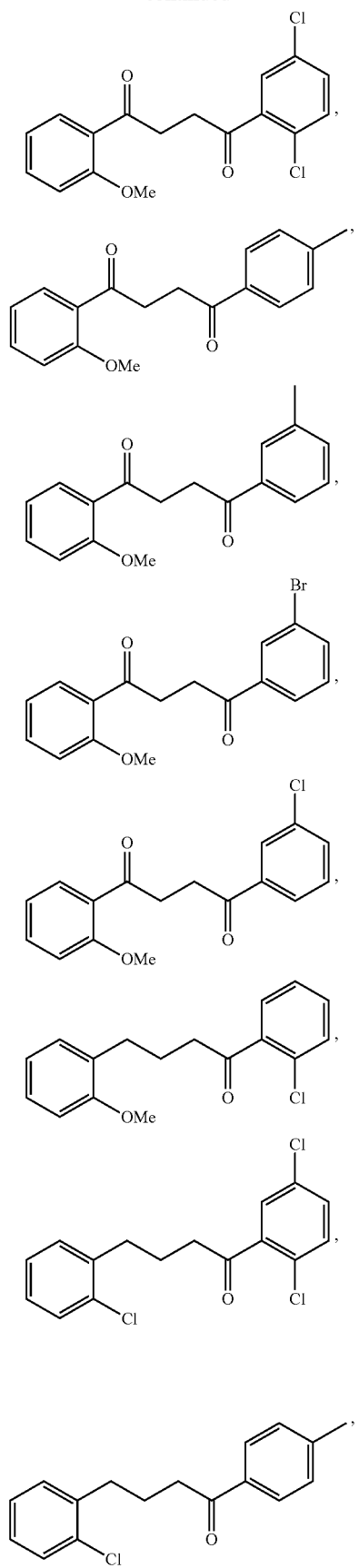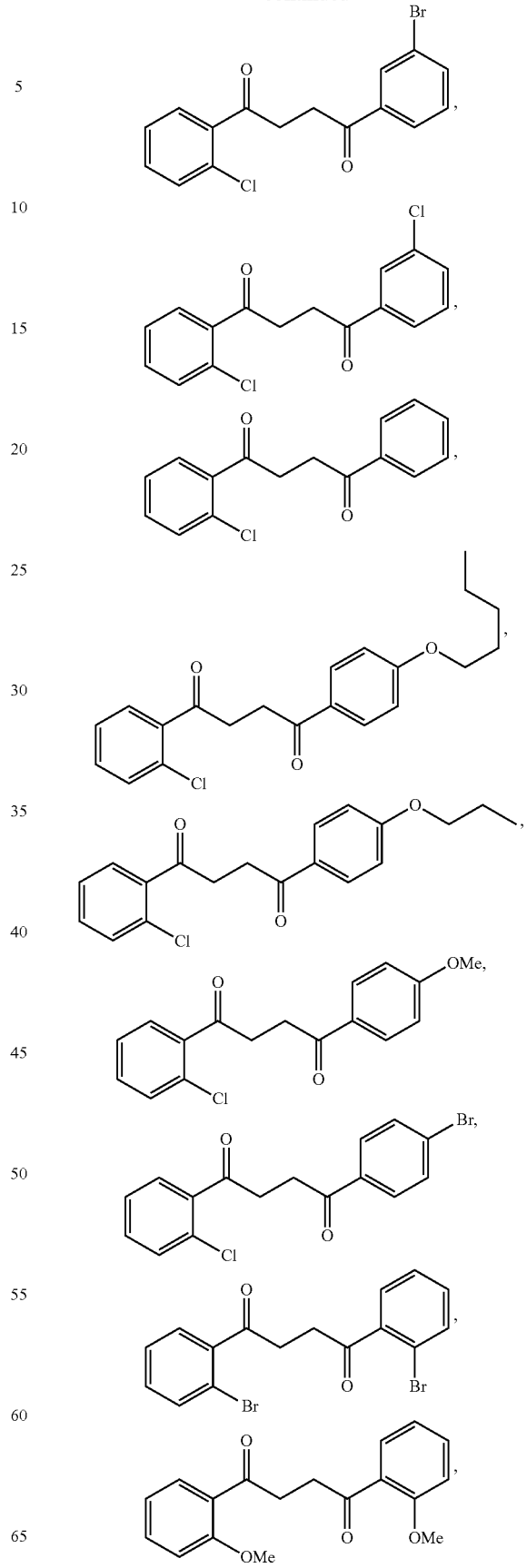

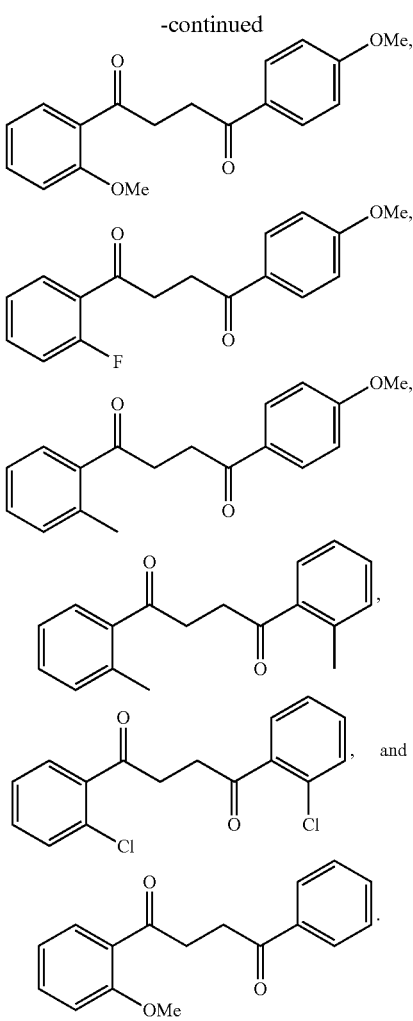

In some embodiments of Formula IIIa and/or IIIc, $R^{10}$ is selected from the group consisting of H, F, Cl, Me, OMe, $CF_3$, and CN.

In some embodiments of Formula IIIa and/or IIIc, $R^{11}$ is selected from the group consisting of F, Cl, Me, OMe, $CF_3$, and CN.

In some embodiments of Formula IIIa and/or IIIc, $R^{10}$ is H; and $R^{11}$ is F.

In some embodiments of Formula IIIa and/or IIIc, $R^{10}$ is H; and $R^{11}$ is Cl.

In some embodiments of Formula IIIa and/or IIIc, $R^{10}$ is H; and $R^{11}$ is Me.

In some embodiments of Formula IIIa and/or IIIc, $R^{10}$ is H; and $R^{11}$ is OMe.

In some embodiments of Formula IIIa and/or IIIc, $R^{10}$ is H; and $R^{11}$ is $CF_3$.

In some embodiments of Formula IIIa and/or IIIc, $R^{10}$ is H; and $R^{11}$ is CN.

In some embodiments of Formula IIIa and/or IIIc, $R^{10}$ is F; and $R^{11}$ is F.

In some embodiments of Formula IIIa and/or IIIc, $R^{10}$ is F; and $R^{11}$ is Cl.

In some embodiments of Formula IIIa and/or IIIc, $R^{10}$ is F; and $R^{11}$ is Me.

In some embodiments of Formula IIIa and/or IIIc, $R^{10}$ is F; and $R^{11}$ is OMe.

In some embodiments of Formula IIIa and/or IIIc, $R^{10}$ is F; and $R^{11}$ is $CF_3$.

In some embodiments of Formula IIIa and/or IIIc, $R^{10}$ is F; and $R^{11}$ is CN.

In some embodiments of Formula IIIa and/or IIIc, $R^{10}$ is $—C_{1-2}$ alkyl.

In some embodiments of Formula IIIa and/or IIIc, $R^{10}$ is $—C_{1-3}$ alkyl.

In some embodiments of Formula IIIa and/or IIIc, $R^{10}$ is $—C_{1-4}$ alkyl.

In some embodiments of Formula IIIa and/or IIIc, $R^{10}$ is $—C_{1-5}$ alkyl.

In some embodiments of Formula IIIa and/or IIIc, $R^{10}$ is $—C_{1-6}$ alkyl.

In some embodiments of Formula IIIa and/or IIIc, $R^{10}$ is $—C_{2-6}$ alkyl.

In some embodiments of Formula IIIa and/or IIIc, $R^{10}$ is $—C_{3-6}$ alkyl.

In some embodiments of Formula IIIa and/or IIIc, $R^{10}$ is $—C_{4-6}$ alkyl.

In some embodiments of Formula IIIa and/or IIIc, $R^{10}$ is $—C_{2-5}$ alkyl.

In some embodiments of Formula IIIa and/or IIIc, $R^{10}$ is $—C_{3-5}$ alkyl.

In some embodiments of Formula IIIa and/or IIIc, $R^{11}$ is $—C_{1-2}$ alkyl.

In some embodiments of Formula IIIa and/or IIIc, $R^{11}$ is $—C_{1-3}$ alkyl.

In some embodiments of Formula IIIa and/or IIIc, $R^{11}$ is $—C_{1-4}$ alkyl.

In some embodiments of Formula IIIa and/or IIIc, $R^{11}$ is $—C_{1-5}$ alkyl.

In some embodiments of Formula IIIa and/or IIIc, $R^{11}$ is $—C_{1-6}$ alkyl.

In some embodiments of Formula IIIa and/or IIIc, $R^{11}$ is $—C_{2-6}$ alkyl.

In some embodiments of Formula IIIa and/or IIIc, $R^{11}$ is $—C_{3-6}$ alkyl.

In some embodiments of Formula IIIa and/or IIIc, $R^{11}$ is $—C_{4-6}$ alkyl.

In some embodiments of Formula IIIa and/or IIIc, $R^{11}$ is $—C_{2-5}$ alkyl.

In some embodiments of Formula IIIa and/or IIIc, $R^{11}$ is $—C_{3-5}$ alkyl.

In some embodiments of Formula IIIa, each $R^{12}$ is selected from the group consisting of H, F, Cl, Me, OMe, $CF_3$, and CN.

In some embodiments of Formula IIIa, $R^{12}$ is H.

In some embodiments of Formula IIIa, $R^{12}$ is a halide.

In some embodiments of Formula IIIa, $R^{12}$ is F.

In some embodiments of Formula IIIa, $R^{12}$ is Cl.

In some embodiments of Formula IIIa, $R^{12}$ is Me.

In some embodiments of Formula IIIa, $R^{12}$ is OH.

In some embodiments of Formula IIIa, $R^{12}$ is OMe.

In some embodiments of Formula IIIa, $R^{12}$ is $CF_3$.

In some embodiments of Formula IIIa, $R^{12}$ is CN.

In some embodiments of Formula IIIa and/or IIIc, q is an integer from 1-4.

In some embodiments of Formula IIIa and/or IIIc, q is an integer from 1-3.

In some embodiments of Formula IIIa, q is an integer from 1-2.

In some embodiments of Formula IIIa and/or IIIc, q is 2.

In some embodiments of Formula IIIa and/or IIIc, q is 1.

In some embodiments of Formula IIIa, $R^{12}$ is F; and q is 1.

In some embodiments of Formula IIIa, $R^{12}$ is F; and q is 2.

In some embodiments of Formula IIIa, $R^{12}$ is Me; and q is 1.

In some embodiments of Formula IIIa, $R^{12}$ is Me; and q is 2.

In some embodiments of Formula IIIa, $R^{12}$ is $CF_3$; and q is 1.

In some embodiments of Formula IIIa, $R^{12}$ is $CF_3$; and q is 2.

In some embodiments of Formula IIIa, $R^{12}$ is OMe; and q is 1.

In some embodiments of Formula IIIa, $R^{12}$ is OMe; and q is 2.

In some embodiments of Formula IIIa, $R^{12}$ is F and Me; and q is 2.

In some embodiments of Formula IIIa, $R^{12}$ is F and $CF_3$; and q is 2.

In some embodiments of Formula IIIa, $R^{12}$ is F and OMe; and q is 2.

In some embodiments of Formula IIIa, $R^{12}$ is CN; and q is 1.

In some embodiments of Formula IIIa, $R^{12}$ is CN; and q is 2.

In some embodiments of Formula IIIa, $R^{12}$ is F and CN; and q is 2.

In some embodiments of Formula IIIa, $R^{12}$ is F or Cl; q is 1.

In some embodiments of Formula IIIa, $R^{12}$ is —$C_{1-2}$ alkyl.

In some embodiments of Formula IIIa, $R^{12}$ is —$C_{1-3}$ alkyl.

In some embodiments of Formula IIIa, $R^{12}$ is —$C_{1-4}$ alkyl.

In some embodiments of Formula IIIa, $R^{12}$ is —$C_{1-5}$ alkyl.

In some embodiments of Formula IIIa, $R^{12}$ is —$C_{1-6}$ alkyl.

In some embodiments of Formula IIIa, $R^{12}$ is —$C_{2-6}$ alkyl.

In some embodiments of Formula IIIa, $R^{12}$ is —$C_{3-6}$ alkyl.

In some embodiments of Formula IIIa, $R^{12}$ is —$C_{4-6}$ alkyl.

In some embodiments of Formula IIIa, $R^{12}$ is —$C_{2-5}$ alkyl.

In some embodiments of Formula IIIa, $R^{12}$ is —$C_{3-5}$ alkyl.

In some embodiments of Formula IIIa and/or IIIc, $R^{12}$ is —$CH_2OH$.

In some embodiments of Formula IIIa and/or IIIc, $R^{11}$ is —$CH_2N(R^{13b})_2$.

In some embodiments of Formula IIIa and/or IIIc, $R^{11}$ is —$CH_2NH_2$.

In some embodiments of Formula IIIa and/or IIIc, $R^{11}$ is —$CH_2NHMe$.

In some embodiments of Formula IIIa and/or IIIc, $R^{11}$ is —$CH_2NMe_2$.

In some embodiments of Formula IIIa and/or IIIc, $R^{11}$ is —$CH_2NHEt$.

In some embodiments of Formula IIIa and/or IIIc, $R^{11}$ is —$CH_2N(Me)(Et)$.

In some embodiments of Formula IIIa and/or IIIc, $R^{11}$ is —$CH_2NEt_2$.

In some embodiments of Formula IIIa and/or IIIc, $R^{13}$ is —$C_{1-2}$ alkyl.

In some embodiments of Formula IIIa and/or IIIc, $R^{13}$ is —$C_{1-3}$ alkyl.

In some embodiments of Formula IIIa and/or IIIc, $R^{13}$ is —$C_{1-4}$ alkyl.

In some embodiments of Formula IIIa and/or IIIc, $R^{13}$ is —$C_{1-5}$ alkyl.

In some embodiments of Formula IIIa and/or IIIc, $R^{13}$ is —$C_{1-6}$ alkyl.

In some embodiments of Formula IIIa and/or IIIc, $R^{13}$ is —$C_{2-6}$ alkyl.

In some embodiments of Formula IIIa and/or IIIc, $R^{13}$ is —$C_{3-6}$ alkyl.

In some embodiments of Formula IIIa and/or IIIc, $R^{13}$ is —$C_{4-6}$ alkyl.

In some embodiments of Formula IIIa and/or IIIc, $R^{13}$ is —$C_{2-5}$ alkyl.

In some embodiments of Formula IIIa and/or IIIc, $R^{13}$ is —$C_{3-5}$ alkyl.

Some additional embodiments of Formula III include compounds of Formula (IIIb):

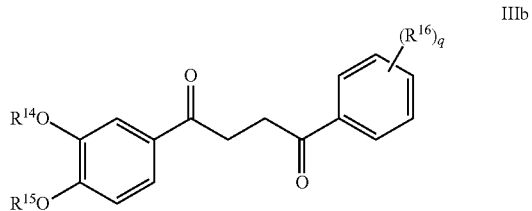

or salts, pharmaceutically acceptable salts, or prodrugs thereof.

In some embodiments of Formula IIIb, $R^{14}$ is selected from the group consisting of unsubstituted —$C_{1-6}$ alkyl, —$C_{1-3}$ haloalkyl, and $CF_3$.

In some embodiments of Formula IIIb, $R^{15}$ is selected from the group consisting of unsubstituted —$C_{1-6}$ alkyl, —$C_{1-3}$ haloalkyl, and $CF_3$.

In some embodiments of Formula IIIb, each $R^{16}$ is a substituent attached to the phenyl ring and is independently selected at each occurrence from the group consisting of H, unsubstituted —$C_{1-6}$ alkyl, —$CH_2OH$, —$CH_2N(R^{17b})_2$, —$C_{1-3}$ haloalkyl, halide, —$OR^{17}$, $CF_3$, and CN.

In some embodiments of Formula IIIb, each $R^{17}$ is independently selected from the group consisting of unsubstituted —$C_{1-6}$ alkyl, —$C_{1-3}$ haloalkyl, and $CF_3$.

In some embodiments of Formula IIIb, each $R^{17b}$ is independently selected from the group consisting of H and unsubstituted —$C_{1-3}$ alkyl.

In some embodiments of Formula IIIb, each q is an integer of 1 to 5.

In some embodiments of Formula IIIb, there is the proviso that a compound of Formula IIIb is not a compound selected from the group consisting of:

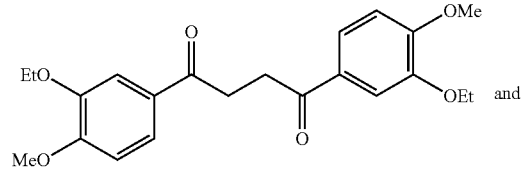

and

-continued

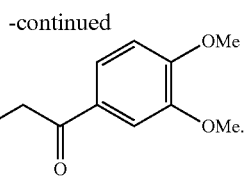

In some embodiments of Formula IIIb and/or IIId, $R^{14}$ is Me

In some embodiments of Formula IIIb and/or IIId, $R^{14}$ is Et.

In some embodiments of Formula IIIb and/or IIId, $R^{14}$ is —$C_{1-2}$ alkyl.

In some embodiments of Formula IIIb and/or IIId, $R^{14}$ is —$C_{1-3}$ alkyl.

In some embodiments of Formula IIIb and/or IIId, $R^{14}$ is —$C_{1-4}$ alkyl.

In some embodiments of Formula IIIb and/or IIId, $R^{14}$ is —$C_{1-5}$ alkyl.

In some embodiments of Formula IIIb and/or IIId, $R^{14}$ is —$C_{1-6}$ alkyl.

In some embodiments of Formula IIIb and/or IIId, $R^{14}$ is —$C_{2-6}$ alkyl.

In some embodiments of Formula IIIb and/or IIId, $R^{14}$ is —$C_{3-6}$ alkyl.

In some embodiments of Formula IIIb and/or IIId, $R^{14}$ is —$C_{4-6}$ alkyl.

In some embodiments of Formula IIIb and/or IIId, $R^{14}$ is —$C_{2-5}$ alkyl.

In some embodiments of Formula IIIb and/or IIId, $R^{14}$ is —$C_{3-5}$ alkyl.

In some embodiments of Formula IIIb and/or IIId, $R^{14}$ is —$C_{1-2}$ haloalkyl.

In some embodiments of Formula IIIb and/or IIId, $R^{14}$ is —$C_{1-3}$ haloalkyl.

In some embodiments of Formula IIIb and/or IIId, $R^{14}$ is —$C_{2-3}$ haloalkyl.

In some embodiments of Formula IIIb and/or IIId, $R^{14}$ is $CF_3$.

In some embodiments of Formula IIIb and/or IIId, $R^{15}$ is Me

In some embodiments of Formula IIIb and/or IIId, $R^{15}$ is Et.

In some embodiments of Formula IIIb and/or IIId, $R^{15}$ is —$C_{1-2}$ alkyl.

In some embodiments of Formula IIIb and/or IIId, $R^{15}$ is —$C_{1-3}$ alkyl.

In some embodiments of Formula IIIb and/or IIId, $R^{15}$ is —$C_{1-4}$ alkyl.

In some embodiments of Formula IIIb and/or IIId, $R^{15}$ is —$C_{1-5}$ alkyl.

In some embodiments of Formula IIIb and/or IIId, $R^{15}$ is —$C_{1-6}$ alkyl.

In some embodiments of Formula IIIb and/or IIId, $R^{15}$ is —$C_{2-6}$ alkyl.

In some embodiments of Formula IIIb and/or IIId, $R^{15}$ is —$C_{3-6}$ alkyl.

In some embodiments of Formula IIIb and/or IIId, $R^{15}$ is —$C_{4-6}$ alkyl.

In some embodiments of Formula IIIb and/or IIId, $R^{15}$ is —$C_{2-5}$ alkyl.

In some embodiments of Formula IIIb and/or IIId, $R^{15}$ is —$C_{3-5}$ alkyl.

In some embodiments of Formula IIIb and/or IIId, $R^{15}$ is —$C_{1-2}$ haloalkyl.

In some embodiments of Formula IIIb and/or IIId, $R^{15}$ is —$C_{1-3}$ haloalkyl.

In some embodiments of Formula IIIb and/or IIId, $R^{15}$ is —$C_{2-3}$ haloalkyl.

In some embodiments of Formula IIIb and/or IIId, $R^{15}$ is $CF_3$.

In some embodiments of Formula IIIb, each $R^{16}$ is selected from the group consisting of H, F, Cl, Me, OMe, $CF_3$, and CN.

In some embodiments of Formula IIIb, $R^{16}$ is H.

In some embodiments of Formula IIIb and/or IIId, $R^{16}$ is a halide.

In some embodiments of Formula IIIb and/or IIId, $R^{16}$ is F.

In some embodiments of Formula IIIb and/or IIId, $R^{16}$ is Cl.

In some embodiments of Formula IIIb and/or IIId, $R^{16}$ is Me.

In some embodiments of Formula IIIb, $R^{16}$ is OH.

In some embodiments of Formula IIIb, $R^{16}$ is OMe.

In some embodiments of Formula IIIb and/or IIId, $R^{16}$ is $CF_3$.

In some embodiments of Formula IIIb and/or IIId, $R^{16}$ is CN.

In some embodiments of Formula IIIb and/or IIId, q is an integer from 1-4.

In some embodiments of Formula IIIb and/or IIId, q is an integer from 1-3.

In some embodiments of Formula IIIb and/or IIId, q is an integer from 1-2.

In some embodiments of Formula IIIb and/or IIId, q is 2.

In some embodiments of Formula IIIb and/or IIId, q is 1.

In some embodiments of Formula IIIb and/or IIId, $R^{16}$ is F; and q is 1.

In some embodiments of Formula IIIb and/or IIId, $R^{16}$ is F; and q is 2.

In some embodiments of Formula IIIb and/or IIId, $R^{16}$ is Me; and q is 1.

In some embodiments of Formula IIIb and/or IIId, $R^{16}$ is Me; and q is 2.

In some embodiments of Formula IIIb and/or IIId, $R^{16}$ is $CF_3$; and q is 1.

In some embodiments of Formula IIIb and/or IIId, $R^{16}$ is $CF_3$; and q is 2.

In some embodiments of Formula IIIb, $R^{16}$ is OMe; and q is 1.

In some embodiments of Formula IIIb, $R^{16}$ is OMe; and q is 2.

In some embodiments of Formula IIIb and/or IIId, $R^{16}$ is F and Me; and q is 2.

In some embodiments of Formula IIIb and/or IIId, $R^{16}$ is F and $CF_3$; and q is 2.

In some embodiments of Formula IIIb, $R^{16}$ is F and OMe; and q is 2.

In some embodiments of Formula IIIb and/or IIId, $R^{16}$ is CN; and q is 1.

In some embodiments of Formula IIIb and/or IIId, $R^{16}$ is CN; and q is 2.

In some embodiments of Formula IIIb and/or IIId, $R^{16}$ is F and CN; and q is 2.

In some embodiments of Formula IIIb and/or IIId, $R^{16}$ is F or Cl; q is 1.

In some embodiments of Formula IIIb and/or IIId, $R^{16}$ is —$C_{1-2}$ alkyl.

In some embodiments of Formula IIIb and/or IIId, $R^{16}$ is —$C_{1-3}$ alkyl.

In some embodiments of Formula IIIb and/or IIId, $R^{16}$ is —$C_{1-4}$ alkyl.

In some embodiments of Formula IIIb and/or IIId, $R^{16}$ is —$C_{1-5}$ alkyl.

In some embodiments of Formula IIIb and/or IIId, $R^{16}$ is —$C_{1-6}$ alkyl.

In some embodiments of Formula IIIb and/or IIId, $R^{16}$ is —$C_{2-6}$ alkyl.

In some embodiments of Formula IIIb and/or IIId, $R^{16}$ is —$C_{3-6}$ alkyl.

In some embodiments of Formula IIIb and/or IIId, $R^{16}$ is —$C_{4-6}$ alkyl.

In some embodiments of Formula IIIb and/or IIId, $R^{16}$ is —$C_{2-5}$ alkyl.

In some embodiments of Formula IIIb and/or IIId, $R^{16}$ is —$C_{3-5}$ alkyl.

In some embodiments of Formula IIIb, $R^{17}$ is —$C_{1-2}$ alkyl.

In some embodiments of Formula IIIb, $R^{17}$ is —$C_{1-3}$ alkyl.

In some embodiments of Formula IIIb, $R^{17}$ is —$C_{1-4}$ alkyl.

In some embodiments of Formula IIIb, $R^{17}$ is —$C_{1-5}$ alkyl.

In some embodiments of Formula IIIb, $R^{17}$ is —$C_{1-6}$ alkyl.

In some embodiments of Formula IIIb, $R^{17}$ is —$C_{2-6}$ alkyl.

In some embodiments of Formula IIIb, $R^{17}$ is —$C_{3-6}$ alkyl.

In some embodiments of Formula IIIb, $R^{17}$ is —$C_{4-6}$ alkyl.

In some embodiments of Formula IIIb, $R^{17}$ is —$C_{2-5}$ alkyl.

In some embodiments of Formula IIIb, $R^{17}$ is —$C_{3-5}$ alkyl.

In some embodiments of Formula IIIb, $R^{16}$ is —$CH_2OH$.

In some embodiments of Formula IIIb, $R^{16}$ is —$CH_2N(R^{17b})_2$.

In some embodiments of Formula IIIb, $R^{16}$ is —$CH_2NH_2$.

In some embodiments of Formula IIIb, $R^{16}$ is —$CH_2NHMe$.

In some embodiments of Formula IIIb, $R^{16}$ is —$CH_2NMe_2$.

In some embodiments of Formula IIIb, $R^{16}$ is —$CH_2NHEt$.

In some embodiments of Formula IIIb, $R^{16}$ is —$CH_2N(Me)(Et)$.

In some embodiments of Formula IIIb, $R^{16}$ is —$CH_2NEt_2$.

Some additional embodiments of Formula III include compounds of Formula (IIIc):

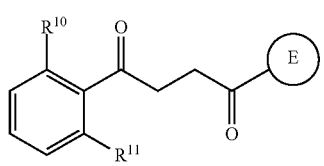

IIIc or salts, pharmaceutically acceptable salts, or prodrugs thereof.

In some embodiments of Formula IIIc, Ring E is selected from the group consisting of

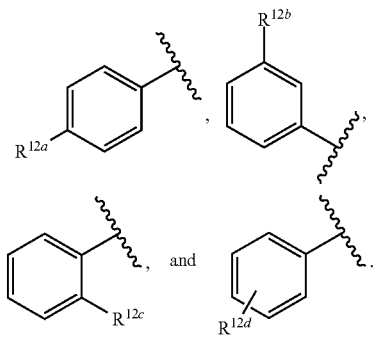

In some embodiments of Formula IIIc, $R^{10}$ is selected from the group consisting of H, unsubstituted —$C_{1-6}$ alkyl, —$C_{1-3}$ haloalkyl, halide, —$OR^{13}$, $CF_3$, and CN.

In some embodiments of Formula IIIc, $R^{11}$ is selected from the group consisting of unsubstituted —$C_{1-6}$ alkyl, —$CH_2OH$, —$CH_2N(R^{13b})_2$, —$C_{1-3}$ haloalkyl, halide, —$OR^{13}$, $CF_3$, and CN.

In some embodiments of Formula IIIc, $R^{12a}$ is a substituent attached to the para position of the phenyl ring and is independently selected at each occurrence from the group consisting of unsubstituted —$C_{2-6}$ alkyl, —$CH_2OH$, —$CH_2N(R^{13b})_2$, —$C_{2-3}$ haloalkyl, Cl, I, -OEt, and CN.

In some embodiments of Formula IIIc, $R^{12b}$ is a substituent attached to the meta position of the phenyl ring and is independently selected at each occurrence from the group consisting of unsubstituted —$C_{2-6}$ alkyl, —$CH_2OH$, —$CH_2N(R^{13b})_2$, —$C_{1-3}$ haloalkyl, iodide, —$OR^{13a}$, and $CF_3$.

In some embodiments of Formula IIIc, $R^{12c}$ is a substituent attached to the ortho position of the phenyl ring and is independently selected at each occurrence from the group consisting of unsubstituted —$C_{2-6}$ alkyl, —$CH_2OH$, —$CH_2N(R^{13b})_2$, —$C_{1-3}$ haloalkyl, F, I, —$OR^{13a}$, $CF_3$, and CN.

In some embodiments of Formula IIIc, $R^{12d}$ is 2-5 substituents, each attached to Ring E and are independently selected at each occurrence from the group consisting of unsubstituted —$C_{1-6}$ alkyl, —$CH_2OH$, —$CH_2N(R^{13b})_2$, —$C_{1-3}$ haloalkyl, F, Br, I, —$OR^{13}$, $CF_3$, and CN.

In some embodiments of Formula IIIc, each $R^{13}$ is independently selected from the group consisting of unsubstituted —$C_{1-6}$ alkyl, —$C_{1-3}$ haloalkyl, and $CF_3$.

In some embodiments of Formula IIIc, each $R^{13a}$ is independently selected from the group consisting of unsubstituted —$C_{2-6}$ alkyl, —$C_{1-3}$ haloalkyl, and $CF_3$.

In some embodiments of Formula IIIc, each $R^{13b}$ is independently selected from the group consisting of H and unsubstituted —$C_{1-3}$ alkyl.

In some embodiments of Formula IIIc, q is an integer of 1 to 5.

In some embodiments of Formula IIIc, $R^{12a}$, $R^{12b}c$, $R^{12}$, $R^{12d}$ and/or $R^{13a}$ is —$C_{2-6}$ alkyl.

In some embodiments of Formula IIIc, $R^{12a}$, $R^{12b}c$, $R^{12}$, $R^{12d}$ and/or $R^{13a}$ is —$C_{2-5}$ alkyl.

In some embodiments of Formula IIIc, $R^{12a}$, $R^{12b}c$, $R^{12}$, $R^{12d}$ and/or $R^{13a}$ is —$C_{2-4}$ alkyl.

In some embodiments of Formula IIIc, $R^{12a}$, $R^{12b}c$, $R^{12}$, $R^{12d}$ and/or $R^{13a}$ is —$C_{3-6}$ alkyl.

In some embodiments of Formula IIIc, $R^{12a}$, $R^{12b}c$, $R^{12}$, $R^{12d}$ and/or $R^{13a}$ is —$C_{4-6}$ alkyl.

In some embodiments of Formula IIIc, $R^{12d}$ and/or $R^{13a}$ is Me.

In some embodiments of Formula IIIc, $R^{12b}$, $R^{12c}$, $R^{12d}$ and/or $R^{13a}$ is $CF_3$.

In some embodiments of Formula IIIc, $R^{12c}$ and/or $R^{12d}$ is F.

In some embodiments of Formula IIIc, $R^{12a}$ is Cl.

In some embodiments of Formula IIIc, $R^{12a}$, $R^{12c}$, and/or $R^{12d}$ is CN.

In some embodiments of Formula IIIc, $R^{12a}$, $R^{12b}$, $R^{12c}$, and/or $R^{12d}$ is —$CH_2OH$.

In some embodiments of Formula IIIc, $R^{12a}$, $R^{12b}$, $R^{12c}$, and/or $R^{12d}$ is —$CH_2N(R^{13b})_2$.

In some embodiments of Formula IIIc, $R^{12a}$, $R^{12b}$, $R^{12c}$, and/or $R^{12d}$ is —$CH_2NH_2$.

In some embodiments of Formula IIIc, $R^{12a}$, $R^{12b}$, $R^{12c}$, and/or $R^{12d}$ is —$CH_2NHMe$.

In some embodiments of Formula IIIc, $R^{12a}$, $R^{12b}$, $R^{12c}$, and/or $R^{12d}$ is —$CH_2NMe_2$.

In some embodiments of Formula IIIc, $R^{12a}$, $R^{12b}$, $R^{12c}$, and/or $R^{12d}$ is —$CH_2NHEt$.

In some embodiments of Formula IIIc, $R^{12a}$, $R^{12b}$, $R^{12c}$, and/or $R^{12d}$ is —$CH_2N(Me)(Et)$.

In some embodiments of Formula IIIa and/or IIIc, $R^{11}$ is —$CH_2NEt_2$.

Some additional embodiments of Formula III include compounds of Formula (IIId):

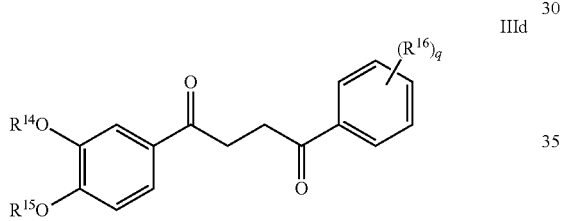

IIId or salts, pharmaceutically acceptable salts, or prodrugs thereof.

In some embodiments of Formula IIId, $R^{14}$ is selected from the group consisting of unsubstituted —$C_{1-6}$ alkyl, —$C_{1-3}$ haloalkyl, and $CF_3$.

In some embodiments of Formula IIId, $R^{15}$ is selected from the group consisting of unsubstituted —$C_{1-6}$ alkyl, —$C_{1-3}$ haloalkyl, and $CF_3$.

In some embodiments of Formula IIId, each $R^{16}$ is a substituent attached to the phenyl ring and is independently selected at each occurrence from the group consisting of unsubstituted —$C_{1-6}$ alkyl, —$CH_2OH$, —$CH_2N(R^{17b})_2$, —$C_{1-3}$ haloalkyl, halide, —$OR^{17a}$, $CF_3$, and CN.

In some embodiments of Formula IIId, each $R^{17a}$ is independently selected from the group consisting of unsubstituted —$C_{3-6}$ alkyl, —$C_{1-3}$ haloalkyl, and $CF_3$.

In some embodiments of Formula IIId, each $R^{17b}$ is independently selected from the group consisting of H and unsubstituted —$C_{1-3}$ alkyl.

In some embodiments of Formula IIId, q is an integer of 1 to 5.

In some embodiments of Formula IIId, $R^{17}$ is —$C_{3-6}$ alkyl.

In some embodiments of Formula IIId, $R^{17}$ is —$C_{4-6}$ alkyl.

In some embodiments of Formula IIId, $R^{17}$ is —$C_{3-5}$ alkyl.

In some embodiments of Formula IIId, $R^{16}$ is —$CH_2OH$.

In some embodiments of Formula IIId, $R^{16}$ is —$CH_2N(R^{17b})_2$.

In some embodiments of Formula IIId, $R^{16}$ is —$CH_2NH_2$.

In some embodiments of Formula IIId, $R^{16}$ is —$CH_2NHMe$.

In some embodiments of Formula IIId, $R^{16}$ is —$CH_2NMe_2$.

In some embodiments of Formula IIId, $R^{16}$ is —$CH_2NHEt$.

In some embodiments of Formula IIId, $R^{16}$ is —$CH_2N(Me)(Et)$.

In some embodiments of Formula IIId, $R^{16}$ is —$CH_2NEt_2$.

Some embodiments of the present disclosure include compounds of Formula (IV):

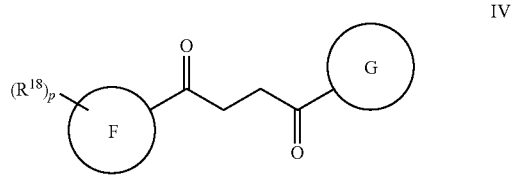

IV or salts, pharmaceutically acceptable salts, or prodrugs thereof.

In some embodiments of Formula IV, Ring F is

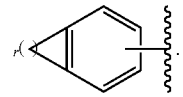

In some embodiments of Formula IV, Ring G is selected from the group consisting of

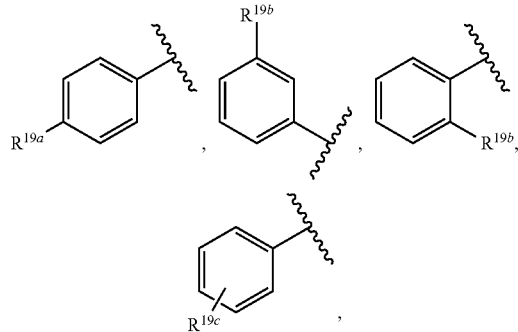

and a 5-6 membered heteroaryl $R^{19d}$, wherein a carbon atom on the ring is attached to the carbonyl carbon.

In some embodiments of Formula IV, each $R^{18}$ is a substituent attached to Ring F and is independently selected at each occurrence from the group consisting of H, —$C_{1-3}$ haloalkyl, halide, —$OR^{20}$, $CF_3$, and CN.

In some embodiments of Formula IV, $R^{19a}$ is a substituent attached to the para position of phenyl and is selected from the group consisting of H, unsubstituted —$C_{2-6}$ alkyl, —$CH_2OH$, —$CH_2N(R^{21})_2$, —$C_{1-3}$ haloalkyl, F, Br, I, —$OR^{20}$, $CF_3$, and CN.

In some embodiments of Formula IV, $R^{19b}$ is a substituent attached to the meta or ortho position of phenyl and is selected from the group consisting of H, unsubstituted —$C_{2-6}$ alkyl, —$CH_2OH$, —$CH_2N(R^{21})_2$, —$C_{1-3}$ haloalkyl, halide, —$OR^{20}$, $CF_3$, and CN.

In some embodiments of Formula IV, $R^{19c}$ is 2-5 substituents, each attached to the phenyl and are independently selected at each occurrence from the group consisting of H, —$CH_2OH$, —$CH_2N(R^{21})_2$, —$C_{1-3}$ haloalkyl, halide, —$OR^{20}$, $CF_3$, and CN.

In some embodiments of Formula IV, $R^{19d}$ is 1-4 substituents, each attached to the heteroaryl ring and is independently selected at each occurrence from the group consisting of H, —$CH_2OH$, —$CH_2N(R^{21})_2$, —$C_{1-3}$ haloalkyl, halide, —$OR^{20}$, $CF_3$, and CN.

In some embodiments of Formula IV, each $R^{20}$ is independently selected from the group consisting of H, unsubstituted —$C_{3-6}$ alkyl, —$C_{1-3}$ haloalkyl, and $CF_3$.

In some embodiments of Formula IV, each $R^{21}$ is independently selected from the group consisting of H and unsubstituted —$C_{1-3}$ alkyl.

In some embodiments of Formula IV, p is an integer of 1 to 13.

In some embodiments of Formula IV, r is an integer of 1 to 5.

In some embodiments of Formula IV,

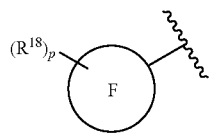

is selected from the group consisting of:

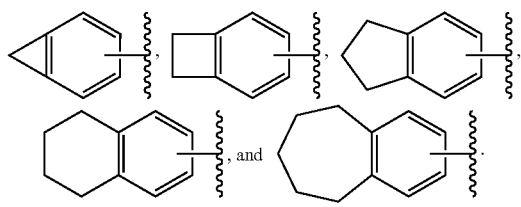

In some embodiments of Formula IV,

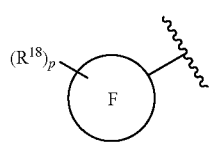

is selected from the group consisting of:

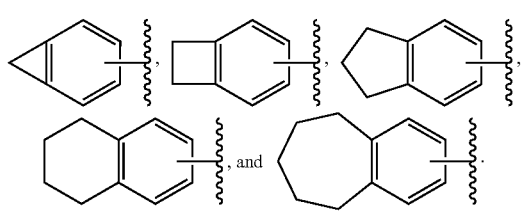

In some embodiments of Formula IV, $R^{19b}$, $R^{19c}$, and/or $R^{19d}$ is selected from the group consisting of H, F, Cl, Me, OMe, $CF_3$, and CN.

In some embodiments of Formula IV, $R^{19a}$, $R^{19b}$, $R^{19c}$, and/or $R^{19d}$ is H.

In some embodiments of Formula IV, $R^{19b}$, $R^{19c}$, and/or $R^{19d}$ is a halide.

In some embodiments of Formula IV, $R^{19a}$, $R^{19b}$, $R^{19c}$, and/or $R^{19d}$ is F.

In some embodiments of Formula IV, $R^{19b}$, $R^{19c}$, and/or $R^{19d}$ is Cl.

In some embodiments of Formula IV, $R^{19a}$, $R^{19b}$, $R^{19c}$, and/or $R^{19d}$ is Me.

In some embodiments of Formula IV, $R^{19a}$, $R^{19b}$, $R^{19c}$, and/or $R^{19d}$ is OH.

In some embodiments of Formula IV, $R^{19a}$, $R^{19b}$, $R^{19c}$, and/or $R^{19d}$ is OMe.

In some embodiments of Formula IV, $R^{19a}$, $R^{19b}$, $R^{19c}$, and/or $R^{19d}$ is $CF_3$.

In some embodiments of Formula IV, $R^{19a}$, $R^{19b}$, $R^{19c}$, and/or $R^{19d}$ is CN.

In some embodiments of Formula IV, $R^{19d}$ is 2 substituents and both are F.

In some embodiments of Formula IV, $R^{19d}$ is 2 substituents and both are Me.

In some embodiments of Formula IV, $R^{19d}$ is 2 substituents and both are $CF_3$.

In some embodiments of Formula IV, $R^{19d}$ is 2 substituents and both are OMe.

In some embodiments of Formula IV, $R^{19d}$ is 2 substituents and are F and Me.

In some embodiments of Formula IV, $R^{19d}$ is 2 substituents and are F and $CF_3$.

In some embodiments of Formula IV, $R^{19d}$ is 2 substituents and are F and OMe.

In some embodiments of Formula IV, $R^{19d}$ is 2 substituents and both are CN.

In some embodiments of Formula IV, $R^{19d}$ is 2 substituents and are F and CN.

In some embodiments of Formula IV, $R^{19d}$ is 2 substituents and are F and Cl.

In some embodiments of Formula IV, $R^{19a}$, $R^{19b}$, $R^{19c}$, and/or $R^{19d}$ is —$C_{1-2}$ alkyl.

In some embodiments of Formula IV, $R^{19a}$, $R^{19b}$, $R^{19c}$, and/or $R^{19d}$ is —$C_{1-3}$ alkyl.

In some embodiments of Formula IV, $R^{19a}$, $R^{19b}$, $R^{19c}$, and/or $R^{19d}$ is —$C_{1-4}$ alkyl.

In some embodiments of Formula IV, $R^{19a}$, $R^{19b}$, $R^{19c}$, and/or $R^{19d}$ is —$C_{1-5}$ alkyl.

In some embodiments of Formula IV, $R^{19a}$, $R^{19b}$, $R^{19c}$, and/or $R^{19d}$ is —$C_{1-6}$ alkyl.

In some embodiments of Formula IV, $R^{19a}$, $R^{19b}$, $R^{19c}$, and/or $R^{19d}$ is —$C_{2-6}$ alkyl.

In some embodiments of Formula IV, $R^{19a}$, $R^{19b}$, $R^{19c}$, and/or $R^{19d}$ is —$C_{3-6}$ alkyl.

In some embodiments of Formula IV, $R^{19a}$, $R^{19b}$, $R^{19c}$, and/or $R^{19d}$ is —$C_{4-6}$ alkyl.

In some embodiments of Formula IV, $R^{19a}$, $R^{19b}$, $R^{19c}$, and/or $R^{19d}$ is —$C_{2-5}$ alkyl.

In some embodiments of Formula IV, $R^{19a}$, $R^{19b}$, $R^{19c}$, and/or $R^{19d}$ is —$C_{3-5}$ alkyl.

In some embodiments of Formula IV, $R^{19a}$, $R^{19b}$, $R^{19c}$, and/or $R^{19d}$ is —$CH_2OH$.

In some embodiments of Formula IV, $R^{19a}$, $R^{19b}$, $R^{19c}$, and/or $R^{19d}$ is —$CH_2N(R^{13b})_2$.

In some embodiments of Formula IV, $R^{19a}$, $R^{19b}$, $R^{19c}$, and/or $R^{19d}$ is —$CH_2NH_2$.

In some embodiments of Formula IV, $R^{19a}$, $R^{19b}$, $R^{19c}$, and/or $R^{19d}$ is —$CH_2NHMe$.

In some embodiments of Formula IV, $R^{19a}$, $R^{19b}$, $R^{19c}$, and/or $R^{19d}$ is —CH$_2$NMe$_2$.

In some embodiments of Formula IV, $R^{19a}$, $R^{19b}$, $R^{19c}$, and/or $R^{19d}$ is —CH$_2$NHEt.

In some embodiments of Formula IV, $R^{19a}$, $R^{19b}$, $R^{19c}$, and/or $R^{19d}$ is —CH$_2$N(Me)(Et).

In some embodiments of Formula IV, $R^{19a}$, $R^{19b}$, $R^{19c}$, and/or $R^{19d}$ is —CH$_2$NEt$_2$.

In some embodiments of Formula IV,

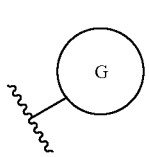

is selected from the group consisting of:

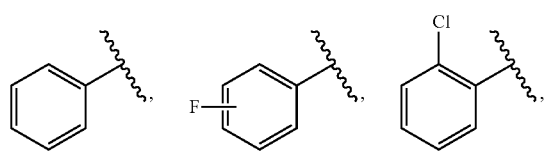

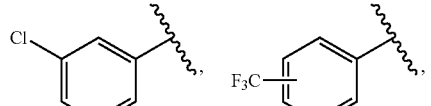

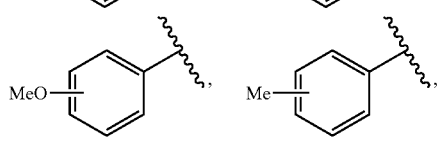

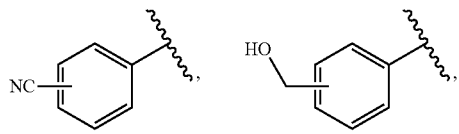

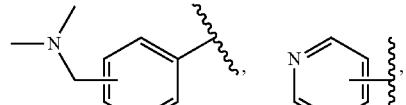

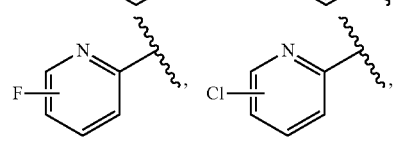

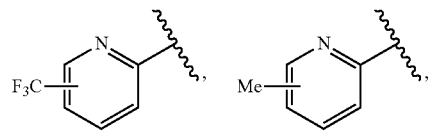

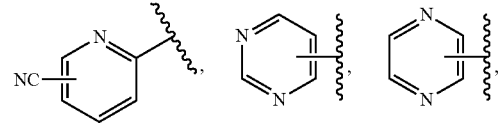

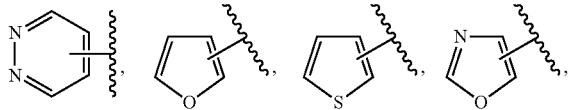

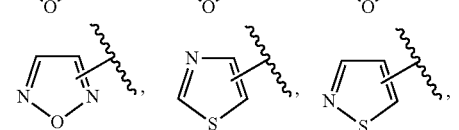

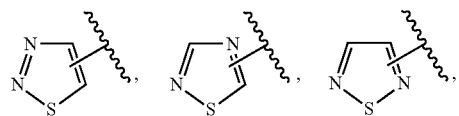

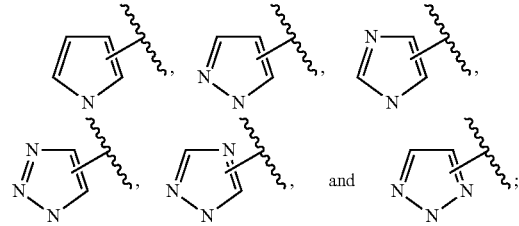

wherein the carbonyl carbon of Formula IV can form a bond with any unsubstituted carbon on the Ring G.

In some embodiments of Formula IV,

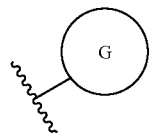

is selected from the group consisting of:

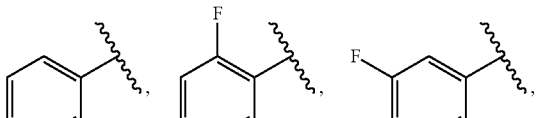

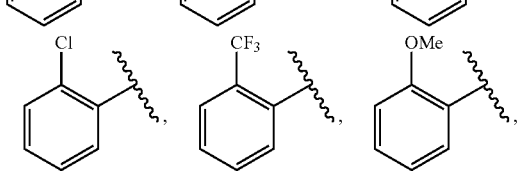

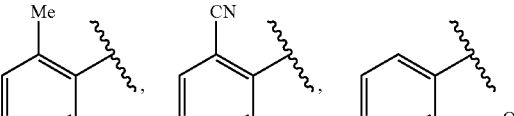

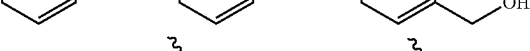

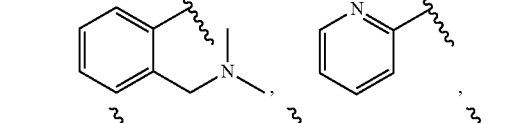

-continued
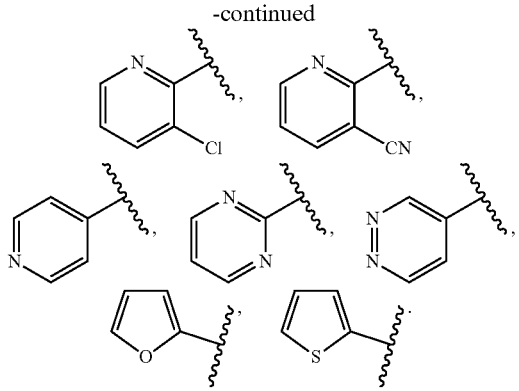
In some embodiments of Formula IV,
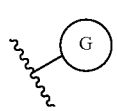
is selected from the group consisting of:
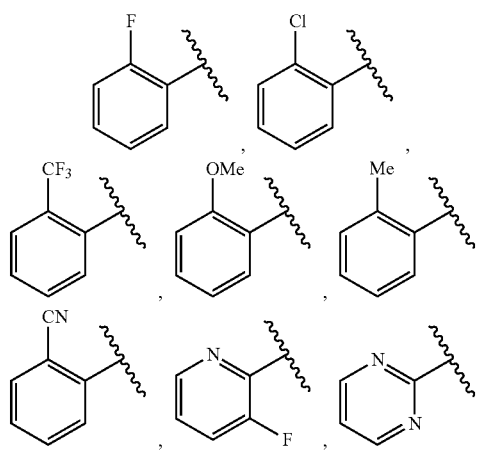
Illustrative compounds of Formulas I, Ia, Ib, Ic, Id, Ie, If, Ig, Ih, Ii, II, IIa, IIb, IIc, IId, IIe, IIf, III, IIIa, IIIb, IIIc, IIId, and IV are shown in Table 1.
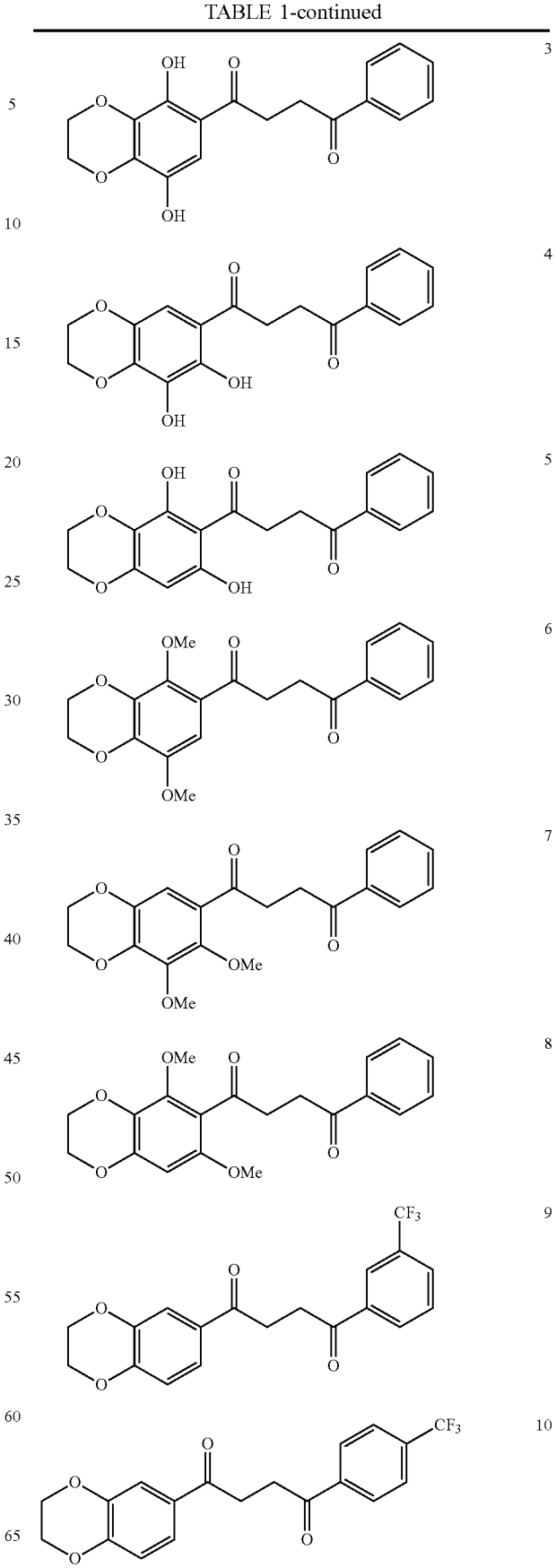

TABLE 1-continued
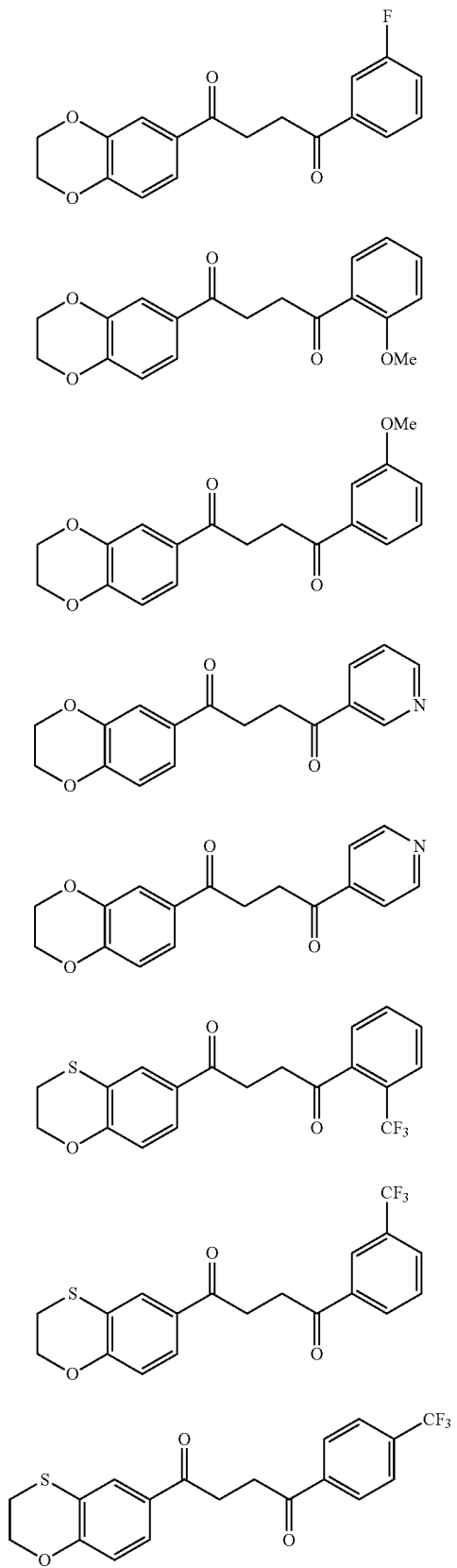
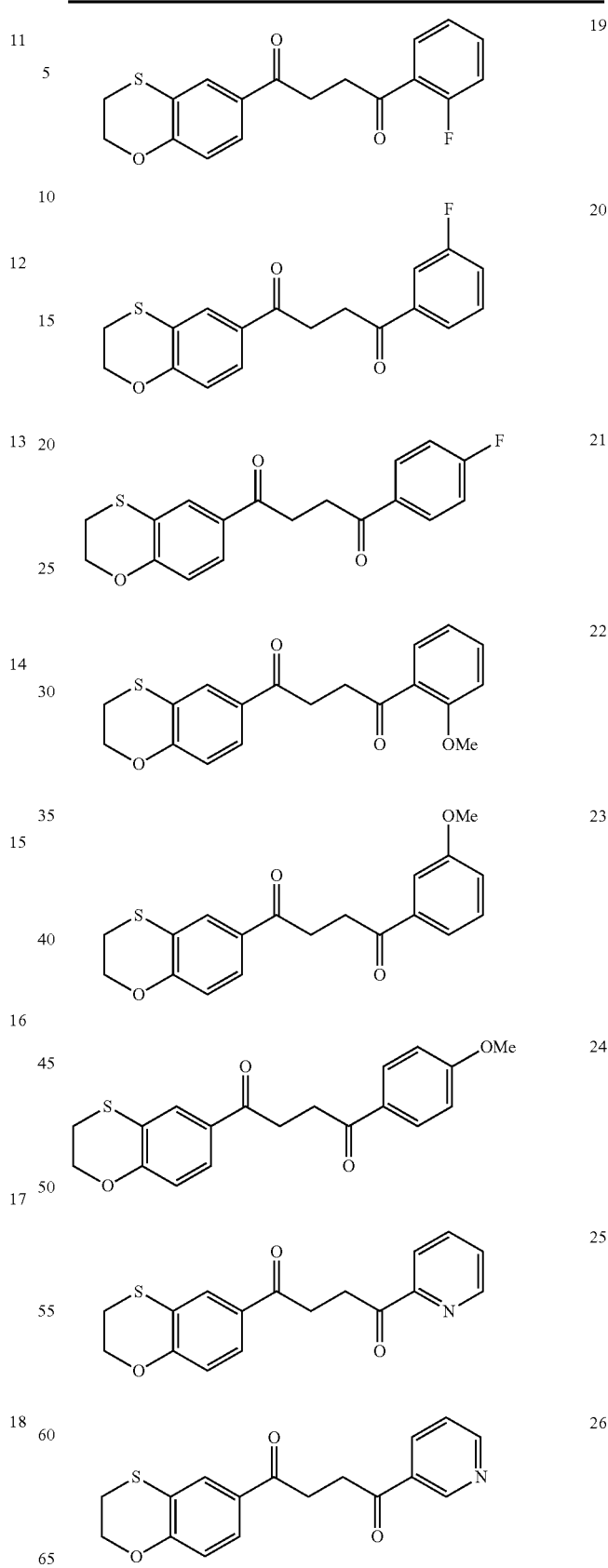

TABLE 1-continued
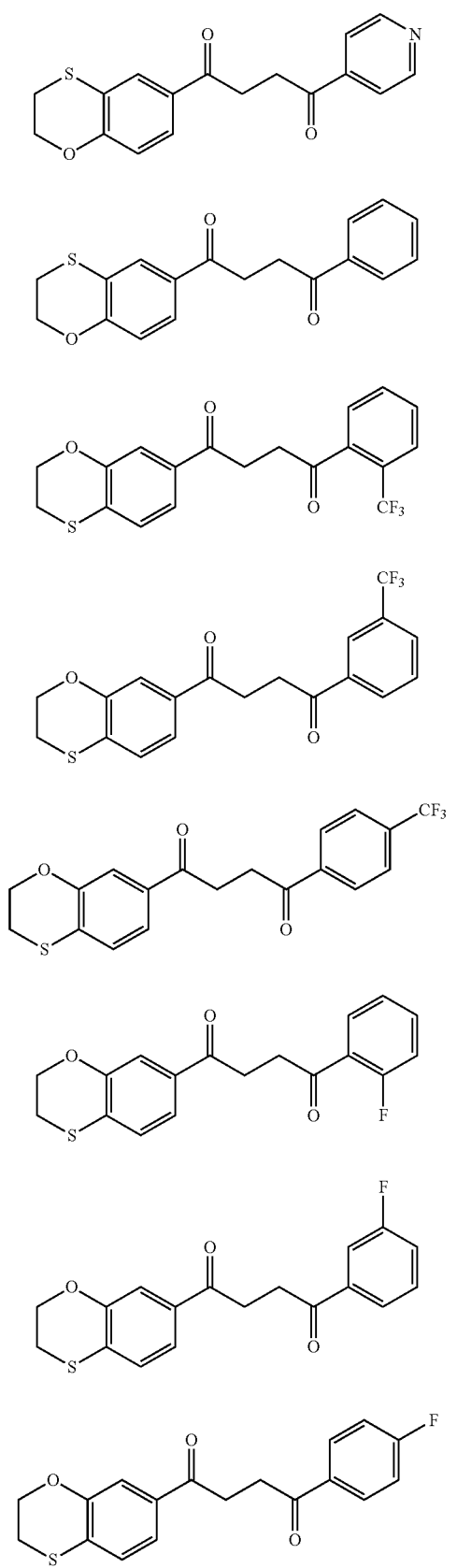
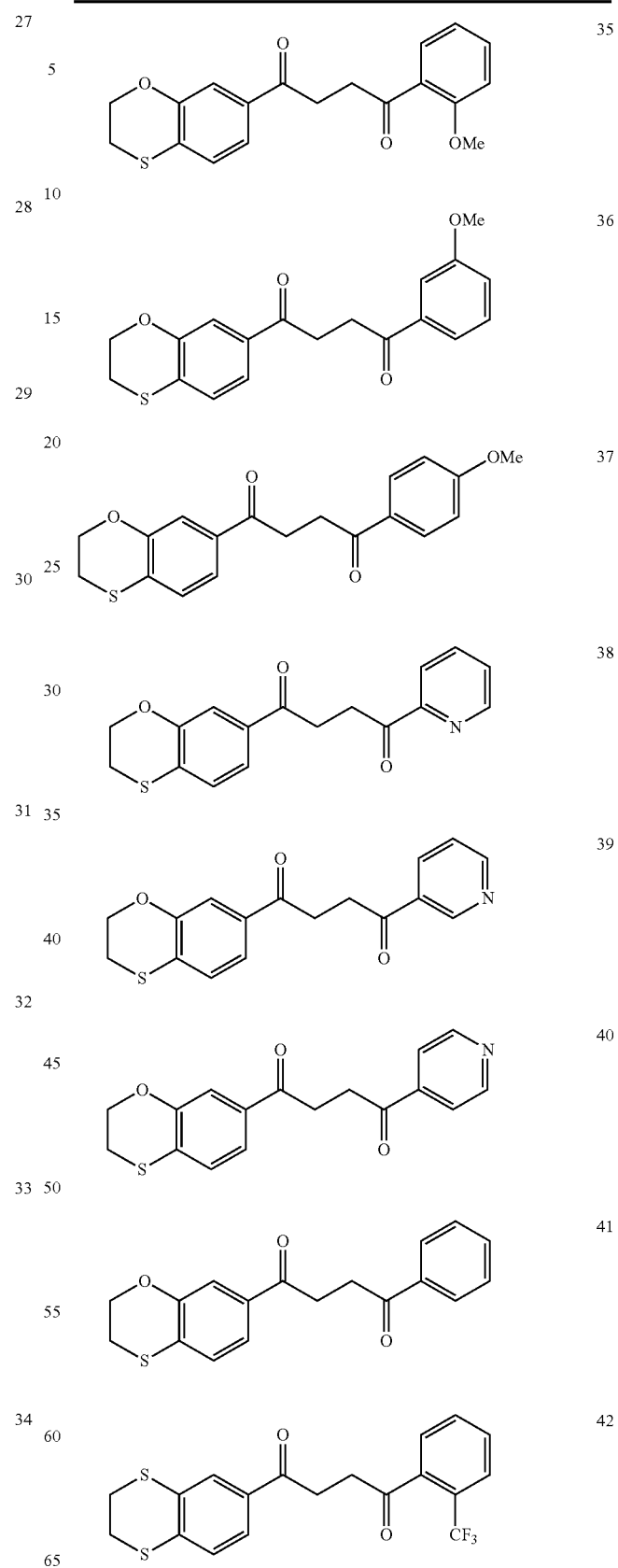

TABLE 1-continued
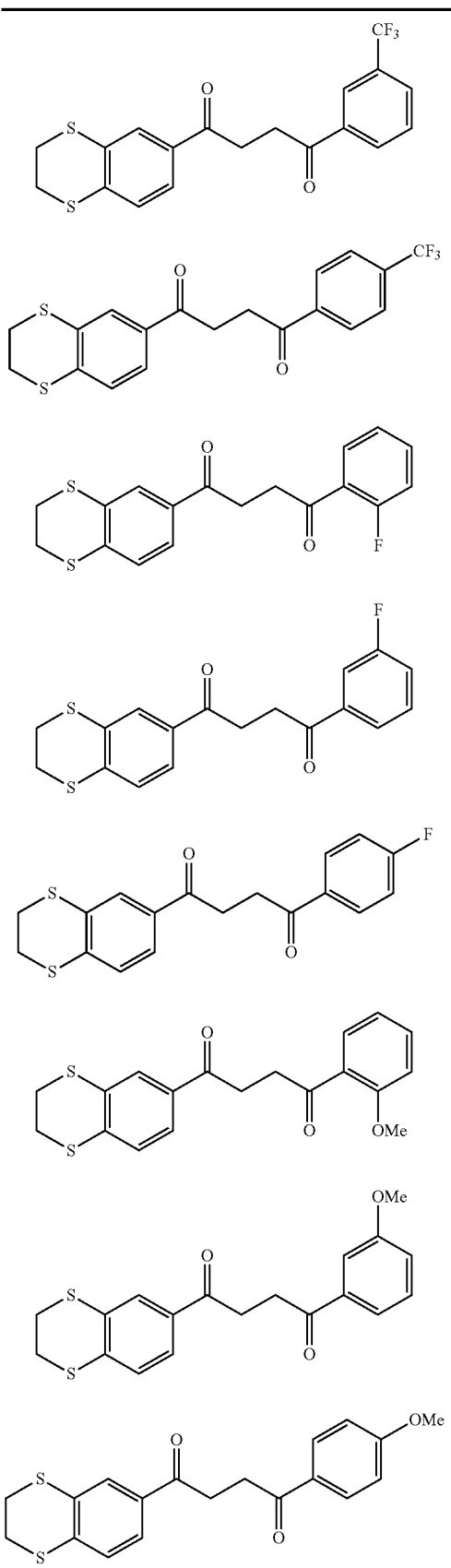
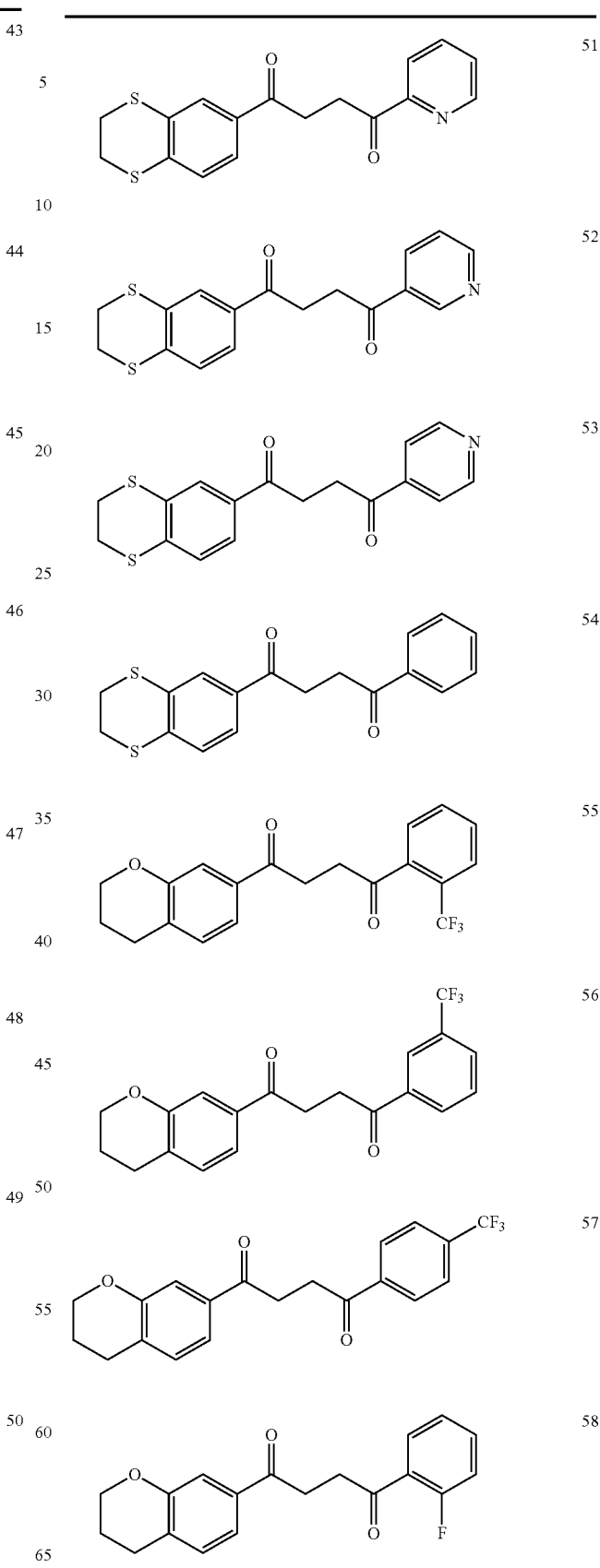

TABLE 1-continued
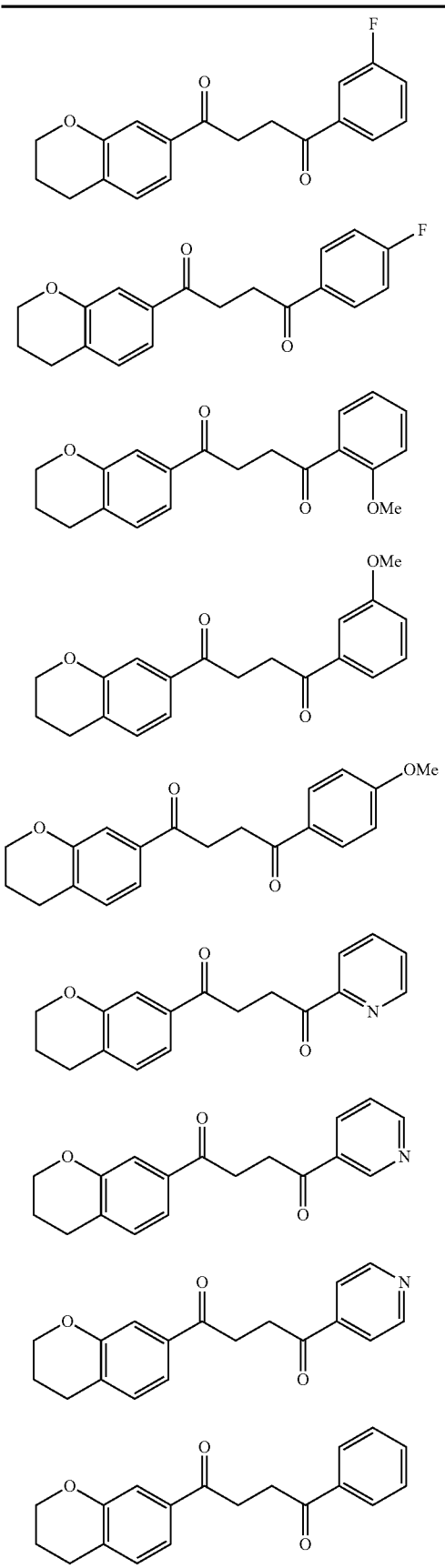
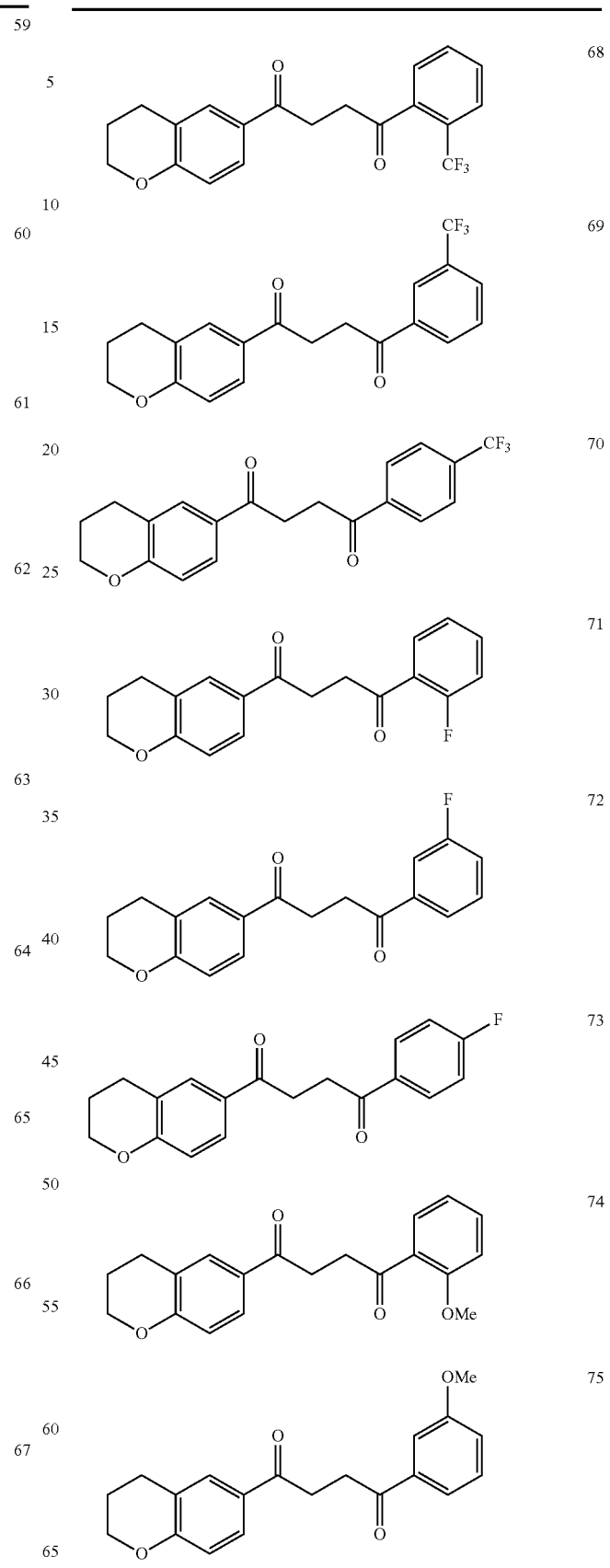

TABLE 1-continued
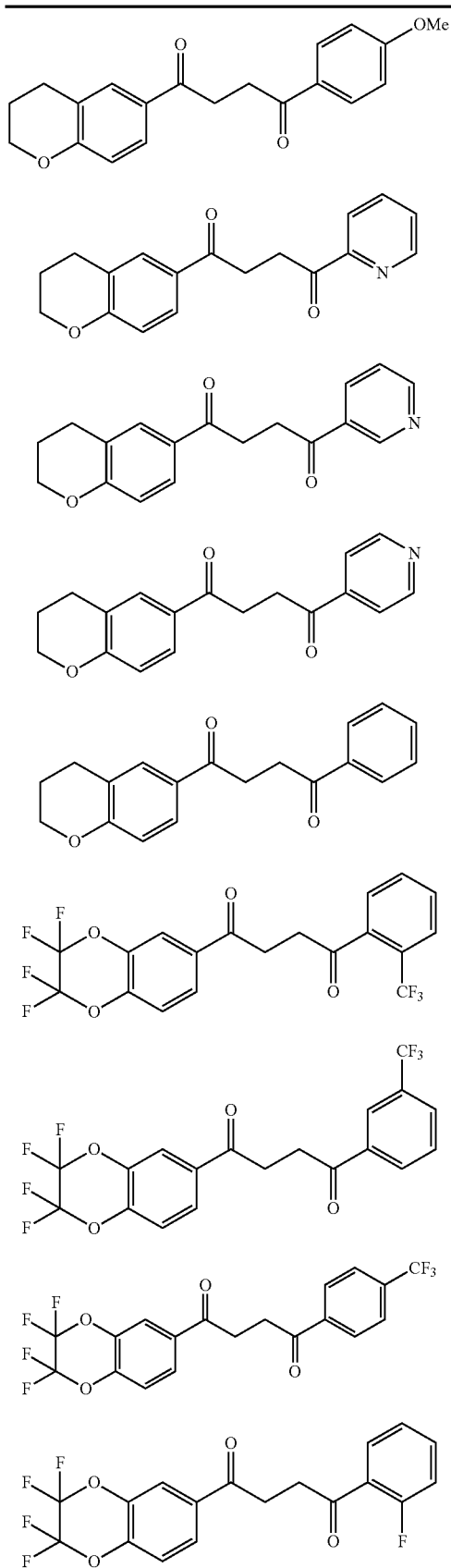
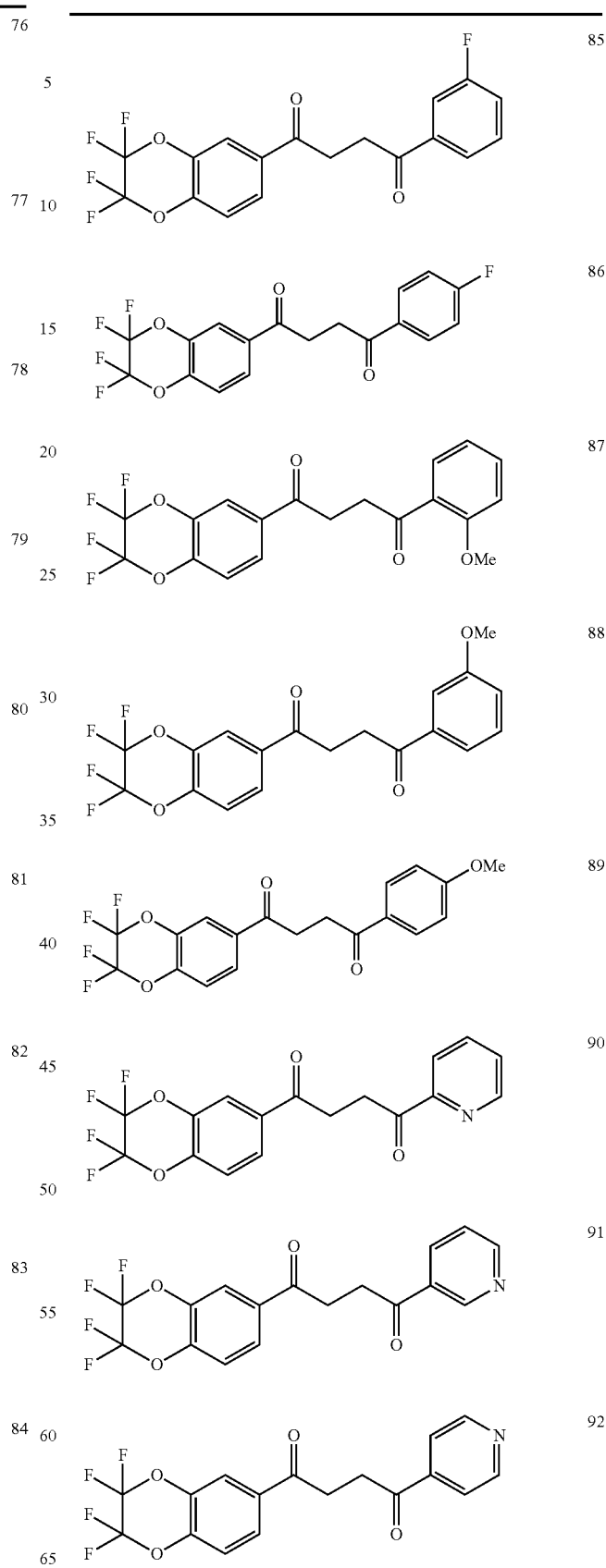

TABLE 1-continued
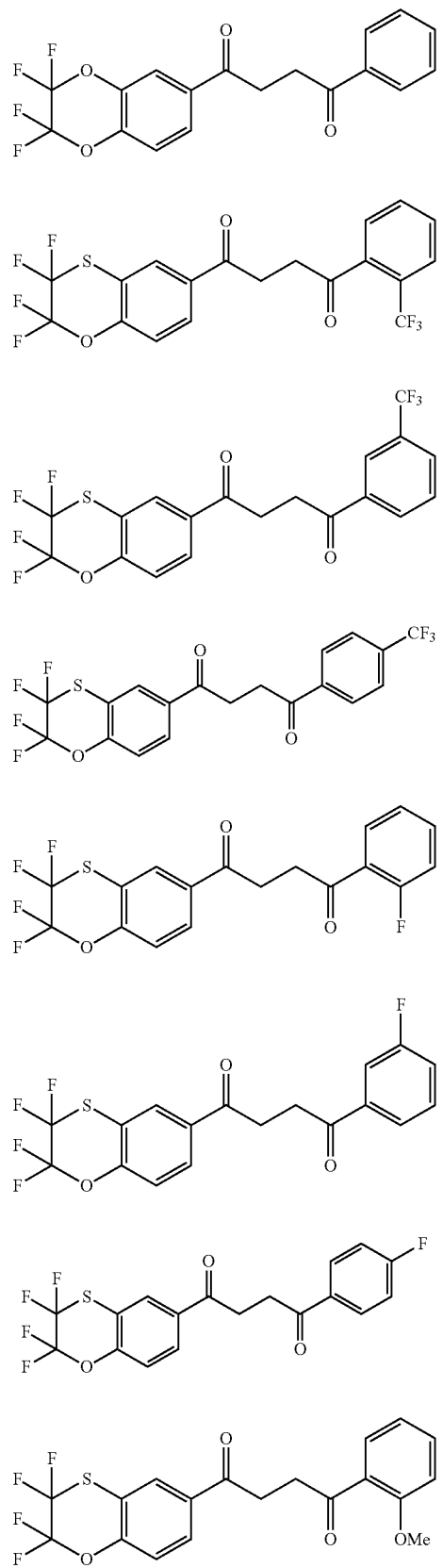
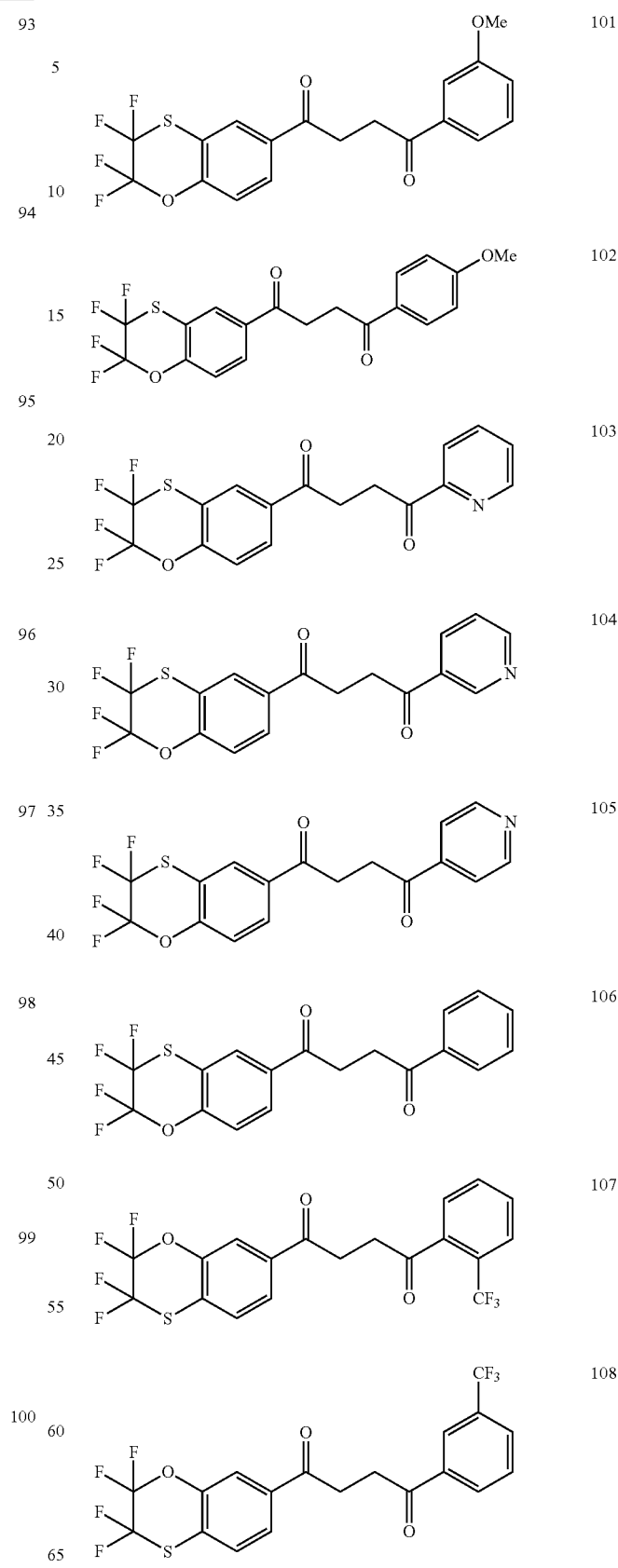

TABLE 1-continued
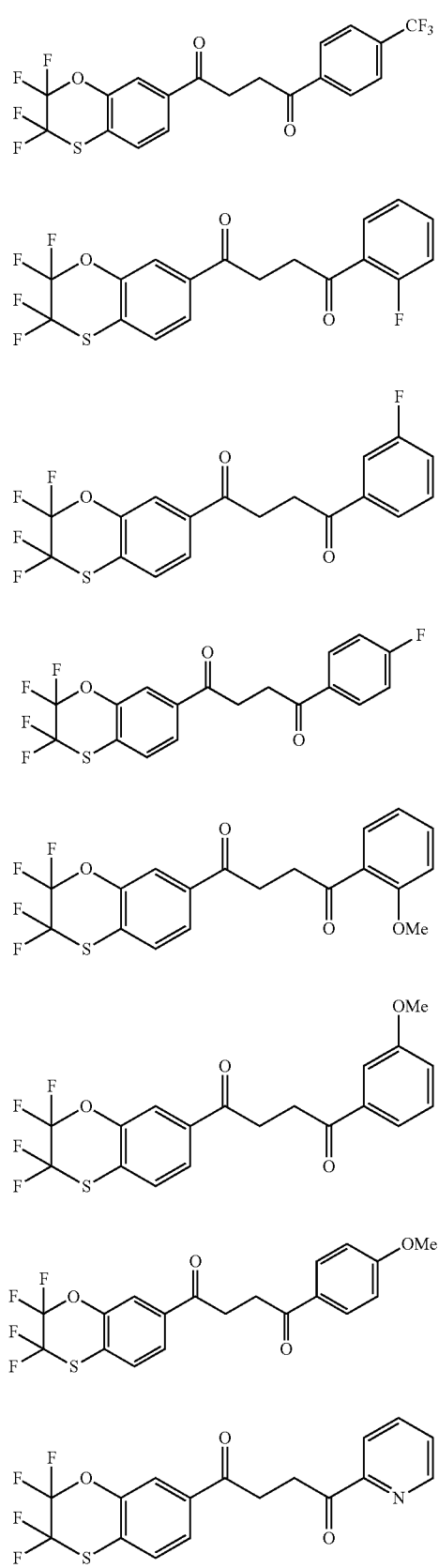
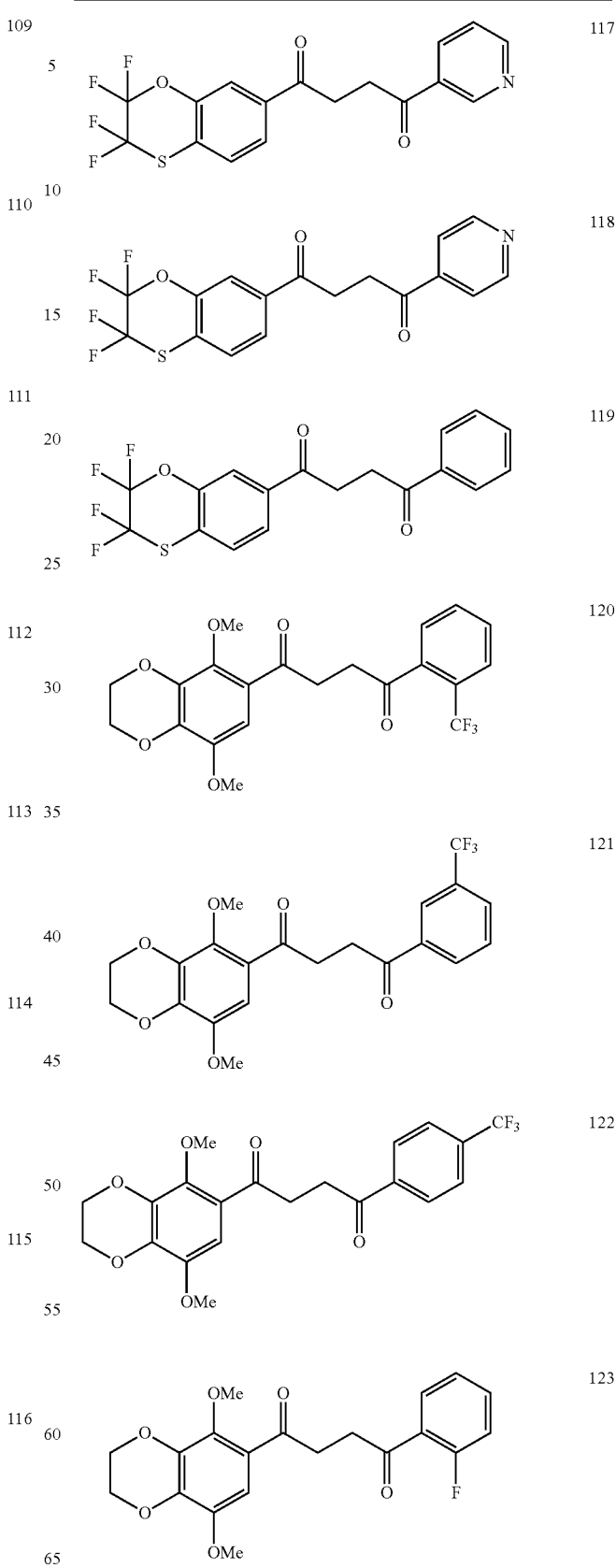

TABLE 1-continued
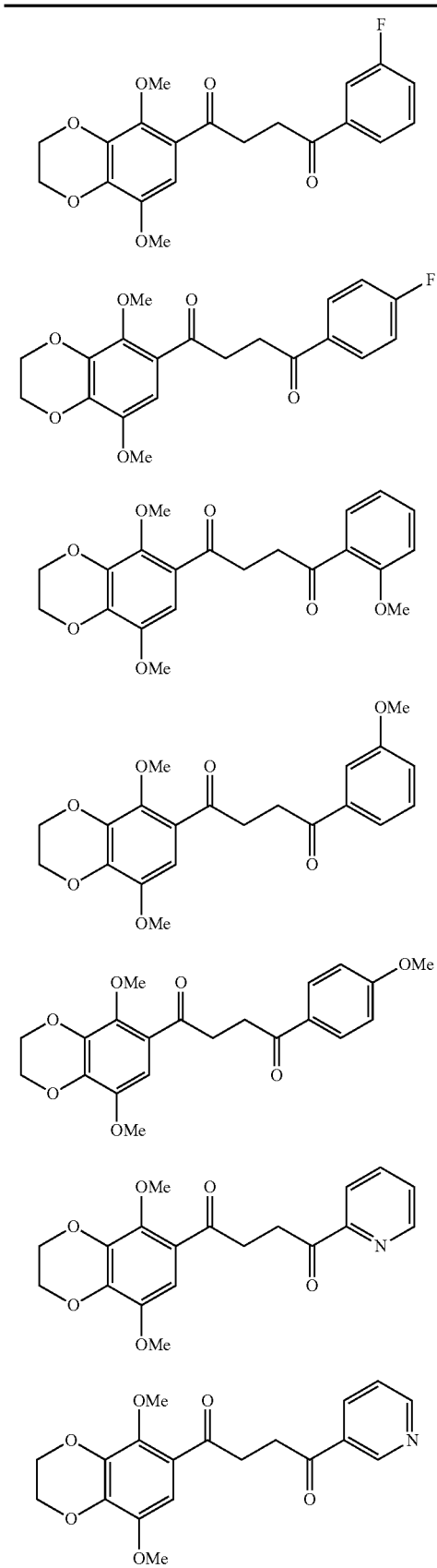
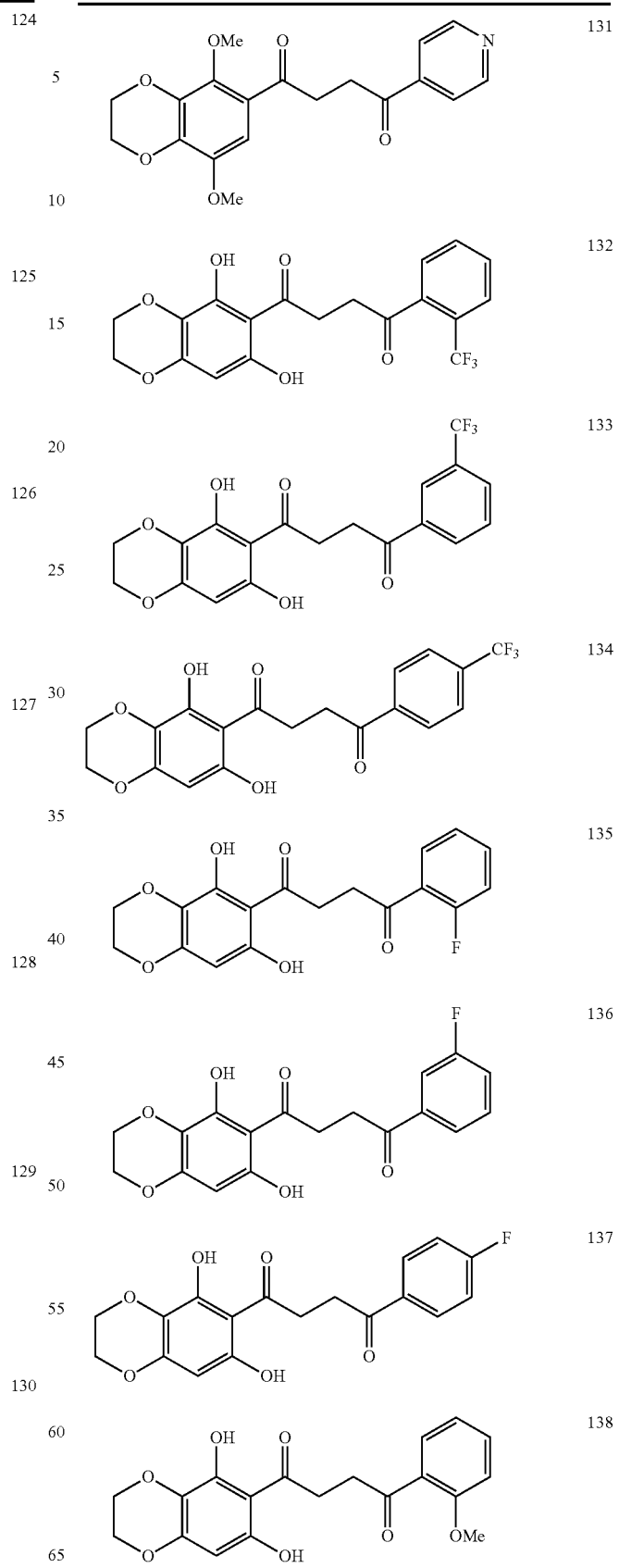

TABLE 1-continued
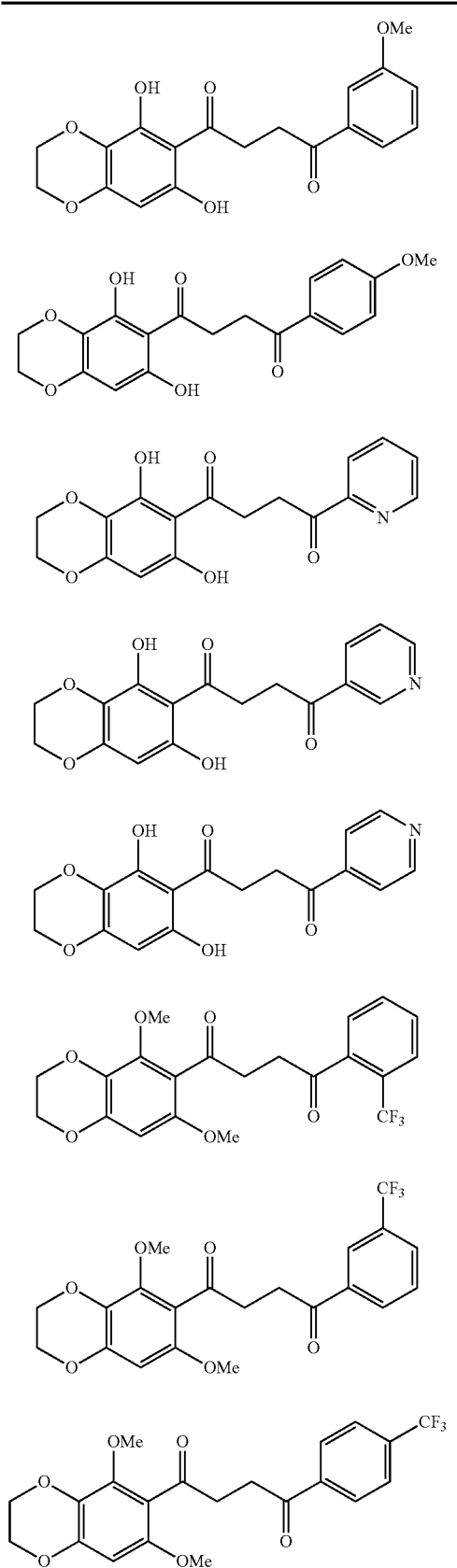
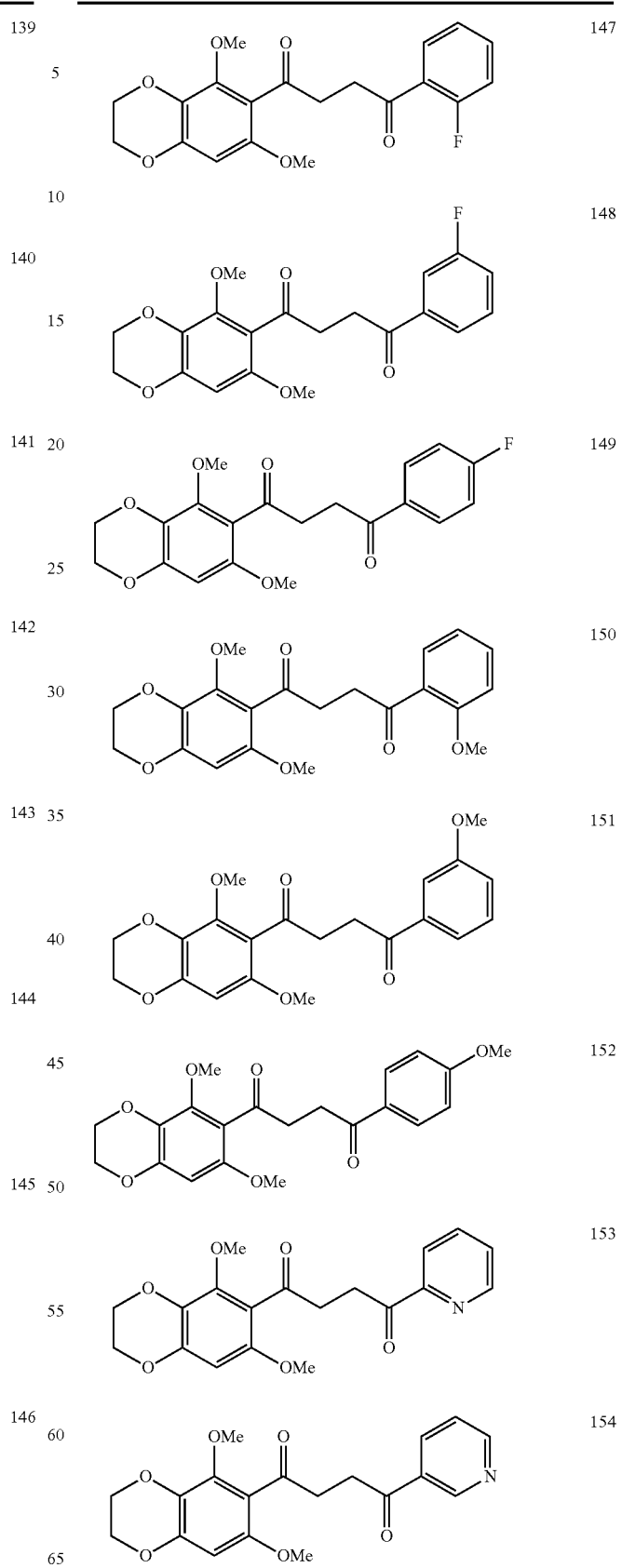

TABLE 1-continued
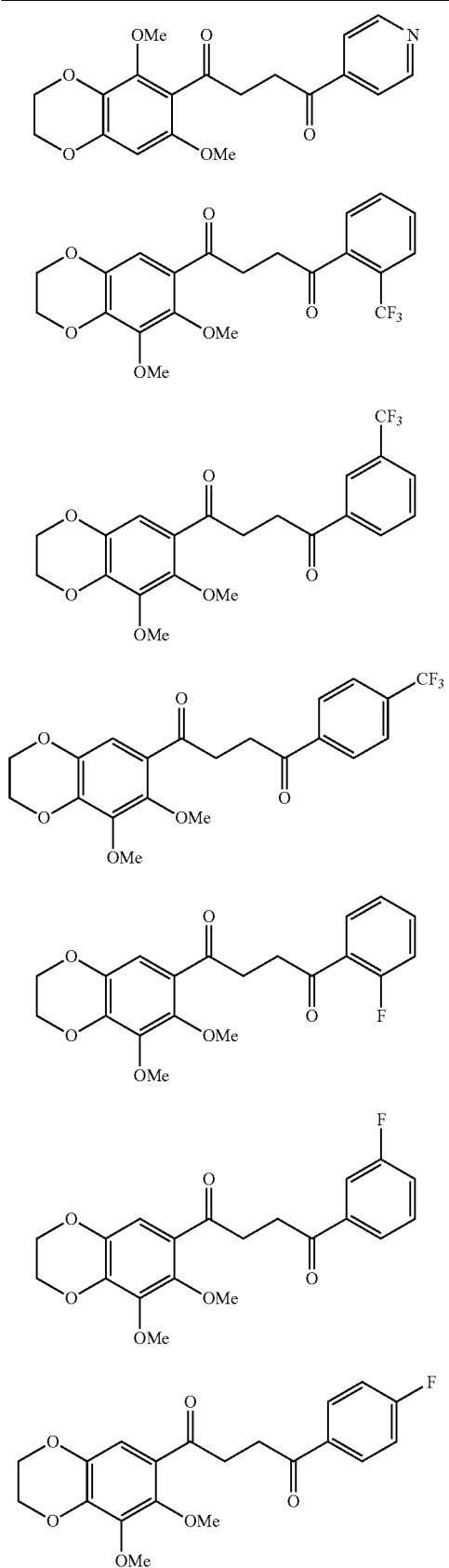
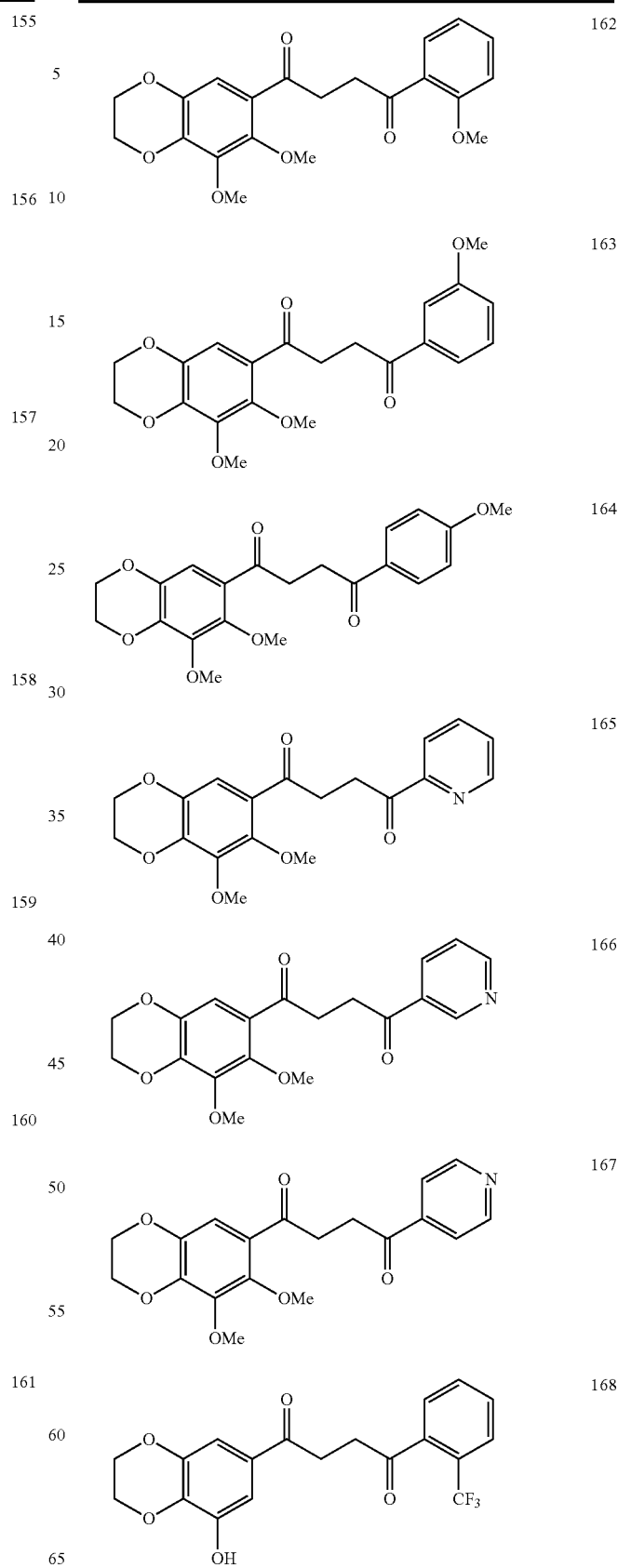

TABLE 1-continued
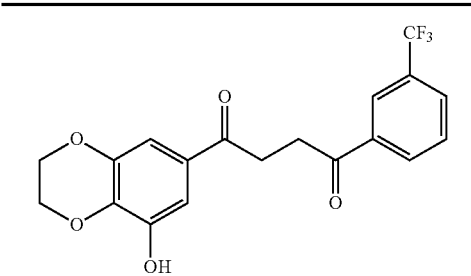 169
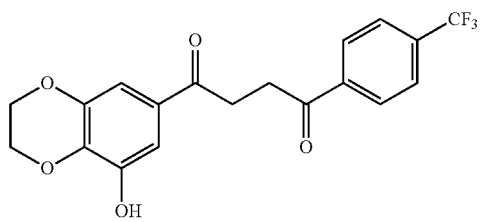 [SMILES: O=C(CCC(=O)c1cc(O)c2c(c1)OCCO2)c1ccc(C(F)(F)F)cc1] 170
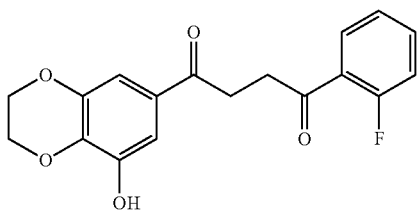 [SMILES: O=C(CCC(=O)c1ccccc1F)c1cc(O)c2c(c1)OCCO2] 171
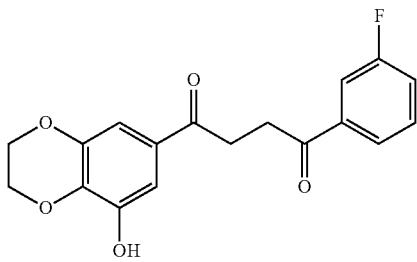 [SMILES: O=C(CCC(=O)c1cc(O)c2c(c1)OCCO2)c1cccc(F)c1] 172
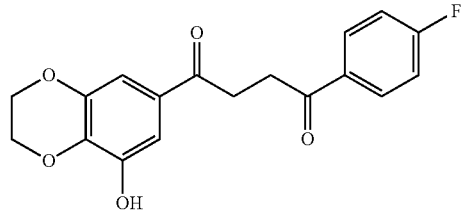 [SMILES: O=C(CCC(=O)c1cc(O)c2c(c1)OCCO2)c1ccc(F)cc1] 173
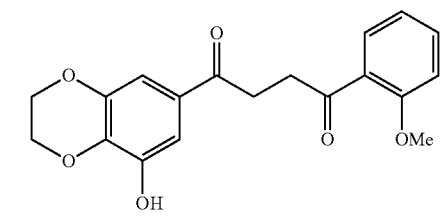 [SMILES: COc1ccccc1C(=O)CCC(=O)c1cc(O)c2c(c1)OCCO2] 174
TABLE 1-continued
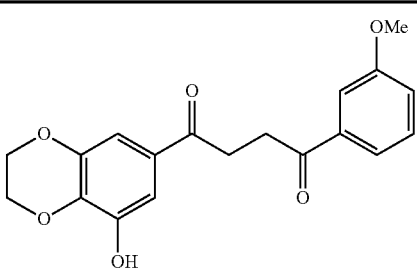 175
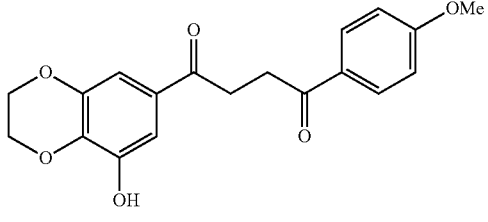 [SMILES: COc1ccc(C(=O)CCC(=O)c2cc(O)c3c(c2)OCCO3)cc1] 176
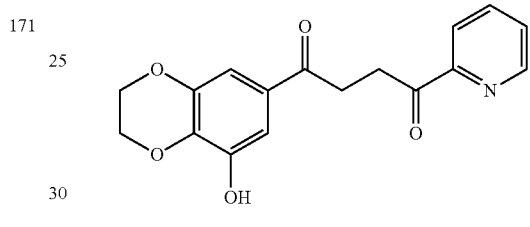 177
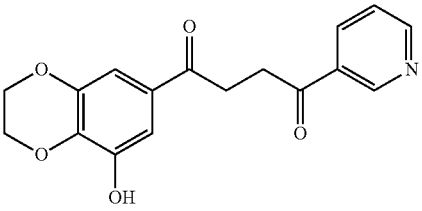 [SMILES: O=C(CCC(=O)c1cc(O)c2c(c1)OCCO2)c1cccnc1] 178
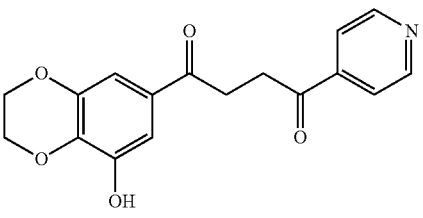 [SMILES: O=C(CCC(=O)c1cc(O)c2c(c1)OCCO2)c1ccncc1] 179
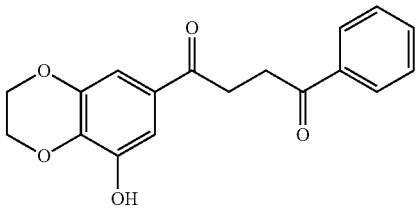 [SMILES: O=C(CCC(=O)c1cc(O)c2c(c1)OCCO2)c1ccccc1] 180
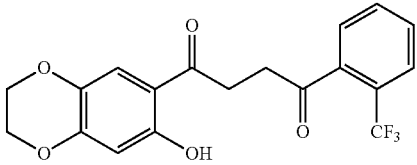 [SMILES: O=C(CCC(=O)c1ccccc1C(F)(F)F)c1cc2c(cc1O)OCCO2] 181

TABLE 1-continued
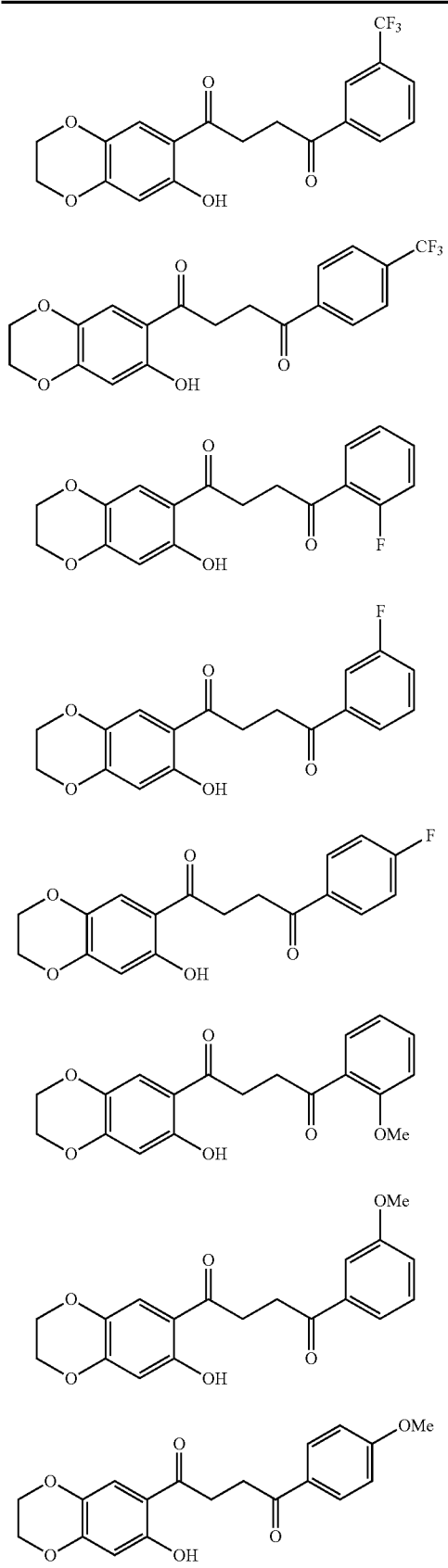
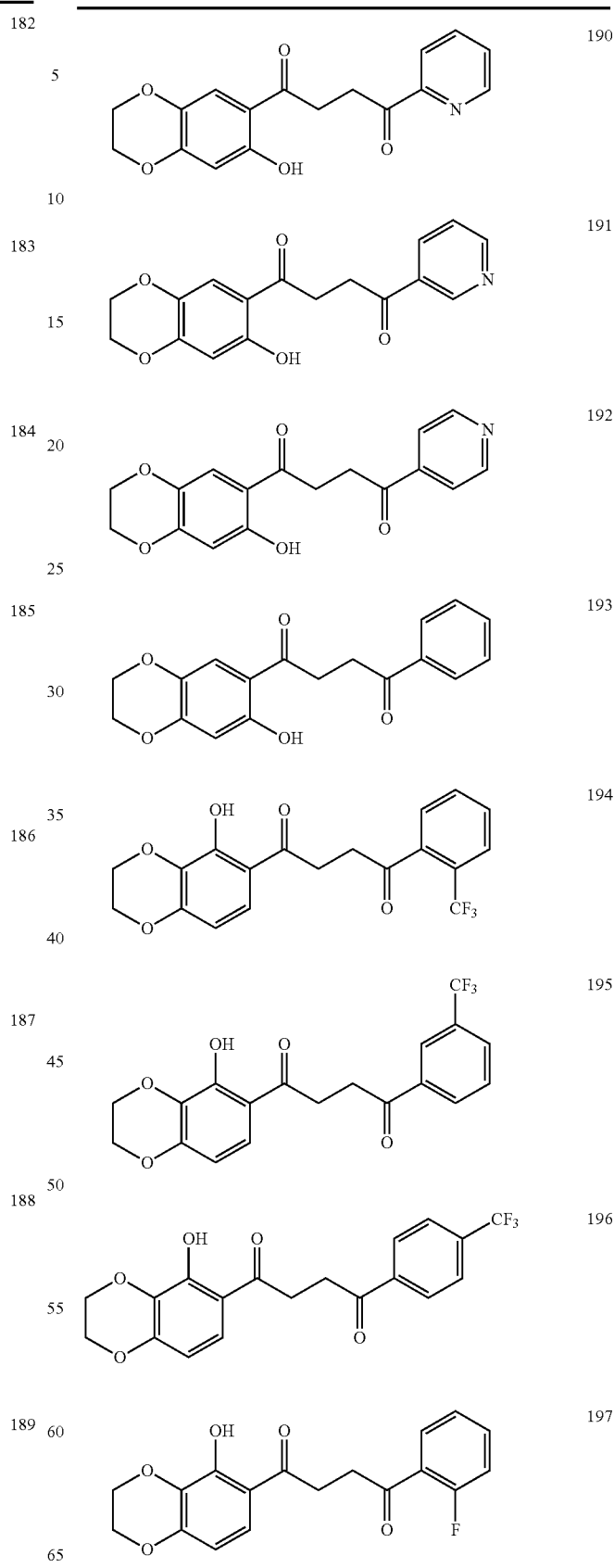

TABLE 1-continued
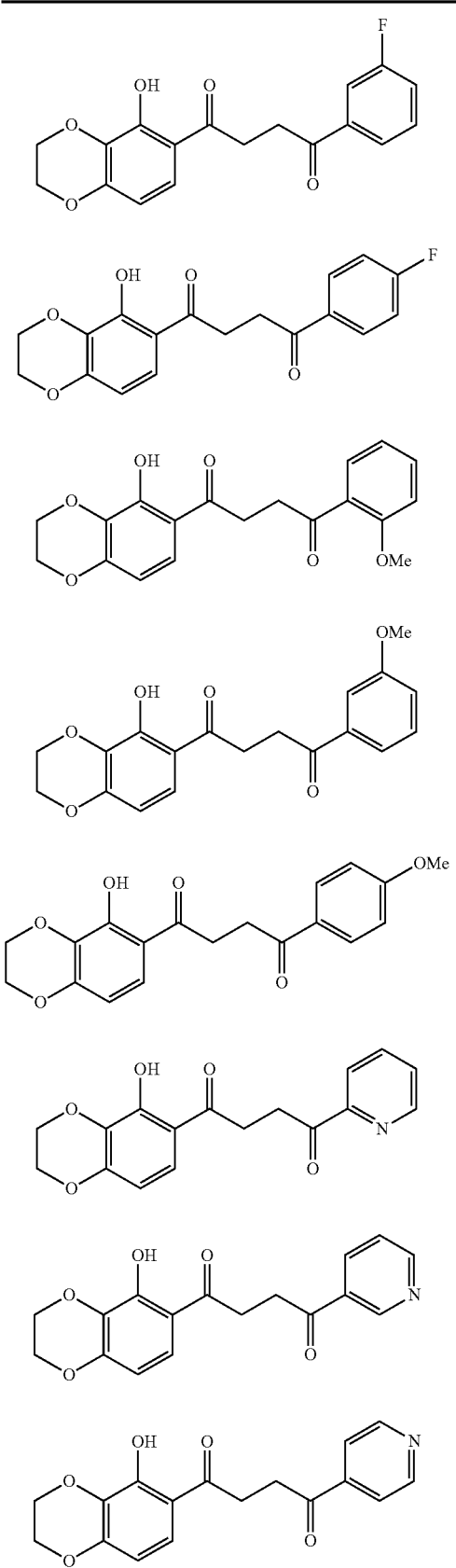
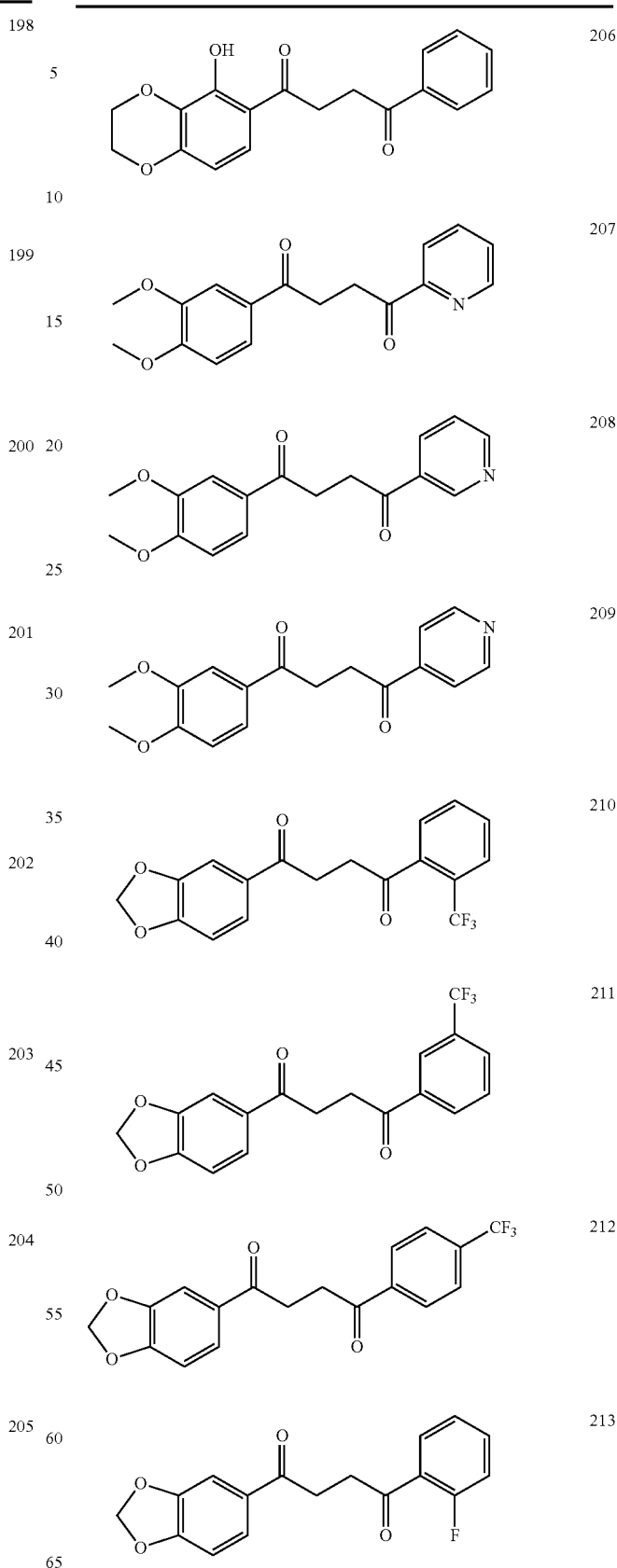

TABLE 1-continued
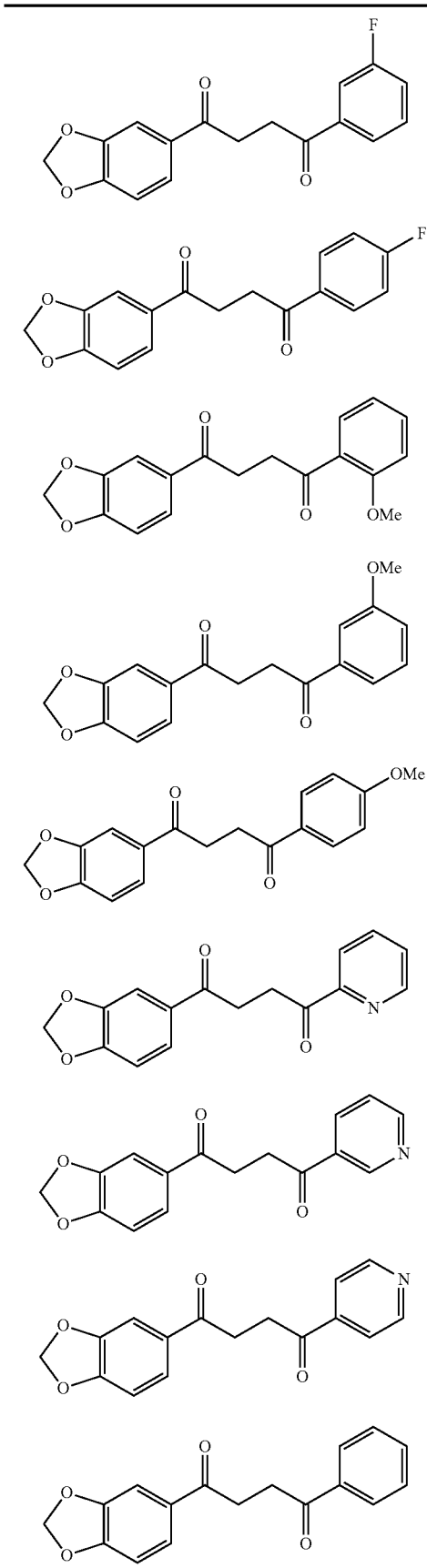
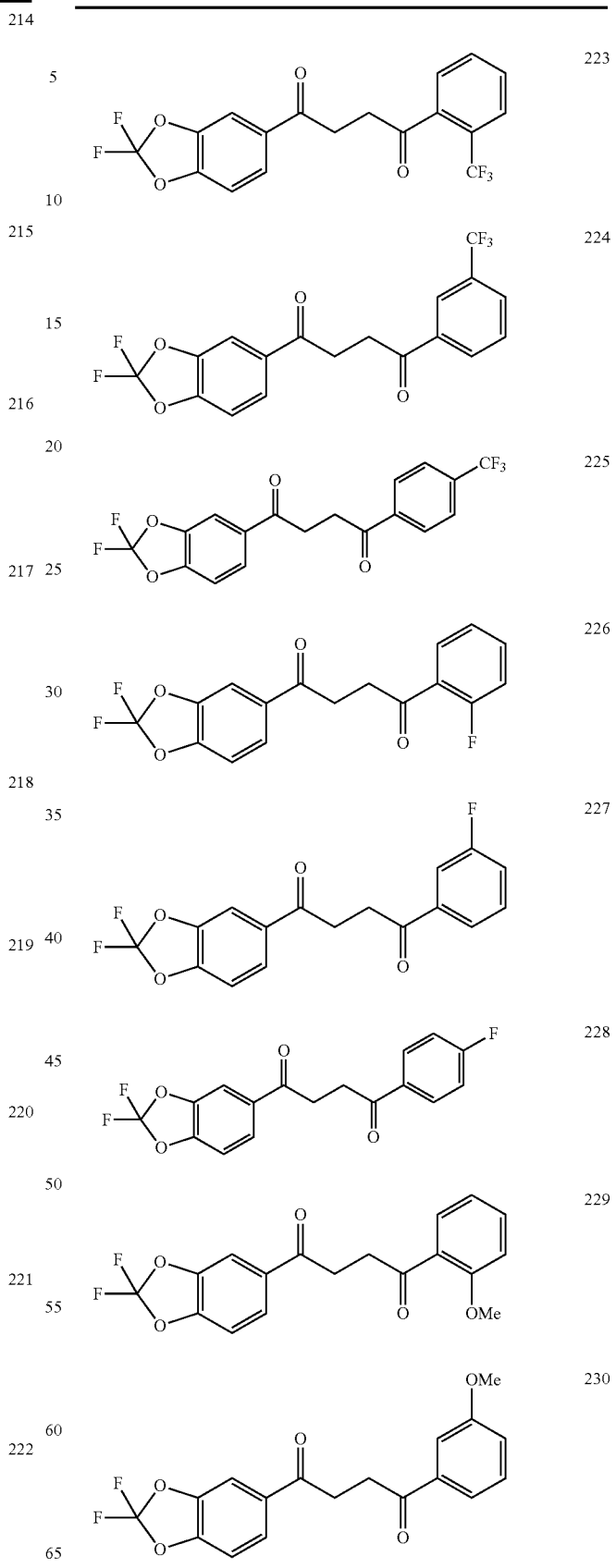

TABLE 1-continued
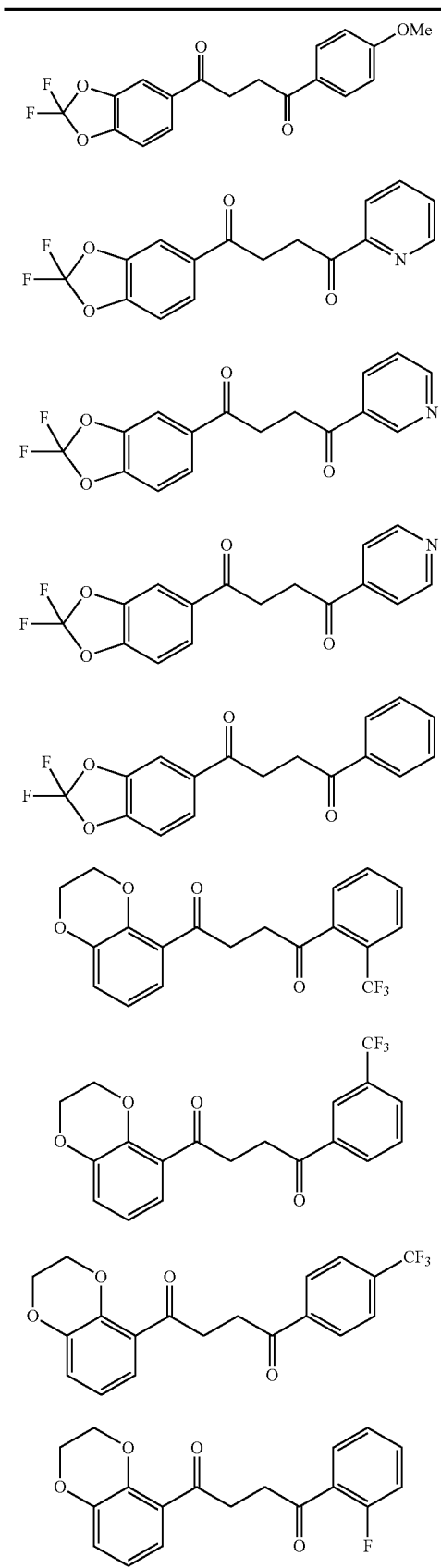
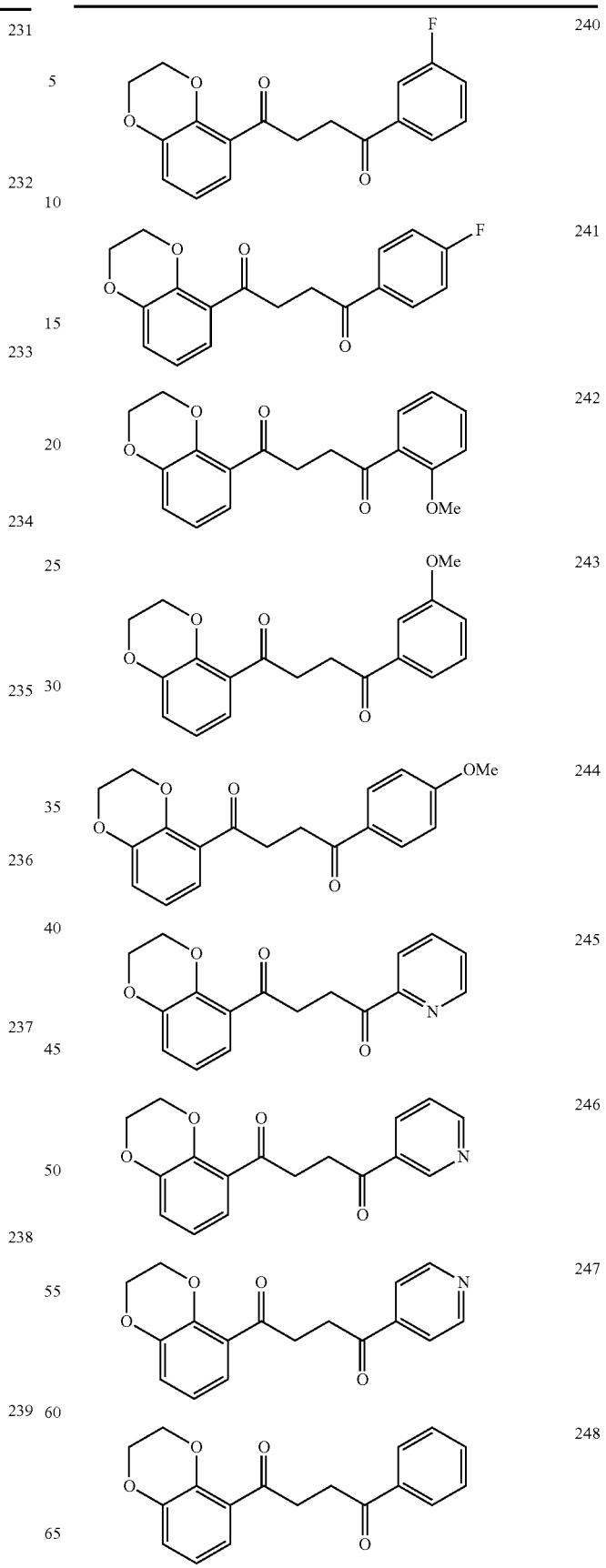

TABLE 1-continued
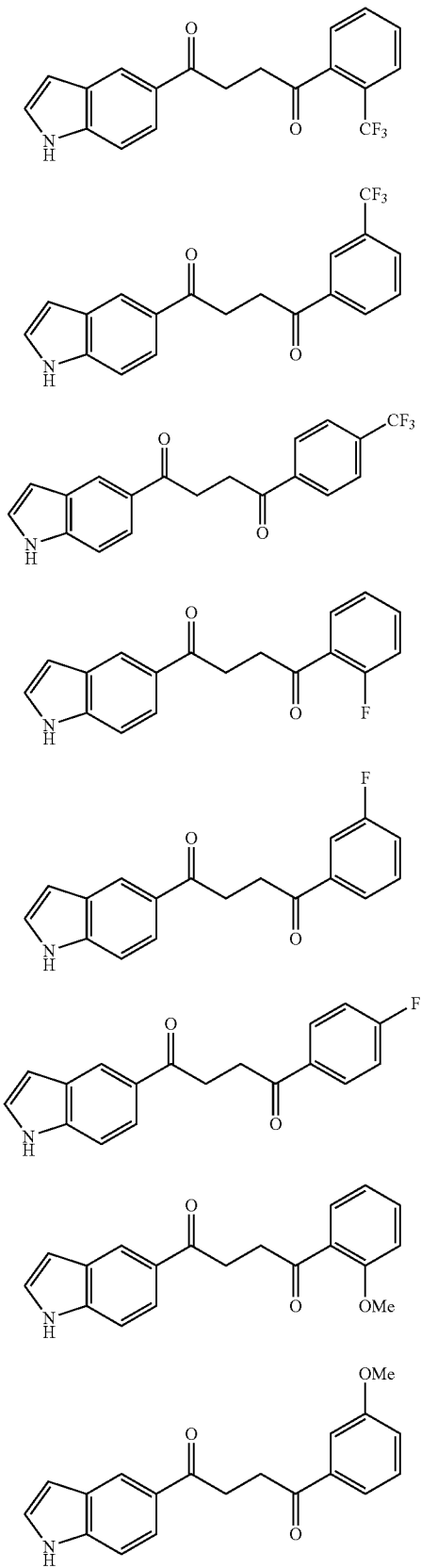
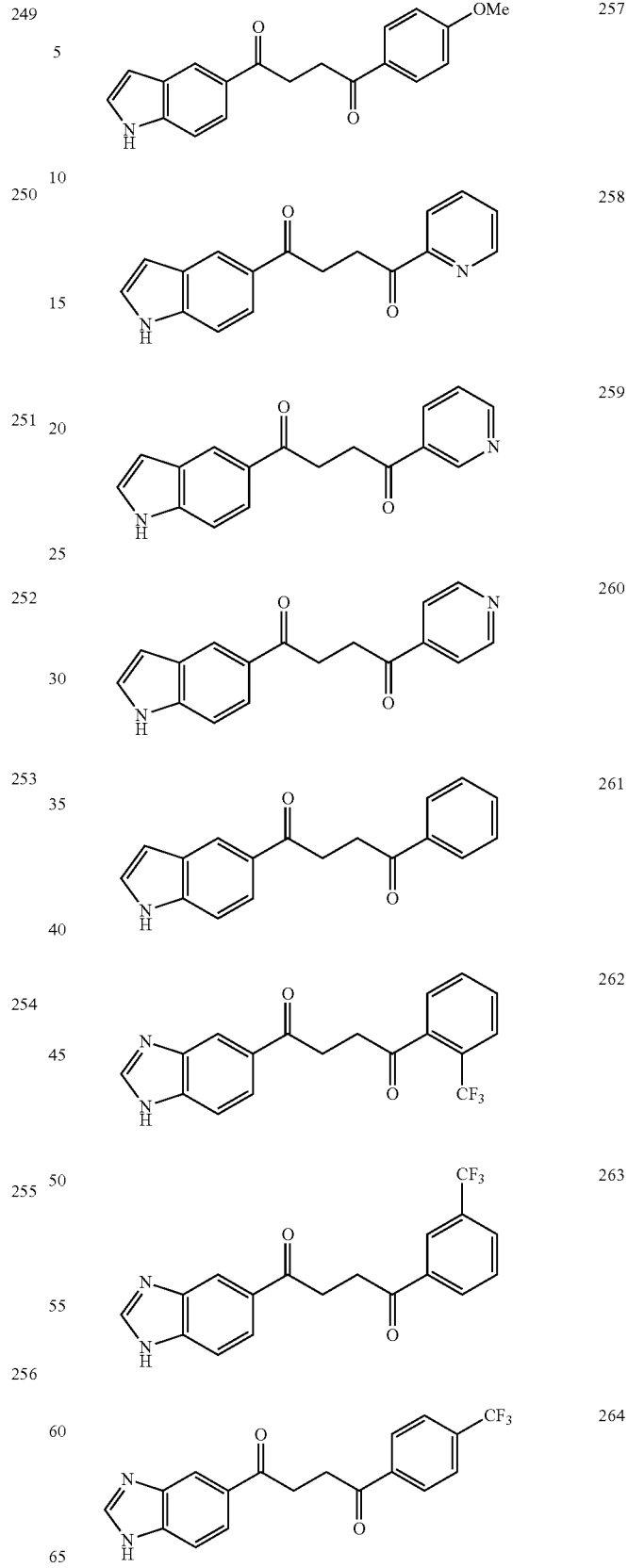

TABLE 1-continued
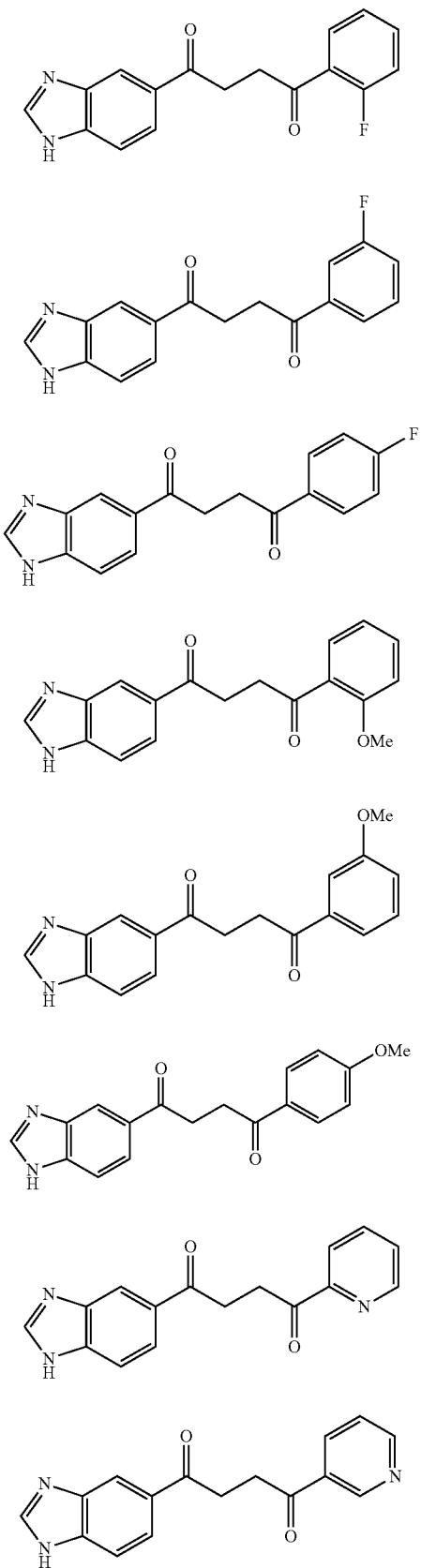
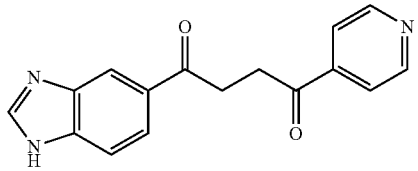 [SMILES: O=C(CCC(=O)c1ccc2[nH]cnc2c1)c1ccncc1]
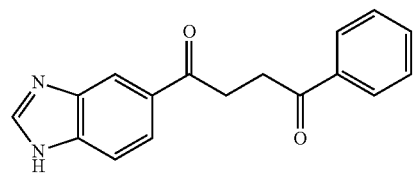 [SMILES: O=C(CCC(=O)c1ccc2[nH]cnc2c1)c1ccccc1]
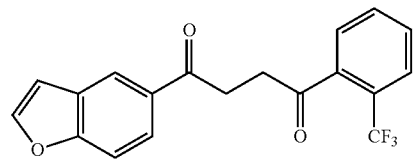 [SMILES: O=C(CCC(=O)c1ccccc1C(F)(F)F)c1ccc2occc2c1]
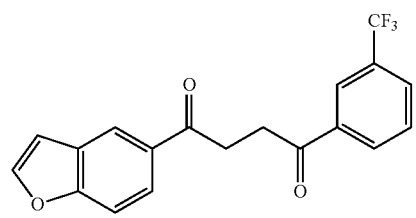 [SMILES: O=C(CCC(=O)c1ccc2occc2c1)c1cccc(C(F)(F)F)c1]
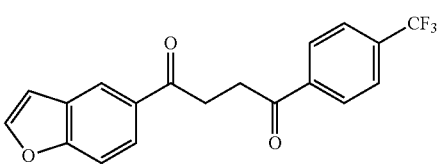 [SMILES: O=C(CCC(=O)c1ccc2occc2c1)c1ccc(C(F)(F)F)cc1]
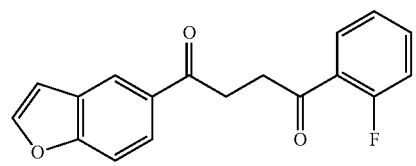 [SMILES: O=C(CCC(=O)c1ccccc1F)c1ccc2occc2c1]
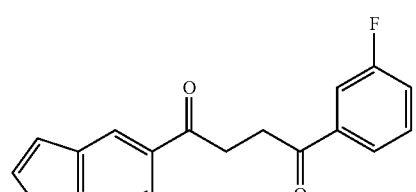
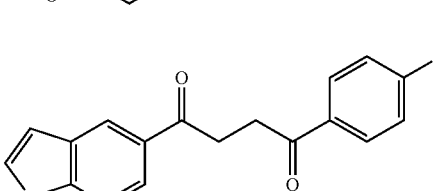

TABLE 1-continued
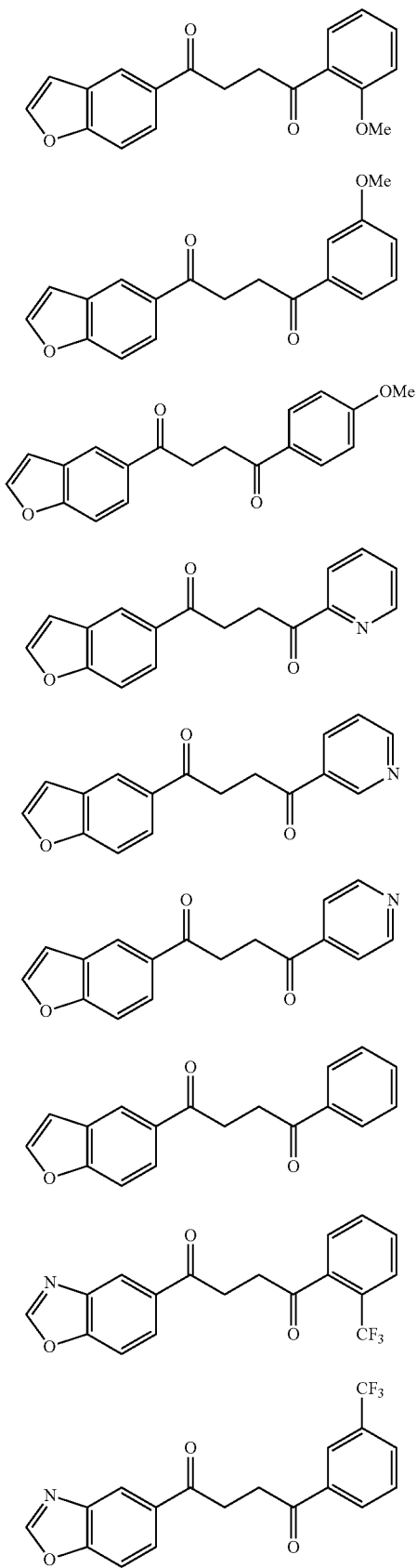
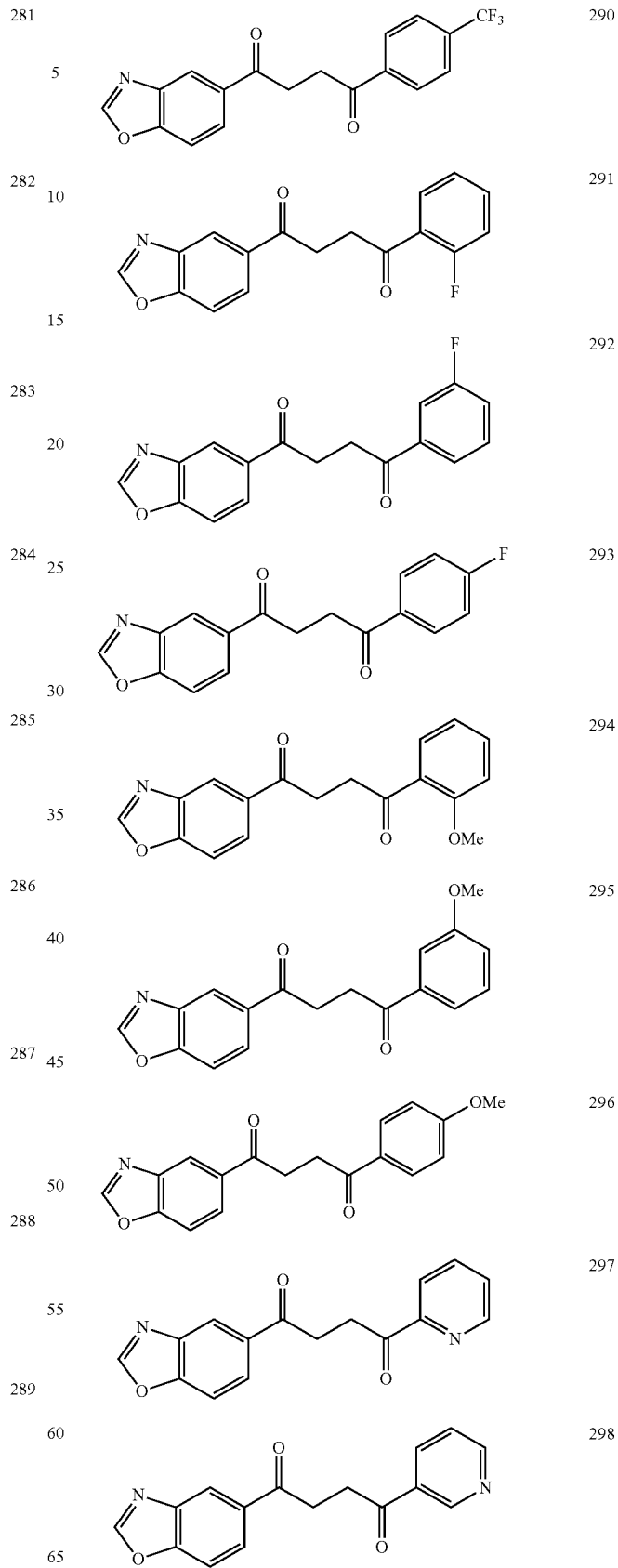

TABLE 1-continued
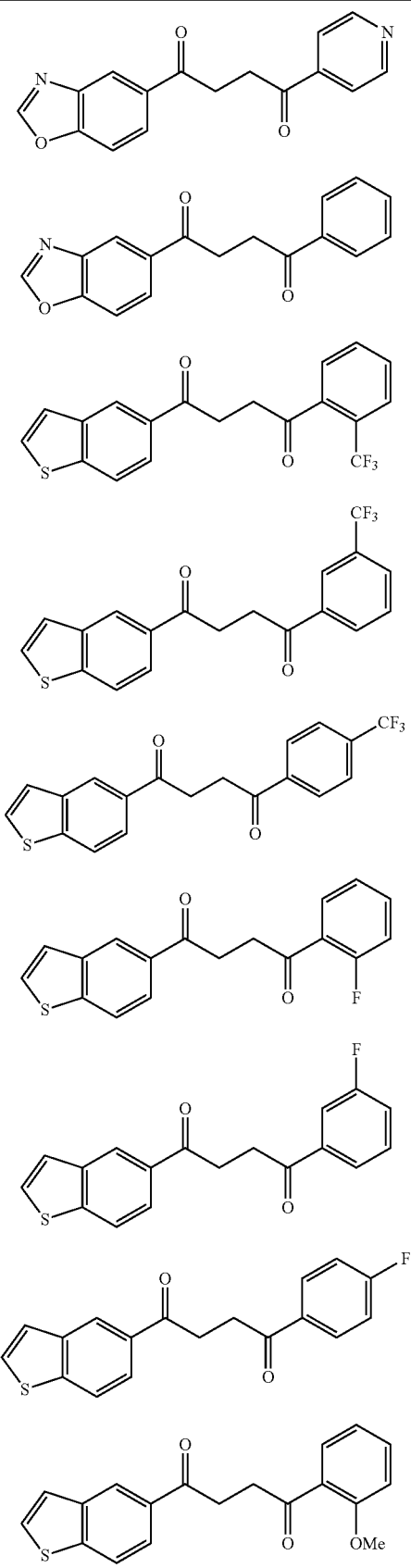
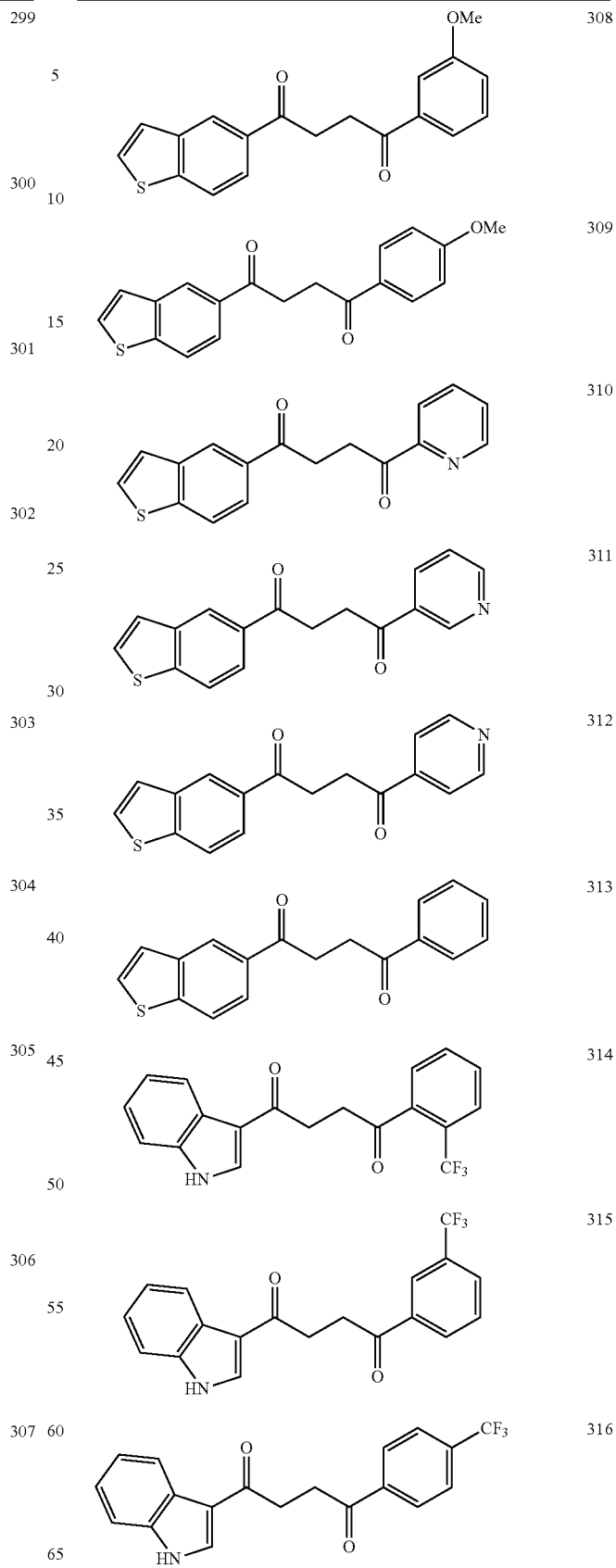

TABLE 1-continued
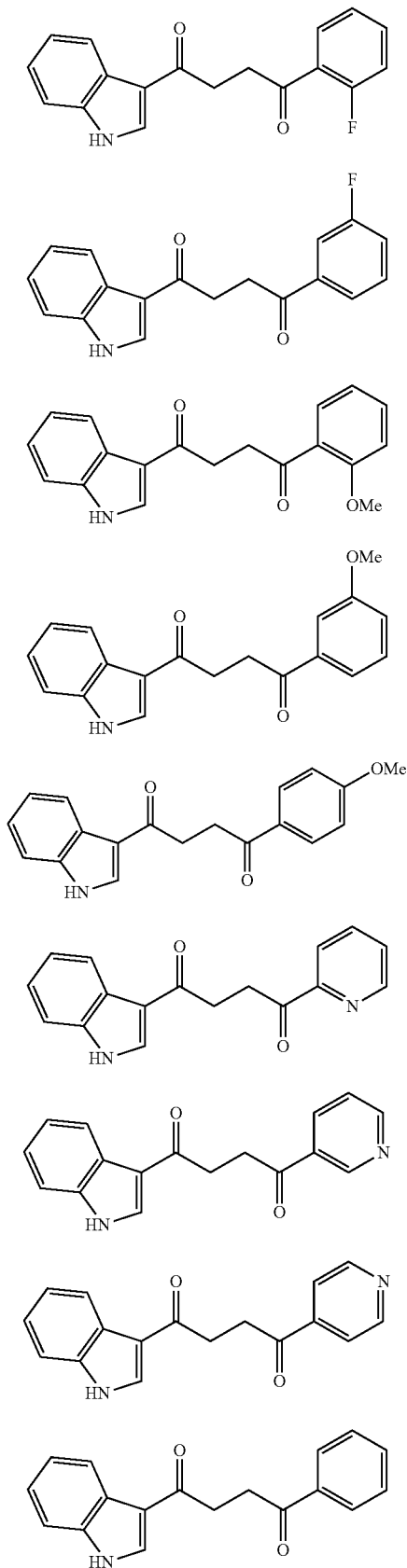
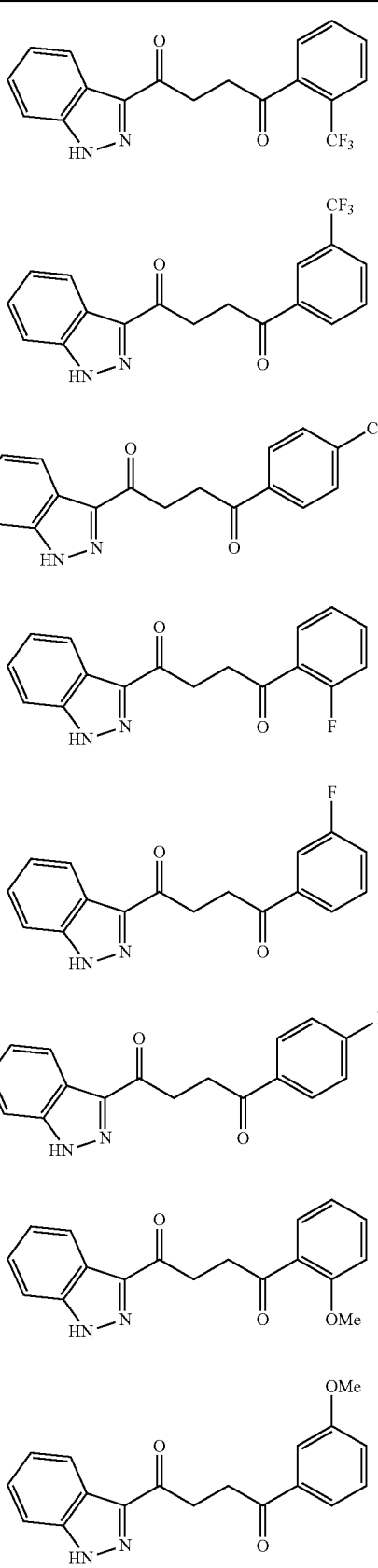

TABLE 1-continued
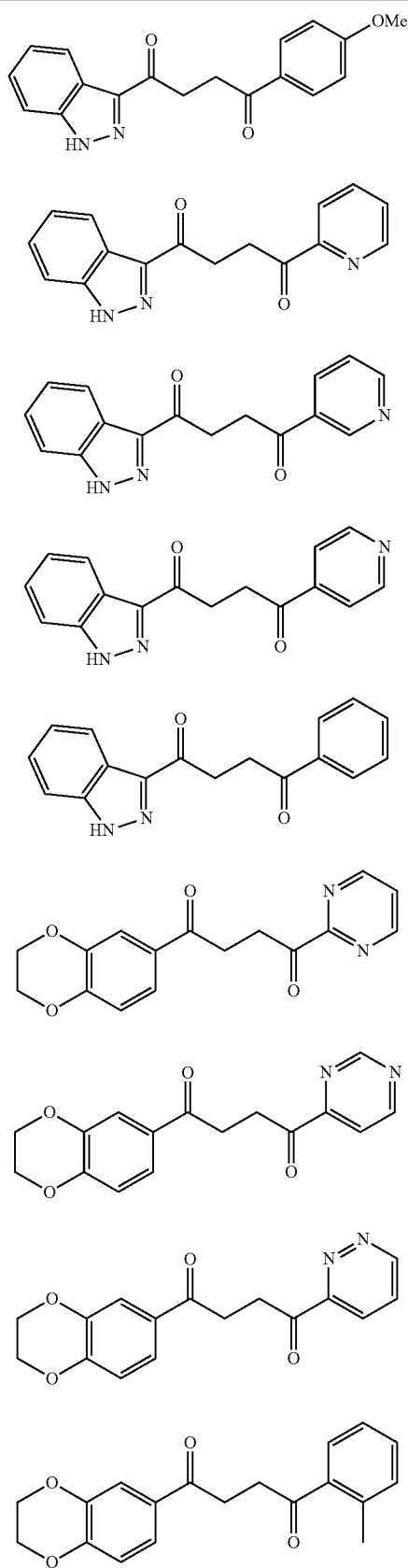
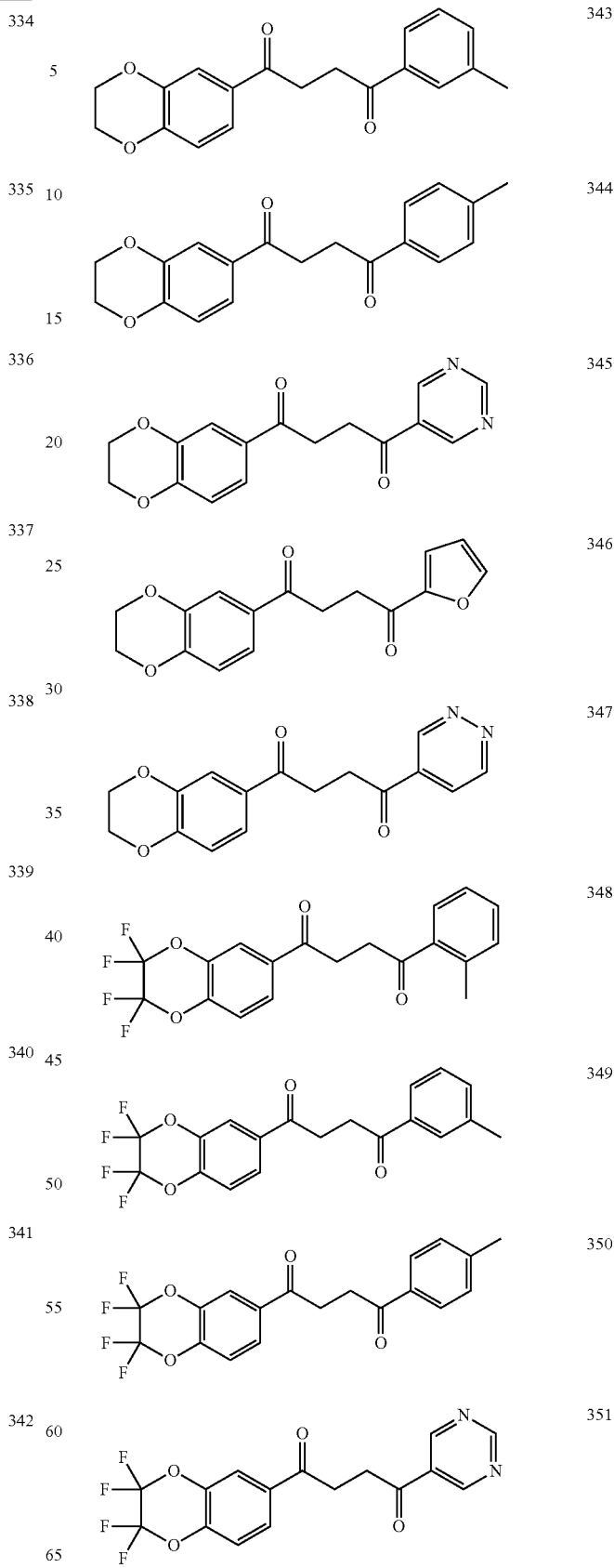

TABLE 1-continued
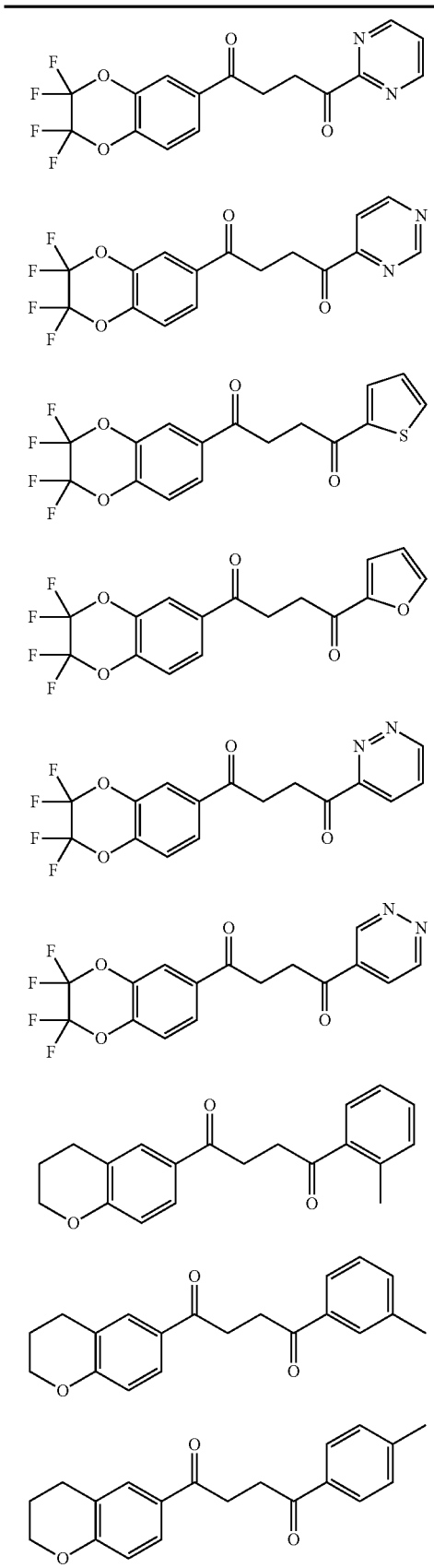
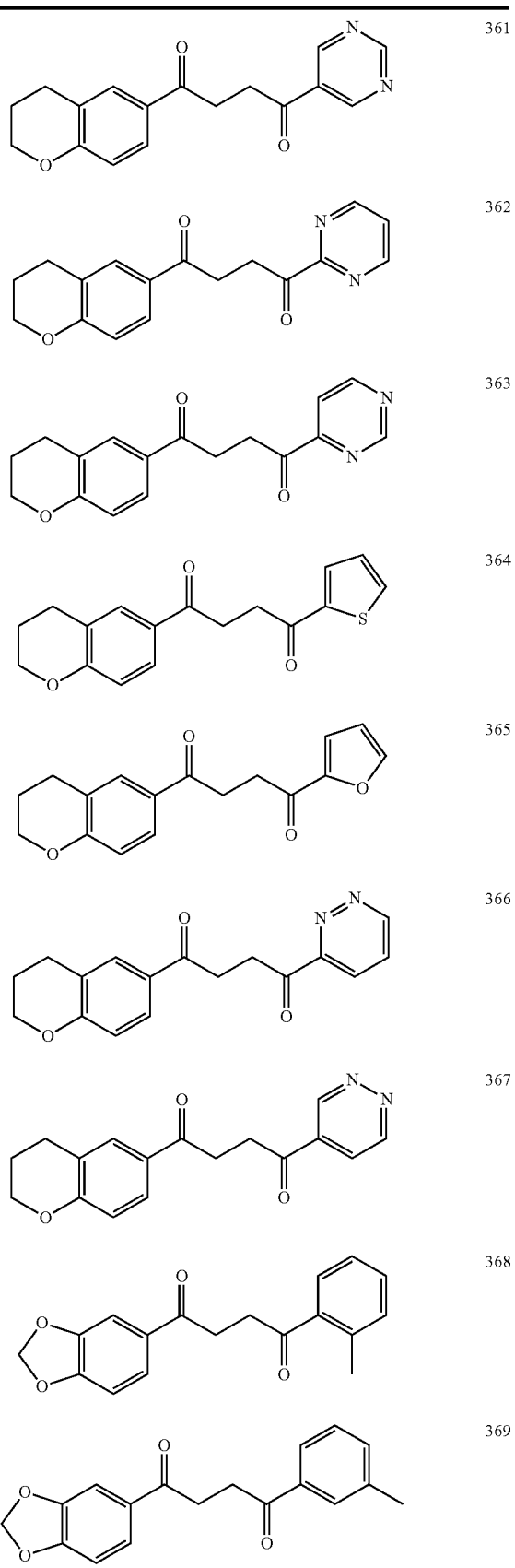

TABLE 1-continued
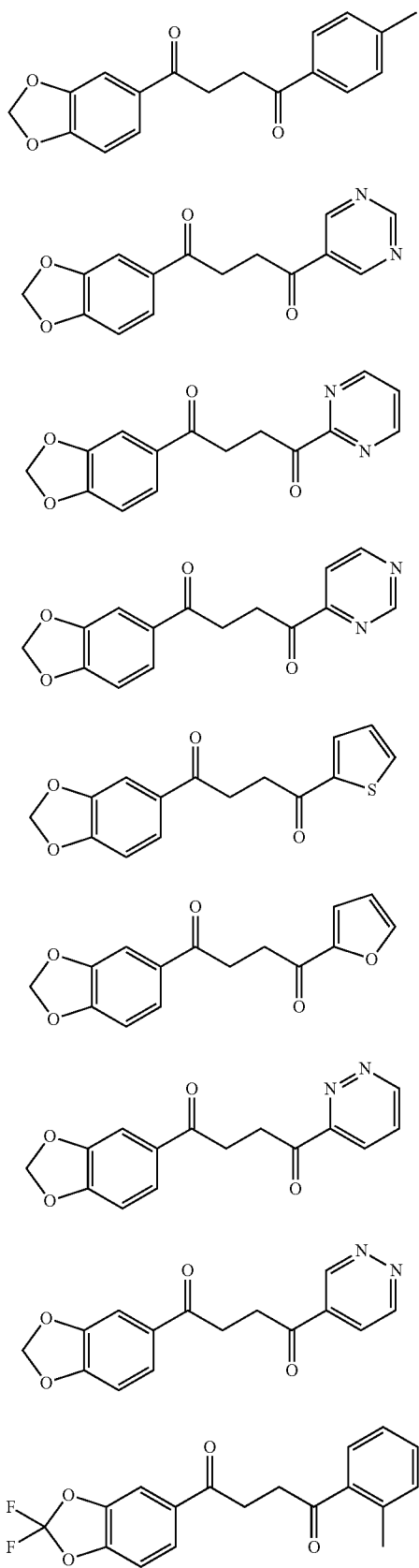
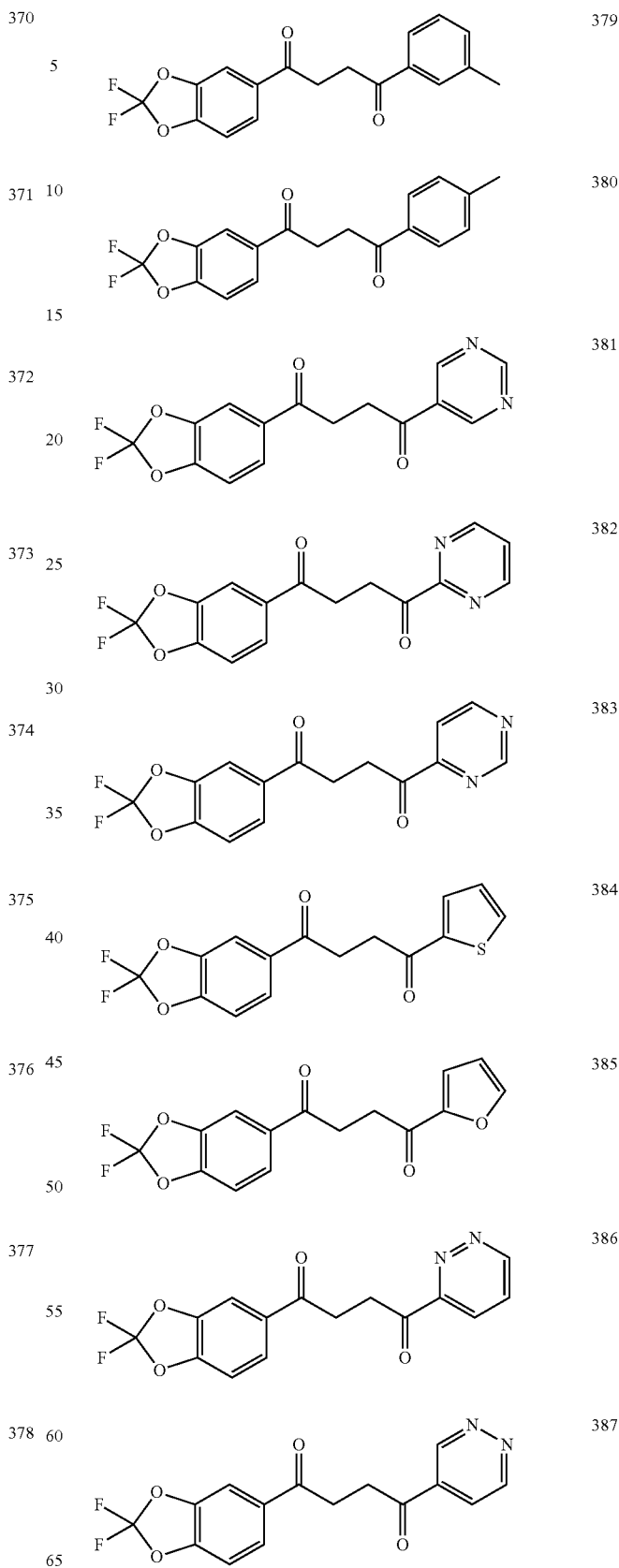

TABLE 1-continued
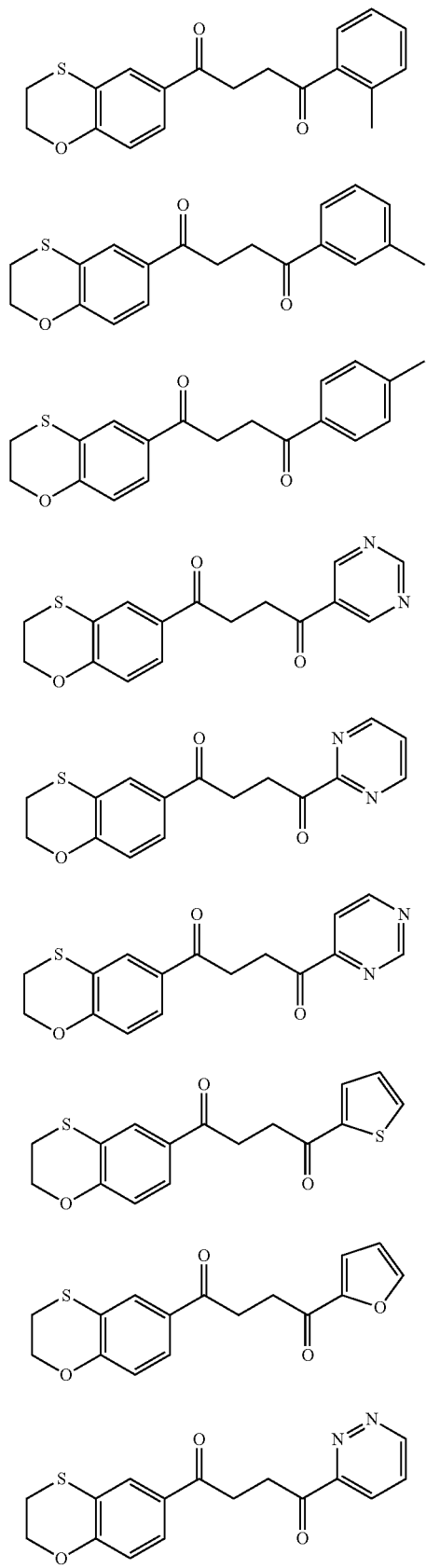
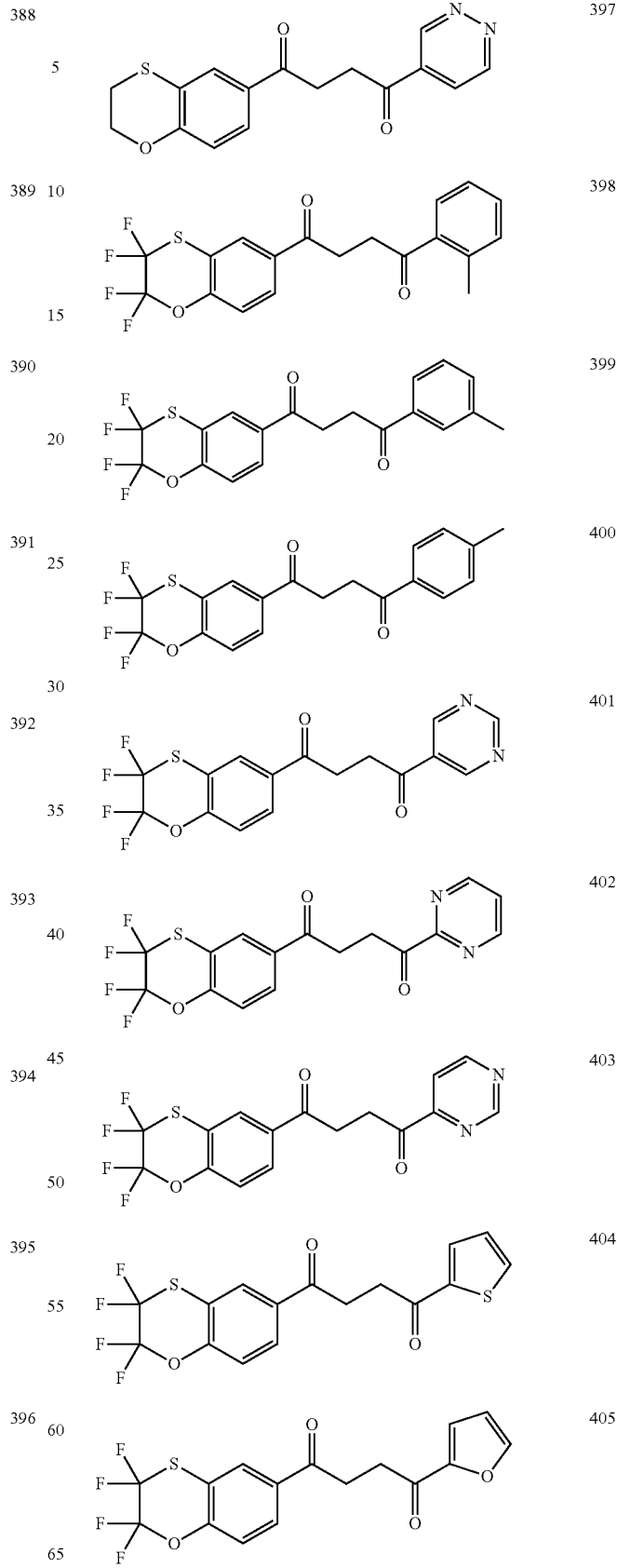

TABLE 1-continued

| Structure | No. |
|---|---|
| (tetrafluoro-benzodioxin-thiopyran)-C(O)-CH2CH2-C(O)-pyridazin-3-yl | 406 |
| (tetrafluoro-benzodioxin-thiopyran)-C(O)-CH2CH2-C(O)-pyridazin-4-yl | 407 |
| (2,3-dihydro-benzo[1,4]dithiin-6-yl)-C(O)-CH2CH2-C(O)-(2-methylphenyl) | 408 |
| (2,3-dihydro-benzo[1,4]dithiin-6-yl)-C(O)-CH2CH2-C(O)-(3-methylphenyl) | 409 |
| (2,3-dihydro-benzo[1,4]dithiin-6-yl)-C(O)-CH2CH2-C(O)-(4-methylphenyl) | 410 |
| (2,3-dihydro-benzo[1,4]dithiin-6-yl)-C(O)-CH2CH2-C(O)-pyrimidin-5-yl | 411 |
| (2,3-dihydro-benzo[1,4]dithiin-6-yl)-C(O)-CH2CH2-C(O)-pyrimidin-2-yl | 412 |
| (2,3-dihydro-benzo[1,4]dithiin-6-yl)-C(O)-CH2CH2-C(O)-pyrimidin-4-yl | 413 |
| (2,3-dihydro-benzo[1,4]dithiin-6-yl)-C(O)-CH2CH2-C(O)-thiophen-2-yl | 414 |
| (2,3-dihydro-benzo[1,4]dithiin-6-yl)-C(O)-CH2CH2-C(O)-furan-2-yl | 415 |
| (2,3-dihydro-benzo[1,4]dithiin-6-yl)-C(O)-CH2CH2-C(O)-pyridazin-3-yl | 416 |
| (2,3-dihydro-benzo[1,4]dithiin-6-yl)-C(O)-CH2CH2-C(O)-pyridazin-4-yl | 417 |
| (3,4-dimethoxyphenyl)-C(O)-CH2CH2-C(O)-(2-fluorophenyl) | 418 |
| (3,4-dimethoxyphenyl)-C(O)-CH2CH2-C(O)-(3-fluorophenyl) | 419 |
| (3,4-dimethoxyphenyl)-C(O)-CH2CH2-C(O)-(4-fluorophenyl) | 420 |
| (3,4-dimethoxyphenyl)-C(O)-CH2CH2-C(O)-(2-trifluoromethylphenyl) | 421 |
| (3,4-dimethoxyphenyl)-C(O)-CH2CH2-C(O)-(3-trifluoromethylphenyl) | 422 |
| (3,4-dimethoxyphenyl)-C(O)-CH2CH2-C(O)-(4-trifluoromethylphenyl) | 423 |

TABLE 1-continued
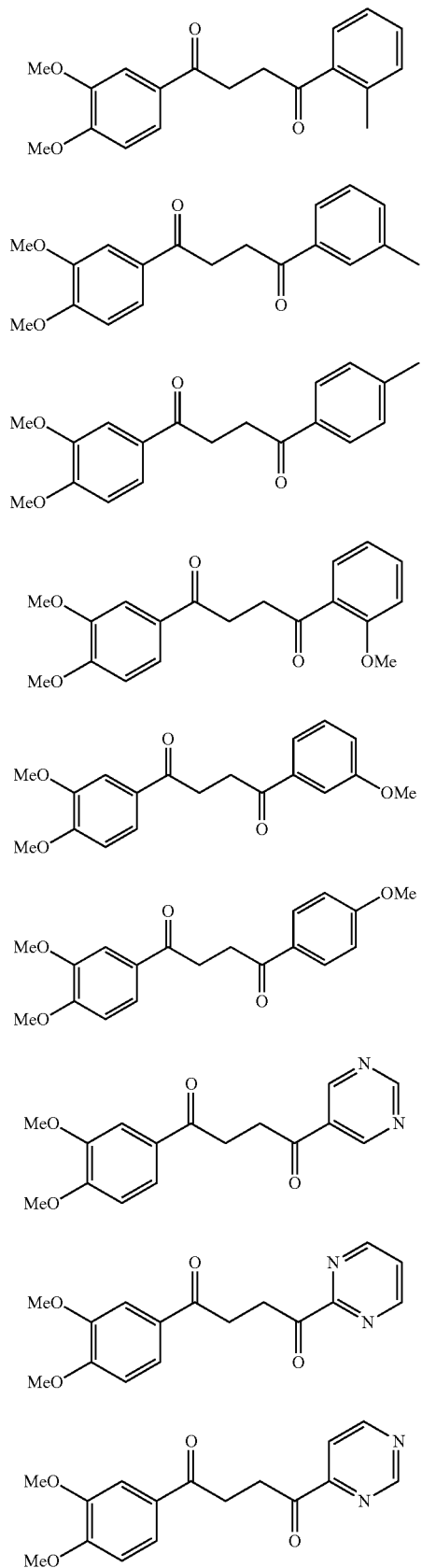
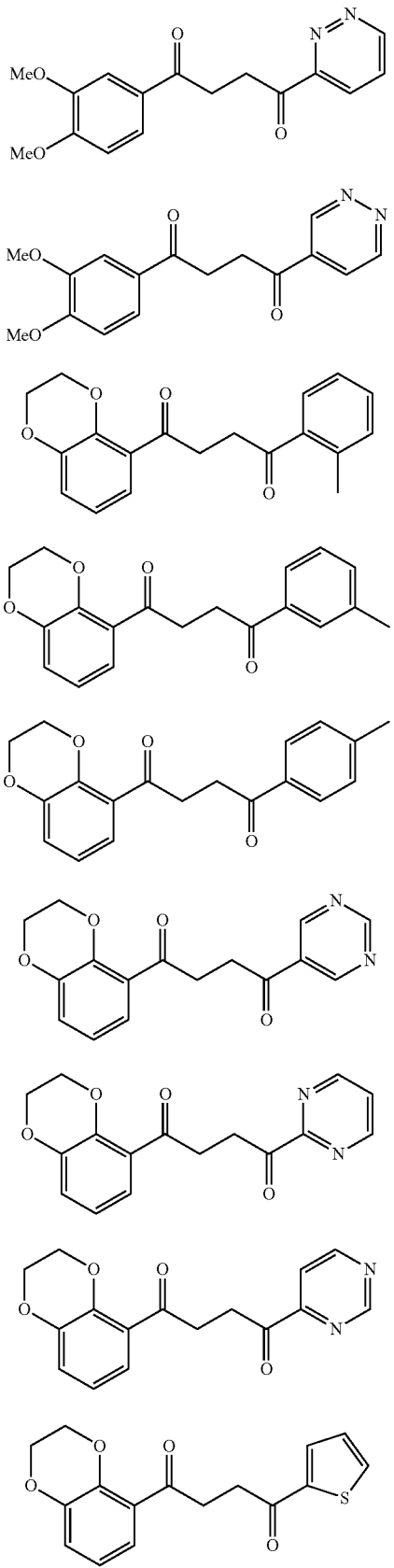

TABLE 1-continued
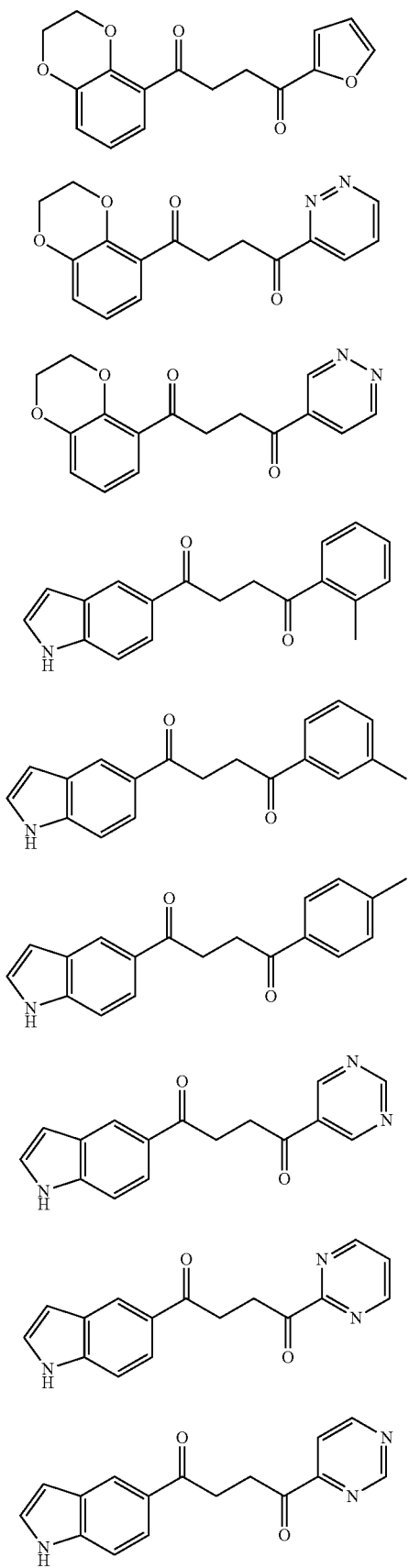
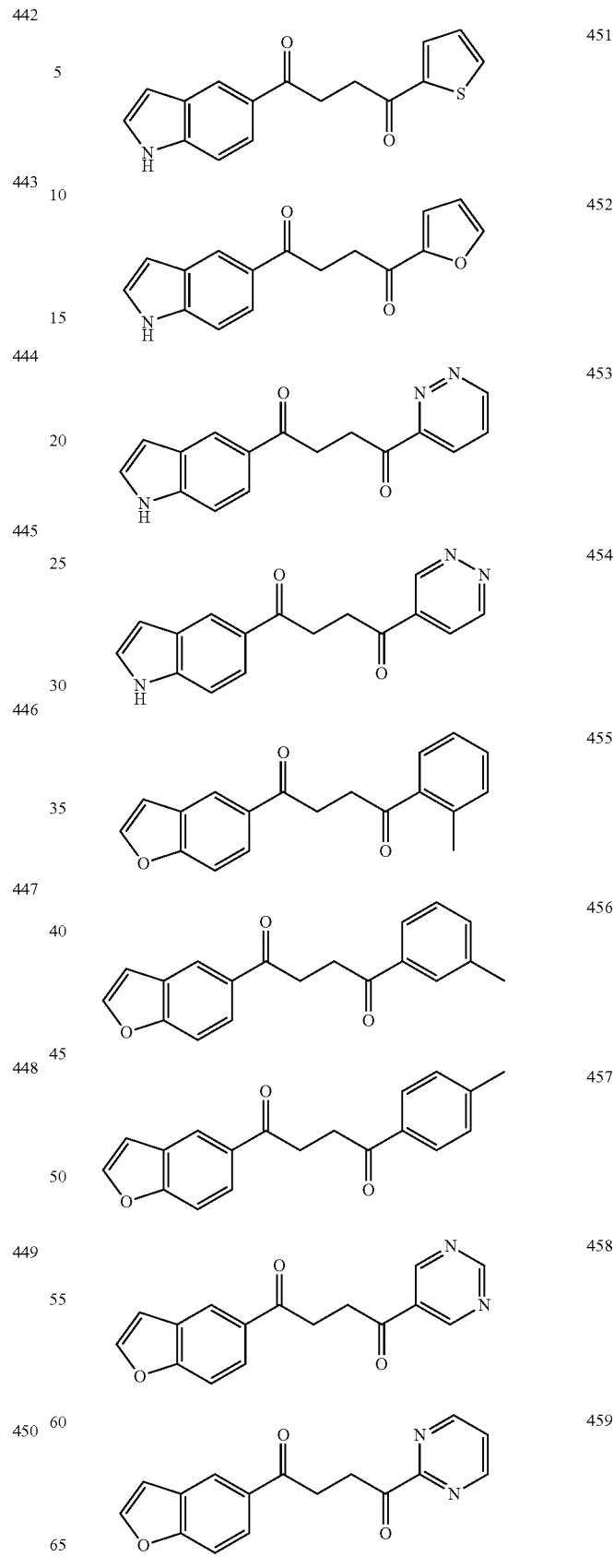

TABLE 1-continued
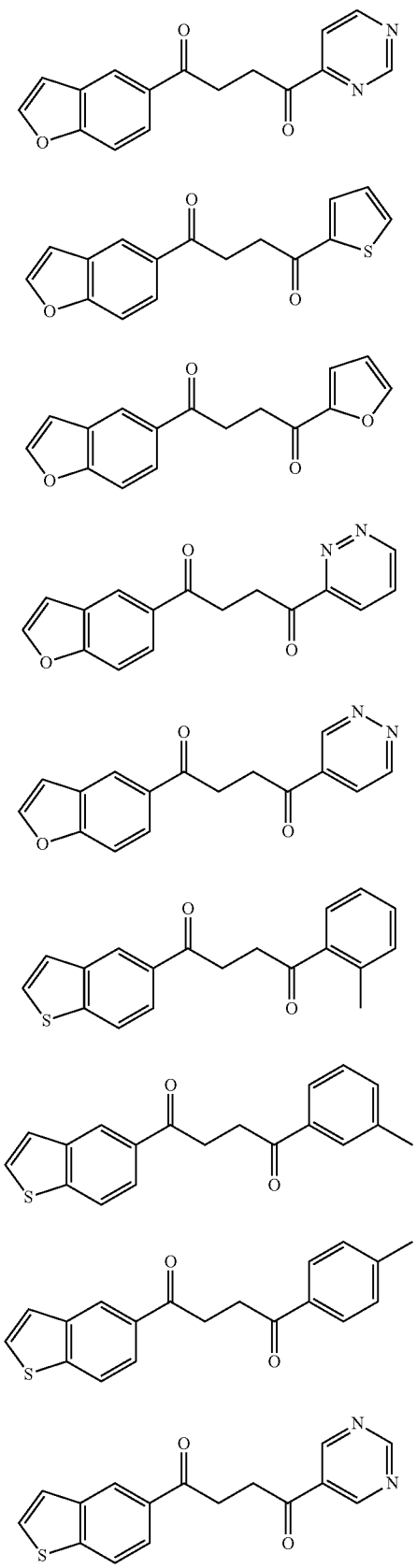
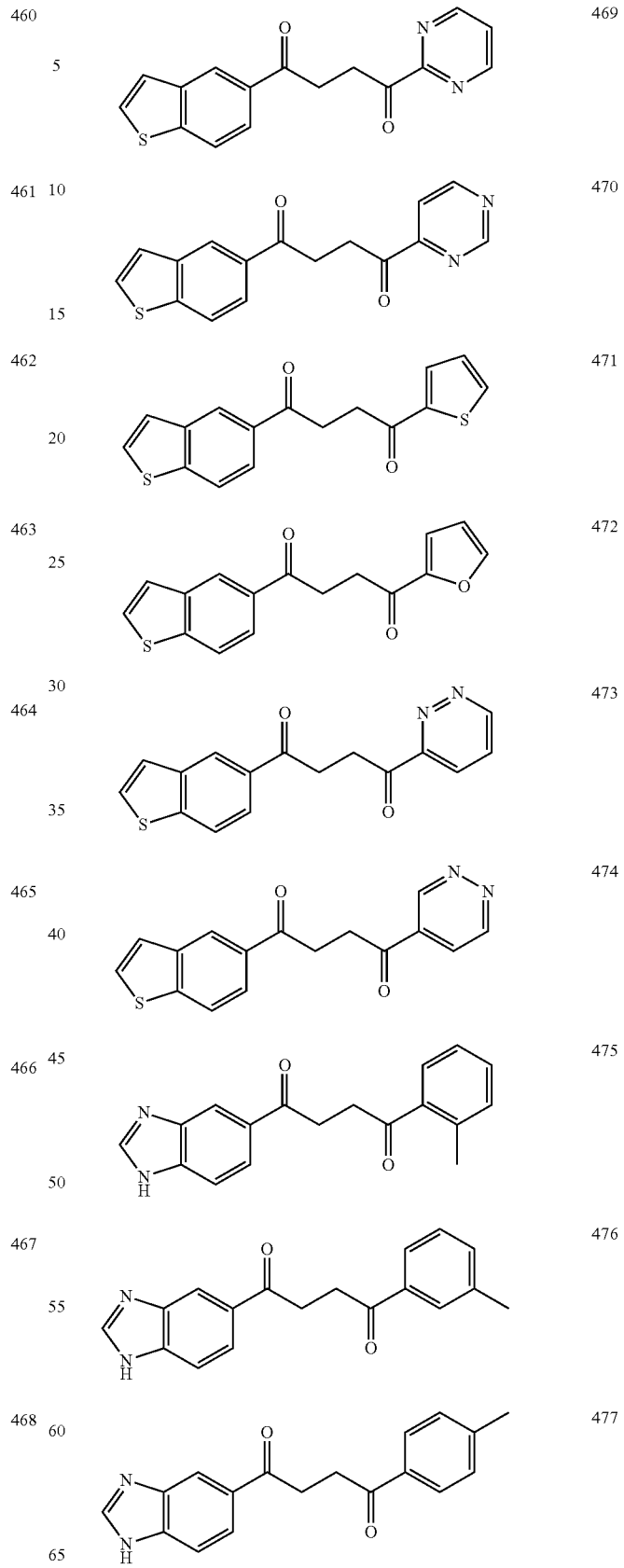

TABLE 1-continued
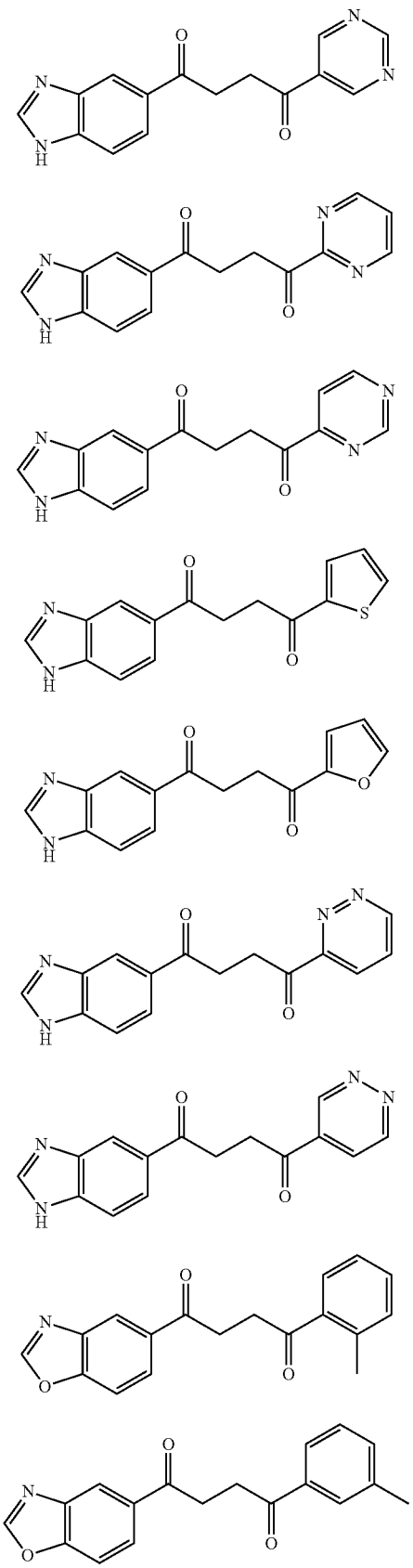
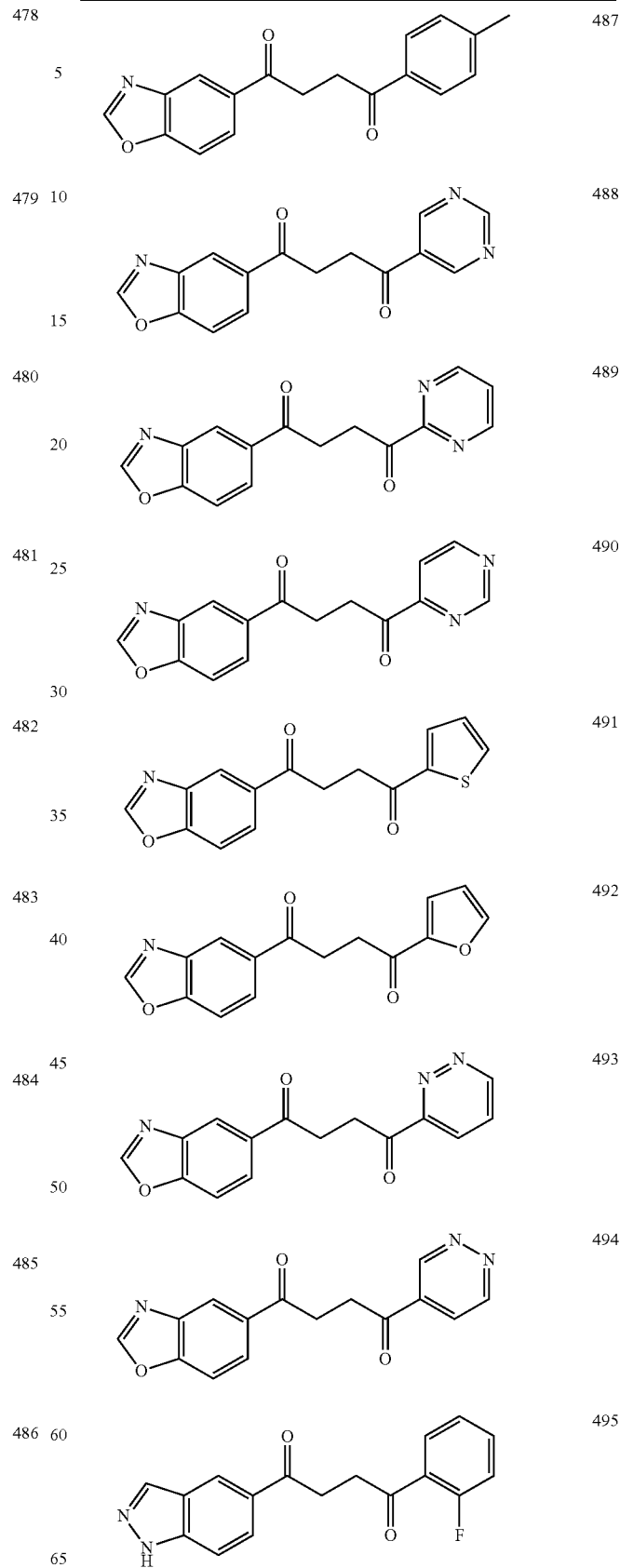

TABLE 1-continued
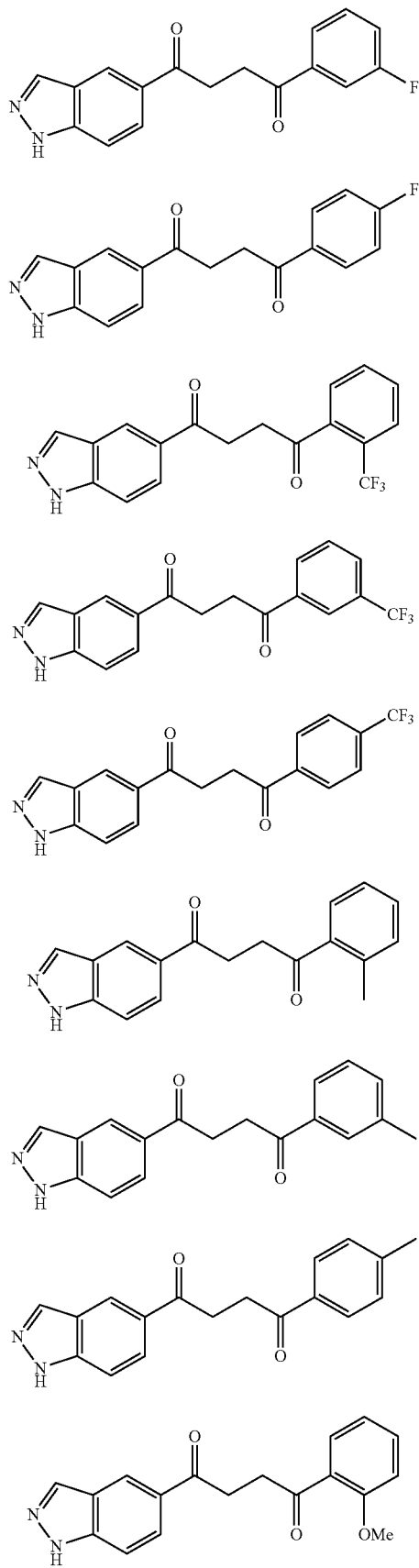
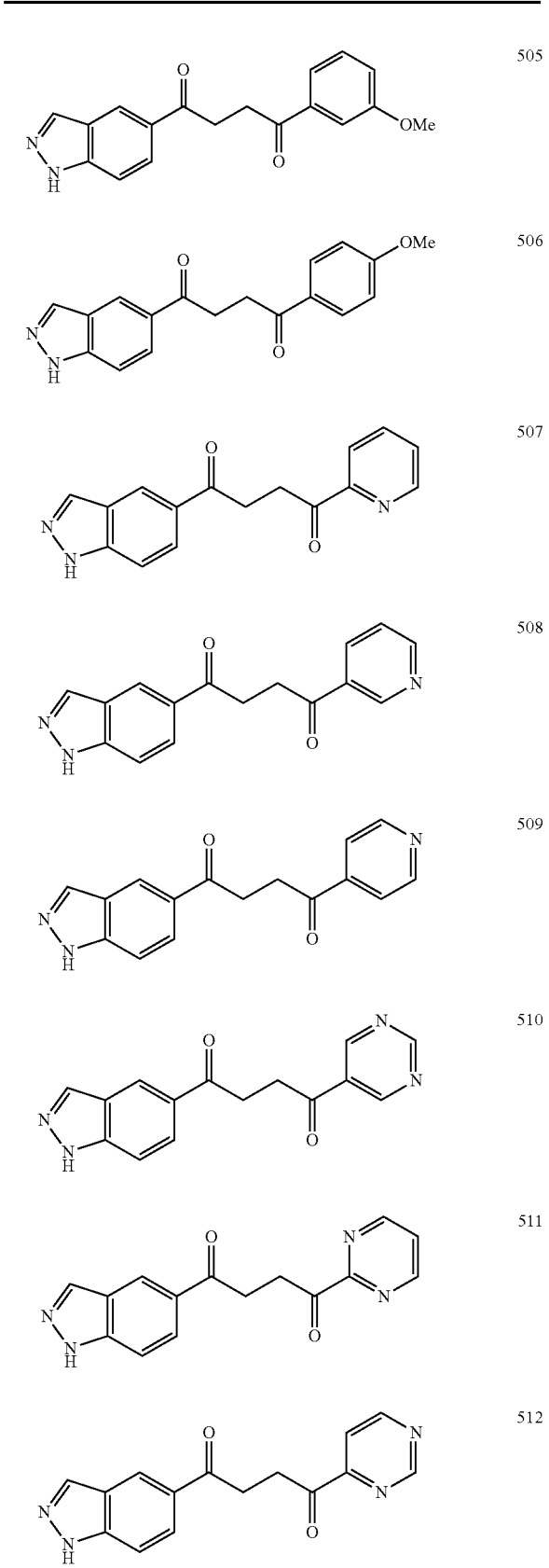

TABLE 1-continued
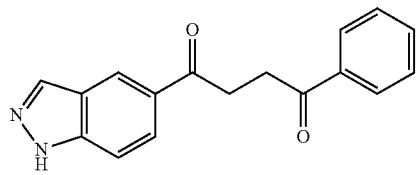 513
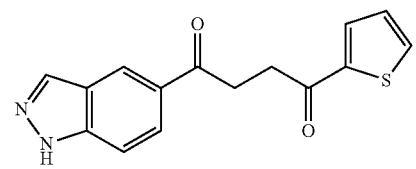 514
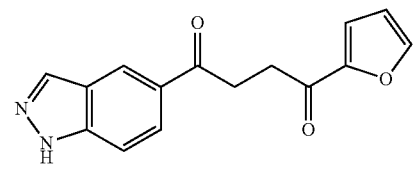 515
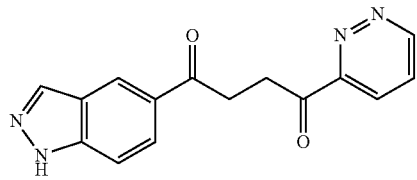 516
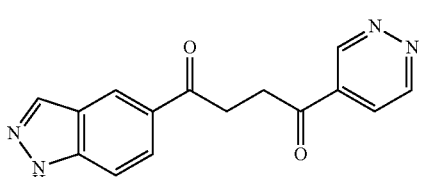 517
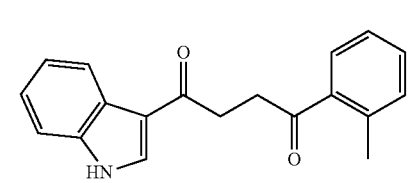 518
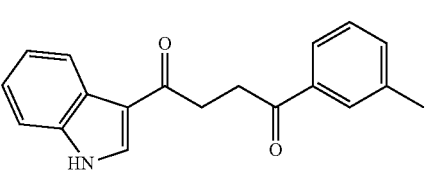 519
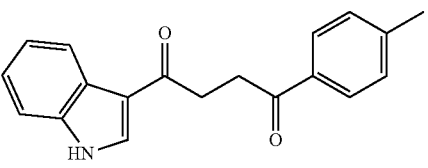 520
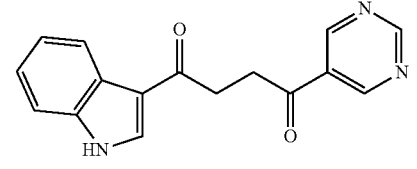 521
TABLE 1-continued
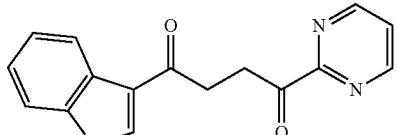 522
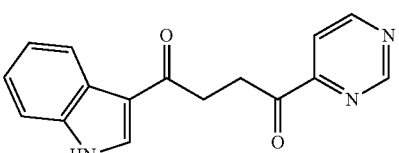 523
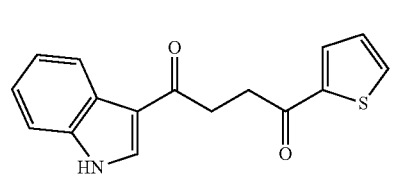 524
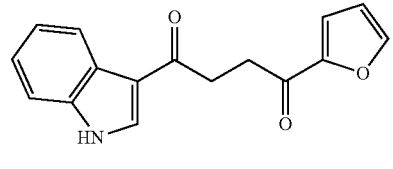 525
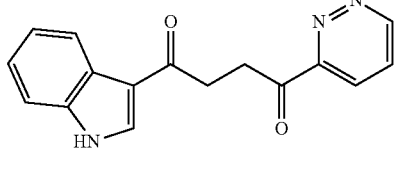 526
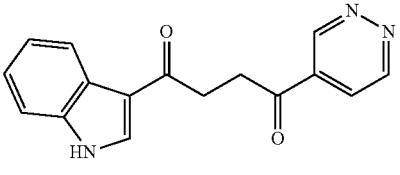 527
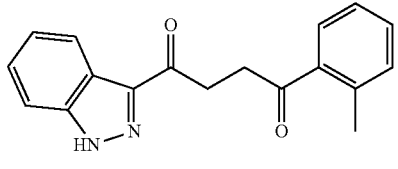 528
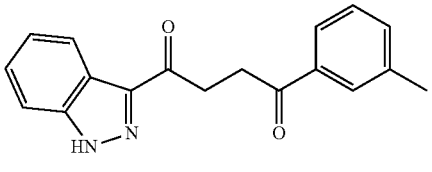 529
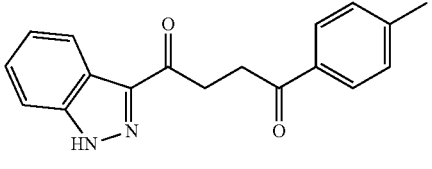 530

TABLE 1-continued

| # | Structure |
|---|---|
| 531 | 1-(1H-indazol-3-yl)-4-(pyrimidin-5-yl)butane-1,4-dione |
| 532 | 1-(1H-indazol-3-yl)-4-(pyrimidin-2-yl)butane-1,4-dione |
| 533 | 1-(1H-indazol-3-yl)-4-(pyrimidin-4-yl)butane-1,4-dione |
| 534 | 1-(1H-indazol-3-yl)-4-(thiophen-2-yl)butane-1,4-dione |
| 535 | 1-(1H-indazol-3-yl)-4-(furan-2-yl)butane-1,4-dione |
| 536 | 1-(1H-indazol-3-yl)-4-(pyridazin-3-yl)butane-1,4-dione |
| 537 | 1-(1H-indazol-3-yl)-4-(pyrazin-2-yl)butane-1,4-dione |
| 538 | 1-(2-fluorophenyl)-4-(pyridin-2-yl)butane-1,4-dione |
| 539 | 1-(3-fluorophenyl)-4-(pyridin-2-yl)butane-1,4-dione |
| 540 | 1-(4-fluorophenyl)-4-(pyridin-2-yl)butane-1,4-dione |
| 541 | 1-(pyridin-2-yl)-4-(2-(trifluoromethyl)phenyl)butane-1,4-dione |
| 542 | 1-(pyridin-2-yl)-4-(3-(trifluoromethyl)phenyl)butane-1,4-dione |
| 543 | 1-(pyridin-2-yl)-4-(4-(trifluoromethyl)phenyl)butane-1,4-dione |
| 544 | 1-(pyridin-2-yl)-4-(o-tolyl)butane-1,4-dione |
| 545 | 1-(pyridin-2-yl)-4-(m-tolyl)butane-1,4-dione |
| 546 | 1-(pyridin-2-yl)-4-(p-tolyl)butane-1,4-dione |
| 547 | 1-(2-methoxyphenyl)-4-(pyridin-2-yl)butane-1,4-dione |
| 548 | 1-(3-methoxyphenyl)-4-(pyridin-2-yl)butane-1,4-dione |

TABLE 1-continued

| # | Structure |
|---|---|
| 549 | 1-(pyridin-2-yl)-4-(pyridin-4-yl)butane-1,4-dione |
| 550 | 1-(pyridin-2-yl)-4-(pyrimidin-5-yl)butane-1,4-dione |
| 551 | 1-(pyridin-2-yl)-4-(pyrimidin-2-yl)butane-1,4-dione |
| 552 | 1-(pyridin-2-yl)-4-(pyrimidin-4-yl)butane-1,4-dione |
| 553 | 1-(pyridin-2-yl)-4-(thiophen-2-yl)butane-1,4-dione |
| 554 | 1-(furan-2-yl)-4-(pyridin-2-yl)butane-1,4-dione |
| 555 | 1-(pyridazin-3-yl)-4-(pyridin-2-yl)butane-1,4-dione |
| 556 | 1-(pyridazin-4-yl)-4-(pyridin-2-yl)butane-1,4-dione |
| 557 | 1-(2-fluorophenyl)-4-(thiophen-2-yl)butane-1,4-dione |
| 558 | 1-(3-fluorophenyl)-4-(thiophen-2-yl)butane-1,4-dione |
| 559 | 1-(thiophen-2-yl)-4-(2-(trifluoromethyl)phenyl)butane-1,4-dione |
| 560 | 1-(2-methylphenyl)-4-(thiophen-2-yl)butane-1,4-dione |
| 561 | 1-(3-methylphenyl)-4-(thiophen-2-yl)butane-1,4-dione |
| 562 | 1-(2-methoxyphenyl)-4-(thiophen-2-yl)butane-1,4-dione |
| 563 | 1-(pyrimidin-5-yl)-4-(thiophen-2-yl)butane-1,4-dione |
| 564 | 1-(pyrimidin-2-yl)-4-(thiophen-2-yl)butane-1,4-dione |
| 565 | 1-(pyrimidin-4-yl)-4-(thiophen-2-yl)butane-1,4-dione |
| 566 | 1-(pyridazin-3-yl)-4-(thiophen-2-yl)butane-1,4-dione |

TABLE 1-continued
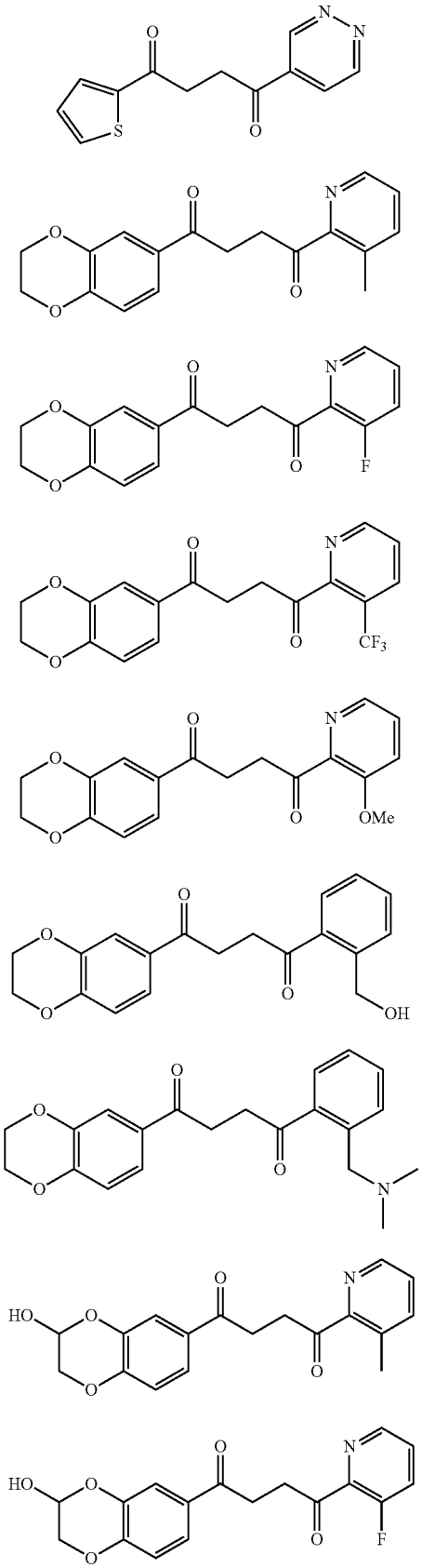
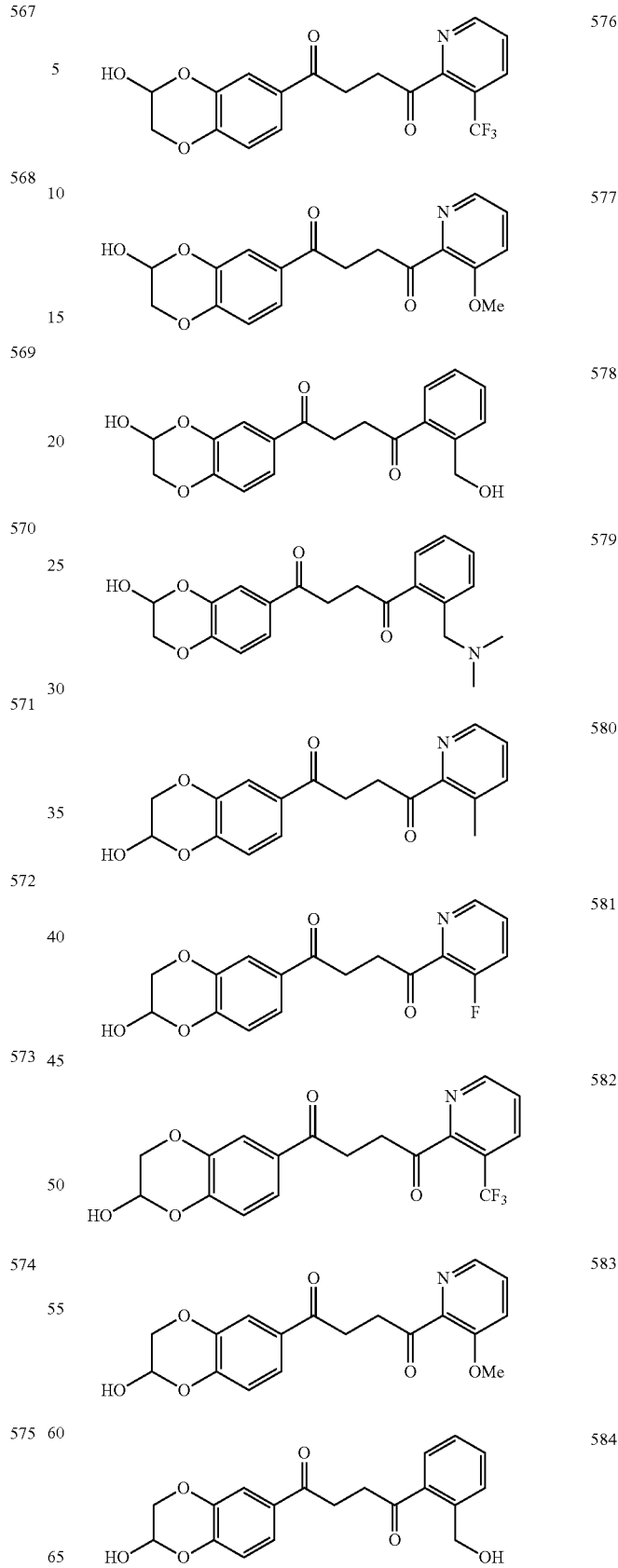

TABLE 1-continued
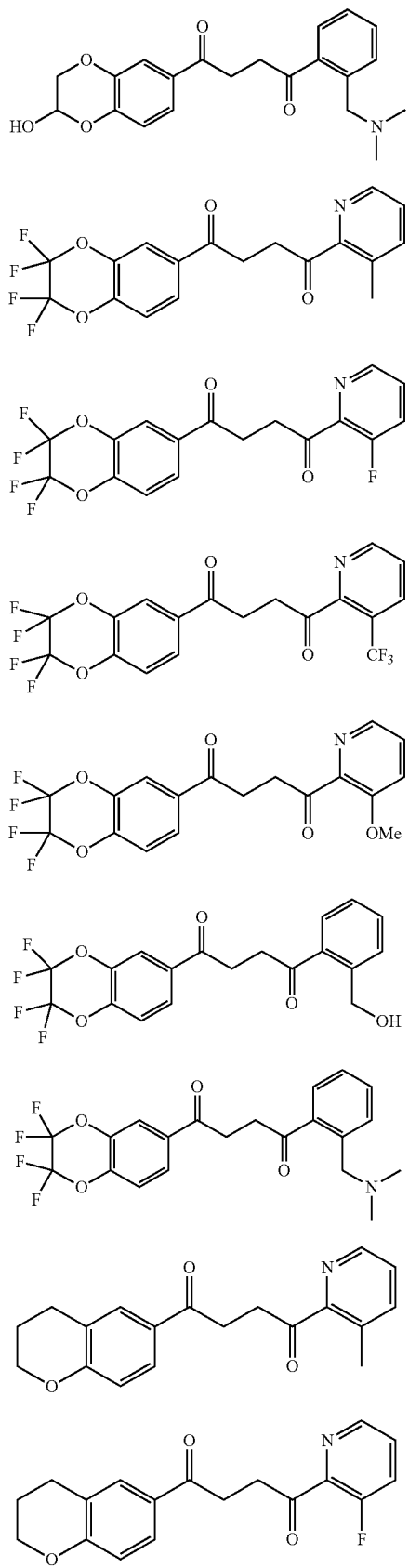
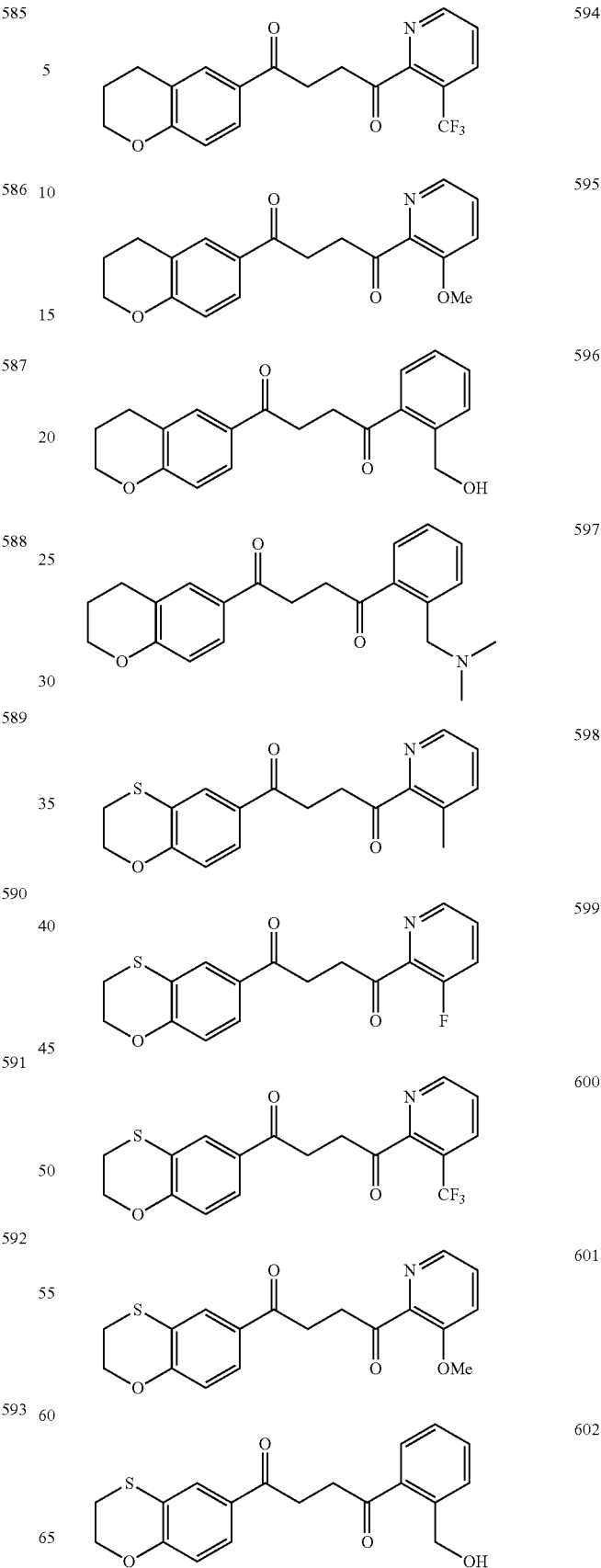

TABLE 1-continued
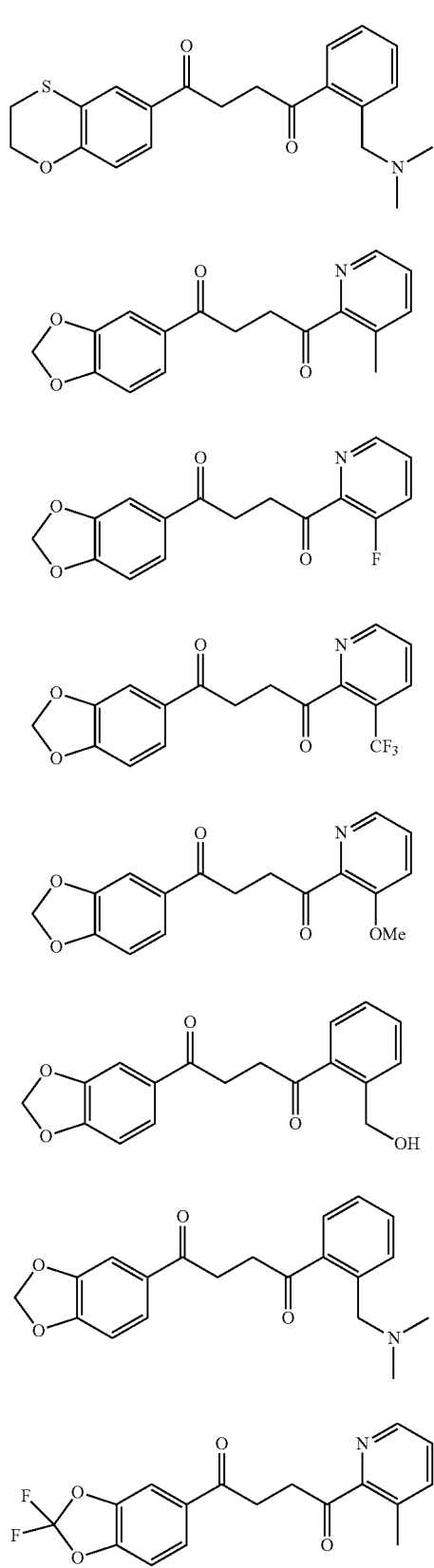
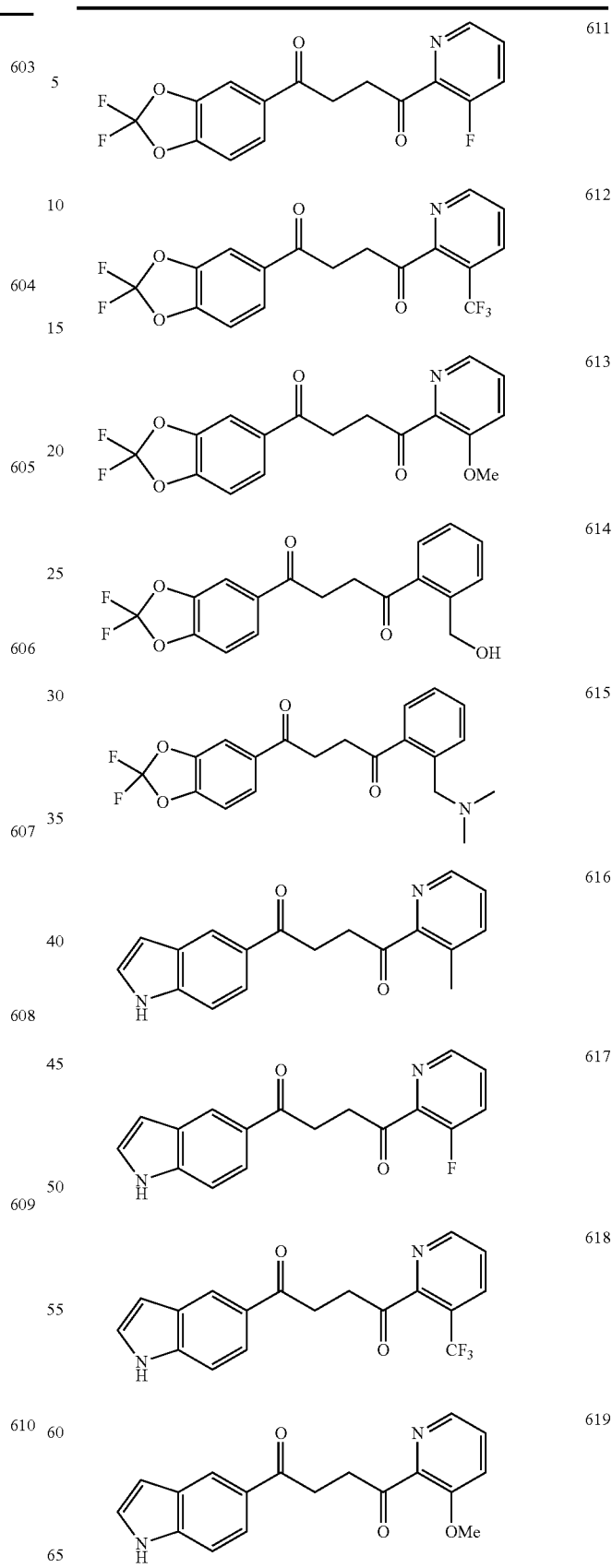

TABLE 1-continued
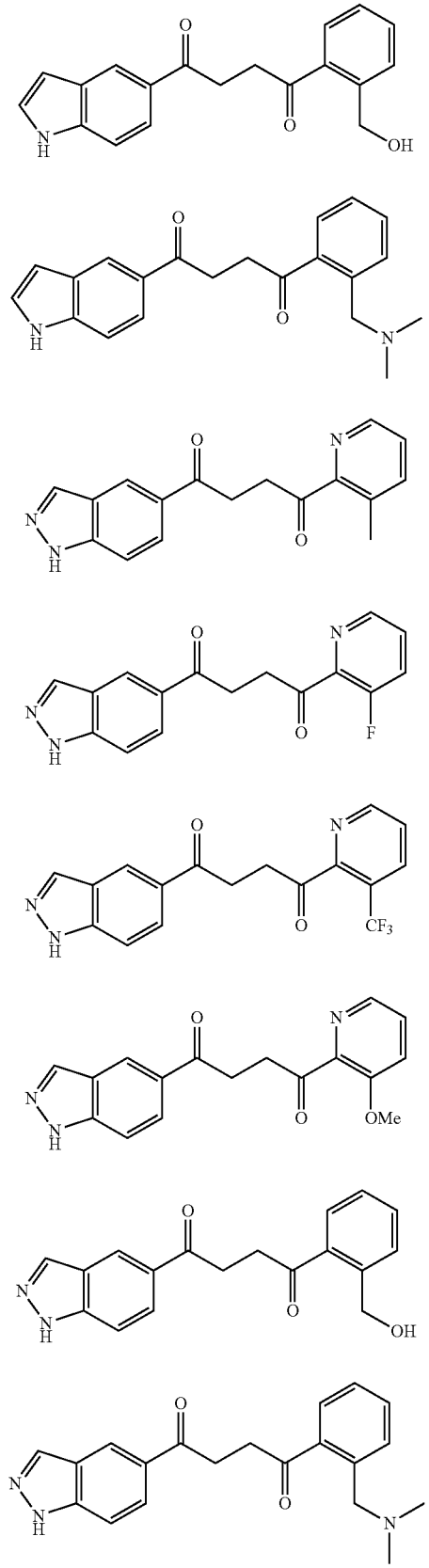
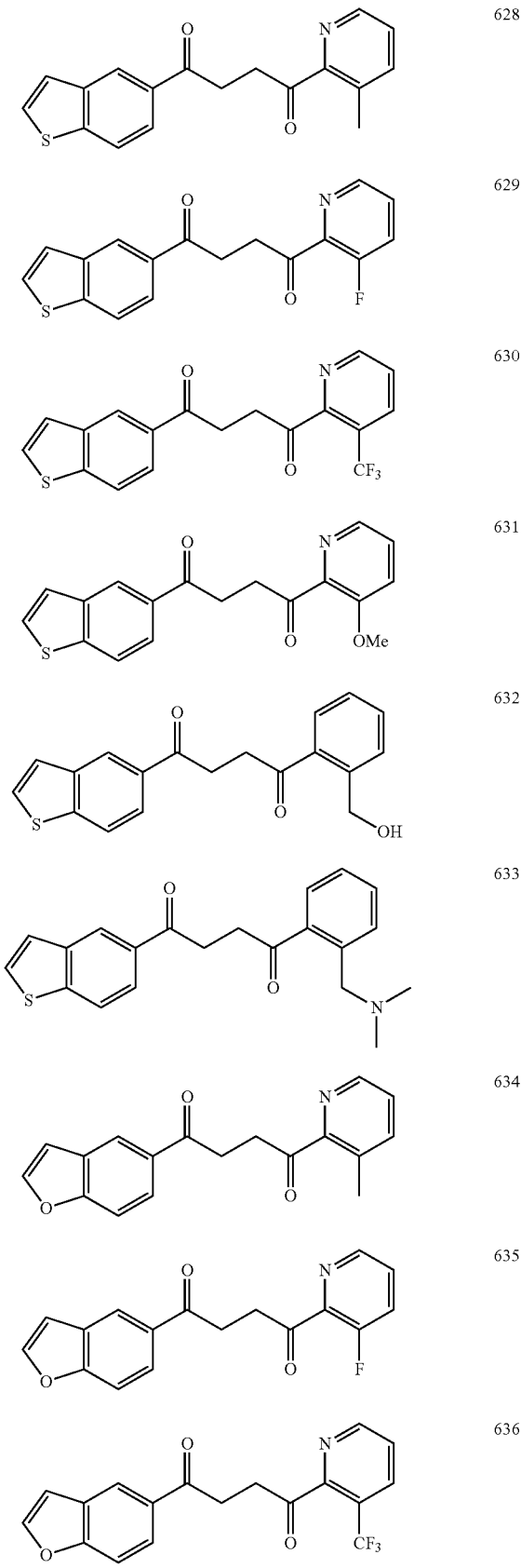

TABLE 1-continued
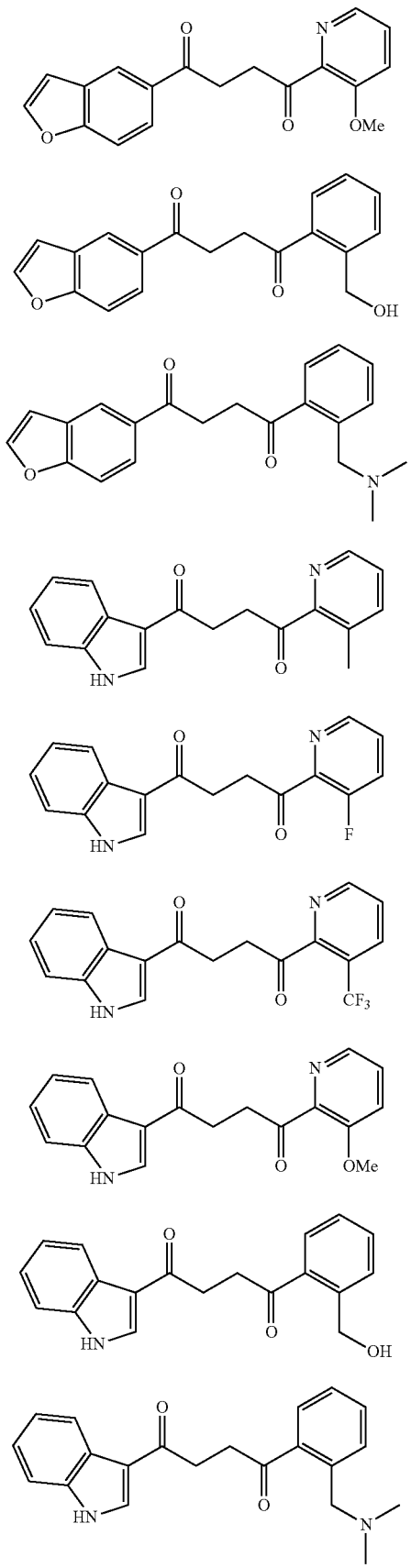
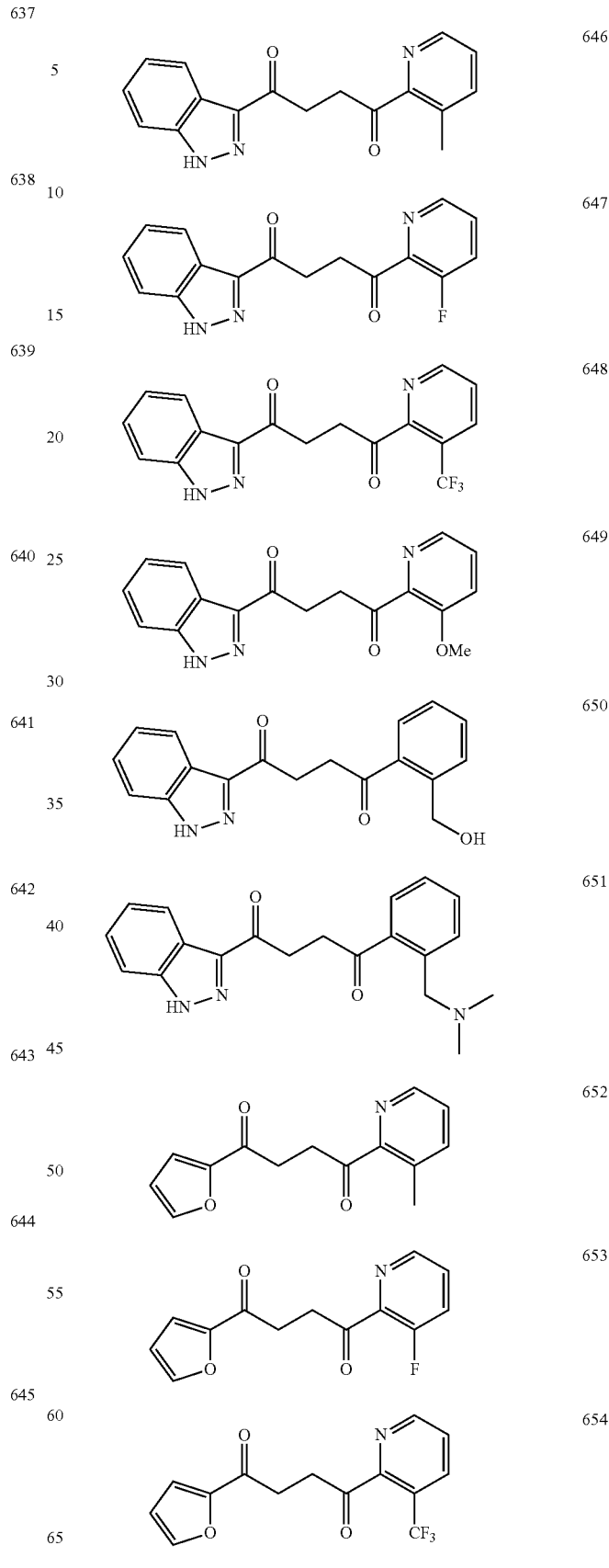

TABLE 1-continued
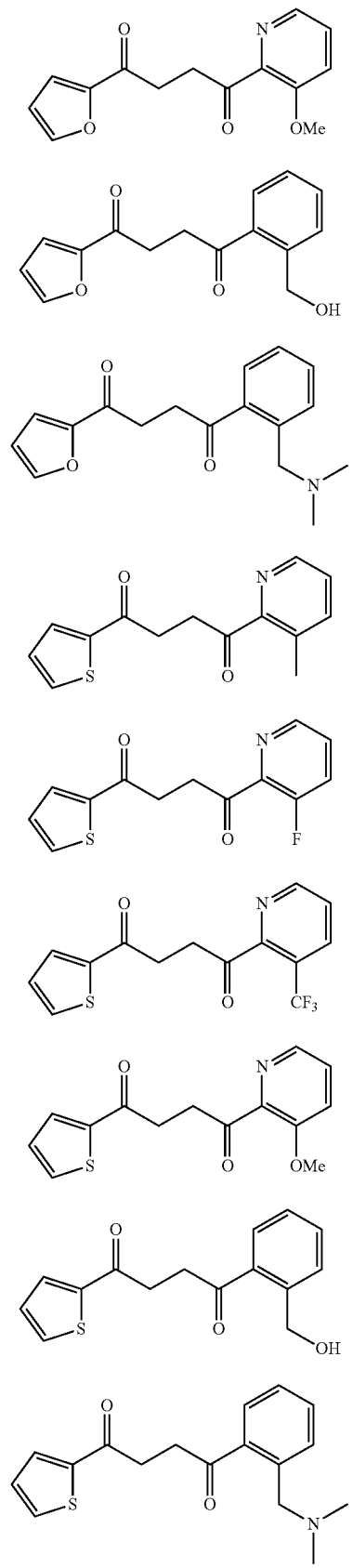
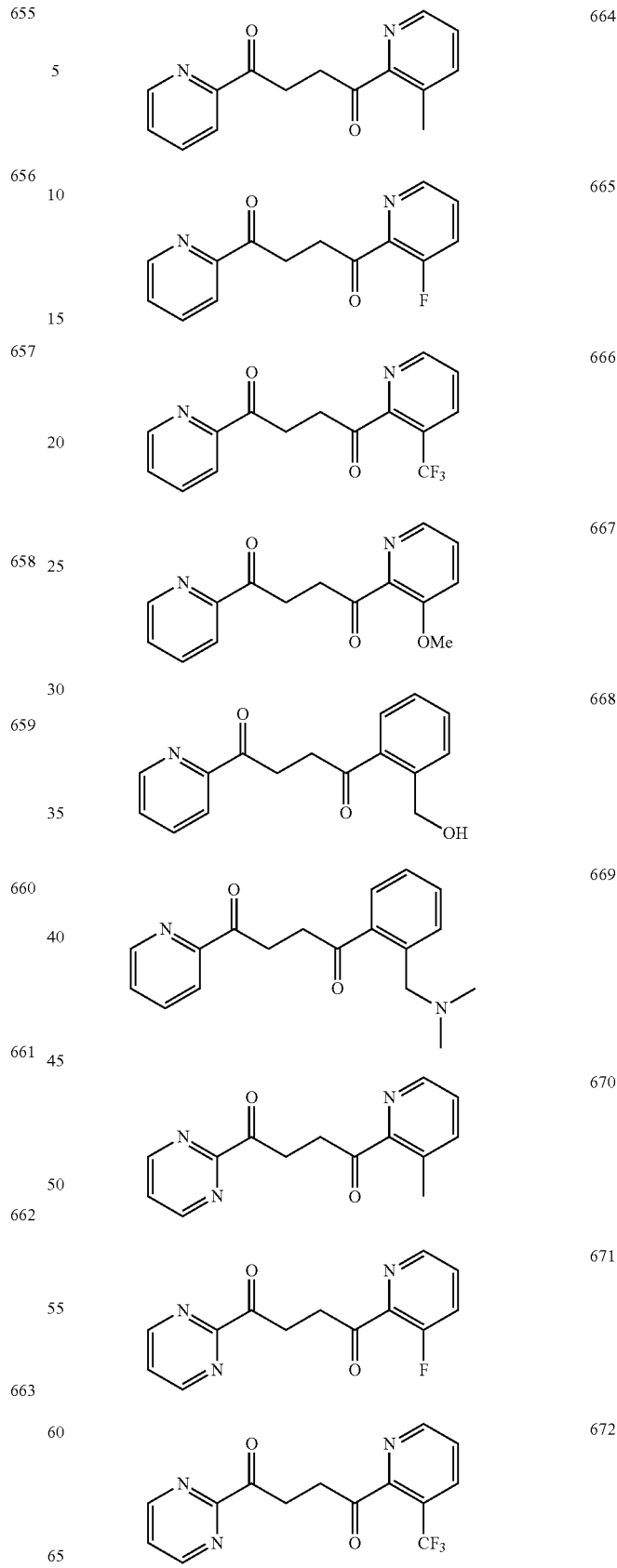

TABLE 1-continued
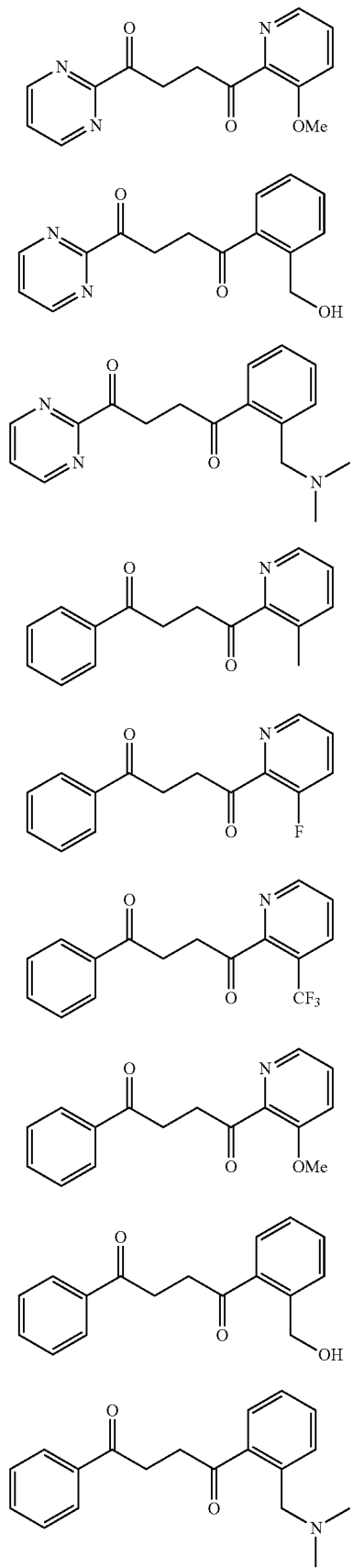
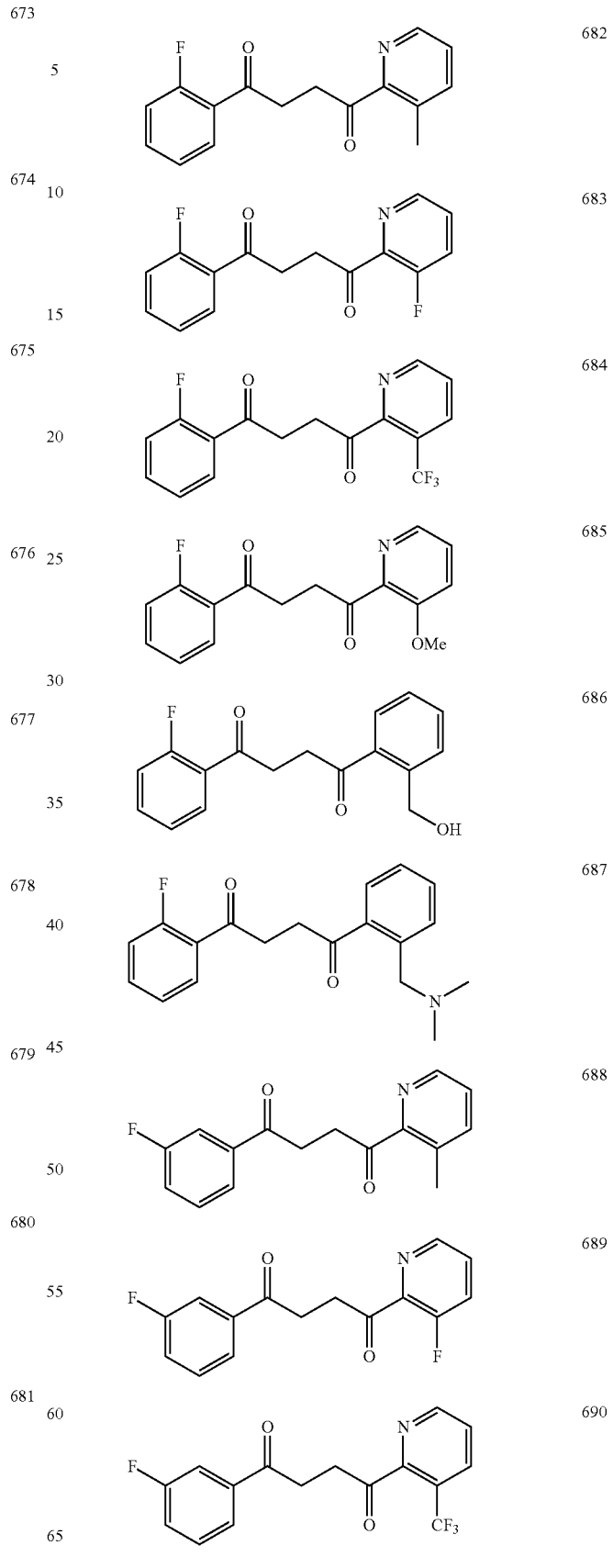

TABLE 1-continued
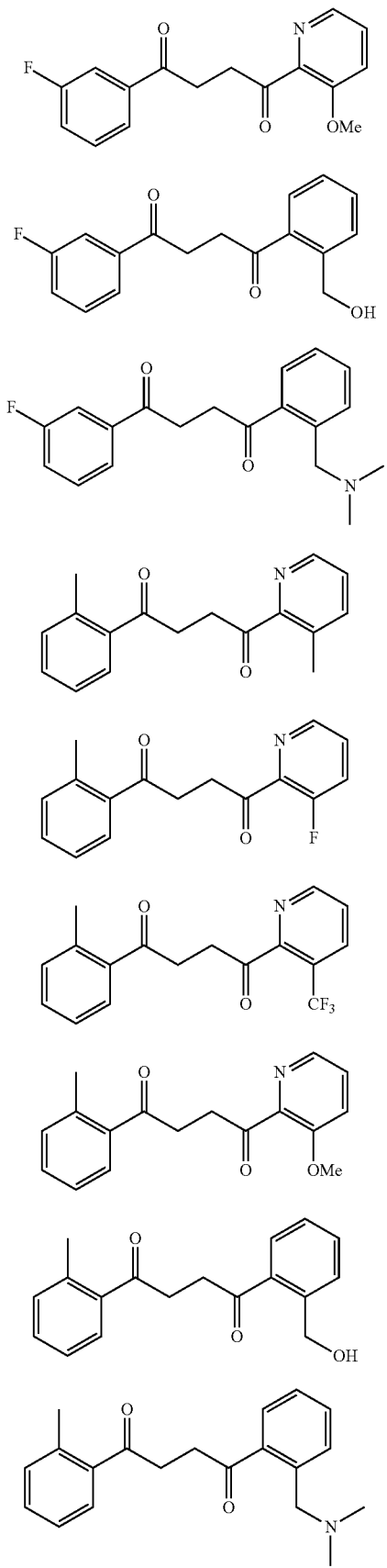
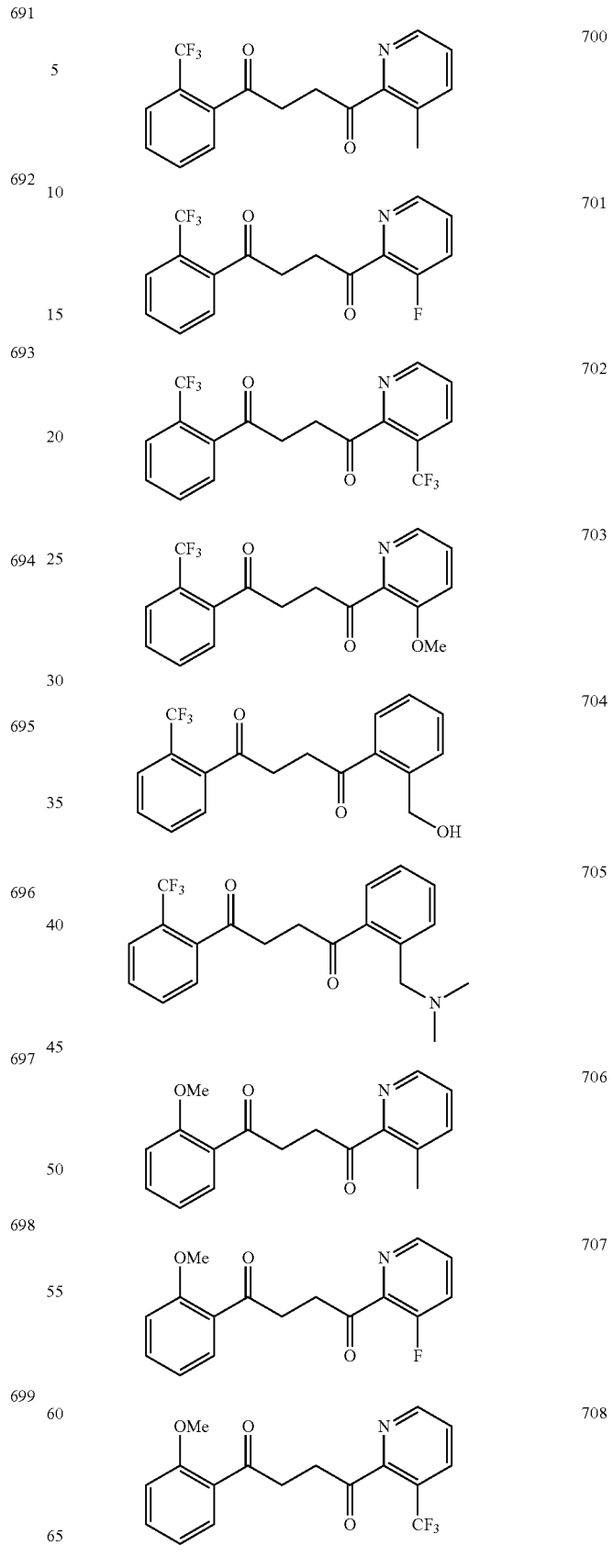

TABLE 1-continued
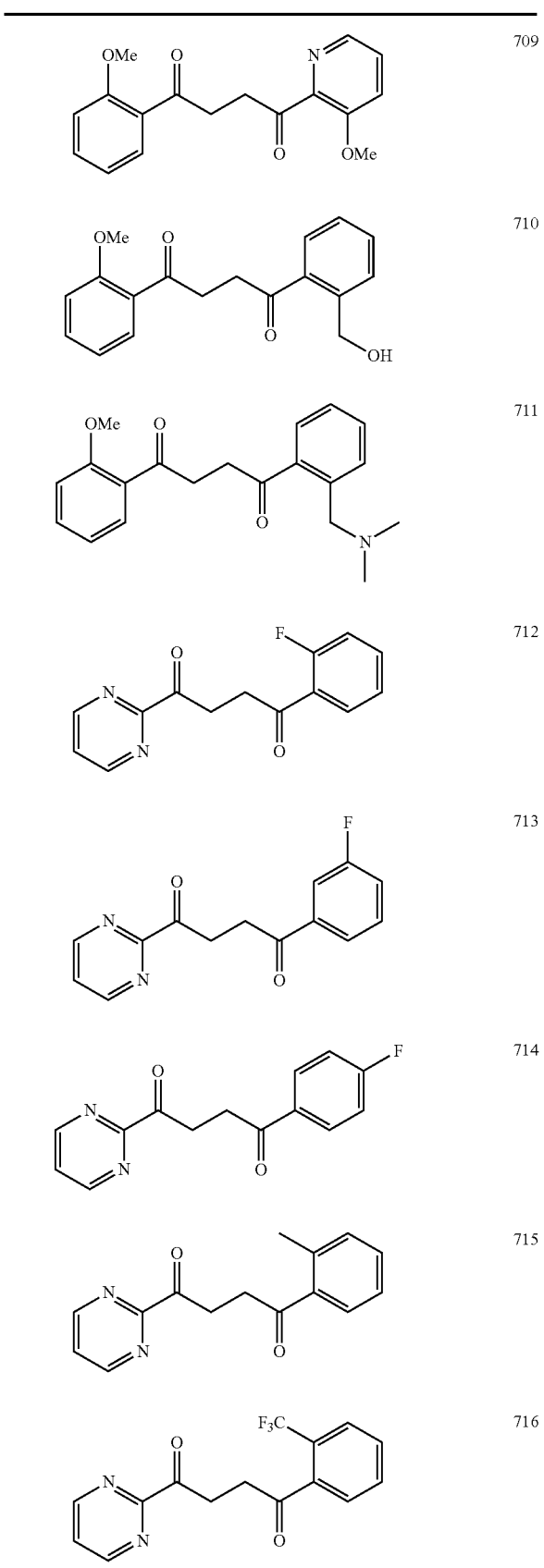
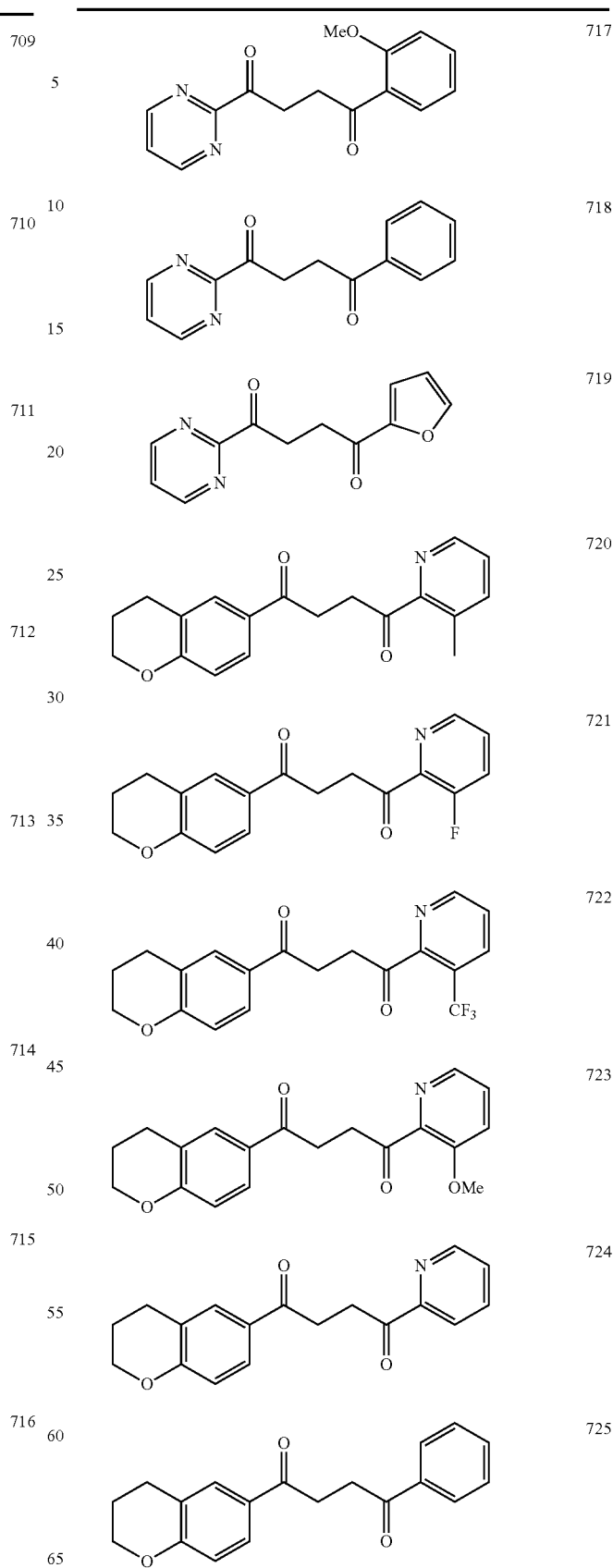

TABLE 1-continued

| | |
|---|---|
| 726 | 735 |
| 727 | 736 |
| 728 | 737 |
| 729 | 738 |
| 730 | 739 |
| 731 | 740 |
| 732 | 741 |
| 733 | 742 |
| 734 | 743 |

TABLE 1-continued
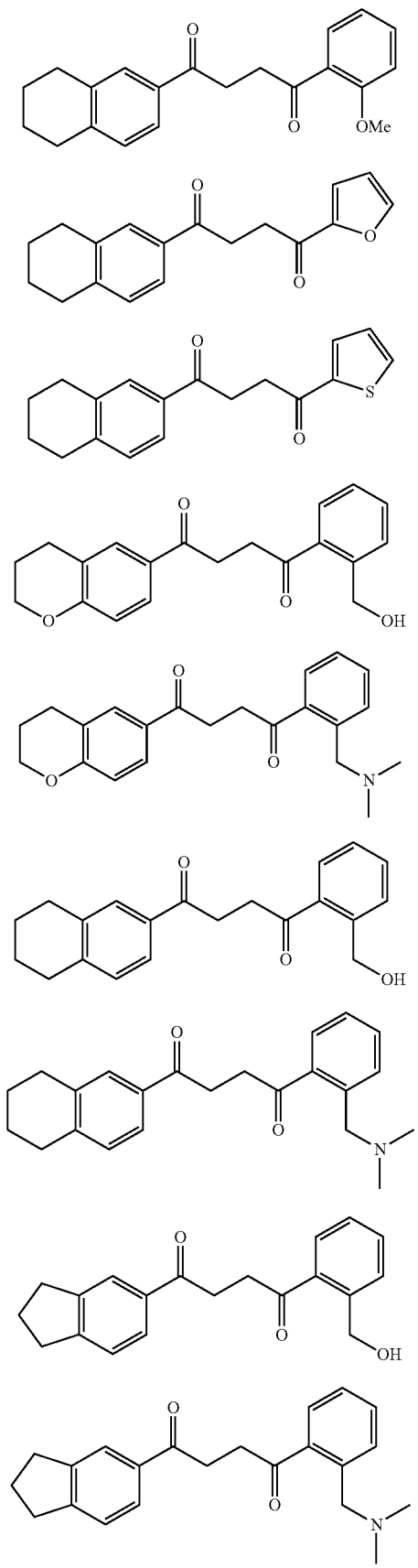
TABLE 1-continued
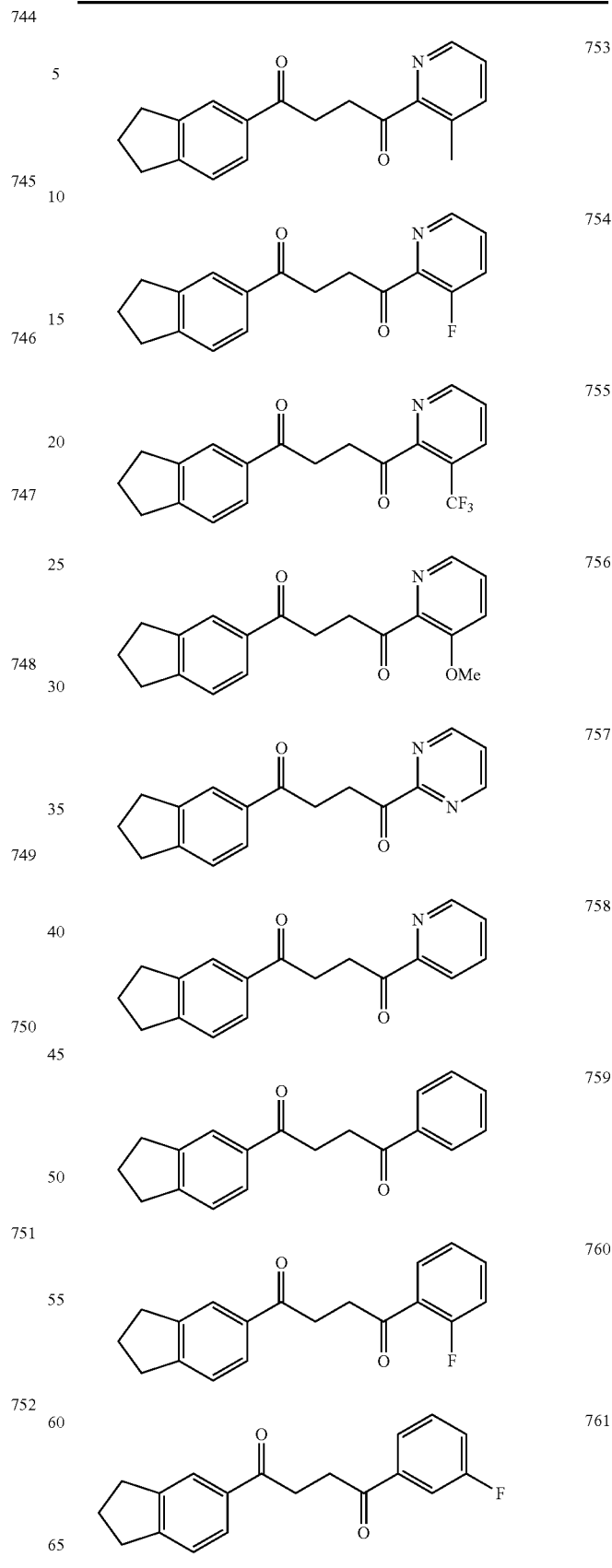

TABLE 1-continued
| | |
|---|---|
| 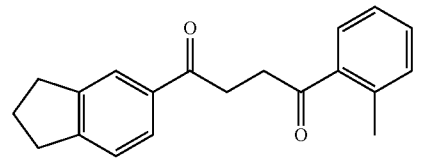 762 | 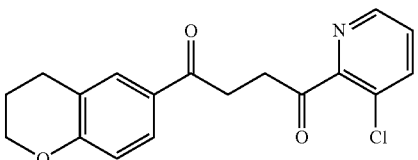 771 |
| 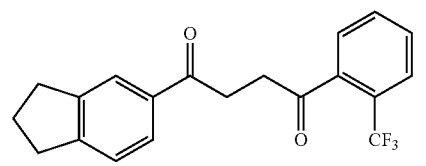 763 | 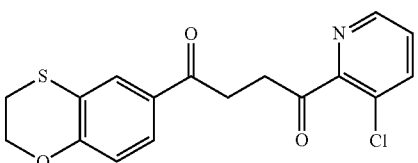 772 |
| 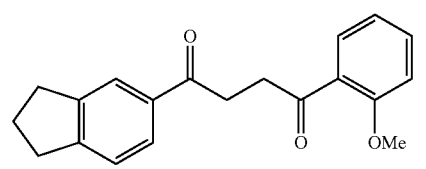 [SMILES: COc1ccccc1C(=O)CCC(=O)c1ccc2occc2c1] 764 | 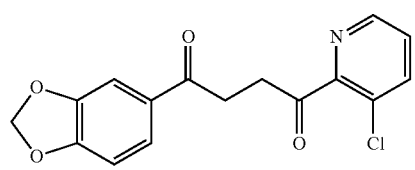 773 |
| 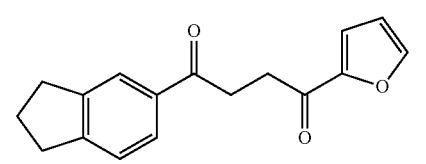 765 | 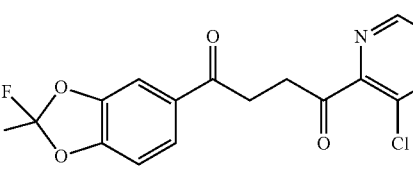 774 |
| 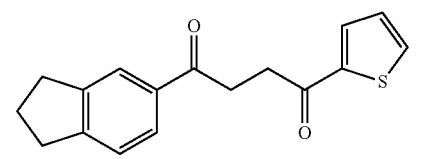 766 | 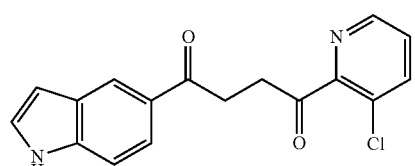 775 |
| 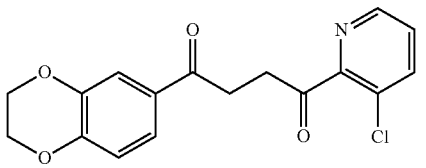 767 | 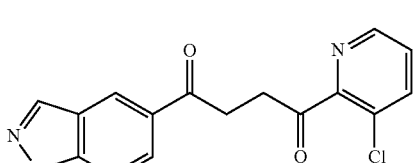 776 |
| 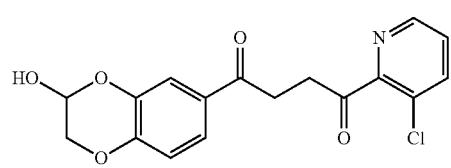 768 | 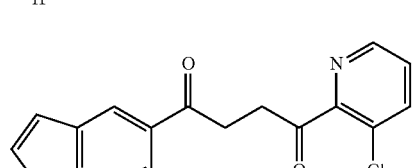 777 |
| 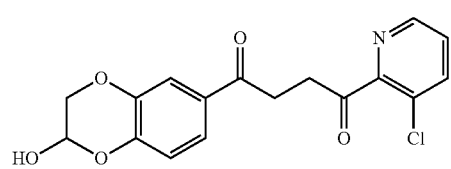 769 | 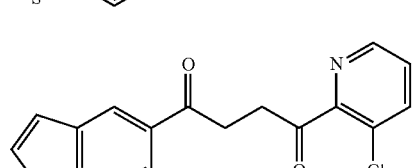 778 |
| 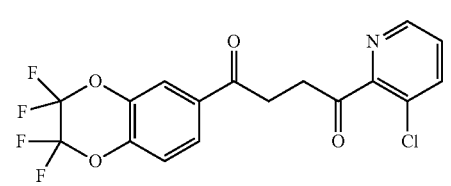 770 | 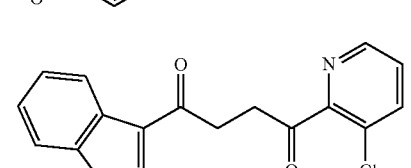 779 |

TABLE 1-continued

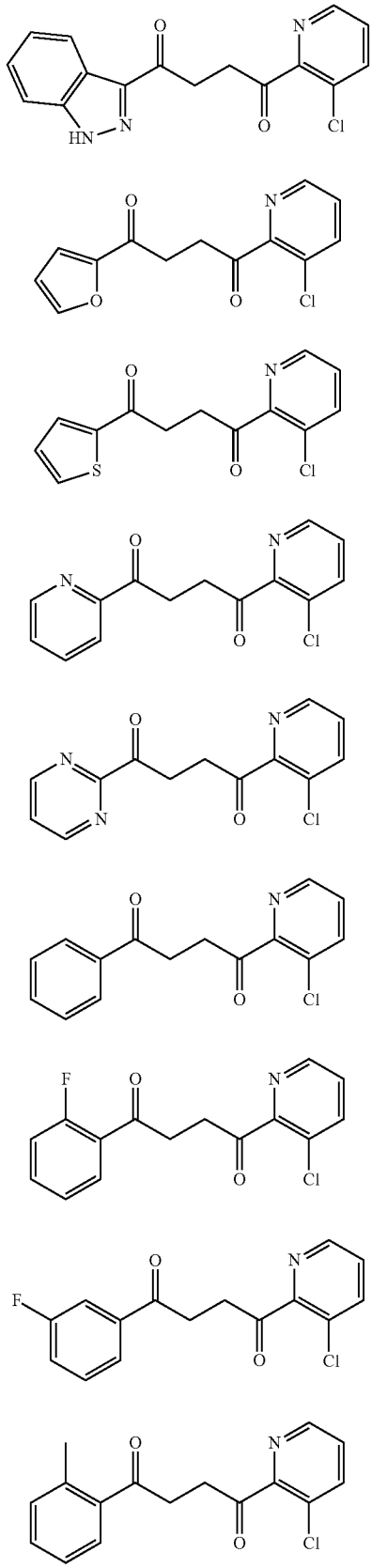

780
781
782
783
784
785
786
787
788

TABLE 1-continued

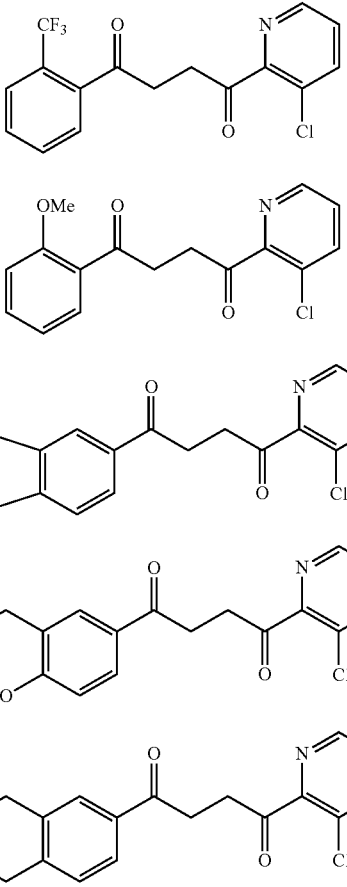

789
790
791
792
793

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt thereof; and (b) a pharmaceutically acceptable carrier.

The compounds provided herein may also be useful in combination (administered together or sequentially) with other known agents.

Non-limiting examples of diseases which can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and other known agents are alopecia, idiopathic pulmonary fibrosis, sensorineural hearing loss (SNHL), spinal cord injury, osteoporosis, Alzheimer's disease, macular degeneration, and retinitis pigmentosa.

In some embodiments, alopecia can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of Minoxidil (Rogaine) and Finasteride (Propecia).

In some embodiments, a composition containing a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV could be applied after a dermatologic surgeon transplants micrografts of skin containing hair follicles. In some embodiments, the micrografts are transplanted from from one area of the scalp to another.

In some embodiments, a composition containing a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV could be applied after scalp reduction, which is the surgical removal of scalp skin without hair, or after flap surgery, which involves moving the scalp with hair to an adjacent area that is lacking hair.

In some embodiments, idiopathic pulmonary fibrosis can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of: pirfenidone (Esbriet), prednisone, azathioprine, N-acetylcysteine, interferon gamma-1b, bosentan, Nintedanib (BIBF 1120), QAX576, and an anti-inflammatory agent such as a corticosteroids.

In some embodiments, sensorineural hearing loss (SNHL) can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of the following therapies: (a) hair cell regeneration using stem cell and gene therapy; (b) with hearing aids; (c) with cochlear implants; (d) with idebenone or combined with vitamin E; (e) with an anti-inflammatory agent such as a corticosteroid; or (f) with high doses of vitamins A, C, and E, and magnesium.

In some embodiments, spinal cord injury can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of the following therapies: (a) surgery to remove any bone fragments from the spinal canal and to stabilize the spine; (b) an anti-inflammatory agent such as a corticosteroid, such as methylprednisolone; (c) with physical therapy and/or mechanical devices; (d) with the promotion of axonal sprouting/regeneration by co-administration of hydrogels or self-assembling nanofibers; (e) by co-administration of carbon nanotubes; or (f) by co-administration of poly-lactic acid microfibers.

In some instances, a compound according to Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is administered in combination with one or more second therapeutic agents, e.g., therapeutic agents useful in the treatment of bone disorders or conditions described herein. For example, certain second therapeutic agents can promote tissue growth or infiltration, such as growth factors. Exemplary growth factors include, without limitation, epidermal growth factor (EGF), vascular endothelial growth factor (VEGF), fibroblast growth factor (FGF), platelet-derived growth factor (PDGF), transforming growth factors (TGFs), parathyroid hormone (PTH), leukemia inhibitory factor (LIF), and insulin-like growth factors (IGFs). Other second therapeutic agents can promote bone growth, such as bone morphogenetic proteins (U.S. Pat. No. 4,761,471; PCT Pub. WO 90/11366), osteogenin [Sampath, et al., *Proc. Natl. Acad. Sci. USA* (1987), 84(20), 7109-7113], NaF [Tencer, et al., *Journal of Biomedical Materials Research* (1989), 23(6), 571-589], and peptide sequences such as IKVAV [Tashiro, et al., *The Journal of Biological Chemistry* (1989), 264(27), 16174-16182].

In some embodiments, osteoporosis can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of: Alendronate (Fosamax), Risedronate (Actonel, Atelvia), Ibandronate (Boniva), Zoledronic acid (Reclast, Zometa), Teriparatide, Raloxifene, Denosumab, and strontium ranelate.

In some embodiments, osteoporosis can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of the following therapies: (a) systemic hormone therapy (e.g., estrogen); (b) estrogen in conjunction with progesterone and/or progestin; and (c) with exercise and/or nutritional changes (e.g., an increase in the intake of sources of calcium and vitamin D, and/or an increase in the intake of sources of vitamin D and/or vitamin K).

In some embodiments, Alzheimer's disease can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of: cholinesterase inhibitors such as Donepezil (Aricept), Glutamine (Razadyne), and Rivastigmine (Exelon); memantine; or with production blockers to reduce the amount of beta-amyloid formed in the brain.

In some embodiments, a composition containing a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV could be combined with immunization strategies to prevent beta-amyloid from clumping into plaques and help the body clear it from the brain.

In some embodiments, macular degeneration can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of: Bevacizumab (Avastin), Ranibizumab (Lucentis), Pegaptanib (Macugen), or Aflibercept (Eylea).

In some embodiments, macular degeneration can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of the following therapies: (a) photodynamic therapy (PDT) (in some cases in combination with a compound like verteporfin (Visudyne)); (b) laser treatment; or (c) increased vitamin intake of antioxidant vitamins and/or zinc. The following vitamins are suggested: vitamin C, vitamin E, β-carotene (often as vitamin A), zinc (as zinc oxide), and copper.

In some embodiments, retinitis pigmentosa can be treated with a combination of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV and one or more of the following active agents or therapies: (a) vitamin A palmitate; (b) the Argus II retinal implant; (c) UF-021 (Ocuseva); (d) stem cell and/or gene therapy; or (e) Pikachurin.

Administration of the compounds disclosed herein or the pharmaceutically acceptable salts thereof can be via any of the accepted modes of administration for agents that serve similar utilities including, but not limited to, orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. In some embodiments, a compound is administered orally or parenterally.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like, are provided herein. The dosage forms may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may also be used. The compounds can also be administered in sustained or controlled release dosage forms, including depot injections, osmotic pumps, pills (tablets and/or capsules), transdermal (including electrotransport) patches, implants and the like, for prolonged and/or timed, pulsed administration at a predetermined rate.

Controlled-release systems can include a component selected from the group consisting of immediate release component(s), pulsatile release component(s), delayed release component(s), sustained release component(s), and combinations thereof. Systems may be in, for example, the form of a matrix, reservoir/membrane, osmotic pump, or hybrids thereof. In some embodiments, a controlled-release system can include compounds entrapped in or otherwise incorporated into or coupled with polymer carriers or polymeric devices, such as micelles, nanoparticles, microspheres, hydrogels, and other types of polymer carriers or devices. In some embodiments, the controlled-release system delivers a compound provided herein at a controlled rate for an extended period of time. In another embodiment, the controlled-release system localizes the action of a compound by spatial placement near where the compound is needed. In another embodiment, the controlled release system includes targeted delivery of a compound to a particular cell type.

The compounds can be administered either alone or more typically in combination with a conventional pharmaceutical carrier, excipient, diluent, or the like. The term "excipient" is used herein to describe any ingredient other than the compound(s) provided herein. Pharmaceutically acceptable excipients include, but are not limited to, ion exchangers; alumina; aluminum stearate; lecithin; self-emulsifying drug delivery systems (SEDDS) such as d-α-tocopherol polyethylene glycol 1000 succinate; surfactants used in pharmaceutical dosage forms such as Tweens, poloxamers or other similar polymeric delivery matrices; serum proteins, such as human serum albumin; buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

In one embodiment, the compositions can take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule) or as a dry powder. Unit dosage forms in which the two active ingredients are physically separated are also contemplated; e.g., capsules with granules (or tablets in a capsule) of each drug; two-layer tablets; two-compartment gel caps, etc. Enteric coated or delayed release oral dosage forms are also contemplated.

In another preferred embodiment, compositions described herein are used as compound-eluting compositions (e.g., controlled release) for a medical device including, but not limited to a temporary or permanent implant, sponge, polymer, or gel.

The implant according to an embodiment of the disclosure is an orthopedic implant including, but not limited to (i) a hip joint, (ii) screws, cannulated screws, nails, meshs, cages, wires, pins, intramedullary nails, rods, posts, anchors, and plates intended to join or attach bone fragments, pieces, or parts with each other, (iii) external skeletal fixators such as monolateral, multiplanar or hybrid fixators, (iv) implants intended for treatment of degenerative instabilities, fractures, tumors, and deformities in respect of the spine, (v) cranio-maxillofacial implants intended for treatment of fractures, reconstruction, and correction of deformities, of mandible, mid-face, or skull, (vi) surgical stents, collagen stents, intramedullary bone stents, (vii) anterior cruciate ligament (ACL) and/or posterior cruciate ligament (PCL) Reconstruction Systems, and (viii) dental implants.

Liquid pharmaceutically administrable compositions can, for example, be prepared by dissolving, dispersing, etc. a compound as provided herein and optional pharmaceutical adjuvants in a carrier (e.g., water, saline, aqueous dextrose, glycerol, glycols, ethanol or the like) to form a solution, colloid, liposome, emulsion, complexes (including inclusion complexes), coacervate, or suspension. If desired, the pharmaceutical composition can also contain auxiliary substances such as wetting agents, emulsifying agents, co-solvents, solubilizing agents, pH buffering agents, and the like (e.g., sodium acetate, sodium citrate, cyclodextrins and derivatives, sorbitan monolaurate, triethanolamine acetate, triethanolamine oleate, and the like).

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for oral systemic delivery is about 0.25 mg/Kg to about 50 mg/Kg.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for systemic delivery is about 0.25 mg/Kg to about 20 mg/Kg.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for local delivery is about 0.050 μg/Kg to about 50 μg/Kg.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for topical delivery is about 0.1 μg/cm² to about 20 μg/cm².

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is about 1.0 μg/eye to about 1 mg/eye.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV loaded into a compound-eluting implant is about 0.1 μg/Kg to about 1 mg/Kg.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for pulmonary delivery is about 1 μg/dose to about 15 mg/dose.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV for parenteral administration is about 0.05 mg/Kg to about 15 mg/Kg.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is about 2.0 mg/Kg to about 13 mg/Kg in humans.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is about 3.0 mg/Kg to about 12 mg/Kg in humans.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is about 4.0 mg/Kg to about 11 mg/Kg in humans.

In some embodiments, the unit dosage of compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloids, liposomes, complexes (like inclusion complexes), coacervate, or suspensions, as emulsions, or in solid forms suitable for reconstitution in liquid prior to injection. The percentage of a compound provided herein contained in such parenteral compositions is dependent on the specific disorder being treated, the activity of the compound, and the needs of the patient. However, percentages of ingredient compound of about 0.01% to about 10% in solution may be used, and could be higher if the composition is a concentrated solid or suspension, which could be subsequently diluted.

In some embodiments, a composition can comprise about 0.01 to about 10% of the compound in solution.

In some embodiments, the composition will comprise about 0.01 to about 5% of the compound in solution.

In some embodiments, the composition will comprise about 0.01 to about 4% of the compound in solution.

In some embodiments, the composition will comprise about 0.05 to about 3% of the compound in solution.

In some embodiments, the composition will comprise about 0.02 to about 2% of the compound in solution.

In some embodiments, the compositions are provided in dosage forms suitable for continuous dosage by intravenous infusion over a period of about 1 to about 96 hours.

In some embodiments, the compositions are provided in dosage forms suitable for continuous dosage by intravenous infusion over a period of about 1 to about 72 hours.

In some embodiments, the compositions are provided in dosage forms suitable for continuous dosage by intravenous infusion over a period of about 1 to about 48 hours.

In some embodiments, the compositions are provided in dosage forms suitable for continuous dosage by intravenous infusion over a period of about 1 to about 24 hours.

In some embodiments, the compositions are provided in dosage forms suitable for continuous dosage by intravenous infusion over a period of about 1 to about 12 hours.

In some embodiments, the compositions are provided in dosage forms suitable for continuous dosage by intravenous infusion over a period of about 1 to about 6 hours.

In some embodiments, these compositions can be administered by intravenous infusion to humans at doses of about 1.5 mg/m² to about 300 mg/m².

In some embodiments, these compositions can be administered by intravenous infusion to humans at doses of about 1.5 mg/m² to about 200 mg/m².

In some embodiments, these compositions can be administered by intravenous infusion to humans at doses of about 1.5 mg/m² to about 100 mg/m².

In some embodiments, these compositions can be administered by intravenous infusion to humans at doses of about 1.0 mg/m² to about 50 mg/m².

In some embodiments, these compositions can be administered by intravenous infusion to humans at doses of about 50 mg/m² to about 200 mg/m².

In some embodiments, these compositions can be administered by intravenous infusion to humans at doses of about 75 mg/m² to about 175 mg/m².

In some embodiments, these compositions can be administered by intravenous infusion to humans at doses of about 100 mg/m² to about 150 mg/m².

It is to be noted that concentrations and dosage values may also vary depending on the specific compound and the severity of the condition to be alleviated. It is to be further understood that for any particular patient, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation, or other suitable device or technique.

In some embodiments, aerosols intended for delivery to the nasal mucosa are provided for inhalation through the nose. For delivery to the nasal cavities, inhaled particle sizes of about 5 to about 100 microns can be used, for example, particle sizes of about 10 to about 60 microns. For nasal delivery, a larger inhaled particle size is can be used. In some embodiments, the larger particles may maximize impaction on the nasal mucosa or minimize or prevent pulmonary deposition of the administered formulation. In some embodiments, aerosols intended for delivery to the lungs are provided for inhalation through the nose or the mouth. For delivery to the lung, inhaled aerodynamic particle sizes of about less than 10 μm can be used, for example, an aerodynamic particle size of about 1 to about 10 microns can be used. Inhaled particles may be defined as liquid droplets containing dissolved compound, liquid droplets containing suspended compound particles (in cases where the compound is insoluble in the suspending medium), dry particles of pure compound, compound incorporated with excipients, liposomes, emulsions, colloidal systems, coacervates, aggregates of compound nanoparticles, or dry particles of a diluent which contain embedded compound nanoparticles.

In some embodiments, compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose®, or the AERx® systems). Propellant-based systems may use suitable pressurized metered-dose inhalers (pMDIs). Dry powders may use dry powder inhaler devices (DPIs), which are capable of dispersing the compound substance effectively. A desired particle size and distribution may be obtained by choosing an appropriate device.

In some embodiments, the compositions of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV disclosed herein intended for delivery to the ear can be administered via an implanted pump and delivery system (e.g., through a needle directly into the middle or inner ear (cochlea) or through a cochlear implant stylet electrode channel or alternative prepared compound delivery channel such as but not limited to a needle through temporal bone into the cochlea).

Other options include delivery via a pump through a thin film coated onto a multichannel electrode or electrode with a specially imbedded compound delivery channel (pathways) carved into the thin film for this purpose. In other embodiments, a compound provided herein can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulations described herein are administered onto the round window membrane via a surgical approach to the round window membrane comprising modification of the crista fenestrae cochleae.

In some embodiments, the compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV are formulated into rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the compound (either as a solution, colloid, suspension, or a complex) can be prepared by mixing the compound with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol.

Solid compositions can be provided in various different types of dosage forms, depending on the physicochemical properties of the compound, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In some embodiments, the solid composition is a highly porous lyophilized form. Such lyophilizates, sometimes also called wafers or lyophilized tablets, can be useful for their rapid disintegration, which can allow for the rapid dissolution of the compound.

In some embodiments, the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid compound dissolution is that of powders, granules, or pellets from water-soluble excipients which are coated with the compound, so that the compound is located at the outer surface of the individual particles. In this type of system, a water-soluble low molecular weight excipient can be useful for preparing the cores of such coated particles, which can be subsequently coated with a coating composition comprising the compound and, in some cases, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with one or more of osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; otic disorders like cochlear hair cell loss; eye diseases including, but not limited to, wet age-related macular degeneration, dry age-related macular degeneration, geographic atrophy, diabetic retinopathy, diabetic macular edema, retinal detachment, retinal degeneration, retinal vein occlusion, retinopathy of prematurity, retinitis pigmentosa, retinopathies, Leber congenital amaurosis and glaucoma, and diseases related to differentiation and growth of stem cell, comprising hair loss, hematopoiesis related diseases, tissue regeneration related diseases, and other diseases associated with abnormalities in development, stem cell differentiation and cell proliferation.

In some embodiments, a compound-eluting coating or a controlled release system comprising a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof, is provided herein.

In some embodiments, a medical device comprising a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof, is provided herein.

In some embodiments, an implant, sponge, polymer, ointment, cream or gel composition suitable for in vivo use comprising a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof, is provided herein.

Methods of Treatment

The compounds and compositions provided herein can be used as activators of one or more members of the Wnt pathway, including one or more Wnt proteins, and thus can be used to treat a variety of disorders and diseases in which aberrant Wnt signaling is implicated, such as osteoporosis and osteoarthropathy; osteogenesis imperfecta, bone defects, bone fractures, periodontal disease, otosclerosis, wound healing, craniofacial defects, oncolytic bone disease, traumatic brain injuries related to the differentiation and development of the central nervous system, comprising Parkinson's disease, strokes, ischemic cerebral disease, epilepsy, Alzheimer's disease, depression, bipolar disorder, schizophrenia; eye diseases including, but not limited to, wet age-related macular degeneration, dry age-related macular degeneration, geographic atrophy, diabetic retinopathy, diabetic macular edema, retinal detachment, retinal degeneration, retinal vein occlusion, retinopathy of prematurity, retinitis pigmentosa, retinopathies, Leber congenital amaurosis and glaucoma and diseases related to differentiation and growth of stem cell, comprising hair loss, hematopoiesis related diseases, tissue regeneration related diseases and other diseases associated with abnormalities in development, stem cell differentiation and cell proliferation.

With respect to hair loss, the canonical Wnt/β-catenin signaling pathway has been linked to hair follicle development and regeneration. Accordingly, the compounds and compositions described herein may be used topically to treat hair loss by modulation of the Wnt/β-catenin signaling pathway.

With respect to neurodegenerative diseases, Wnt/β-catenin signal transduction system plays a role in the differentiation and development of nerve cells for the central nervous system. Consequently, the compounds and compositions described herein may be used to reactivate lost Wnt signaling function involved in neurodegeneration.

Other neurodegenerative diseases can also be treated with the compounds and compositions described herein.

More particularly, neurodegenerative diseases that may be treated by the compound, compositions and methods described herein include, but are not limited to, the following:

Parkinson's disease, schizophrenia, Huntington's disease, amyotrophic lateral sclerosis (Lou Gehrig's disease), primary lateral sclerosis (PLS), progressive muscular atrophy (PMA), bipolar disorder, depression, strokes, spinal cord injury, ischemic cerebral disease, epilepsy, brain damage, and spinocerebellar ataxia type 1 (SCA1).

With respect to eye diseases, Wnt/β-catenin signal transduction system is thought to regulate the maintenance of a retinal progenitor population in the ciliary marginal zone (CMZ), and thus can function as a putative stem cell factor in the retina.

Other eye diseases can also be treated with the compounds and compositions described herein.

More particularly, eye diseases that may be treated by the compound, compositions and methods described herein include, but are not limited to, the following:

wet age-related macular degeneration, dry age-related macular degeneration, geographic atrophy, diabetic retinopathy, diabetic macular edema, retinal detachment, retinal degeneration, retinal vein occlusion, retinopathy of prematurity, retinitis pigmentosa, retinopathies, Leber congenital amaurosis and glaucoma.

With respect to diseases associated with differentiation and growth of stem cell, Wnt/β-catenin signaling participates in the self-renewal of stem cells in many different tissues, including the skin, intestine, brain, and blood. Therefore, the compounds and compositions described herein may be used to treat disorders and diseases related to abnormalities in development.

In some embodiments, the disclosure provides a method for activating the Wnt signaling in order to treat a disorder or disease in a patient, the method comprising administering to the patient a therapeutically effective amount of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof.

In some embodiments, the disorder or disease is neurodegenerative disease.

In some embodiments, the neurodegenerative disease is Parkinson's disease, stroke, spinal cord injury, ischemic cerebral disease, epilepsy, Alzheimer's disease, dementia, depression, bipolar disorder, or schizophrenia.

In some embodiments, the disorder or disease is an eye disease.

In some embodiments, the eye diseases include, but are not limited to, wet age-related macular degeneration, dry age-related macular degeneration, geographic atrophy, diabetic retinopathy, diabetic macular edema, retinal detachment, retinal degeneration, retinal vein occlusion, retinopathy of prematurity, retinitis pigmentosa, retinopathies, Leber congenital amaurosis and glaucoma.

In some embodiments, the disorder or disease is related to differentiation and growth of stem cells such as hair loss, hematopoiesis related diseases, tissue regeneration related diseases and other diseases associated with abnormalities in development, stem cell differentiation, and cell proliferation.

In some embodiments, the disorder or disease is osteoporosis, osteoarthropathy, osteogenesis imperfecta, bone defects, bone fractures, periodontal disease, otosclerosis, wound healing, mucositis (oral and gastrointestinal), craniofacial defects, and oncolytic bone disease.

In some embodiments, the patient is a mammal. In some embodiments, the patient is a human.

In some embodiments, a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV activates one or more proteins in the Wnt pathway.

In some embodiments, a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV activates signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, a pharmaceutical composition provided herein comprises a therapeutically effective amount of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, or a pharmaceutically acceptable salt thereof, and a pharmaceutically acceptable excipient.

In some embodiments, the pharmaceutical composition comprises a therapeutically effective amount of a compound of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV, wherein the composition is suitable for use as or inclusion in a compound-eluting coating for a medical device.

EXAMPLES

Compound Preparation

The starting materials used in preparing the compounds of the disclosure are known, made by known methods, or are commercially available. It will be apparent to the skilled artisan that methods for preparing precursors and those compounds functionality related to the compounds provided herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis*, 4$^{th}$ Ed., John Wiley & Sons (2007).

Trademarks used herein are examples only and reflect illustrative materials used at the time of the invention. The skilled artisan will recognize that variations in lot, manufacturing processes, and the like, are expected. Hence the examples, and the trademarks used in them are non-limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
Ac$_2$O=acetic anhydride
BBr$_3$=boron tribromide
BF$_3$*Et$_2$O=boron trifluoride ethyl etherate
Boc$_2$O=di-t-butyl dicarbonate
B(OiPr)$_3$=boron tri-isopropoxide
brine=saturated aqueous sodium chloride
CDCl$_3$=deuterated chloroform
CH(OMe)$_3$=trimethyl orthoformate
Cs$_2$CO$_3$=cesium carbonate
CuBr$_2$=copper(II) bromide
CuI=copper(I) iodide or cuprous iodide
DCM=dichloromethane
DMAP=4-dimethylaminopyridine
DMF=dimethylforamide
DMSO-d$_6$=deuterated dimethylsulfoxide
ESIMS=electron spray mass spectrometry
EtOAc=ethyl acetate
HCl=hydrochloric acid
HOAc=acetic acid
HPLC=high-performance liquid chromatography
K$_2$CO$_3$=potassium carbonate
LAH=lithium aluminium hydride
m-CPBA=meta-chloroperoxybenzoic acid
MeCN=acetonitrile
MeOH=methanol
MgSO$_4$=magnesium sulfate
NaH=sodium hydride
NBS=N-bromosuccinimide
NMR=nuclear magnetic resonance
Pd(Ph$_3$)$_4$=tetrakis(triphenylphosphorus) palladium(0)
PE=petroleum ether
POCl$_3$=phosphorus oxychloride
TEA=triethylamine
THF=tetrahydrofuran
TLC=thin layer chromatography The following example schemes are provided for the guidance of the reader, and collectively represent exemplary methods for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with the same numberings in other sections of the disclosure. Unless otherwise indicated, all variables are as defined above.

General Procedures

Compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV of the present disclosure can be prepared as depicted in Scheme 1.

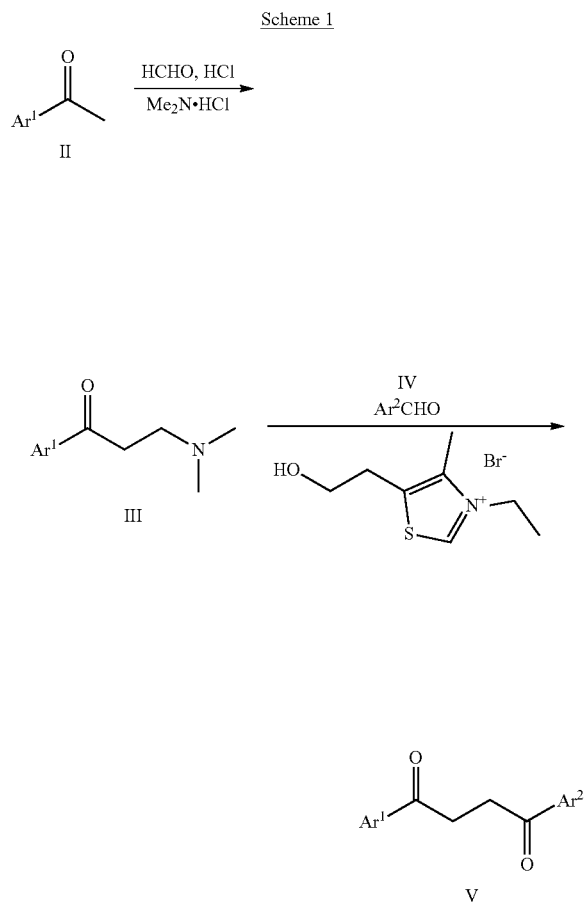

Scheme 1 describes a method for the preparation of unsubstituted 1,4-diketones derivatives (V) by the modified Stetter reaction of a Mannich base as a vinyl ketone precursor with aldehyde. The Mannich base is formed by first reacting an aryl methyl ketone (II) with paraformaldehyde and dimethylamine hydrochloride to form the 3-dimethyl-amino-propan-1-one (III). Next, Mannich base (III) was reacted with various aryl aldehydes (IV) under standard Stetter conditions using a thiazolium salt as the catalyst yields unsubstituted 1,4-diketone derivatives (V).

Compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV of the present disclosure can also be prepared from a methyl ketone and -bromo ketone as depicted in Scheme 2.

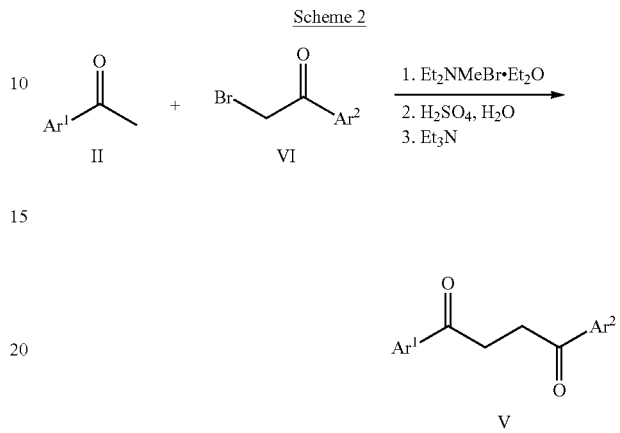

Scheme 2 describes a method for the preparation of 1,4-diketones derivatives (V) by the method of Kel'in and Kulinkovich [*Synthesis* (1996), (3), 330-2] which is based on the application of magnesium reagents in the cross-aldol condensation of aryl methyl ketones with α-bromo ketones. An aryl methyl ketone (II) is reacted with a substituted α-bromo ketone (VI) in the presence of diethylamidomagnesium bromide and acid followed by treatment with TEA to produce the desired 1,4-diketone derivatives (V).

Compounds of Formula I, Ia, Ib, Ic, Id, Ie, If, Ig, Ih, Ii, II, IIa, IIb, IIc, IId, IIe, IIf, III, IIIa, IIIb, IIIc, IIId, and/or IV of the present disclosure can also be prepared from an α-bromo ketone and a 1,3-diketone as depicted in Scheme 3.

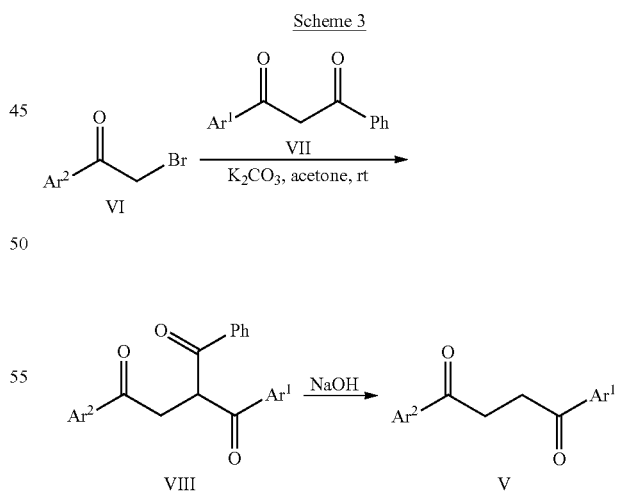

Scheme 3 describes a method for preparation of unsubstituted 1,4-diketones derivatives (V) by first reacting an α-bromo ketone (VI) with a 1,3-diketone in the presence of a mild base to form the triketone (VIII). Next, the triketone (VIII) was debenzoylated with strong base to yield unsubstituted 1,4-diketone derivatives (V).

Illustrative Compound Examples

Preparation of intermediate (XVI) is depicted below in Scheme 4.

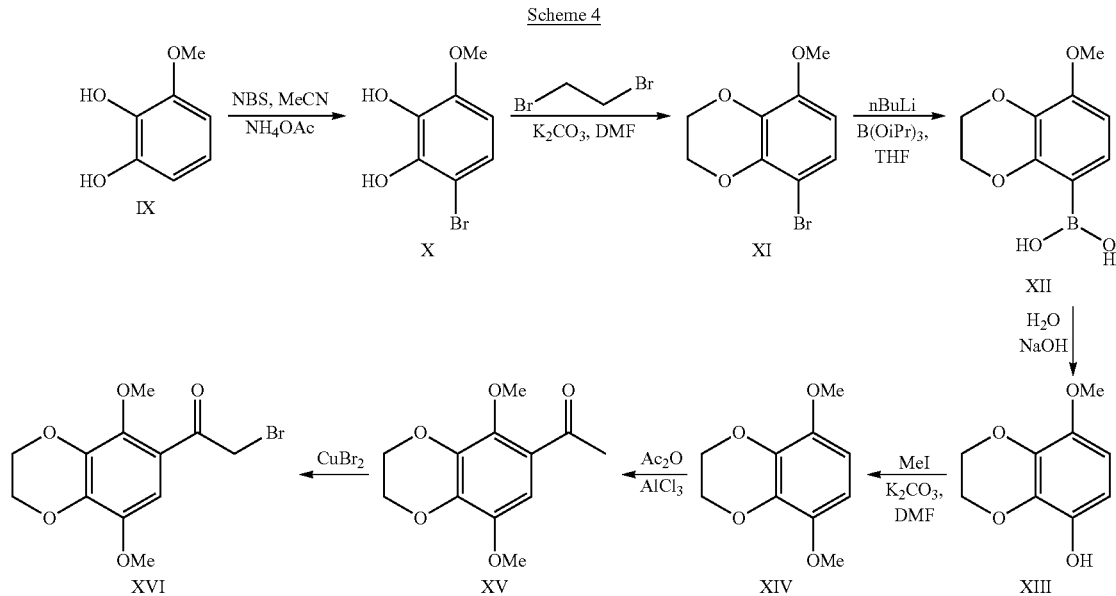

Scheme 4

Step 1

To a solution of 3-methoxybenzene-1,2-diol (IX) (15 g, 0.107 mol), and NH$_4$OAc (0.83 g, 10.7 mmol) in MeCN (500 mL) was added NBS (20 g, 0.112 mol) portion wise at room temperature and stirred for an hour. The reaction mixture was concentrated under vacuum, diluted with EtOAc (300 mL), washed with an aqueous solution of 50% NaHSO$_3$ (200 mL), and brine (200 mL). The EtOAc layer was dried over anhydrous Na$_2$SO$_4$, concentrated under vacuum and purified on a silica gel column (100% DCM) to give 3-bromo-6-methoxybenzene-1,2-diol (X) (18 g, 82.2 mmol, 76% yield) as a white solid. $^1$H NMR (CDCl$_3$, 500 MHz) δ ppm 3.87 (s, 3H), 5.54 (s, 1H), 5.60 (s, 1H), 6.42 (d, J=8.78 Hz, 1H), 6.98 (d, J=8.78 Hz, 1H).

Step 2

To a solution of 3-bromo-6-methoxybenzene-1,2-diol (X) (18 g, 82.2 mmol), K$_2$CO$_3$ (25 g, 0.18 mol) and 1,2-dibromoethane (18.53 g, 0.98.6 mmol) in DMF (100 mL) was stirred at 100° C. for 2 h. The reaction mixture was diluted with water (300 mL) and extracted with EtOAc (3×200 mL). The combined organic layers were washed with brine (2×100 mL), dried over Na$_2$SO$_4$, and concentrated under vacuum. The residue was purified by column chromatography on silica gel (100% DCM) to produce 5-bromo-8-methoxy-2,3-dihydrobenzo[b][1,4]dioxine (XI) (16 g, 65.3 mmol, 80% yield) as a white solid. $^1$H NMR (CDCl$_3$, 500 MHz) δ ppm 3.86 (s, 3H), 4.35 (dd, J=13.05 Hz, 4.27 Hz, 4H), 6.42 (d, J=8.78 Hz, 1H), 7.03 (d, J=8.78 Hz, 1H).

Step 3

To a solution of 5-bromo-8-methoxy-2,3-dihydrobenzo[b][1,4]dioxine (XI) (16 g, 65.3 mmol) in anhydrous THF (150 mL) was slowly added n-butyllithium (31.5 mL, 78.4 mmol) dropwise at −78° C. This mixture was stirred at −78° C. for an hour before adding triisopropylborate (14.8 g, 78.4 mmol) dropwise. The reaction was allowed warm to room temperature and stir overnight before quenching with 2N HCl (100 mL). The mixture was extracted with EtOAc (2×200 mL). The combined organic layers were washed with brine, dried over anhydrous Na$_2$SO$_4$ and concentrated under vacuum. The crude solid was recrystallized with EtOAc/PE to yield 8-methoxy-2,3-dihydrobenzo[b][1,4]dioxin-5-ylboronic acid (XII) (12 g, 57.1 mmol, 87.5% yield) as a white solid. $^1$H NMR (CDCl$_3$, 500 MHz) δ ppm 3.91 (s, 3H), 4.30-4.44 (m, 4H), 5.46 (s, 2H), 6.58 (d, J=8.28 Hz, 1H), 7.36 (d, J=8.28 Hz, 1H).

Step 4

To a solution of 8-methoxy-2,3-dihydrobenzo[b][1,4]dioxin-5-ylboronic acid (XII) (12 g, 57.14 mmol) in water (60 mL) and THF (60 mL) was added NaOH (4 g, 0.1 mmol) at 0° C. and stirred for 20 min. To this clear solution was added H$_2$O$_2$ (19.4 mL, 0.17 mol) dropwise at 0° C. The reaction mixture was quenched with 50% aqueous NaHSO$_3$ (100 mL), water (50 mL), and extracted with EtOAc (2×200 mL). The EtOAc layer was washed with brine, dried over anhydrous Na$_2$SO$_4$ and concentrated to give crude 8-methoxy-2,3-dihydrobenzo[b][1,4]dioxin-5-ol (XIII) (12 g, 57.1 mmol, quantitative yield). The crude product was used for the next step without any additional purification.

Step 5

A solution of 8-methoxy-2,3-dihydrobenzo[b][1,4]dioxin-5-ol (XIII), K$_2$CO$_3$ (10 g, 70.9 mmol), and MeI (16 g, 0.19 mmol) in DMF (50 mL) was stirred at 40° C. for 5 h. This reaction mixture was cooled, diluted with water (150 mL), and extracted with EtOAc (2×100 mL). The combined organic layers were washed with brine, dried over anhydrous Na$_2$SO$_4$, concentrated under vacuum, and purified using a silica gel column (20% EtOAc/PE) to give 5,8-dimethoxy-2,3-dihydrobenzo[b][1,4]dioxine (XIV) (3 g, 15.3 mmol, 50% yield) as a yellow oil. $^1$H NMR (CDCl$_3$, 500 MHz) δ ppm 3.84 (s, 6H), 4.34 (s, 4H), 6.40 (s, 2H).

Step 6

A solution of 5,8-dimethoxy-2,3-dihydrobenzo[b][1,4]dioxine (XIV) (0.75 g, 3.82 mmol), ZnCl$_2$ (3.13 g, 23 mmol) and Ac$_2$O in CH$_3$NO$_2$ (25 mL) was stirred at 50° C. for 1 h. The reaction mixture was cooled, diluted with EtOAc (100 mL), and washed with brine (30 mL). The EtOAc layer was dried over anhydrous Na$_2$SO$_4$ and concentrated under vacuum. The residue was purified by the silica gel column (20% EtOAc/PE) to give 1-(5,8-dimethoxy-2,3-dihydrobenzo[b][1,4]dioxin-6-yl)ethanone (XV) (800 mg, 3.36 mmol, 88% yield) as a white solid. $^1$H NMR (CDCl$_3$, 500 MHz) δ ppm 2.64 (s, 3H), 3.89 (d, J=3.26 Hz, 6H), 4.37 (dd, J=14.56 Hz, 4.77 Hz, 4H), 6.96 (s, 1H).

Step 7

A solution of 1-(5,8-dimethoxy-2,3-dihydrobenzo[b][1,4]dioxin-6-yl)ethanone (XV) (800 mg, 3.36 mmol), CuBr$_2$ (1.13 g, 5.04 mmol) in EtOAc (20 mL), CHCl$_3$ (20 mL) and MeOH (1 mL) was stirred at 50-60° C. for 5 h. This reaction mixture was cooled, diluted with sat aqueous NH$_4$Cl solution (30 mL), and extracted with EtOAc (50 mL). The organic layer was washed with brine, dried over anhydrous Na$_2$SO$_4$, and concentrated under vacuum to give a crude 2-bromo-1-(5,8-dimethoxy-2,3-dihydrobenzo[b][1,4]dioxin-6-yl)ethanone (XVI) (1.1 g, 3.47 mmol). The crude product was used for the next step without any additional purification.

Preparation of intermediate (XXIII) is depicted below in Scheme 5.

Step 2

A solution of 1-(5-hydroxy-2,3-dihydrobenzo[b][1,4]dioxin-6-yl) ethanone (XVIII) (11 g, 56.65 mmol), K$_2$CO$_3$ (15.6 g, 0.113 mol) and MeI (16 g, 0.113 mol) DMF (80 mL) was stirred at room temperature for 18 h. This reaction mixture was diluted with water (300 mL), and extracted with 20% EtOAc/PE (2×200 mL). The combined organic layers were washed with brine (2×100 mL), dried with Na$_2$SO$_4$, and concentrated under vacuum to give 1-(5-methoxy-2,3-dihydrobenzo[b][1,4]dioxin-6-yl)ethanone (XIX) (11 g, 52.8 mmol, 94% yield) as a yellow oil. $^1$H NMR (CDCl$_3$, 500 MHz) δ ppm 2.60 (s, 3H), 3.93 (s, 3H), 4.32 (s, 4H), 6.67 (d, J=8.78 Hz, 1H), 7.31 (d, J=9.03 Hz, 1H).

Step 3

A solution of 1-(5-methoxy-2,3-dihydrobenzo[b][1,4]dioxin-6-yl)ethanone (XIX) (11 g, 53 mmol) and m-CPBA (55 g, 0.23 mol), in DCM (120 mL), was heated to 50-60° C. for 18 h. This reaction mixture was cooled and filtered. The filtrate was diluted with DCM (250 mL) and washed with a 50% aqueous NaHSO$_3$ solution (200 mL), sat NaHCO$_3$ (200 mL) and brine. The DCM layer was dried over anhydrous Na$_2$SO$_4$ and concentrated under vacuum, purified by column chromatography on silica gel (20% EtOAc/PE) to give 5-methoxy-2,3-dihydrobenzo[b][1,4]dioxin-6-yl acetate Scheme 5

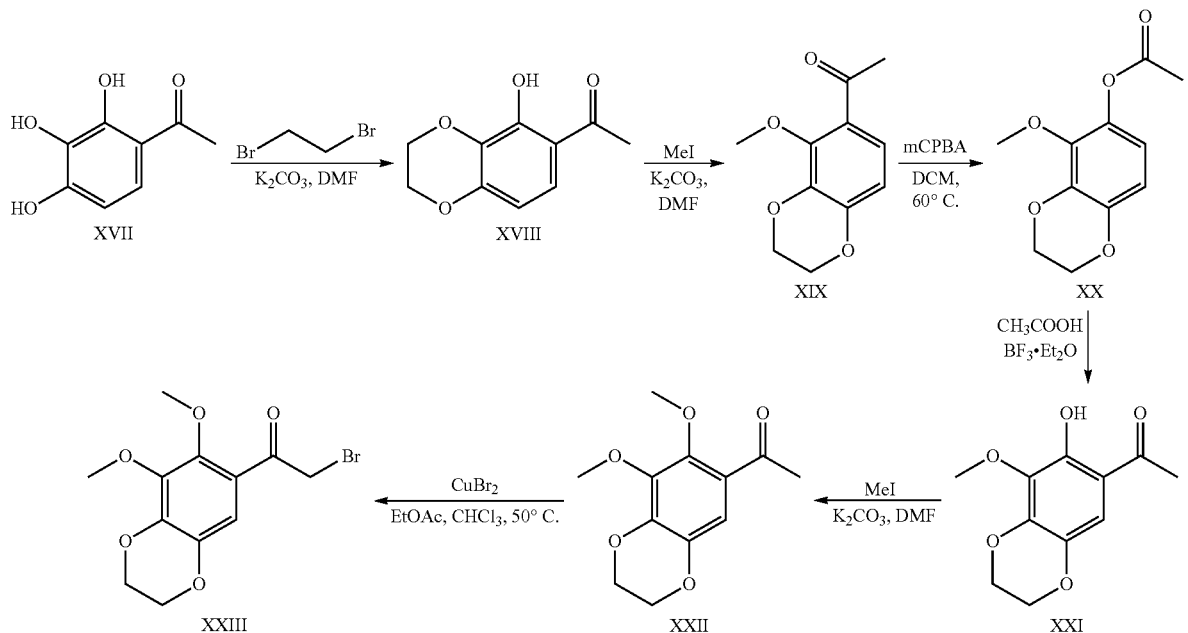

Step 1

A solution of 1-(2,3,4-trihydroxyphenyl)ethanone (XVII) (30 g, 0.18 mol), 1,2-dibromoethane (33.52 g, 0.18 mol), and K$_2$CO$_3$ (74 g, 0.53 mol) in DMF (200 mL) was stirred at 100° C. for 2 h under N$_2$. The black reaction mixture was cooled, diluted with water (1000 mL), and extracted with 40% EtOAc/PE (3×300 mL). The combined organic layers were washed with brine (3×50 mL), dried over Na$_2$SO$_4$ and concentrated under vacuum to give 1-(5-hydroxy-2,3-dihydrobenzo[b][1,4]dioxin-6-yl)ethanone (XVIII) (11 g, 56.6 mmol, 33% yield) as a yellow solid. $^1$H NMR (CDCl$_3$, 500 MHz) δ ppm 2.58 (s, 3H), 4.35 (s, 4H), 6.45 (d, J=8.78 Hz, 1H), 7.28 (d, J=9.03 Hz, 1H), 12.86 (s, 1H).

(XX) (6 g, 26.8 mmol, 55% yield) as a white solid. $^1$H NMR (CDCl$_3$, 500 MHz) δ ppm 2.31 (s, 3H), 3.85 (s, 3H), 4.19-4.43 (m, 4H), 6.49-6.56 (m, 1H), 6.58-6.65 (m, 1H).

Step 4

A solution of 5-methoxy-2,3-dihydrobenzo[b][1,4]dioxin-6-yl acetate (XX) (6 g, 26.8 mmol) in HOAc (3 mL), and BF$_3$*Et$_2$O (6 mL) was stirred at 100° C. for 2 h. The black reaction solution was cooled down, diluted with EtOAc (150 mL), washed with water (2×50 mL), sat NaHCO$_3$ solution (50 mL), and brine (50 mL). The EtOAc layer was dried over anhydrous Na$_2$SO$_4$ and concentrated under vacuum. The crude 1-(7-hydroxy-8-methoxy-2,3-dihydrobenzo[b][1,4]dioxin-6-yl)ethanone (XXI) was used directly for the next step without any additional purification.

Step 5

A solution of crude 1-(7-hydroxy-8-methoxy-2,3-dihydrobenzo[b][1,4]dioxin-6-yl)ethanone (XXI), K₂CO₃ (10 g, 70.9 mmol), and MeI (16 g, 0.19 mmol) in DMF (50 mL) was stirred at 40° C. for 5 h. This reaction mixture was cooled, diluted with water (150 mL), and extracted with EtOAc (2×100 mL). The combined organic layers were washed with brine, dried over anhydrous Na₂SO₄, concentrated under vacuum, and purified by column chromatography on silica gel (20% EtOAc/PE) to produce 1-(7,8-dimethoxy-2,3-dihydrobenzo[b][1,4]dioxin-6-yl)ethanone (XXII) (3 g, 12.6 mmol, 47.0% yield for two steps) as a yellow oil. ¹H NMR (CDCl₃, 500 MHz) δ ppm 2.59 (s, 3H), 3.90 (d, J=5.27 Hz, 6H), 4.17-4.27 (m, 2H), 4.28-4.41 (m, 2H), 7.09 (s, 1H).

Step 6

A solution of 1-(7,8-dimethoxy-2,3-dihydrobenzo[b][1,4]dioxin-6-yl) ethanone (XXII) (0.5 g, 2.1 mmol), and CuBr₂ (0.562 g, 2.5 mmol) in a mixture of EtOAc (20 mL), CHCl₃ (20 mL), and MeOH (1 mL) was stirred at 50-60° C. for 5 h. The reaction mixture was cooled, diluted with EtOAc (60 mL), washed with a sat aqueous NH₄Cl solution (30 mL), brine (30 mL), dried over anhydrous Na₂SO₄ and concentrated under vacuum to give a crude 2-bromo-1-(7,8-dimethoxy-2,3-dihydrobenzo[b][1,4]dioxin-6-yl)ethanone (XXIII) as an oil (920 mg) which was used directly for the next step without any further purification.

Preparation of intermediate (XXXII) is depicted below in Scheme 6.

anhydrous Na₂SO₄, and concentrated to give 5-bromobenzene-1,2,3-triol (XXV) as a pale solid. (40 g, 0.195 mol, 96.4% yield)¹H NMR (DMSO-d₆, 400 MHz): δ ppm 6.40 (s, 1H), 9.28 (brs, 3H); ESIMS found C₆H₅BrO₃ m/z 205.0 (M+H).

Step 2

The mixture of 5-bromobenzene-1,2,3-triol (XXV) (20 g, 97.6 mmol), K₂CO₃ (23.8 g, 0.146 mol) and 1,2-dibromoethane (20.16 g, 107.3 mmol) in DMF (200 mL) was stirred at 100° C. for 2 h. The reaction mixture was cooled and diluted with water (600 mL), extracted with 50% EtOAc/PE (3×400 mL). The combined organic layers were washed with brine (3×200 mL), dried over anhydrous Na₂SO₄, and concentrated under vacuo. The residue was purified by column chromatography on silica gel (20% EtOAc/PE) to give 7-bromo-2,3-dihydrobenzo[b][1,4]dioxin-5-ol (XXVI) as a white solid. (4 g, 17.3 mmol, 17.7% yield)¹H NMR (CDCl₃, 400 MHz): δ ppm 4.19-4.38 (m, 4H), 5.37 (brs, 1H), 6.62 (d, J=2.01 Hz, 1H), 6.69 (d, J=2.01 Hz, 1H); ESIMS found C₈H₇BrO₃ m/z 230.9 (M+H).

Step 3

To the mixture of 7-bromo-2,3-dihydrobenzo[b][1,4]dioxin-5-ol (XXVI) (6 g, 26.0 mmol), and TEA (5.3 g, 52 mmol) in DCM (200 mL), was added acetyl chloride (3 g, 39 mmol) at 0° C. dropwise which was then stirred at room temperature for 2 h. The reaction mixture was quenched with sat. aq. NaHCO₃ (200 mL), and the water layer was separated. The DCM was washed with brine (100 mL), dried over anhydrous Na₂SO₄, and concentrated under vacuum.

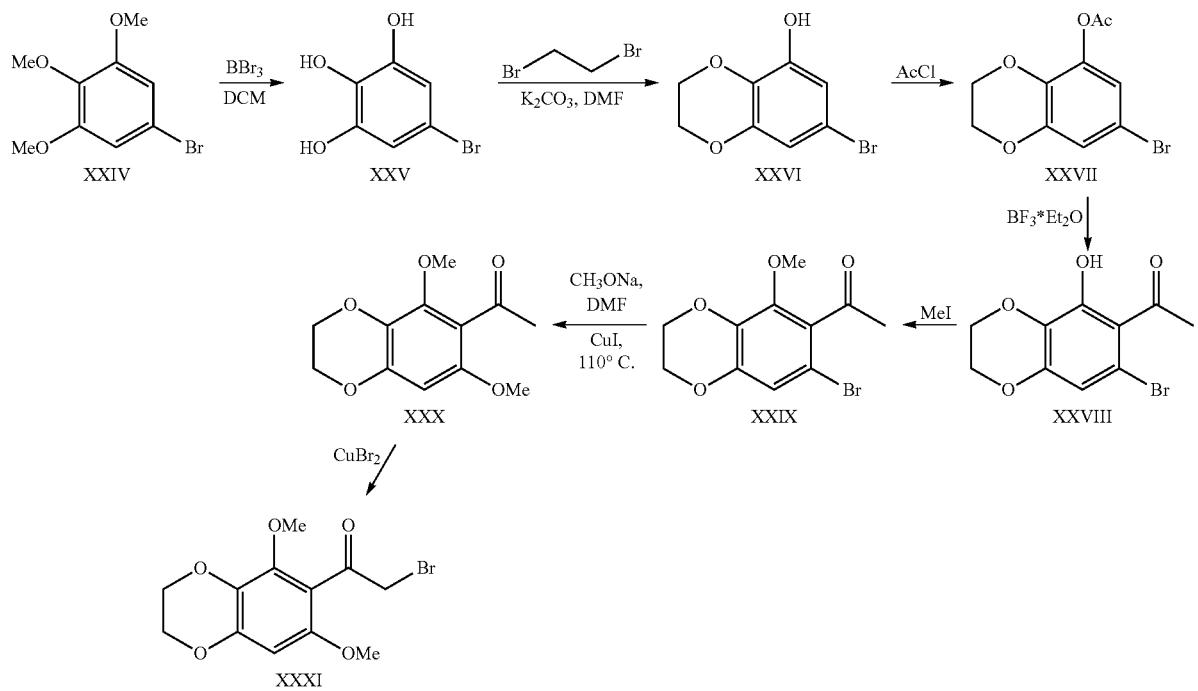

Scheme 6

The residue was purified by column chromatography on silica gel (20% EtOAc/PE) to give 7-bromo-2,3-dihydrobenzo[b][1,4]dioxin-5-yl acetate (XXVII) as a white solid. (6.5 g, 23.8 mmol, 91.5% yield)¹H NMR (CDCl₃, 400 MHz): δ ppm 2.30 (s, 3H), 4.18-4.34 (m, 4H), 6.80 (d, J=2.26 Hz, 1H), 6.94 (d, J=2.26 Hz, 1H); ESIMS found C₁₀H₉BrO₄ m/z 272.9 (M+H).

Step 1

The mixture of 5-bromo-1,2,3-trimethoxybenzene (XXIV) (50 g, 0.2 mol) in anhydrous DCM (500 mL) was added BBr₃ (167.3 g, 0.66 mol) at −78° C. dropwise while stirring. The black reaction mixture was allowed warm to room temperature and stir overnight. The reaction mixture was poured into ice water (1000 mL), and extracted with EtOAc (2×1000 mL). The EtOAc layers were dried over Step 4

The mixture of 7-bromo-2,3-dihydrobenzo[b][1,4]dioxin-5-yl acetate (XXVII) (6 g, 22.0 mmol) in HOAc (20 mL), and BF$_3$*Et$_2$O (20 mL) was stirred at 100° C. for 3 h. The reaction solution was cooled, diluted with EtOAc (250 mL), washed with water (2×100 mL), sat. aq. NaHCO$_3$ solution (2×150 mL), and brine (100 mL). The EtOAc layer was dried over anhydrous Na$_2$SO$_4$ and concentrated. Crude 1-(7-bromo-5-hydroxy-2,3-dihydrobenzo[b][1,4]dioxin-6-yl) ethan-1-one (XXVIII) was used for the next step directly without any purification. ESIMS found C$_{10}$H$_9$BrO$_4$ m/z 273.0 (M+H).

Step 5

A solution of the 1-(7-bromo-5-hydroxy-2,3-dihydrobenzo[b][1,4]dioxin-6-yl)ethan-1-one (XXVIII), K$_2$CO$_3$ (6.6 g, 47.6 mmol), and MeI (6.76 g, 47.6 mmol) in DMF (50 mL) was stirred at room temperature overnight. The reaction mixture was diluted with water (150 mL) and extracted with EtOAc (2×100 mL). The combined organic layers were washed with brine, dried over anhydrous Na$_2$SO$_4$, concentrated under vacuum, and purified by column chromatography on silica gel (20% EtOAc/PE) to give 1-(7-bromo-5-methoxy-2,3-dihydrobenzo[b][1,4]dioxin-6-yl)ethan-1-one (XXIX) as a yellow oil. (3 g, 10.4 mmol, 47.5% yield for 2 steps)$^1$H NMR (CDCl$_3$, 400 MHz): δ ppm 2.50 (s, 3H), 3.83 (s, 3H), 4.20-4.37 (m, 4H), 6.87 (s, 1H); ESIMS found C$_{11}$H$_{11}$BrO$_4$ m/z 287.0 (M+H).

Step 6

A solution of 1-(7-bromo-5-methoxy-2,3-dihydrobenzo[b][1,4]dioxin-6-yl)ethan-1-one (XXIX) (800 mg, 2.79 mmol) in DMF:H$_2$O (95:5)(16 mL) was heated at 80° C. for 30 minutes. To this solution was added a solution of 25% NaOMe (1.44 g of Na in 16 mL MeOH) in four portions. The temperature of the resulting solution was raised to 110° C. followed by addition of the catalyst CuBr (112 mg, 0.8 mmol). The reaction mixture was heated under reflux for 6 h. The reaction was cooled and diluted with sat. aq. NH$_4$Cl (40 mL), extracted with EtOAc (2×). The combined EtOAc layers were dried over anhydrous Na$_2$SO$_4$, concentrated, and purified by preparative TLC (10% EtOAc/PE) to give 1-(5,7-dimethoxy-2,3-dihydrobenzo[b][1,4]dioxin-6-yl)ethan-1-one (XXX) as a yellow oil. (70 mg, 0.294 mmol, 10.5% yield)$^1$H NMR (CDCl$_3$, 400 MHz): δ ppm 2.47 (s, 3H), 3.72 (s, 3H), 3.85 (s, 3H), 4.20-4.33 (m, 4H), 6.22 (s, 1H); ESIMS found C$_{12}$H$_{14}$O$_5$ m/z 239.1 (M+H).

Step 7

A mixture of 1-(5,7-dimethoxy-2,3-dihydrobenzo[b][1,4]dioxin-6-yl)ethan-1-one (XXX) (130 mg, 0.546 mmol), CuBr$_2$ (183 mg, 0.82 mmol) in EtOAc (10 mL), CHCl$_3$ (10 mL) and MeOH (0.2 mL) was stirred at 50-60° C. for 5 h. The reaction mixture was cooled, diluted with sat. aq. NH$_4$Cl (30 mL), and extracted with EtOAc (50 mL). The combined organic layers were washed with brine, dried over anhydrous Na$_2$SO$_4$, and concentrated under vacuum to give a crude 2-bromo-1-(5,7-dimethoxy-2,3-dihydrobenzo[b][1,4]dioxin-6-yl)ethan-1-one (XXXI) which directly used for the next step without further purification (170 mg). ESIMS found C$_{12}$H$_{13}$BrO$_5$ m/z 317.0 (M+H).

Preparation of 1-(2,3-dihydrobenzo[b][1,4]dioxin-6-yl)-3-(dimethylamino)propan-1-one (XXXIII) is depicted below in Scheme 7.

Scheme 7

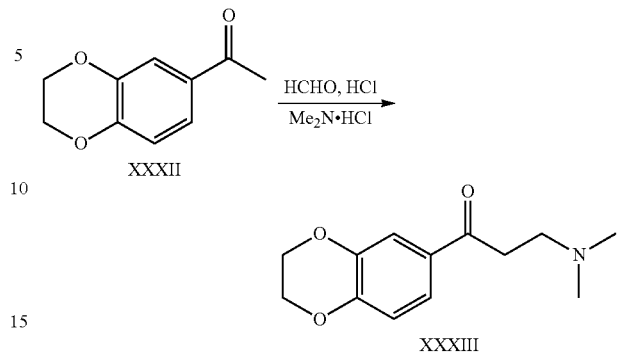

Step 1

A solution of 1-(2,3-dihydrobenzo[b][1,4]dioxin-6-yl) ethanone (XXXII) (4.68 g, 26.3 mmol), dimethylamine hydrochloride (2.78 g, 34.1 mmol), paraformaldehyde (1.18 g, 39.4 mmol) and 12 N HCl (50 μL) in ethanol (8.0 mL) was refluxed overnight. The solution was cooled to room temperature and the ethanol was evaporated under vacuum. The residue was treated with EtOAc, heated slightly and sonicated to disperse into fine particles. The solids were filtered and dried at room temperature to produce 1-(2,3-dihydrobenzo[b][1,4]dioxin-6-yl)-3-(dimethylamino) propan-1-one hydrochloride as a white solid, (7.73 g, quantitative yield). The solid was cooled in minimum about of water (12 mL) and cooled to 0° C. A 20% aqueous solution of NaOH was added until pH=10. The solution was extracted with DCM, dried and evaporated to produce 1-(2,3-dihydrobenzo [b][1,4]dioxin-6-yl)-3-(dimethylamino) propan-1-one (XXXIII) a colorless oil (2.485 g, 10.6 mmol, 40.2% yield) $^1$H NMR (CDCl$_3$, 500 MHz): δ ppm 2.77 (s, 6H), 3.41 (m, 2H), 3.56 (m, 2H), 4.25 (m, 4H), 6.85 (m, 1H), 7.45 (m, 2H); ESIMS found C$_{13}$H$_{17}$NO$_3$ m/z 236 (M+H).

The following intermediates were prepared in accordance with the procedure described in the above Scheme 7.

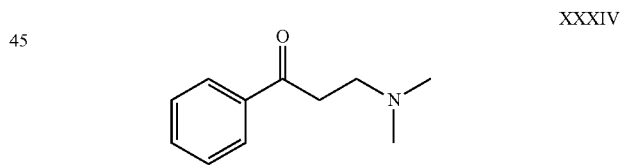

3-(Dimethylamino)-1-phenylpropan-1-one (XXXIV): Yellow oil, (3.9 g, 22.0 mmol, 52.7% yield). $^1$H NMR (DMSO-d$_6$, 400 MHz) δ ppm 2.81 (s, 6H), 3.40 (t, J=7.6 Hz, 2H), 3.65 (t, J=7.6 Hz, 2H), 7.58 (t, J=7.6 Hz, 2H), 7.70 (t, J=7.6 Hz, 1H), 8.03 (d, J=7.2 Hz, 2H); ESIMS found C$_{11}$H$_{15}$NO m/z 178.0 (M+H).

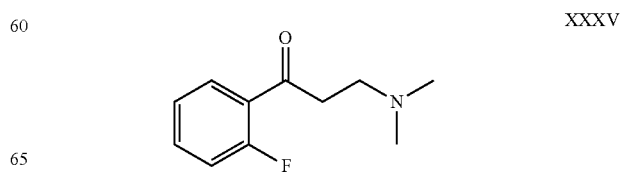

3-(Dimethylamino)-1-(2-fluorophenyl)propan-1-one (XXXV): Yellow oil, (11.8 g, 60.4 mmol, 84.0% yield). ESIMS found C₁₁H₁₄FNO m/z 196.2 (M+H).

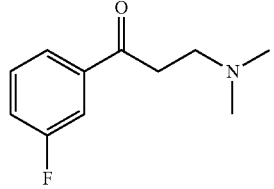
XXXVI 3-(Dimethylamino)-1-(3-fluorophenyl)propan-1-one (XXXVI): Yellow oil, (10.3 g, 52.8 mmol, 72.8% yield). ¹H NMR (CDCl₃, 400 MHz) δ ppm 2.31 (s, 6H), 2.78 (t, J=7.2 Hz, 2H), 3.15 (t, J=7.2 Hz, 2H), 7.29 (t, 1H), 7.47 (dq, J=8.0 Hz, J=2.4 Hz, 1H), 7.66 (d, J=9.6 Hz, 1H), 7.76 (d, J=8.0 Hz, 1H); ESIMS found C₁₁H₁₄FNO m/z 196.1 (M+H).

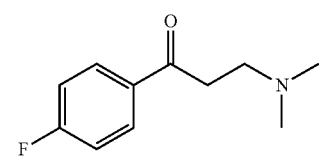
XXXVII 3-(Dimethylamino)-1-(4-fluorophenyl)propan-1-one (XXXVII): Yellow oil, (12.0 g, 61.5 mmol, 85.0% yield). ESIMS found C₁₁H₁₄FNO m/z 196.1 (M+H).

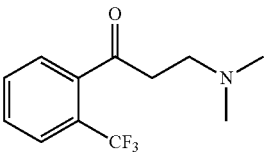
XXXVIII 3-(Dimethylamino)-1-(2-(trifluoromethyl)phenyl)propan-1-one (XXXVIII): Yellow oil, (1.6 g, 6.5 mmol, 24.6% yield). ¹H NMR (CDCl₃, 400 MHz) δ ppm 2.27 (s, 6H), 2.72 (t, J=7.2 Hz, 2H), 3.04 (t, J=7.2 Hz, 2H), 7.47 (d, J=7.2 Hz, 1H), 7.52-7.67 (m, 2H), 7.72 (d, J=7.2 Hz, 1H); ESIMS found C₁₂H₁₄F₃NO m/z 246.0 (M+H).

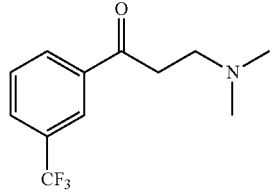
XXXIX 3-(Dimethylamino)-1-(3-(trifluoromethyl)phenyl)propan-1-one (XXXIX): Yellow oil, (7.9 g, 32.2 mmol, 64.0% yield). ESIMS found C₁₂H₁₄F₃NO m/z 246.1 (M+H).

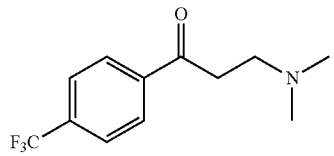
XL 3-(Dimethylamino)-1-(4-(trifluoromethyl)phenyl)propan-1-one (XL): Yellow oil, (9.5 g, 38.7 mmol, 77.0% yield). ESIMS found C₁₂H₁₄F₃NO m/z 246.1 (M+H).

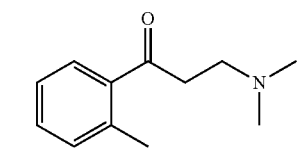
XLI 3-(Dimethylamino)-1-(o-tolyl)propan-1-one (XLI): Yellow oil, (5.1 g, 26.7 mmol, 71.8% yield). ¹H NMR (CDCl₃, 400 MHz) δ ppm 2.28 (s, 6H), 2.50 (s, 3H), 2.73 (t, J=7.6 Hz, 2H), 3.09 (t, J=7.6 Hz, 2H), 7.27 (t, J=8.4 Hz, 2H), 7.38 (t, J=7.6 Hz, 1H), 7.65 (d, J=7.6 Hz, 1H); ESIMS found C₁₂H₁₇NO m/z 192.1 (M+H).

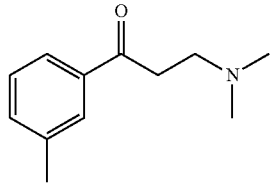
XLII 3-(Dimethylamino)-1-(m-tolyl)propan-1-one (XLII): Yellow oil, (5.2 g, 27.2 mmol, 73.2% yield). ¹H NMR (CDCl₃, 400 MHz) δ ppm 2.30 (s, 6H), 2.42 (s, 3H), 2.67 (t, J=7.6 Hz, 2H), 3.15 (t, J=7.6 Hz, 2H), 7.31-7.43 (m, 2H), 7.71-7.82 (m, 2H); ESIMS found C₁₂H₁₇NO m/z 192.1 (M+H).

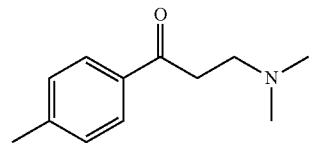
XLIII 3-(Dimethylamino)-1-(p-tolyl)propan-1-one (XLIII): Yellow oil, (5.1 g, 25.6 mmol, 71.8% yield). ¹H NMR (CDCl₃, 400 MHz) δ ppm 2.31 (s, 6H), 2.43 (s, 3H), 2.77 (t, J=7.6 Hz, 2H), 3.15 (t, J=7.6 Hz, 2H), 7.28 (d, J=8.0 Hz, 2H), 7.88 (d, J=8.0 Hz, 2H); ESIMS found C₁₂H₁₇NO m/z 192.0 (M+H).

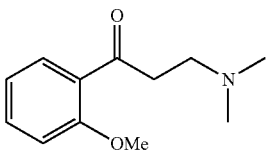

XLIV 3-(Dimethylamino)-1-(2-methoxyphenyl)propan-1-one (XLIV): Yellow oil, (3.1 g, 15.0 mmol, 45.6% yield). $^1$H NMR (CDCl$_3$, 400 MHz) δ ppm 2.25 (s, 6H), 2.69 (t, J=7.2 Hz, 2H), 3.17 (t, J=7.2 Hz, 2H), 3.88 (s, 3H), 6.88-7.03 (m, 2H), 7.43 (t, J=7.8 Hz, 1H), 7.67 (d, J=8 Hz, 1H); ESIMS found C$_{12}$H$_{17}$NO$_2$ m/z 208.1 (M+H).

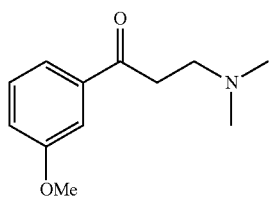

XLV 3-(Dimethylamino)-1-(3-methoxyphenyl)propan-1-one (XLV): Yellow oil, (5.0 g, 24.1 mmol, 72.4% yield). $^1$H NMR (CDCl$_3$, 400 MHz) δ ppm 2.32 (s, 6H), 2.79 (t, J=7.6 Hz, 2H), 3.17 (t, J=7.6 Hz, 2H), 3.86 (s, 3H), 7.12 (dd, J=8.4 Hz, J=2.8 Hz, 1H), 7.38 (t, J=8.0 Hz, 1H), 7.51 (d, J=2.5 Hz, 1H), 7.56 (d, J=8.0 Hz, 1H); ESIMS found C$_{12}$H$_{17}$NO$_2$ m/z 208.1 (M+H).

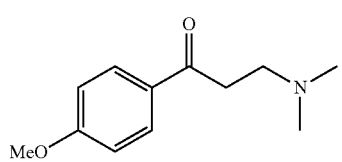

XLVI 3-(Dimethylamino)-1-(4-methoxyphenyl)propan-1-one (XLVI): Yellow oil, (5.0 g, 24.1 mmol, 72.4% yield). $^1$H NMR (CDCl$_3$, 400 MHz) δ ppm 2.29 (s, 6H), 2.74 (t, J=7.6 Hz, 2H), 3.10 (t, J=7.6 Hz, 2H), 3.86 (s, 3H), 6.93 (d, J=8.6 Hz, 2H), 7.95 (d, J=8.6 Hz, 2H); ESIMS found C$_{12}$H$_{17}$NO$_2$ m/z 208.1 (M+H).

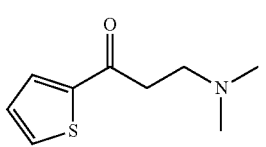

XLVII 3-(Dimethylamino)-1-(thiophen-2-yl)propan-1-one (XLVII): Yellow oil, (5.1 g, 27.8 mmol, 69.9% yield). $^1$H NMR (CDCl$_3$, 400 MHz) δ ppm 2.30 (s, 6H), 2.77 (t, J=7.4 Hz, 2H), 3.10 (t, J=7.4 Hz, 2H), 7.14 (t, J=7.6 Hz, 1H), 7.64 (dd, J=5.2 Hz, J=0.4 Hz, 1H), 7.74 (dd, J=4.0 Hz, J=0.8 Hz, 1H); ESIMS found C$_9$H$_{13}$NOS m/z 184 (M+H).

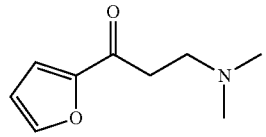

XLVIII 3-(Dimethylamino)-1-(furan-2-yl)propan-1-one (XLVIII): Yellow oil, (4.3 g, 25.7 mmol, 56.6% yield). $^1$H NMR (CDCl$_3$, 400 MHz) δ ppm 2.27 (s, 6H), 2.73 (t, J=7.4 Hz, 2H), 3.00 (t, J=7.4 Hz, 2H), 6.53 (td, J=3.6 Hz, J=1.6 Hz, 1H), 7.19 (d, J=3.6 Hz, 1H), 7.58 (d, J=5.2 Hz, 1H); ESIMS found C$_9$H$_{13}$NO$_2$ m/z 168 (M+H).

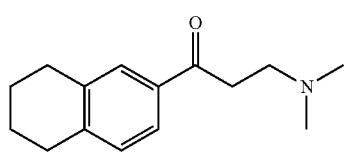

XLIX 3-(Dimethylamino)-1-(5,6,7,8-tetrahydronaphthalen-2-yl)propan-1-one (XLIX): White solid (7.3 g, 31.5 mmol, 93% yield). $^1$H NMR (DMSO-d$_6$, 500 MHz) δ ppm 1.75-1.77 (m, 4H), 2.79 (s, 6H), 2.78-2.81 (m, 4H), 3.36-3.39 (m, 2H), 3.54-3.57 (m, 2H), 7.23 (d, J=7.9 Hz, 1H), 7.70-7.72 (m, 2H), 10.53 (brs, 1H); ESIMS found C$_{15}$H$_{21}$NO m/z 232.0 (M+H).

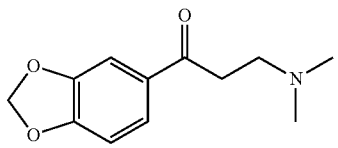

L 1-(Benzo[d][1,3]dioxol-5-yl)-3-(dimethylamino)propan-1-one (L): White solid (16.9 g, 76.4 mmol, 100% yield). $^1$H NMR (DMSO-d$_6$, 500 MHz) δ ppm 2.79 (s, 6H), 3.35-3.38 (m, 2H), 3.51-3.54 (m, 2H), 6.16 (s, 2H), 7.09 (d, J=8.2 Hz, 1H), 7.49 (d, J=1.7 Hz, 1H), 7.67 (dd, J=1.7 Hz, J=8.2 Hz, 1H), 10.51 (brs, 1H); ESIMS found C$_{12}$H$_{15}$NO$_3$ m/z 221.9 (M+H).

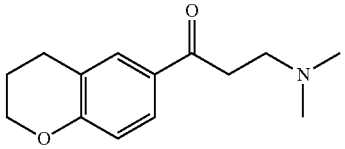

LI 1-(Chroman-6-yl)-3-(dimethylamino)propan-1-one (LI): White solid (3.99 g, 17.1 mmol, 99.5% yield). $^1$H NMR (DMSO-d$_6$, 500 MHz) δ ppm 1.95 (quin, J=5.80 Hz, 2H), 2.77-2.85 (m, 9H), 3.37 (t, J=7.14 Hz, 2H), 3.51 (t, J=7.14 Hz, 2H), 4.23 (t, J=5.00 Hz, 2H), 6.86 (d, J=8.78 Hz, 1H), 7.74 (dd, J=8.51, 2.47 Hz, 1H), 7.78 (d, J=2.20 Hz, 1H), 10.44 (brs, 1H); ESIMS found C$_{14}$H$_{19}$NO$_2$ m/z 234.1 (M+H).

Preparation of chromane-6-carbaldehyde (LIV) is depicted below in Scheme 8.

Scheme 8

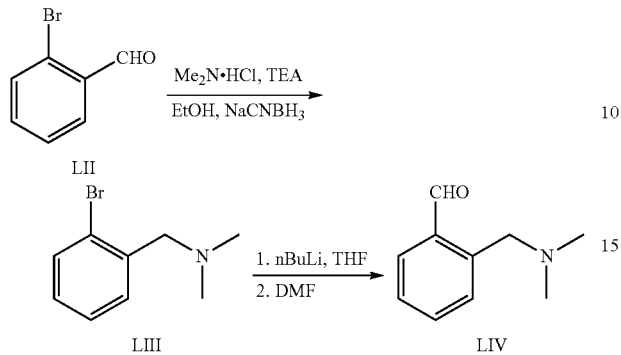

Step 1
To a solution of dimethylamine hydrochloride (2.25 g, 27.6 mmol) in EtOH (212 mL) was added TEA (3.84 mL, 27.6 mmol). 2-Bromobenzaldehyde (LII) (5.1 g, 27.6 mmol) was then added and the reaction was stirred overnight. NaCNBH₃ (3.47 g, 55.1 mmol) was then added and the reaction stirred at room temperature for 6 h. The solvent was removed under nigh vacuum. The residue was dissolved in DCM, washed with sat. aq. NaHCO₃, washed with water and then with brine, dried over MgSO₄ and concentrated. The crude product was purified on a silica gel column (100% EtOAc→15% hexane/EtOAc) to give 1-(2-bromophenyl)-N,N-dimethylmethanamine (LIII) as a colorless liquid (3.46 g, 16.2 mmol, 58.6% yield). $^1$H NMR (DMSO-$d_6$, 500 MHz) δ ppm 2.19 (s, 6H), 3.45 (s, 2H), 7.18-7.22 (m, 1H), 7.35-7.38 (m, 1H), 7.45 (dd, J=1.7 Hz, J=7.6 Hz, 1H), 7.59 (dd, J=1.1 Hz, J=8.0 Hz, 1H); ESIMS found $C_9H_{12}BrN$ m/z 213.8 (M+H).

Step 2
To a solution of 1-(2-bromophenyl)-N,N-dimethylmethanamine (LIII) in THF (25 mL) cooled to −78° C. under N₂ was added a 2.5M solution of nBuLi in hexane (3.37 mL, 8.42 mmol). The reaction was stirred at −78° C. under N₂ for 1.5 h before adding DMF (0.68 mL, 8.79 mmol). The reaction was stirred at −78° C. under N₂ for 1 h and then warmed to room temperature. The solvent was removed under reduced pressure and purified on a silica column (100% CHCl₃→10% MeOH/CHCl₃) to produce 2-((dimethylamino)methyl)benzaldehyde (LIV) as a light yellow oil (305 mg, 1.87 mmol, 25.5% yield). $^1$H NMR (DMSO-$d_6$, 500 MHz) δ ppm 2.14 (s, 6H), 3.72 (s, 2H), 7.42 (d, J=7.6 Hz, 1H), 7.45-7.48 (m, 1H), 7.57-7.59 (m, 1H), 7.78 (dd, J=1.2 Hz, J=7.6 Hz, 1H), 10.34 (s, 1H); ESIMS found $C_9H_{12}BrN$ m/z 163.9 (M+H).

Preparation of chromane-6-carbaldehyde (LVII) is depicted below in Scheme 9.

Scheme 9

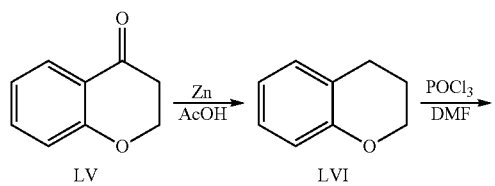

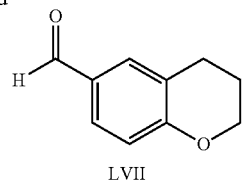

Step 1
To a suspension of zinc dust (100 g, 1.56 mol) in HOAc (300 mL) was added chroman-4-one (LV) (10 g, 67.6 mol). The mixture was stirred at 110° C. for 6 h. Then the mixture was cooled and filtrated. The filtrate was poured into water (500 mL) and extracted with EtOAc (3×100 mL). The organic layer was concentrated to give chromane (LVI) as colorless oil. (8.05 g, 60.0 mmol, 88.7% yield). $^1$H NMR (CDCl₃, 400 MHz) δ ppm 2.04 (q, J=4.3 Hz, 2H), 2.81 (t, J=6.6 Hz, 2H), 4.21 (t, J=5.2 Hz, 2H), 6.72-6.92 (m, 2H), 7.00-7.17 (m, 2H); ESIMS found $C_9H_{10}O$ m/z 135.0 (M+H).

Step 2
To a solution of chromane (LVI) (3 g, 22.4 mmol, 1.0 eq) and DMF (3.3 g, 45.2 mmol, 2 eq) in DCE (20 mL) was added phosphorus oxychloride (3.4 g, 45.2 mmol, 2 eq) dropwise over 30 min below 50° C. The mixture was stirred at 85° C. for 12 h. The reaction was quenched by water and extracted with EtOAc (3×300 mL). The combined organic phase was dried over anhydrous Na₂SO₄, filtered and concentrated in vacuo. The residue was purified by chromatography on silica gel (PE:EtOAc=8:1) to give chromane-6-carbaldehyde (LVII) as yellow oil. (2.0 g, 12.3 mmol, 55.1% yield). $^1$H NMR (CDCl₃, 400 MHz) δ ppm 2.01 (q, J=45.8 Hz, 2H), 2.82 (t, J=6.4 Hz, 2H), 4.24 (t, J=5.2 Hz, 2H), 6.85 (d, J=8.4 Hz, 1H), 7.52-7.64 (m, 2H), 9.79 (s, 1H); ESIMS found $C_{10}H_{10}O_2$ m/z 163.1 (M+H).

Preparation of benzo[d]oxazole-5-carbaldehyde (LXI) is depicted below in Scheme 10.

Scheme 10

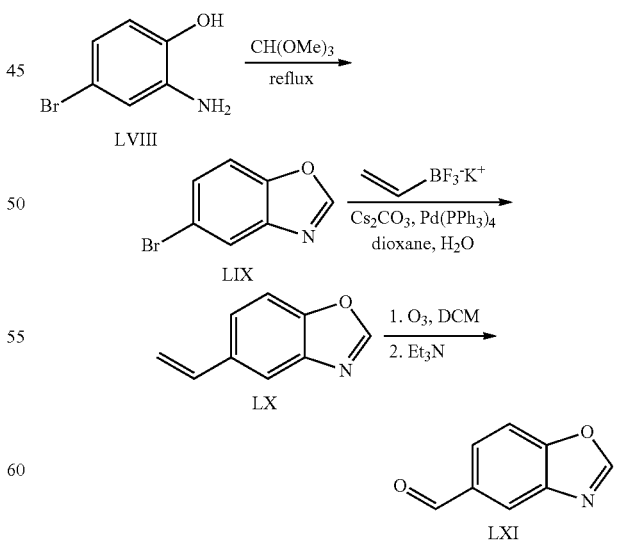

Step 1
A solution of 2-amino-4-bromophenol (LVIII) (10 g, 53.5 mmol, 1 eq) in trimethyl orthoformate (200 mL) was stirred at reflux for 2 h. After cooling, the solution was concentrated under reduced pressure to remove trimethyl orthoformate to give 5-bromobenzo[d]oxazole (LIX) (10.06 g, 50.8 mmol, 95.0%). Used in the next reaction without additional purification.

Step 2

To a suspension of 5-bromobenzo[d]oxazole (LIX) (10.06 g, 50.8 mmol, 1 eq) in dioxane (200 mL) and water (10 mL) was added potassium (ethenyl)trifluoroborate (8.17 g, 61 mmol, 1.2 eq), cesium carbonate (13.8 g, 101.6 mmol, 2 eq) and tetrakis(triphenylphosphorus) palladium(0) (2.9 g, 2.54 mmol, 0.05 eq). The mixture was stirred at reflux under nitrogen for 5 h. The mixture was then poured onto ice-water (200 mL) and extracted with EtOAc (3×300 mL). The organic phases were combined, dried over anhydrous Na$_2$SO$_4$, filtered and concentrated in vacuo, the residue was purified by chromatography on silica gel (PE:EtOAc=20:1-10:1) to afford 5-vinylbenzo[d]oxazole (LX) (6.11 g, 42.1 mmol, 82.9%) as an oil. Used in the next reaction directly without additional purification.

Step 3

To a solution of 5-vinylbenzo[d]oxazole (LX) (6.1 g, 42.1 mmol, 1.0 eq) in DCM (100 mL) was bubbled ozone at −78° C. until the solution turn to blue. The solution was then purged with O2 followed by N$_2$ for 5 minutes. TEA (12.8 g, 126.3 mmol, 3 eq) was added and the mixture was stirred at 25° C. for 1 h. The solution was poured into water (200 mL) and extracted with EtOAc (3×300 mL). The combined organic phase was dried, filtered and concentrated in vacuo. The residue was purified by chromatography on silica gel eluted (PE:EtOAc=10:1→1:1) to give benzo[d]oxazole-5-carbaldehyde (LXI) (2.1 g, 14.3 mmol, 33.9%) as a colorless oil. $^1$H NMR (CDCl$_3$, 400 MHz) δ ppm 7.75 (d, J=8.4 Hz, 1H), 8.02 (dd, J=8.4 Hz, J=1.2 Hz, 1H), 8.22 (s, 1H), 8.33 (s, 1H), 10.13 (s, 1H); ESIMS found C$_8$H$_5$NO$_2$ m/z 148.0 (M+H).

Preparation of 2,3-dihydrobenzo[b][1,4]oxathiine-6-carbaldehyde (LXIV) is depicted below in Scheme 11.

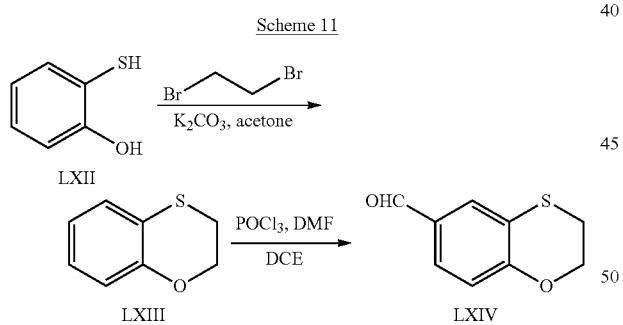

Scheme 11

Step 1

To a solution of 2-mercaptophenol (LXII) (10 g, 79 mmol, 1.0 eq) in acetone (500 mL) was added potassium carbonate (21.8 g, 158 mmol, 2 eq) and 1,2-dibromoethane (14.92 g, 79 mmol, 1 eq) in acetone (100 mL) dropwise over 3 h. The mixture was stirred at 30° C. for 12 h. The solid was filtered off and the filtrate was concentrated in vacuo. The residue was purified by chromatography on silica gel (100% PE) to give 2,3-dihydrobenzo[b][1,4]oxathiine (LXIII) as colorless oil. (4.02 g, 26.4 mmol, 33.3%) as a colorless oil. $^1$H NMR (CDCl$_3$, 400 MHz) δ ppm 3.14 (t, J=4.6 Hz, 2H), 4.43 (t, J=4.6 Hz, 2H), 6.71-6.92 (m, 2H), 7.02 (td, J=7.6 Hz, J=1.6 Hz, 1H), 7.07 (dd, J=7.6 Hz, J=1.2 Hz, 1H); ESIMS found C$_8$H$_8$OS m/z 153.0 (M+H).

Step 2

To a solution of 2,3-dihydrobenzo[b][1,4]oxathiine (LXIII) (4 g, 26.3 mmol, 1.0 eq) and DMF (7.2 g, 47.2 mmol, 2 eq) in DCE (20 mL) was added phosphorus oxychloride (3.4 g, 47.2 mmol, 2 eq) dropwise over 30 minutes below 50° C. The mixture was stirred at 85° C. for 12 h. The reaction was quenched by water and extracted with EtOAc (3×300 mL). The combined organic phase was dried, filtered and concentrated in vacuo, the residue was purified by chromatography on silica gel (PE:EtOAc=10:1-5:1) to give 2,3-dihydrobenzo[b][1,4]oxathiine-6-carbaldehyde (LXIV) as yellow oil. (300 mg, 1.67 mmol, 6.3%) as a colorless oil. $^1$H NMR (CDCl$_3$, 400 MHz) δ ppm 3.15 (t, J=4.6 Hz, 2H), 4.50 (t, J=4.6 Hz, 2H), 6.92 (d, J=8.4 Hz, 1H), 7.51 (dd, J=8.8 Hz, J=2.0 Hz, 1H), 7.59 (s, 1H), 9.80 (s, 1H); ESIMS found C$_9$H$_8$O$_2$S m/z 181.1 (M+H).

Preparation of 2,3-dihydrobenzo[b][1,4]dioxine-5-carbaldehyde (LXVI) is depicted below in Scheme 12.

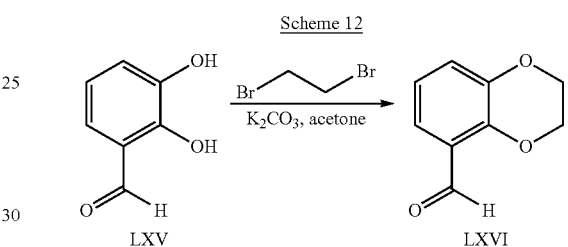

Scheme 12

Step 1

To a solution of 2,3-dihydroxybenzaldehyde (LXV) (5 g, 36.2 mmol, 1.0 eq) in acetone (300 mL) was added potassium carbonate (10 g, 72.5 mmol, 2 eq) and 1,2-dibromoethane (6.8 g, 36.2 mmol, 1 eq) in acetone (50 mL) dropwise over 2 h. The mixture was stirred at 30° C. for 12 h. The solid was filtered off, the filtrate was concentrated in vacuo and purified by chromatography on silica gel (PE:EtOAc=10:1) to give 2,3-dihydrobenzo[b][1,4]dioxine-5-carbaldehyde (LXVI) as a colorless oil. (4.02 g, 26.4 mmol, 68%) ESIMS found C$_9$H$_8$O$_3$ m/z 165.0 (M+H).

Preparation of benzo[b]thiophene-5-carbaldehyde (LXXI) is depicted below in Scheme 13.

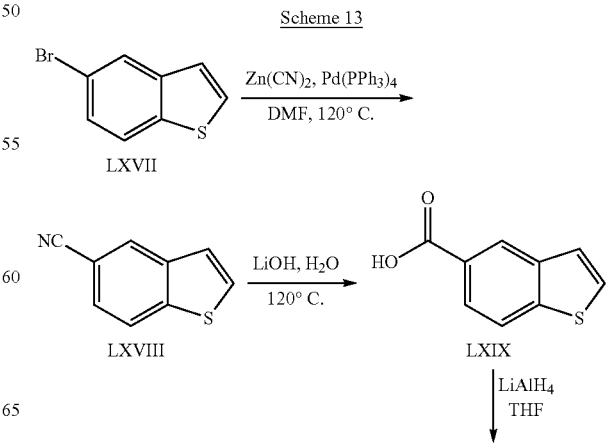

Scheme 13

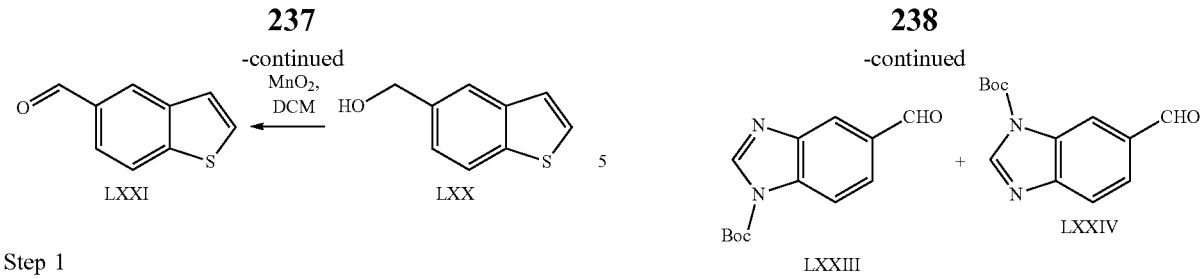

Step 1

A solution of 5-bromobenzo[b]thiophene (LXVII) (1.2 g, 6 mmol), zinc cyanide (0.66 g, 6 mmol) and tetrakis(triphenylphosphorus)palladium (0) (0.65 g, 0.6 mmol) in dry DMF (10 mL) was stirred at reflux under nitrogen atmosphere for 1 h. The mixture was poured into cold water and extracted with EtOAc (3×). The combined organic layers were concentrated in vacuum to give the crude benzo[b]thiophene-5-carbonitrile (LXVIII) as a white solid. (0.90 g, 6 mmol, 100%) ESIMS found $C_9H_5NS$ m/z 160.0 (M+H).

Step 2

A suspension of benzo[b]thiophene-5-carbonitrile (LXVIII) (0.9 g, 5.1 mmol) and LiOH (10 g, 0.24 mol) in water (50 ml) was stirred at reflux for 2 h. The reaction was washed with water, acidified to pH 3 with 1M HCl and extracted with EtOAc. The combined organic layers were dried over anhydrous $Na_2SO_4$, filtered and concentrated in vacuum to give the crude benzo[b]thiophene-5-carboxylic acid (LXIX) as a white solid. (0.9 g, 5.1 mmol, 88.6%) ESIMS found $C_9H_6O_2S$ m/z 179.1 (M+H).

Step 3

To a solution of benzo[b]thiophene-5-carboxylic acid (LXIX) (0.9 g, 5.1 mmol) in THF (20 mL) was added LAH (0.28 g, 7 mmol) in portions at 0° C. under nitrogen atmosphere. The reaction was quenched by water, washed with 20% aq. NaOH (4 mL) and extracted with EtOAc. The EtOAc phase was concentrated in vacuo to give the crude benzo[b]thiophen-5-ylmethanol (LXX) as yellow solid. (~1 g, used without further purification) ESIMS found $C_9H_8OS$ m/z 165.0 (M+H).

Step 4

To a solution of benzo[b]thiophen-5-ylmethanol (LXX) (~1 g, crude) in DCM (20 mL) was added manganese oxide (6.36 g, 0.07 mol). The mixture was stirred at room temperature overnight. The mixture was filtered and the filtrate was concentrated in vacuo. The residue was purified by chromatography on silica gel (PE:EtOAc=10:1) to give benzo[b]thiophene-5-carbaldehyde (LXXI) as an orange solid. (570 mg, 3.51 mmol, 68.9% yield for 2 steps) $^1$H NMR (DMSO-$d_6$, 400 MHz) δ ppm 7.68 (d, J=5.2 Hz, 1H), 7.85 (d, J=8.4 Hz, 1H), 7.95 (d, J=5.2 Hz, 1H), 8.23 (d, J=8.4 Hz, 1H), 8.48 (s, 1H), 10.11 (s, 1H); ESIMS found $C_9H_6OS$ m/z 163.0 (M+H).

Preparation of tert-butyl 5-formyl-1H-benzo[d]imidazole-1-carboxylate (LXXIII) and tert-butyl 6-formyl-1H-benzo[d]imidazole-1-carboxylate (LXXIV) is depicted below in Scheme 14.

Scheme 14

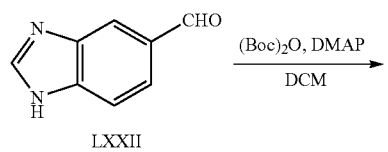

Step 1

A solution of 1H-benzo[d]imidazole-5-carbaldehyde (LXXII) (787 mg, 4.92 mmol, 1 eq) in DCM (5 mL) was added $Boc_2O$ (1.13 g, 5.2 mmol, 1.05 eq) and DMAP (60 mg, 0.492 mmol, 0.1 eq). The mixture was then stirred at 25° C. for 30 minutes before being poured into water (100 mL) and extracted with EtOAc (3×100 mL), the organic phases were combined, dried over anhydrous $Na_2SO_4$, filtered and concentrated in vacuo to give a mixture of tert-butyl 5-formyl-1H-benzo[d]imidazole-1-carboxylate (LXXIII) and tert-butyl 6-formyl-1H-benzo[d]imidazole-1-carboxylate (LXXIV) as a white solid. (850 mg, 63.5%) $^1$H NMR (CDCl$_3$, 400 MHz) δ ppm 1.73 (s, 9H), 7.93 (s, 1H), 7.98 (dd, J=8.4 Hz, J=1.2 Hz, 1H), 8.16 (d, J=8.4 Hz, 1H), 8.30 (s, 1H), 8.55 (s, 1H), 8.60 (s, 1H), 10.12 (s, 1H); ESIMS found $C_{13}H_{14}N_2O_3$ m/z 247.1 (M+H).

The following intermediates were prepared in accordance with the procedure described in the above Scheme 14.

tert-Butyl 5-formyl-1H-indole-1-carboxylate (LXXV): White solid, (8.5 g, 34.7 mmol, 50.3% yield). $^1$H NMR (CDCl$_3$, 400 MHz) δ ppm 1.70 (s, 9H), 6.70 (d, J=4.0 Hz, 1H), 7.70 (d, J=4.0 Hz, 1H), 7.87 (dd, J=8.8 Hz, J=1.6 Hz, 1H), 8.11 (s, 1H), 8.30 (d, J=8.8 Hz, 1H), 10.08 (s, 1H); ESIMS found $C_{14}H_{15}NO_3$ m/z 246.1 (M+H).

tert-Butyl 5-formyl-1H-indazole-1-carboxylate (LXXVI): White solid, (1.8 g, 7.3 mmol, 93.3% yield). $^1$H NMR (CDCl$_3$, 400 MHz) δ ppm 1.76 (s, 9H), 8.10 (d, J=8.8 Hz, 1H), 8.30 (s, 1H), 8.34 (s, 1H), 8.35 (d, J=8.8 Hz, 1H), 10.13 (s, 1H); ESIMS found $C_{13}H_{14}N_2O_3$ m/z 247.1 (M+H).

LXXVIIa & b

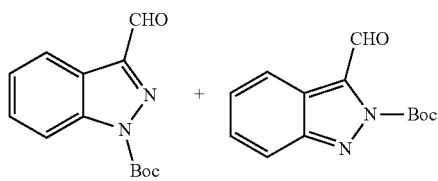

tert-Butyl 3-formyl-1H-indazole-1-carboxylate (LXXVIIa) and tert-butyl 3-formyl-2H-indazole-2-carboxylate (LXXVIIb): White solid, (1.6 g, 6.5 mmol, 38.1% yield). $^1$H NMR (CDCl$_3$, 400 MHz) δ ppm 1.77 (s, 9H), 7.45 (t, J=7.4 Hz, 1H), 7.60 (t, J=7.4 Hz, 1H), 8.18 (d, J=8.4 Hz, 1H), 8.32 (d, J=8.4 Hz, 1H), 10.34 (s, 1H); ESIMS found C$_{13}$H$_{14}$N$_2$O$_3$ m/z 247.1 (M+H).

Example 1

Preparation of 1-(2,3-dihydrobenzo[b][1,4]dioxin-6-yl)-4-(3-(trifluoromethyl)phenyl)butane-1,4-dione (1) is depicted below in Scheme 15.

Scheme 15

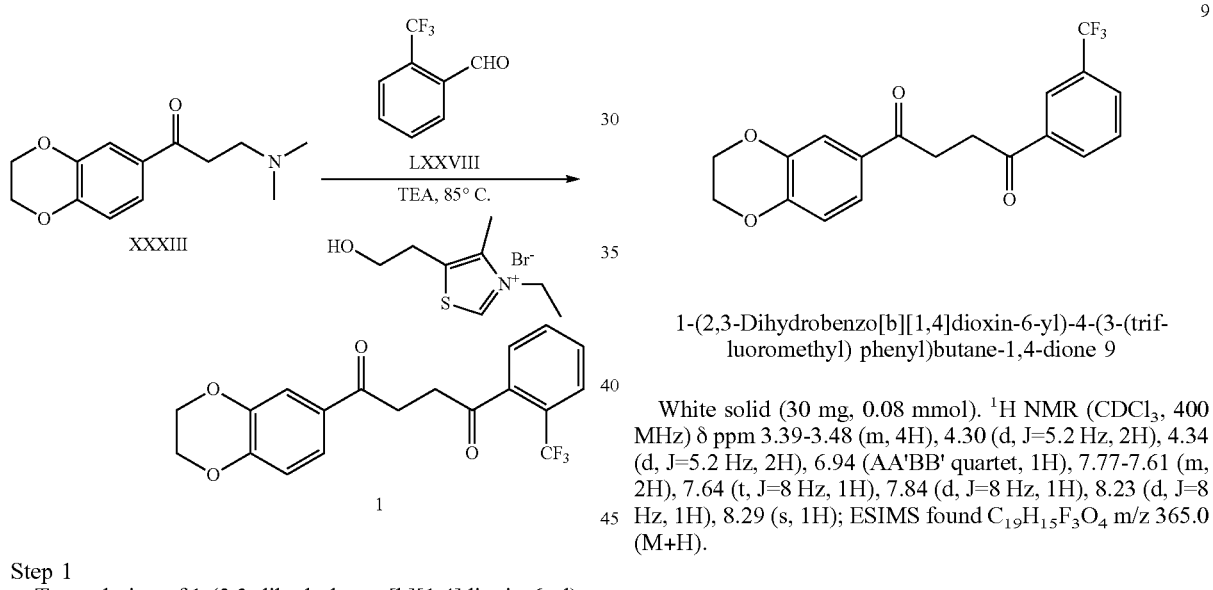

Step 1

To a solution of 1-(2,3-dihydrobenzo[b][1,4]dioxin-6-yl)-3-(dimethylamino)propan-1-one (XXXIII) (1.05 g, 4.4 mmol) and 2-(trifluoromethyl) benzaldehyde (LXXVIII) (703 μL, 5.3 mmol) in TEA (2.0 mL, 14.2 mmol) and was added 3-ethyl-5-(2-hydroxyethyl)-4-methylthiazolium bromide (336 mg, 1.3 mmol). The solution was heated overnight at 85° C. The solution was cooled and excess solvent was evaporated under vacuum. The residue was partitioned between EtOAc and water. The organic phase was dried over MgSO$_4$, filtered and concentrated. The residue was purified by silica gel flash chromatography using (100% hexane→EtOAc/hexane=1:9) to yield 1-(2,3-dihydrobenzo[b][1,4]dioxin-6-yl)-4-(3-(trifluoromethyl)phenyl)butane-1,4-dione 1 as an opaque oil (127.3 mg, 0.35 mmol, 7.8% yield). $^1$H NMR (DMSO-d$_6$, 500 MHz) δ ppm 3.22-3.25 (m, 2H), 3.33-3.35 (m, 2H), 4.29-4.30 (m, 2H), 4.33-4.35 (m, 2H), 6.99 (d, J=8.4 Hz, 1H), 7.50 (d, J=2.2 Hz, 1H), 7.55 (dd, J=8.4 Hz, J=2.0 Hz, 1H), 7.72-7.75 (m, 1H), 7.82-7.86 (m, 2H), 7.94 (d, J=7.5 Hz, 1H); ESIMS found C$_{19}$H$_{15}$F$_3$O$_4$ m/z 365 (M+H).

The following compounds were prepared in accordance with the procedure described in the above Example 1.

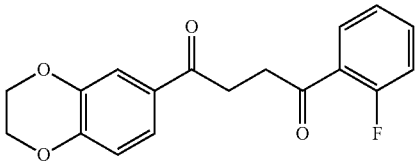

1-(2,3-dihydrobenzo[b][1,4]dioxin-6-yl)-4-(3-fluorophenyl)butane-1,4-dione 2

White solid (308.2 mg, 0.98 mmol, 10.4% yield). $^1$H NMR (DMSO-d$_6$, 500 MHz) δ ppm 3.29-3.33 (m, 2H), 4.29-4.30 (m, 2H), 4.33-4.34 (m, 2H), 6.99 (d, J=8.5 Hz, 1H), 7.34-7.39 (m, 2H), 7.47 (d, J=2.1 Hz, 1H), 7.54 (dd, J=8.5 Hz, J=2.1 Hz, 1H), 7.67-7.69 (m, 1H), 7.82-7.86 (m, 1H); ESIMS found C$_{18}$H$_{15}$FO$_4$ m/z 315.0 (M+H).

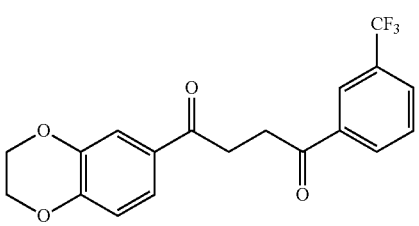

1-(2,3-Dihydrobenzo[b][1,4]dioxin-6-yl)-4-(3-(trifluoromethyl) phenyl)butane-1,4-dione 9

White solid (30 mg, 0.08 mmol). $^1$H NMR (CDCl$_3$, 400 MHz) δ ppm 3.39-3.48 (m, 4H), 4.30 (d, J=5.2 Hz, 2H), 4.34 (d, J=5.2 Hz, 2H), 6.94 (AA'BB' quartet, 1H), 7.77-7.61 (m, 2H), 7.64 (t, J=8 Hz, 1H), 7.84 (d, J=8 Hz, 1H), 8.23 (d, J=8 Hz, 1H), 8.29 (s, 1H); ESIMS found C$_{19}$H$_{15}$F$_3$O$_4$ m/z 365.0 (M+H).

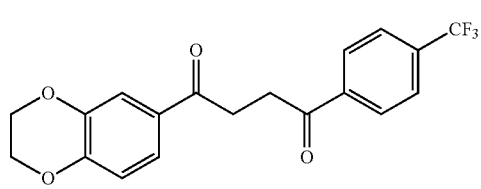

1-(2,3-Dihydrobenzo[b][1,4]dioxin-6-yl)-4-(4-(trifluoromethyl) phenyl)butane-1,4-dione 10

White solid (25 mg, 0.07 mmol). $^1$H NMR (CDCl$_3$, 400 MHz) δ ppm 3.45 (s, 4H), 4.32 (d, J=5.2 Hz, 2H), 4.35 (d, J=5.2 Hz, 2H), 6.96 (AA'BB' quartet, 1H), 7.56-7.64 (m, 2H), 7.77 (d, J=8.4 Hz, 2H), 8.16 (d, J=8 Hz, 2H); ESIMS found C$_{19}$H$_{15}$F$_3$O$_4$ m/z 365.1 (M+H).

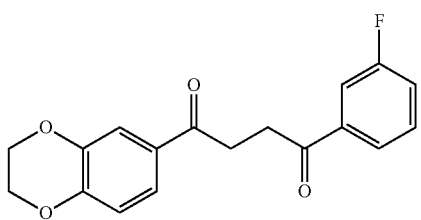

1-(2,3-Dihydrobenzo[b][1,4]dioxin-6-yl)-4-(3-fluorophenyl)butane-1,4-dione 11

White solid (35 mg, 0.11 mmol). $^1$H NMR (CDCl$_3$, 400 MHz) δ ppm 3.42 (s, 4H), 4.31 (t, J=5.6 Hz, 2H), 4.35 (t, J=5.6 Hz, 2H), 6.95 (AA'BB' quartet, 1H), 7.27-7.32 (m, 1H), 7.48 (q, J=5.6 Hz, 1H), 7.60 (dd, J=4 Hz, J=2.4 Hz, 2H), 7.73 (d, J=9.2 Hz, 1H), 7.85 (d, J=8 Hz, 1H); ESIMS found C$_{18}$H$_{15}$FO$_4$ m/z 314.9 (M+H).

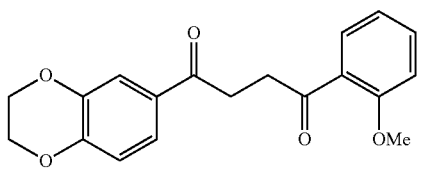

1-(2,3-Dihydrobenzo[b][1,4]dioxin-6-yl)-4-(2-methoxyphenyl)butane-1,4-dione 12

White solid (20 mg, 0.06 mmol). $^1$H NMR (CDCl$_3$, 400 MHz) δ ppm 3.33 (t, J=6.4 Hz, 2H), 3.43 (t, J=6.4 Hz, 2H), 3.93 (s, 3H), 4.24-4.38 (m, 4H), 6.92 (AA'BB' quartet, 1H), 6.95-7.07 (m, 2H), 7.47 (dt, 1H), 7.53-7.62 (m, 2H), 7.76 (dd, J=1.6 Hz, J=7.6 Hz, 1H); ESIMS found C$_{19}$H$_{18}$O$_5$ m/z 327.0 (M+H).

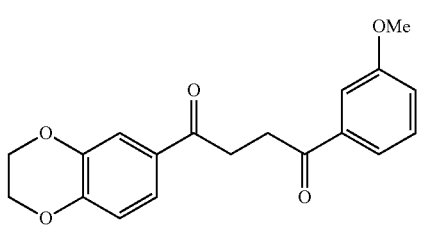

1-(2,3-Dihydrobenzo[b][1,4]dioxin-6-yl)-4-(3-methoxyphenyl)butane-1,4-dione 13

White solid (13 mg, 0.04 mmol). $^1$H NMR (CDCl$_3$, 400 MHz) δ ppm 3.37-3.43 (m, 2H), 3.43-3.48 (m, 2H), 3.88 (s, 3H), 4.29-4.33 (m, 2H), 4.33-4.37 (m, 2H), 6.95 (AA'BB' quartet, 1H), 7.12 (dd, J=4 Hz, J=8.8 Hz, 1H), 7.41 (t, J=7.6 Hz, 2H), 7.56 (t, J=2.4 Hz, 1H), 7.57-7.62 (m, 2H), 7.66 (d, J=8.4 Hz, 1H); ESIMS found C$_{19}$H$_{18}$O$_5$ m/z 327.1 (M+H).

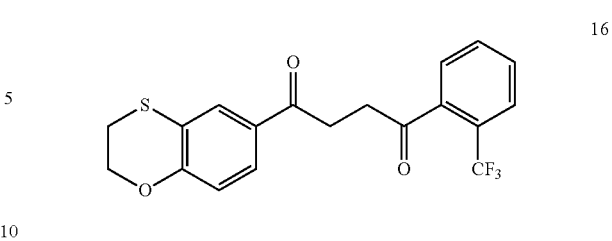

1-(2,3-Dihydrobenzo[b][1,4]oxathiin-6-yl)-4-(2-(trifluoromethyl) phenyl)butane-1,4-dione 16

Yellow oil (16 mg, 0.04 mmol). $^1$H NMR (CDCl$_3$, 400 MHz) δ ppm 3.13-3.19 (m, 2H), 3.22-3.30 (m, 2H), 3.36-3.45 (m, 2H), 4.47-4.55 (m, 2H), 6.89 (d, J=8.58 Hz, 1H), 7.57 (t, J=7.76 Hz, 1H), 7.62-7.80 (m, 5H); ESIMS found C$_{19}$H$_{15}$F$_3$O$_3$S m/z 380.9 (M+H).

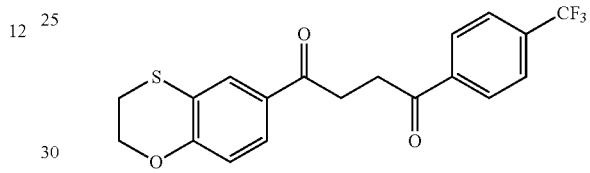

1-(2,3-Dihydrobenzo[b][1,4]oxathiin-6-yl)-4-(4-(trifluoromethyl) phenyl)butane-1,4-dione 18

White solid (52 mg, 0.14 mmol). $^1$H NMR (DMSO-d$_6$, 400 MHz) δ ppm 3.24 (dd, J=5.27 Hz, J=4.02 Hz, 2H), 3.36-3.39 (m, 2H), 3.39-3.45 (m, 2H), 4.39-4.49 (m, 2H), 6.95 (d, J=8.53 Hz, 1H), 7.67 (dd, J=8.66 Hz, J=2.13 Hz, 1H), 7.77 (d, J=2.01 Hz, 1H), 7.93 (d, J=8.28 Hz, 2H), 8.21 (d, J=8.28 Hz, 2H); ESIMS found C$_{19}$H$_5$F$_3$O$_3$S m/z 380.9 (M+H).

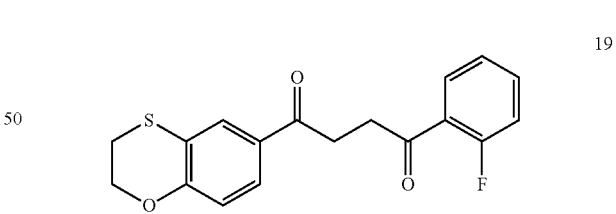

1-(2,3-Dihydrobenzo[b][1,4]oxathiin-6-yl)-4-(2-fluorophenyl)butane-1,4-dione 19

Yellow oil (11 mg, 0.03 mmol). $^1$H NMR (CDCl$_3$, 400 MHz) δ ppm 3.14-3.18 (m, 2H), 3.34-3.40 (m, 2H), 3.41-3.45 (m, 2H), 4.47-4.52 (m, 2H), 6.88 (d, J=8.53 Hz, 1H), 7.12-7.20 (m, 1H), 7.24 (td, J=7.76, 1.00 Hz, 1H), 7.47-7.58 (m, 2H), 7.69 (dd, J=8.53, 2.26 Hz, 1H), 7.78 (d, J=2.01 Hz, 1H), 7.91 (td, J=7.65, 2.01 Hz, 1H); ESIMS found C$_{18}$H$_{15}$FO$_3$S m/z 330.9 (M+H).

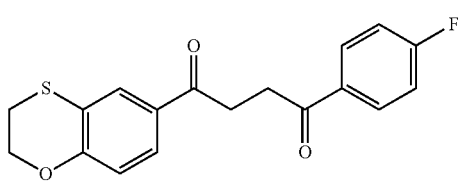

1-(2,3-Dihydrobenzo[b][1,4]oxathiin-6-yl)-4-(4-fluorophenyl)butane-1,4-dione 21

White solid (15 mg, 0.05 mmol). $^1$H NMR (CDCl$_3$, 400 MHz) δ ppm 3.15-3.20 (m, 2H), 3.38-3.43 (m, 4H), 4.49-4.58 (m, 2H), 6.90 (d, J=8.53 Hz, 1H), 7.12-7.21 (m, 2H), 7.70 (dd, J=8.53 Hz, J=2.26 Hz, 1H), 7.80 (d, J=2.01 Hz, 1H), 8.05-8.11 (m, 2H); ESIMS found C$_{17}$H$_{15}$NO$_4$ m/z 330.9 (M+H).

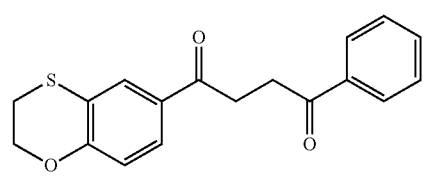

1-(2,3-Dihydrobenzo[b][1,4]oxathiin-6-yl)-4-phenylbutane-1,4-dione 28

White solid (8 mg, 0.03 mmol). $^1$H NMR (CDCl$_3$, 400 MHz) δ ppm 3.14-3.20 (m, 2H), 3.36-3.43 (m, 2H), 3.43-3.49 (m, 2H), 4.48-4.56 (m, 2H), 6.90 (d, J=8.53 Hz, 1H), 7.46-7.53 (m, 2H), 7.57-7.63 (m, 1H), 7.71 (dd, J=8.53 Hz, J=2.26 Hz, 1H), 7.81 (d, J=2.26 Hz, 1H), 8.02-8.10 (m, 2H); ESIMS found C$_{18}$H$_{16}$O$_3$S m/z 312.9 (M+H).

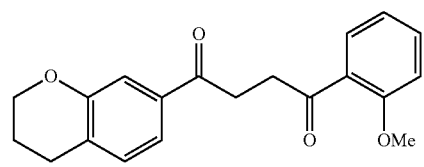

1-(Chroman-7-yl)-4-(2-methoxyphenyl)butane-1,4-dione 61

Yellow oil (30 mg, 0.09 mmol). $^1$H NMR (CDCl$_3$, 400 MHz) δ ppm 2.84 (t, J=6.40 Hz, 2H), 3.31-3.38 (m, 2H), 3.40-3.48 (m, 2H), 3.93 (s, 3H), 4.21-4.29 (m, 2H), 6.83 (d, J=8.28 Hz, 1H), 6.95-7.08 (m, 2H), 7.4207.52 (m, 1H), 7.74-7.83 (m, 3H); ESIMS found C$_{20}$H$_{20}$O$_4$ m/z 325.0 (M+H).

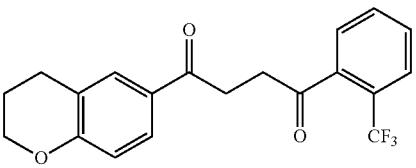

1-(Chroman-6-yl)-4-(2-(trifluoromethyl)phenyl)butane-1,4-dione 68

Yellow oil (35 mg, 0.10 mmol). $^1$H NMR (CDCl$_3$, 400 MHz) δ ppm 1.99-2.08 (m, 2H), 2.84 (t, J=6.40 Hz, 2H), 3.27 (t, J=6.04 Hz, 2H), 3.43 (t, J=7.32 Hz, 2H), 4.26 (t, J=5.28 Hz, 2H), 6.84 (d, J=8.15 Hz, 1H), 7.57 (t, J=7.52 Hz, 1H), 7.66 (t, J=7.52 Hz, 1H), 7.69-7.83 (m, 4H); ESIMS found C$_{20}$H$_{17}$F$_3$O$_3$ m/z 363.0 (M+H).

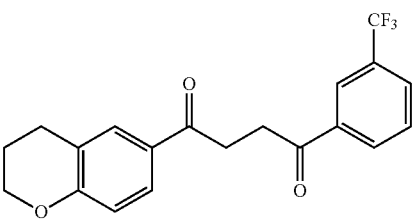

1-(Chroman-6-yl)-4-(3-(trifluoromethyl)phenyl)butane-1,4-dione 69

White solid (52 mg, 0.14 mmol). $^1$H NMR (DMSO-d$_6$, 400 MHz) δ ppm 1.90-2.03 (m, 2H), 2.82 (t, J=6.40 Hz, 2H), 3.37 (d, J=2.76 Hz, 2H), 3.41-3.48 (m, 1H), 4.19-4.29 (m, 2H), 6.85 (d, J=8.53 Hz, 1H), 7.75 (dd, J=8.53 Hz, J=2.26 Hz, 1H), 7.78-7.85 (m, 2H), 8.05 (d, J=7.78 Hz, 1H), 8.26 (s, 1H), 8.34 (d, J=7.78 Hz, 1H); ESIMS found C$_{20}$H$_{17}$F$_3$O$_3$ m/z 363.1 (M+H).

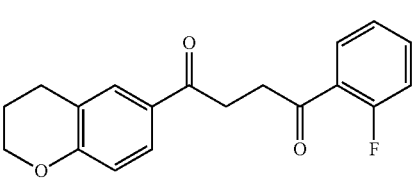

1-(Chroman-6-yl)-4-(2-fluorophenyl)butane-1,4-dione 71

White solid (20 mg, 0.06 mmol). $^1$H NMR (CDCl$_3$, 400 MHz) δ ppm 1.98-2.11 (m, 2H), 2.85 (t, J=6.8 Hz, 2H), 3.34-3.48 (m, 4H), 4.26 (t, J=5.6 Hz, 2H), 6.84 (d, J=8.4 Hz, 1H), 7.16 (ABX quartet, 1H), 7.24 (t, J=7.6 Hz, 1H), 7.47-7.58 (m, 1H), 7.78 (s, 1H), 7.81 (d, J=2 Hz, 1H), 7.91 (dt, J=1.6 Hz, J=7.6 Hz, 1H); ESIMS found C$_{19}$H$_{17}$FO$_3$ m/z 313.0 (M+H).

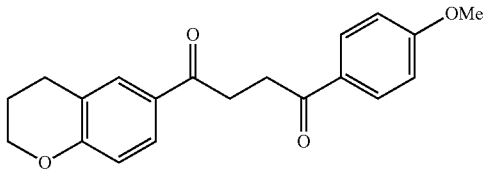

1-(Chroman-6-yl)-4-(4-methoxyphenyl)butane-1,4-dione 76

White solid (20 mg, 0.06 mmol). $^1$H NMR (CDCl$_3$, 400 MHz) δ ppm 2.04 (quin, J=6 Hz, 2H), 2.84 (t, J=6.4 Hz, 2H), 3.33-3.46 (m, 4H), 3.89 (s, 3H), 4.26 (t, J=5.6 Hz, 2H), 6.84 (d, J=8.8 Hz, 1H), 6.96 (d, J=8.8 Hz, 2H), 7.80 (A$_2$X doublet, 2H), 8.03 (d, J=8.8 Hz, 2H); ESIMS found C$_{20}$H$_{20}$O$_4$ m/z 325.0 (M+H).

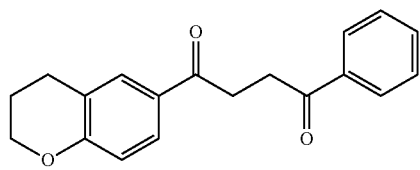

1-(Chroman-6-yl)-4-phenylbutane-1,4-dione 80

White solid (16 mg, 0.05 mmol). $^1$H NMR (CDCl$_3$, 400 MHz) δ ppm 2.05 (q, J=6.4 Hz, 2H), 2.85 (t, J=6.4 Hz, 2H), 3.41 (d, J=5.6 Hz, 2H), 3.44 (d, J=5.2 Hz, 2H), 4.26 (t, J=5.2 Hz, 2H), 6.84 (d, J=8.4 Hz, 1H), 7.49 (t, J=7.6 Hz, 2H), 7.58 (t, J=7.6 Hz, 1H), 7.81 (d, J=9.2 Hz, 2H), 8.05 (d, J=7.2 Hz, 2H); ESIMS found C$_{19}$H$_{18}$O$_3$ m/z 295.0 (M+H).

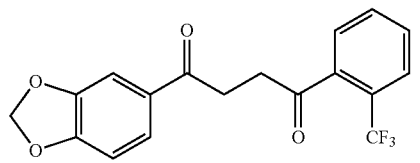 [SMILES: O=C(CCC(=O)c1ccccc1C(F)(F)F)c1ccc2ocnc2c1]

1-(Benzo[d][1,3]dioxol-5-yl)-4-(2-(trifluoromethyl) phenyl)butane-1,4-dione 210

White solid (66 mg, 0.19 mmol). $^1$H NMR (CDCl$_3$, 400 MHz) δ ppm 3.26 (t, J=6.4 Hz, 2H), 3.40 (t, J=6.4 Hz, 2H), 6.05 (s, 2H), 6.87 (d, J=8 Hz, 1H), 7.48 (d, J=1.6 Hz, 1H), 7.57 (t, 1H), 7.60-7.68 (m, 2H), 7.68-7.79 (m, 2H); ESIMS found C$_{18}$H$_{13}$F$_3$O$_4$ m/z 350.9 (M+H).

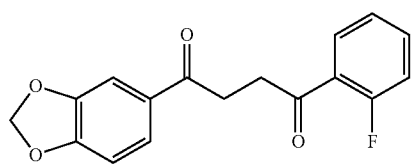 [SMILES: O=C(CCC(=O)c1ccccc1F)c1ccc2ocnc2c1]

1-(Benzo[d][1,3]dioxol-5-yl)-4-(2-fluorophenyl) butane-1,4-dione 213

White solid (10 mg, 0.03 mmol). $^1$H NMR (CDCl$_3$, 400 MHz) δ ppm 3.32-3.40 (m, 2H), 3.40-3.50 (m, 2H), 6.06 (s, 2H), 6.88 (d, J=8.03 Hz, 1H), 7.17 (dd, J=11.17, 8.41 Hz, 1H), 7.24 (t, J=7.65 Hz, 1H), 7.49 (d, J=1.51 Hz, 1H), 7.50-7.59 (m, 1H), 7.66 (dd, J=8.16, 1.63 Hz, 1H), 7.91 (td, J=7.65, 1.76 Hz, 1H); ESIMS found C$_{17}$H$_{13}$FO$_4$ m/z 301.0 (M+H).

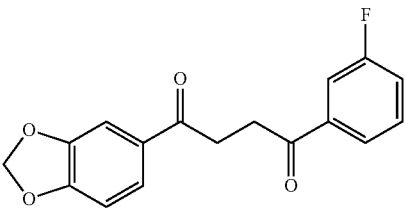 [SMILES: O=C(CCC(=O)c1ccc2ocnc2c1)c1cccc(F)c1]

1-(Benzo[d][1,3]dioxol-5-yl)-4-(3-fluorophenyl) butane-1,4-dione 214

White solid (30 mg, 0.10 mmol). $^1$H NMR (CDCl$_3$, 400 MHz) δ ppm 3.41 (s, 4H), 6.06 (s, 2H), 6.89 (d, J=8.4 Hz, 1H), 7.29 (dt, J=2.4 Hz, J=7.2 Hz, 1H), 7.43-7.53 (m, 2H), 7.67 (dd, J=1.2 Hz, J=8 Hz, 1H), 7.70 (d, J=8.4 Hz, 1H), 7.83 (d, J=8 Hz, 1H); ESIMS found C$_{17}$H$_{13}$FO$_4$ m/z 323.0 (M+H).

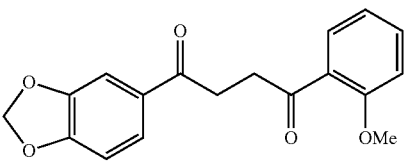 [SMILES: COc1ccccc1C(=O)CCC(=O)c1ccc2ocnc2c1]

1-(Benzo[d][1,3]dioxol-5-yl)-4-(2-methoxyphenyl) butane-1,4-dione 216

White solid (30 mg, 0.10 mmol). $^1$H NMR (CDCl$_3$, 400 MHz) δ ppm 3.34 (t, J=6.4 Hz, 2H), 3.45 (t, J=6.4 Hz, 2H), 3.93 (s, 3H), 6.05 (s, 2H), 6.87 (d, J=8 Hz, 1H), 6.96-7.06 (m, 2H), 7.48 (t, 1H), 7.50 (d, J=1.2 Hz, 1H), 7.66 (dd, J=1.6 Hz, J=8 Hz, 1H), 7.77 (dd, J=1.6 Hz, J=8 Hz, 1H); ESIMS found C$_{18}$H$_{16}$O$_5$ m/z 313.0 (M+H).

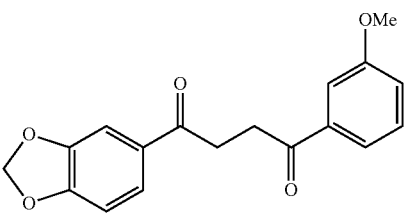 [SMILES: COc1cccc(C(=O)CCC(=O)c2ccc3ocnc3c2)c1]

1-(Benzo[d][1,3]dioxol-5-yl)-4-(3-methoxyphenyl) butane-1,4-dione 217

White solid (30 mg, 0.10 mmol). $^1$H NMR (CDCl$_3$, 400 MHz) δ ppm 3.35-3.41 (m, 2H), 3.41-3.47 (m, 2H), 3.87 (s, 3H), 6.06 (s, 2H), 6.88 (d, J=8.28 Hz, 1H), 7.13 (ddd, J=8.16, 2.64, 1.00 Hz, 1H), 7.40 (t, J=7.91 Hz, 1H), 7.50 (d, J=1.52 Hz, 1H), 7.55 (dd, J=2.52, J=1.52 Hz, 1H), 7.64 (dt, J=7.84, 1.10 Hz, 1H), 7.68 (dd, J=8.03, 1.76 Hz, 1H); ESIMS found $C_{18}H_{16}O_5$ m/z 313.0 (M+H).

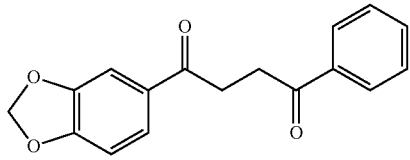 [SMILES: O=C(CCC(=O)c1ccc2ocnc2c1)c1ccccc1]

1-(Benzo[d][1,3]dioxol-5-yl)-4-phenylbutane-1,4-dione 222

White solid (48 mg, 0.17 mmol). $^1$H NMR (CDCl$_3$, 400 MHz) δ ppm 3.39 (t, J=5.6 Hz, 2H), 3.45 (t, J=5.6 Hz, 2H), 6.06 (s, 2H), 6.88 (d, J=8.4 Hz, 1H), 7.43-7.53 (m, 3H), 7.58 (t, J=7.6 Hz, 1H), 7.68 (d, J=8.4 Hz, 1H), 8.04 (d, J=7.6 Hz, 2H); ESIMS found $C_{17}H_{14}O_4$ m/z 283.0 (M+H).

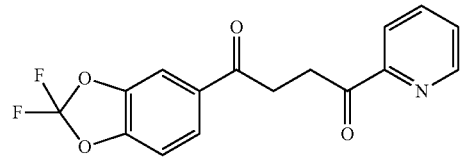

1-(2,2-Difluorobenzo[d][1,3]dioxol-5-yl)-4-(pyridin-2-yl)butane-1,4-dione 232

White solid (11 mg, 0.03 mmol). $^1$H NMR (CDCl$_3$, 400 MHz) δ ppm 3.44 (t, J=6 Hz, 2H), 3.73 (t, J=6 Hz, 2H), 7.18 (d, J=8.4 Hz, 1H), 7.53 (t, J=4 Hz, 1H), 7.78 (s, 1H), 7.83-7.95 (m, 2H), 8.07 (d, J=8 Hz, 1H), 8.75 (d, J=4 Hz, 1H); ESIMS found $C_{16}H_{11}F_2NO_4$ m/z 320.1 (M+H).

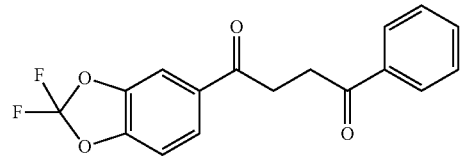

1-(2,2-Difluorobenzo[d][1,3]dioxol-5-yl)-4-phenylbutane-1,4-dione 235

White solid (20 mg, 0.06 mmol). $^1$H NMR (CDCl$_3$, 400 MHz) δ ppm 3.43 (t, J=6 Hz, 2H), 3.50 (t, J=6 Hz, 2H), 7.19 (d, J=8.4 Hz, 1H), 7.51 (t, J=7.6 Hz, 2H), 7.62 (t, J=7.6 Hz, 1H), 7.78 (d, J=2 Hz, 1H), 7.91 (dd, J=1.5 Hz, J=8.4 Hz, 1H), 8.06 (d, J=7.2 Hz, 2H); ESIMS found $C_{17}H_{12}F_2O_4$ m/z 318.9 (M+H).

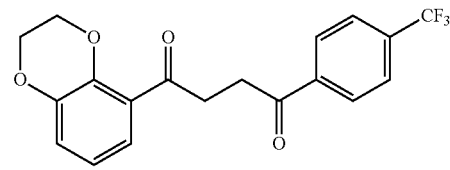

1-(2,3-Dihydrobenzo[b][1,4]dioxin-5-yl)-4-(4-(trifluoromethyl)phenyl)butane-1,4-dione 238

White solid (14 mg, 0.04 mmol). $^1$H NMR (CDCl$_3$, 400 MHz) δ ppm 3.43 (t, J=6 Hz, 2H), 3.51 (t, J=6 Hz, 2H), 4.34 (t, J=4 Hz, 2H), 4.42 (t, J=4 Hz, 2H), 6.91 (t, J=8 Hz, 1H), 7.06 (dd, J=1.2 Hz, J=8 Hz, 1H), 7.38 (dd, J=1.6 Hz, J=8 Hz, 1H), 7.77 (d, J=8 Hz, 2H), 8.16 (d, J=8.4 Hz, 2H); ESIMS found $C_{19}H_{15}F_3O_4$ m/z 365.0 (M+H).

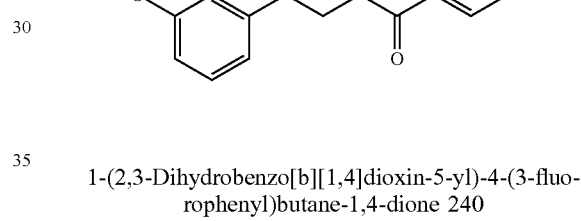

1-(2,3-Dihydrobenzo[b][1,4]dioxin-5-yl)-4-(3-fluorophenyl)butane-1,4-dione 240

White solid (79 mg, 0.25 mmol). $^1$H NMR (CDCl$_3$, 400 MHz) δ ppm 3.40 (t, J=6 Hz, 2H), 3.48 (t, J=6 Hz, 2H), 4.34 (dd, J=4 Hz, J=6 Hz, 2H), 4.41 (dd, J=4 Hz, J=6 Hz, 2H), 6.91 (t, J=7.6 Hz, 1H), 7.05 (dd, J=1.6 Hz, J=8 Hz, 1H), 7.26-7.32 (m, 1H), 7.38 (dd, J=1.6 Hz, J=8 Hz, 1H), 7.48 (dd, J=7.6 Hz, J=8.8 Hz, 1H), 7.73 (d, J=8.8 Hz, 1H), 7.85 (d, J=7.6 Hz, 1H); ESIMS found $C_{18}H_{15}FO_4$ m/z 314.9 (M+H).

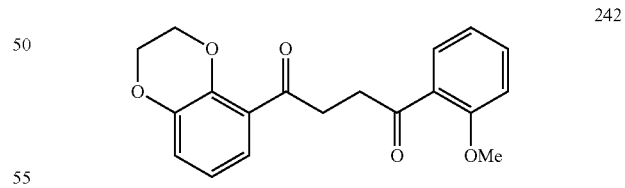

1-(2,3-Dihydrobenzo[b][1,4]dioxin-5-yl)-4-(2-methoxyphenyl)butane-1,4-dione 242

White solid (40 mg, 0.12 mmol). $^1$H NMR (CDCl$_3$, 400 MHz) δ ppm 3.29-3.46 (m, 4H), 3.93 (s, 3H), 4.25-4.35 (m, 2H), 4.35-4.43 (m, 2H), 6.88 (t, J=8 Hz, 1H), 6.94-7.07 (m, 3H), 3.34 (dd, J=1.6 Hz, J=8 Hz, 1H), 7.46 (dt, J=1.6 Hz, J=7.6 Hz, 1H), 7.76 (dd, J=1.6 Hz, J=7.6 Hz, 1H); ESIMS found $C_{19}H_{18}O_5$ m/z 327.0 (M+H).

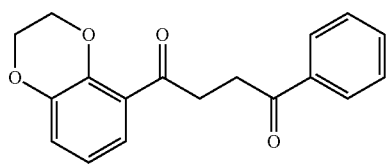

248

1-(2,3-Dihydrobenzo[b][1,4]dioxin-5-yl)-4-phenylbutane-1,4-dione 248

White solid (28 mg, 0.10 mmol). ¹H NMR (CDCl₃, 400 MHz) δ ppm 3.39-3.54 (m, 4H), 4.28-4.35 (m, 2H), 4.35-4.44 (m, 2H), 6.89 (t, J=7.6 Hz, 1H), 7.03 (dd, J=2.4 Hz, J=7.6 Hz, 1H), 7.36 (dd, J=1.2 Hz, J=7.6 Hz, 1H), 7.48 (t, J=7.6 Hz, 2H), 7.58 (t, J=7.6 Hz, 1H), 8.04 (dd, J=1.2 Hz, J=8 Hz, 2H); ESIMS found $C_{18}H_{16}O_4$ m/z 297.0 (M+H).

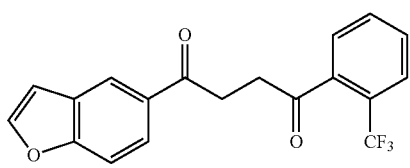

275

1-(Benzofuran-5-yl)-4-(2-(trifluoromethyl)phenyl)butane-1,4-dione 275

Oil (27 mg, 0.08 mmol). ¹H NMR (CDCl₃, 400 MHz) δ ppm 3.34 (t, J=6 Hz, 2H), 3.57 (t, J=6 Hz, 2H), 6.89 (d, J=1.2 Hz, 1H), 7.60 (t, J=8.4 Hz, 2H), 7.68 (t, J=7.2 Hz, 1H), 7.71-7.74 (m, 2H), 7.78 (t, J=7.2 Hz, 1H), 8.05 (dd, J=1.6 Hz, J=8.4 Hz, 1H), 8.36 (s, 1H); ESIMS found $C_{19}H_{13}F_3O_3$ m/z 346.9 (M+H).

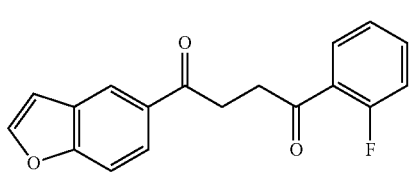

278

1-(Benzofuran-5-yl)-4-(2-fluorophenyl)butane-1,4-dione 278

White solid (34 mg, 0.11 mmol). ¹H NMR (DMSO-d₆, 400 MHz) δ ppm 3.34-3.46-3.52 (m, 2H), 7.12 (t, J=1.50 Hz, 1H), 7.32-7.44 (m, 2H), 7.65-7.71 (m, 1H), 7.73 (d, J=8.78 Hz, 1H), 7.86 (td, J=7.65, 1.76 Hz, 1H), 7.99 (dd, J=8.78, 1.76 Hz, 1H), 8.13 (d, J=2.26 Hz, 1H), 7.12 (d, J=1.50 Hz, 1H); ESIMS found $C_{18}H_{13}FO_3$ m/z 297.0 (M+H).

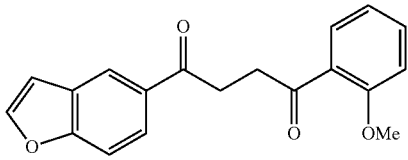

281

1-(Benzofuran-5-yl)-4-(2-methoxyphenyl)butane-1,4-dione 281

White solid (50 mg, 0.16 mmol). ¹H NMR (CDCl₃, 400 MHz) δ ppm 3.45-3.53 (m, 4H), 3.94 (s, 3H), 6.88 (dd, J=2.26, 0.75 Hz, 1H), 6.95-7.08 (m, 2H), 7.49 (ddd, J=8.34, 7.34, 1.88 Hz, 1H), 7.57 (d, J=8.53 Hz, 1H), 7.70 (d, J=2.26 Hz, 1H), 7.79 (dd, J=7.65, 1.88 Hz, 1H), 8.05 (dd, J=8.78, 1.76 Hz, 1H), 8.36 (d, J=1.76 Hz, 1H); ESIMS found $C_{19}H_{16}O_4$ m/z 309.1 (M+H).

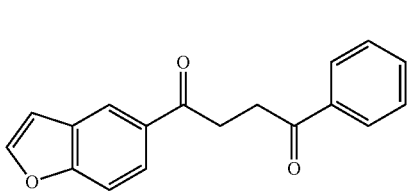

287

1-(Benzofuran-5-yl)-4-phenylbutane-1,4-dione 287

White solid (16 mg, 0.06 mmol). ¹H NMR (DMSO-d₆, 400 MHz) δ ppm 3.41-3.47 (m, 2H) 3.47-3.52 (m, 2H) 7.13 (dd, J=2.13 Hz, J=0.88 Hz, 1H) 7.57 (t, J=7.56 Hz, 2H) 7.67 (t, J=6.99 Hz, 1H) 7.74 (d, J=8.78 Hz, 1H) 8.00 (dd, J=8.53 Hz, J=1.76 Hz, 1H) 8.02-8.06 (m, 2H) 8.14 (d, J=2.26 Hz, 1H) 8.44 (d, J=1.76 Hz, 1H); ESIMS found $C_{18}H_{14}O_3$ m/z 279.1 (M+H).

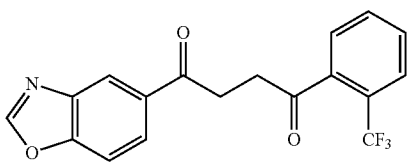

288

1-(Benzo[d]oxazol-5-yl)-4-(2-(trifluoromethyl)phenyl)butane-1,4-dione 288

White solid (15 mg, 0.04 mmol). ¹H NMR (CDCl₃, 400 MHz) δ ppm 3.31-3.38 (m, 2H), 3.54-3.60 (m, 2H), 7.59 (t, J=7.66 Hz, 1H), 7.66-7.71 (m, 2H), 7.74 (d, J=7.78 Hz, 1H), 7.79 (d, J=7.53 Hz, 1H), 8.15 (dd, J=1.6 Hz, J=8.31 Hz, 1H), 8.21 (s, 1H), 8.50 (d, J=1.51 Hz, 1H); ESIMS found $C_{18}H_{12}F_3NO_3$ m/z 348.1 (M+H).

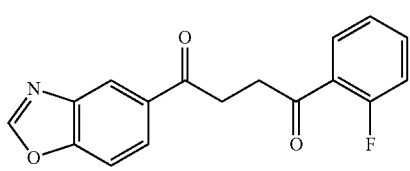

1-(Benzo[d]oxazol-5-yl)-4-(2-fluorophenyl)butane-1,4-dione 291

White solid (12 mg, 0.04 mmol). $^1$H NMR (CDCl$_3$, 400 MHz) δ ppm 3.45-3.59 (m, 4H), 7.18 (ddd, J=11.23, 8.34, 1.00 Hz, 1H), 7.22-7.27 (m, 1H), 7.49-7.60 (m, 1H), 7.68 (d, J=8.78 Hz, 1H), 7.92 (td, J=7.65, 1.76 Hz, 1H), 8.17 (dd, J=8.56, 1.76 Hz, 1H), 8.20 (s, 1H), 8.51 (d, J=1.25 Hz, 1H); ESIMS found C$_{17}$H$_{12}$FNO$_3$ m/z 298.1 (M+H).

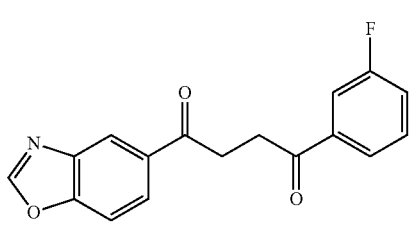

1-(Benzo[d]oxazol-5-yl)-4-(3-fluorophenyl)butane-1,4-dione 292

White solid (28 mg, 0.09 mmol). $^1$H NMR (CDCl$_3$, 400 MHz) δ ppm 3.45-3.52 (m, 2H), 3.54-3.61 (m, 2H), 7.31 (dt, J=1.00 Hz, J=8.28 Hz, 1H), 7.50 (td, J=8.03 Hz, J=5.52 Hz, 1H), 7.70 (d, J=8.53 Hz, 1H), 7.72-7.78 (m, 1H), 7.87 (dt, J=7.78 Hz, J=1.13 Hz, 1H), 8.18 (d, J=8.73 Hz, 1H), 8.21 (s, 1H), 8.53 (d, J=1.51 Hz, 1H); ESIMS found C$_{17}$H$_{12}$FNO$_3$ m/z 298.0 (M+H).

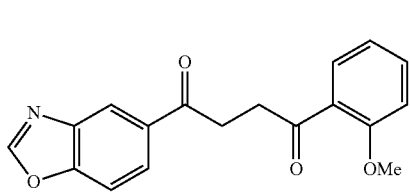

1-(Benzo[d]oxazol-5-yl)-4-(2-methoxyphenyl)butane-1,4-dione 294

White solid (10 mg, 0.03 mmol). $^1$H NMR (CDCl$_3$, 400 MHz) δ ppm 3.44-3.56 (m, 4H), 3.95 (s, 3H), 6.95-7.08 (m, 2H), 7.49 (td, J=7.80, 1.50 Hz, 1H), 7.67 (d, J=8.53 Hz, 1H), 7.79 (dd, J=7.65, 1.63 Hz, 1H), 8.16 (dd, J=8.80, 1.50 Hz, 1H), 8.19 (s, 1H), 8.51 (d, J=1.00 Hz, 1H); ESIMS found C$_{18}$H$_{15}$NO$_4$ m/z 310.1 (M+H).

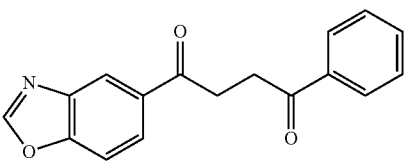

1-(Benzo[d]oxazol-5-yl)-4-phenylbutane-1,4-dione 300

White solid (50 mg, 0.18 mmol). $^1$H NMR (CDCl$_3$, 400 MHz) δ ppm 3.48-3.59 (m, 4H), 7.46-7.55 (m, 2H), 7.60 (tt, J=1.24 Hz, J=7.52 Hz, 1H), 7.68 (d, J=8.53 Hz, 1H), 8.03-8.09 (m, 2H), 8.17 (dd, J=8.78 Hz, J=1.76 Hz, 1H), 8.20 (s, 1H), 8.53 (d, J=1.51 Hz, 1H); ESIMS found C$_{17}$H$_{13}$NO$_3$ m/z 280.0 (M+H).

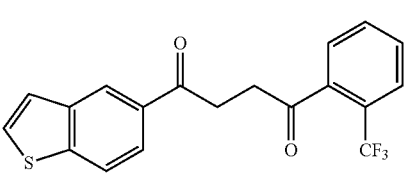

1-(Benzo[b]thiophen-5-yl)-4-(2-(trifluoromethyl)phenyl)butane-1,4-dione 301

White solid (83 mg, 0.23 mmol). $^1$H NMR (DMSO-d$_6$, 400 MHz) δ ppm 3.30-3.37 (m, 2H), 3.48-3.57 (m, 2H), 7.65 (d, J=5.27 Hz, 1H), 7.75 (t, J=7.61 Hz, 1H), 7.85 (t, J=7.76 2H), 7.91 (d, J=5.27 Hz, 1H), 7.95-8.01 (m, 2H), 8.17 (d, J=8.53 Hz, 1H), 8.65 (d, J=1.25 Hz, 1H); ESIMS found C$_{19}$H$_{13}$F$_3$O$_2$S m/z 362.9 (M+H).

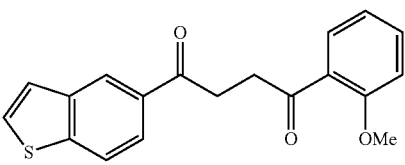

1-(Benzo[b]thiophen-5-yl)-4-(2-methoxyphenyl)butane-1,4-dione 307

Brown solid (20 mg, 0.06 mmol). $^1$H NMR (CDCl$_3$, 400 MHz) δ ppm 3.52 (s, 2H), 3.95 (s, 2H), 6.97-7.09 (m, 2H), 7.43-7.52 (m, 2H), 7.54 (d, J=5.52 Hz, 1H), 7.79 (dd, J=7.78, 1.76 Hz, 1H), 7.96 (d, J=8.52 Hz, 1H), 8.02 (dd, J=8.52, 1.24 Hz, 1H), 8.54 (d, J=1.00 Hz, 1H); ESIMS found C$_{19}$H$_{16}$O$_3$S m/z 324.9 (M+H).

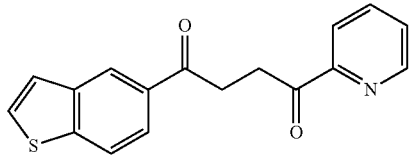

1-(Benzo[b]thiophen-5-yl)-4-(pyridin-2-yl)butane-1,4-dione 310

White solid (20 mg, 0.07 mmol). $^1$H NMR (DMSO-$d_6$, 400 MHz) δ ppm 3.50-3.55 (m, 2H), 3.55-3.61 (m, 2H), 7.63 (d, J=5.52 Hz, 1H), 7.69 (ddd, J=1.52 Hz, J=5.52 Hz, J=7.52 Hz, 1H), 7.89 (d, J=5.52 Hz, 1H), 7.92-7.98 (m, 2H), 8.02 (dt, J=1.76, J=7.67 Hz, 1H), 8.15 (d, J=8.53 Hz, 1H), 8.62 (d, J=1.51 Hz, 1H), 8.77 (d, J=4.79 Hz, 1H); ESIMS found $C_{17}H_{13}NO_2S$ m/z 296.1 (M+H).

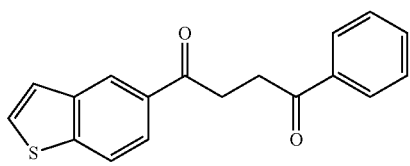

1-(Benzo[b]thiophen-5-yl)-4-phenylbutane-1,4-dione 313

White solid (105 mg, 0.36 mmol). $^1$H NMR (DMSO-$d_6$, 400 MHz) δ ppm 3.41-3.48 (m, 2H), 3.48-3.55 (m, 2H), 7.51-7.61 (m, 2H), 7.62-7.71 (m, 2H), 7.91 (d, J=5.52 Hz, 1H), 7.96 (dd, J=8.53 Hz, J=1.51 Hz, 1H), 8.03 (d, J=7.36 Hz, 2H), 8.16 (d, J=8.53 Hz, 1H), 8.64 (d, J=1.51 Hz, 1H); ESIMS found $C_{18}H_{14}O_2S$ m/z 295.1 (M+H).

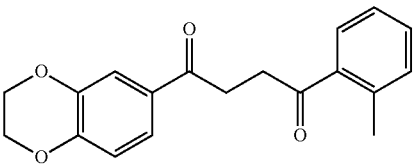

1-(2,3-Dihydrobenzo[b][1,4]dioxin-6-yl)-4-(o-tolyl)butane-1,4-dione 342

White solid (15 mg, 0.05 mmol). $^1$H NMR (CDCl$_3$, 400 MHz) δ ppm 2.52 (s, 3H), 3.35 (t, J=5.2 Hz, 2H), 3.39 (t, J=5.2 Hz, 2H), 4.31 (d, J=5.2 Hz, 2H), 4.35 (d, J=5.2 Hz, 2H), 6.95 (AA'BB' quartet, 1H), 7.26-7.35 (m, 2H), 7.40 (t, J=7.6 Hz, 1H), 7.56-7.61 (m, 2H), 7.83 (d, J=7.2 Hz, 1H); ESIMS found $C_{19}H_{18}O_4$ m/z 311.1 (M+H).

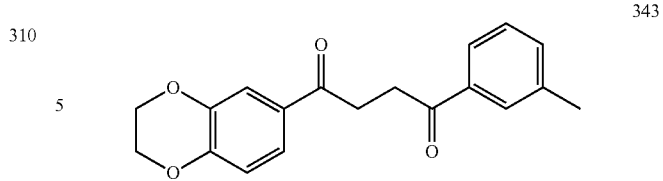

1-(2,3-Dihydrobenzo[b][1,4]dioxin-6-yl)-4-(m-tolyl)butane-1,4-dione 343

White solid (13 mg, 0.04 mmol). $^1$H NMR (CDCl$_3$, 400 MHz) δ ppm 2.43 (s, 3H), 3.39 (t, J=4.8 Hz, 2H), 3.43 (t, J=4.8 Hz, 2H), 4.30 (d, J=5.2 Hz, 2H), 4.33 (d, J=5.2 Hz, 2H), 6.93 (AA'BB' quartet, 1H), 7.34-7.42 (m, 2H), 7.56-7.62 (m, 2H), 7.84 (d, J=7.6 Hz, 2H); ESIMS found $C_{19}H_{18}O_4$ m/z 311.1 (M+H).

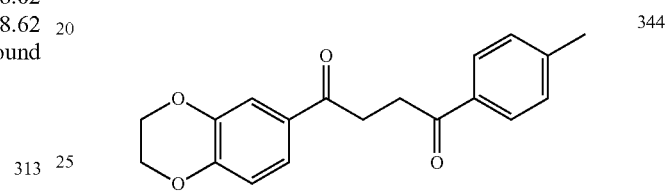

1-(2,3-Dihydrobenzo[b][1,4]dioxin-6-yl)-4-(p-tolyl)butane-1,4-dione 344

White solid (26 mg, 0.08 mmol). $^1$H NMR (CDCl$_3$, 400 MHz) δ ppm 2.43 (s, 3H), 3.35-3.45 (m, 4H), 4.30 (d, J=5.6 Hz, 2H), 4.33 (d, J=5.6 Hz, 2H), 6.93 (AA'BB' quartet, 1H), 7.26-7.33 (m, 2H), 7.57-7.63 (m, 2H), 7.94 (d, J=8 Hz, 2H); ESIMS found $C_{19}H_{18}O_4$ m/z 311.1 (M+H).

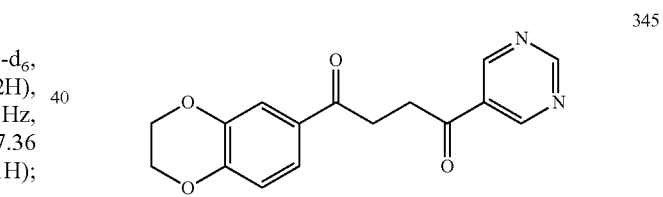

1-(2,3-Dihydrobenzo[b][1,4]dioxin-6-yl)-4-(pyrimidin-5-yl)butane-1,4-dione 345

White solid (9 mg, 0.03 mmol). $^1$H NMR (CDCl$_3$, 400 MHz) δ ppm 3.40 (t, J=6 Hz, 2H), 3.48 (t, J=6 Hz, 2H), 4.28-4.39 (m, 4H), 6.96 (AA'BB' quartet, 1H), 7.55-7.62 (m, 2H), 9.34 (s, 2H), 9.41 (s, 1H); ESIMS found $C_{16}H_{14}N_2O_4$ m/z 299.0 (M+H).

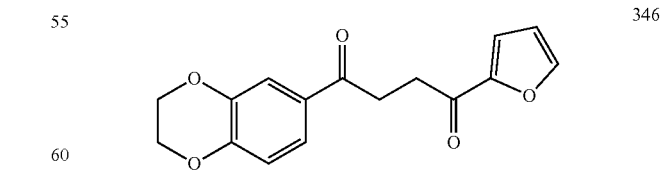

1-(2,3-Dihydrobenzo[b][1,4]dioxin-6-yl)-4-(furan-2-yl)butane-1,4-dione 346

White solid (42 mg, 0.15 mmol). $^1$H NMR (CDCl$_3$, 400 MHz) δ ppm 3.29 (t, J=6 Hz, 2H), 3.38 (t, J=6 Hz, 2H), 4.26-4.31 (m, 2H), 4.31-4.36 (m, 2H), 6.56 (dd, J=2 Hz, J=5.2 Hz, 1H), 6.92 (AA'BB' quartet, 1H), 7.25-7.29 (m, 1H), 7.55-7.64 (m, 2H), 7.61 (s, 1H); ESIMS found $C_{16}H_{14}O_5$ m/z 287.1 (M+H).

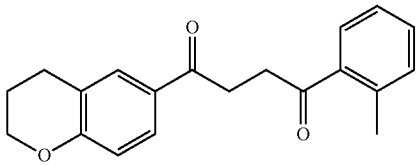

358

1-(Chroman-6-yl)-4-(o-tolyl)butane-1,4-dione 358

Yellow solid (28 mg, 0.09 mmol). $^1$H NMR (CDCl$_3$, 400 MHz) δ ppm 1.99-2.08 (m, 2H), 2.51 (s, 3H), 2.84 (t, J=6.53 Hz, 2H), 3.31-3.36 (m, 2H), 3.36-3.42 (m, 2H), 4.26 (t, J=5.28 Hz, 2H), 6.84 (d, J=8.28 Hz, 1H), 7.24-7.32 (m, 2H), 7.39 (td, J=7.50, 1.52 Hz, 1H), 7.77-7.84 (m, 3H); ESIMS found $C_{20}H_{20}O_3$ m/z 309.2 (M+H).

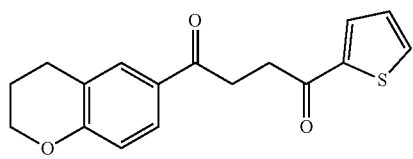

364

1-(Chroman-6-yl)-4-(thiophen-2-yl)butane-1,4-dione 364

Yellow solid (18 mg, 0.06 mmol). $^1$H NMR (DMSO-d$_6$, 400 MHz) δ ppm 1.94 (quin, J=5.02 Hz, 2H), 2.80 (t, J=6.15 Hz, 2H), 3.31 (s, 4H), 3.36 (s, 4H), 4.21 (t, J=4.76 Hz, 2H), 6.83 (d, J=8.53 Hz, 1H), 7.26 (t, J=4.27 Hz, 1H), 7.73 (d, J=8.53 Hz, 1H), 7.77 (s, 1H), 8.00 (d, J=4.77 Hz, 1H), 8.04 (d, J=3.76 Hz, 1H); ESIMS found $C_{17}H_{16}O_3S$ m/z 301.1 (M+H).

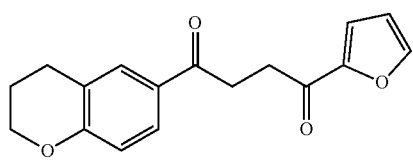

365

1-(Chroman-6-yl)-4-(furan-2-yl)butane-1,4-dione 365

White solid (11 mg, 0.04 mmol). $^1$H NMR (CDCl$_3$, 400 MHz) δ ppm 2.04 (quin, J=5.00 Hz, 2H), 2.84 (t, J=6.40 Hz, 2H), 3.26-3.32 (m, 2H), 3.35-3.42 (m, 2H), 4.25 (t, J=5.04 Hz, 2H), 6.56 (dd, J=3.51, 1.76 Hz, 1H), 6.83 (d, J=8.28 Hz, 1H), 7.25-7.28 (m, 1H), 7.61 (d, J=0.75 Hz, 1H), 7.74-7.81 (m, 2H); ESIMS found $C_{17}H_{16}O_4$ m/z 285.2 (M+H).

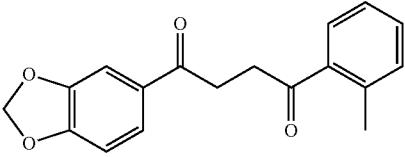 [SMILES: Cc1ccccc1C(=O)CCC(=O)c1ccc2c(c1)OCO2]

368

1-(Benzo[d][1,3]dioxol-5-yl)-4-(o-tolyl)butane-1,4-dione 368

White solid (66 mg, 0.22 mmol). $^1$H NMR (DMSO-d$_6$, 400 MHz) δ ppm 2.37 (s, 3H), 3.24 (t, J=6 Hz, 2H), 3.27-3.35 (m, 2H), 6.14 (s, 2H), 7.06 (d, J=8 Hz, 1H), 7.30 (t, J=7.2 Hz, 1H), 7.35 (d, 1H), 7.43 (t, 1H), 7.48 (s, 1H), 7.68 (dd, J=1.6 Hz, J=8.4 Hz, 1H), 7.84 (d, J=7.2 Hz, 1H); ESIMS found $C_8H_{16}O_4$ m/z 297.0 (M+H).

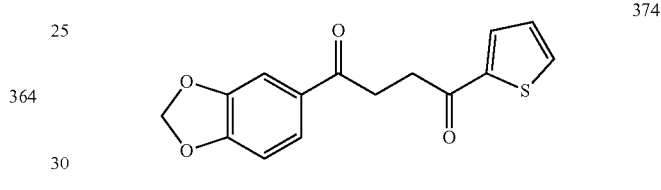

374

1-(Benzo[d][1,3]dioxol-5-yl)-4-(thiophen-2-yl)butane-1,4-dione 374

White solid (23 mg, 0.08 mmol). $^1$H NMR (DMSO-d$_6$, 400 MHz) δ ppm 3.30-3.36 (m, 4H), 6.14 (s, 2H), 7.06 (d, J=8.03 Hz, 1H), 7.27 (dd, J=5.02, 3.76 Hz, 1H), 7.46 (d, J=1.51 Hz, 1H), 7.66 (dd, J=8.28, 1.76 Hz, 1H), 8.00 (dd, J=5.02, 1.00 Hz, 1H), 8.04 (dd, J=3.76, 1.25 Hz, 1H); ESIMS found $C_{15}H_{12}O_4S$ m/z 288.9 (M+H).

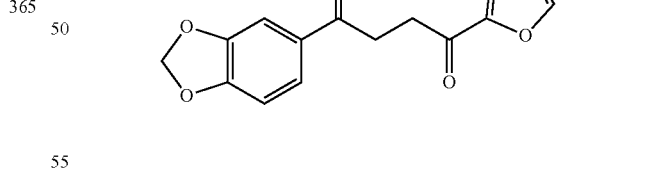

375

1-(Benzo[d][1,3]dioxol-5-yl)-4-(furan-2-yl)butane-1,4-dione 375

White solid (10 mg, 0.04 mmol). $^1$H NMR (DMSO-d$_6$, 400 MHz) δ ppm 3.13-3.20 (m, 2H), 3.28-3.35 (m, 2H), 6.14 (s, 2H), 6.73 (dd, J=3.51, 1.76 Hz, 1H), 7.05 (d, J=8.03 Hz, 1H), 7.46 (d, J=1.76 Hz, 1H), 7.49 (d, J=3.86 Hz, 1H), 7.66 (dd, J=8.16, 1.63 Hz, 1H), 8.00 (d, J=1.00 Hz, 1H); ESIMS found $C_{15}H_{12}O_5$ m/z 273.0 (M+H).

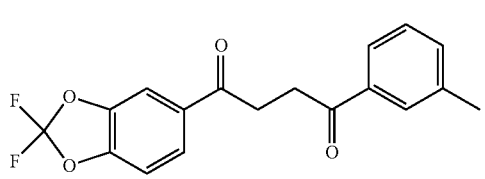

1-(2,2-Difluorobenzo[d][1,3]dioxol-5-yl)-4-(m-tolyl)butane-1,4-dione 379

White solid (308.2 mg, 0.98 mmol). $^1$H NMR (CDCl$_3$, 400 MHz) δ ppm 2.43 (s, 3H), 3.41 (t, J=5.6 Hz, 2H), 3.47 (t, J=5.6 Hz, 2H), 7.17 (d, J=8.4 Hz, 1H), 7.39 (q, J=8.8 Hz, 2H), 7.77 (d, J=1.6 Hz, 1H), 7.84 (d, J=6.8 Hz, 2H), 7.90 (dd, J=1.6 Hz, J=8.4 Hz, 1H); ESIMS found C$_{18}$H$_{14}$F$_2$O$_4$ m/z 333.1 (M+H).

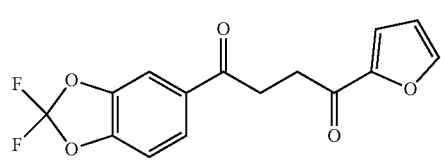

1-(2,2-Difluorobenzo[d][1,3]dioxol-5-yl)-4-(furan-2-yl)butane-1,4-dione 385

White solid (11 mg, 0.04 mmol). $^1$H NMR (CDCl$_3$, 400 MHz) δ ppm 3.33 (t, J=6 Hz, 2H), 3.39 (t, J=6 Hz, 2H), 6.57 (dd, J=2.5 Hz, J=3.5 Hz, 1H), 7.15 (d, J=7.6 Hz, 1H), 7.23-7.31 (m, 1H), 7.62 (s, 1H), 7.74 (d, J=1.6 Hz, 1H), 7.86 (dd, J=1.6 Hz, J=7.6 Hz, 1H); ESIMS found C$_{15}$H$_{10}$F$_2$O$_5$ m/z 309.1 (M+H).

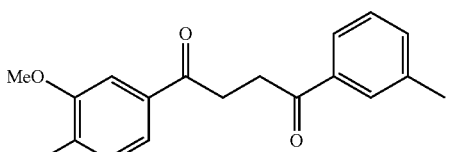

1-(3,4-Dimethoxyphenyl)-4-(m-tolyl)butane-1,4-dione 425

White solid (27 mg, 0.09 mmol). $^1$H NMR (CDCl$_3$, 400 MHz) δ ppm 2.43 (s, 3H), 3.45 (s, 4H), 3.95 (s, 3H), 3.97 (s, 3H), 6.93 (d, J=8.53 Hz, 1H), 7.35-7.44 (m, 2H), 7.58 (d, J=2.01 Hz, 1H), 7.72 (dd, J=8.53, 2.01 Hz, 1H), 7.83-7.89 (m, 2H); ESIMS found C$_{19}$H$_{20}$O$_4$ m/z 313.1 (M+H).

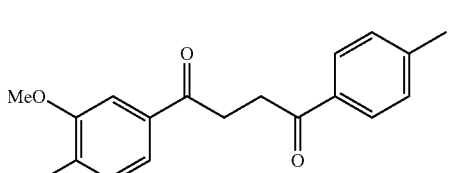

1-(3,4-Dimethoxyphenyl)-4-(p-tolyl)butane-1,4-dione 426

White solid (34 mg, 0.11 mmol). 1H NMR (CDCl$_3$, 400 MHz) δ ppm 2.43 (s, 3H), 3.44 (s, 4H), 3.94 (s, 3H), 3.97 (s, 3H), 6.93 (d, J=8.53 Hz, 1H), 7.29 (d, J=8.03 Hz, 2H), 7.57 (d, J=2.01 Hz, 1H), 7.72 (dd, J=8.41, 2.13 Hz, 1H), 7.95 (d, J=7.71 Hz, 2H); ESIMS found C$_{19}$H$_{20}$O$_4$ m/z 313.0 (M+H).

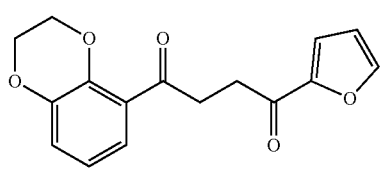

1-(2,3-Dihydrobenzo[b][1,4]dioxin-5-yl)-4-(furan-2-yl)butane-1,4-dione 442

White solid (23 mg, 0.08 mmol). $^1$H NMR (CDCl$_3$, 400 MHz) δ ppm 3.26 (t, J=6.4 Hz, 2H), 3.44 (t, J=6.4 Hz, 2H), 4.27-4.35 (m, 2H), 4.35-4.42 (m, 2H), 6.56 (dd, J=1.6 Hz, J=3.6 Hz, 1H), 6.88 (t, J=8 Hz, 1H), 7.03 (dd, J=1.6 Hz, J=8 Hz, 1H), 7.24-7.29 (m, 1H), 7.35 (dd, J=1.6 Hz, J=7.6 Hz, 1H), 7.61 (s, 1H); ESIMS found C$_{16}$H$_{14}$O$_5$ m/z 286.9 (M+H).

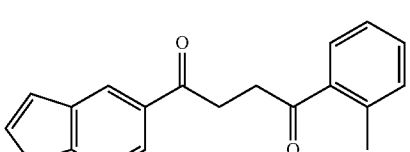

1-(Benzofuran-5-yl)-4-(o-tolyl)butane-1,4-dione 455

White solid (12 mg, 0.04 mmol). $^1$H NMR (CDCl$_3$, 400 MHz) δ ppm 2.52 (s, 3H), 3.35-3.43 (m, 2H), 3.51-3.57 (m, 2H), 6.88 (dd, J=2.26, 0.75 Hz, 1H), 7.24-7.34 (m, 2H), 7.40 (td, J=7.52, 1.24 Hz, 1H), 7.57 (d, J=8.53 Hz, 1H), 7.71 (d, J=2.26 Hz, 1H), 7.84 (dd, J=7.65, 1.13 Hz, 1H), 8.05 (dd, J=8.78, 1.76 Hz, 1H), 8.36 (d, J=1.76 Hz, 1H); ESIMS found C$_{19}$H$_{16}$O$_3$ m/z 293.0 (M+H).

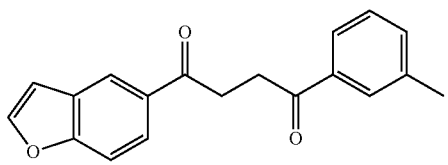

456

1-(Benzofuran-5-yl)-4-(m-tolyl)butane-1,4-dione 456

White solid (19 mg, 0.07 mmol). $^1$H NMR (CDCl$_3$, 400 MHz) δ ppm 2.44 (s, 3H), 3.50 (d, J=5.2 Hz, 2H), 3.53 (d, J=5.2 Hz, 2H), 6.88 (s, 1H), 7.39 (d, J=7.2 Hz, 2H), 7.58 (d, J=8.4 Hz, 1H), 7.71 (d, J=2 Hz, 1H), 7.86 (d, J=6.8 Hz, 2H), 8.06 (d, J=8.4 Hz, 1H), 8.37 (s, 1H); ESIMS found C$_{19}$H$_{16}$O$_3$ m/z 293.1 (M+H).

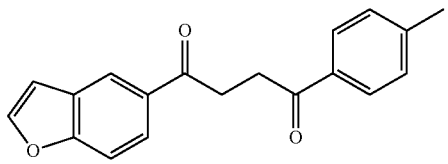

457

1-(Benzofuran-5-yl)-4-(p-tolyl)butane-1,4-dione 457

White solid (73 mg, 0.25 mmol). $^1$H NMR (CDCl$_3$, 400 MHz) δ ppm 2.43 (s, 3H), 3.45-3.51 (m, 2H), 3.51-3.57 (m, 2H), 6.89 (dd, J=2.13, 0.88 Hz, 1H), 7.29 (d, J=8.03 Hz, 2H), 7.57 (d, J=8.53 Hz, 1H), 7.71 (d, J=2.26 Hz, 1H), 7.96 (d, J=7.72 Hz, 2H), 8.06 (dd, J=8.66, 1.88 Hz, 1H), 8.37 (d, J=1.76 Hz, 1H); ESIMS found C$_{19}$H$_{16}$O$_3$ m/z 293.0 (M+H).

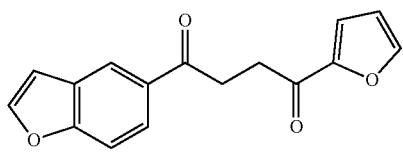

462

1-(Benzofuran-5-yl)-4-(furan-2-yl)butane-1,4-dione 462

White solid (25 mg, 0.09 mmol). $^1$H NMR (CDCl$_3$, 400 MHz) δ ppm 3.35 (t, J=6.4 Hz, 2H), 3.53 (t, J=6.4 Hz, 2H), 6.57 (dd, J=2 Hz, J=3.6 Hz, 1H), 6.88 (d, J=1.6 Hz, 1H), 7.24-7.31 (m, 1H), 7.57 (d, J=8.8 Hz, 1H), 7.62 (s, 1H), 7.71 (d, J=2 Hz, 1H), 8.03 (dd, J=1.2 Hz, J=8.8 Hz, 1H), 8.34 (d, J=1.2 Hz, 1H); ESIMS found C$_{16}$H$_{12}$O$_4$ m/z 269.2 (M+H).

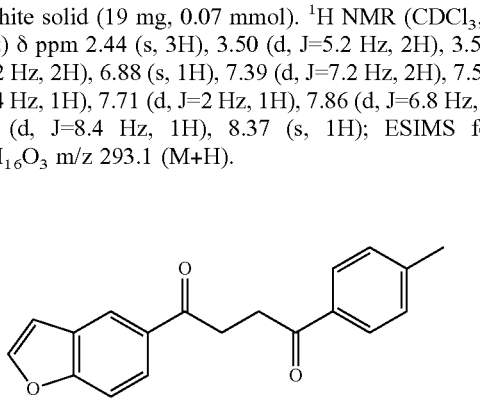

485

1-(Benzo[d]oxazol-5-yl)-4-(o-tolyl)butane-1,4-dione 485

White solid (15 mg, 0.05 mmol). $^1$H NMR (CDCl$_3$, 400 MHz) δ ppm 2.52 (s, 3H), 3.38-3.44 (m, 2H), 3.51-3.57 (m, 2H), 7.2-7.35 (m, 2H), 7.40 (dt, J=1.48 Hz, J=7.52 Hz, 1H), 7.68 (d, J=8.33 Hz, 1H), 7.85 (dd, J=7.53 Hz, J=1.25 Hz, 1H), 8.17 (dd, J=1.76 Hz, J=8.63 Hz, 1H), 8.20 (s, 1H), 8.52 (d, J=1.51 Hz, 1H); ESIMS found C$_{18}$H$_{15}$NO$_3$ m/z 294.2 (M+H).

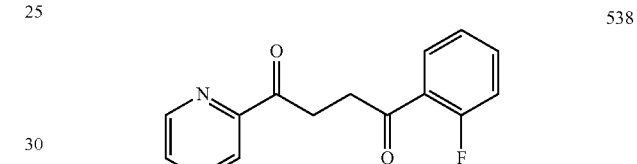

538

1-(2-Fluorophenyl)-4-(pyridin-2-yl)butane-1,4-dione 538

White solid (30 mg, 0.12 mmol). $^1$H NMR (CDCl$_3$, 400 MHz) δ ppm 3.50 (t, J=6 Hz, 2H), 3.70 (t, J=6 Hz, 2H), 7.18 (t, J=8.8 Hz, 1H), 7.27 (t, J=7.2 Hz, 1H), 7.45-7.62 (m, 2H), 7.86 (dt, J=1.6 Hz, J=7.6 Hz, 1H), 7.93 (dt, J=2 Hz, 1H), 8.07 (d, J=8 Hz, 1H), 8.74 (d, J=4 Hz, 1H); ESIMS found C$_{15}$H$_{12}$FNO$_2$ m/z 258.0 (M+H).

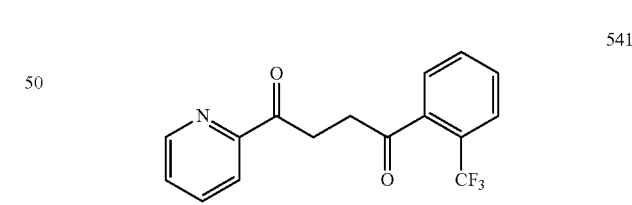

541

1-(Pyridin-2-yl)-4-(2-(trifluoromethyl)phenyl)butane-1,4-dione 541

Oil (41 mg, 0.13 mmol). $^1$H NMR (CDCl$_3$, 400 MHz) δ ppm 3.31 (t, J=6.4 Hz, 2H), 3.73 (t, J=6.4 Hz, 2H), 7.50 (t, J=4.8 Hz, 1H), 7.58 (t, J=7.6 Hz, 1H), 7.66 (t, J=7.6 Hz, 1H), 7.70-7.77 (m, 2H), 7.85 (dt, J=1.2 Hz, J=7.6 Hz, 1H), 8.05 (d, J=8 Hz, 1H), 8.72 (d, J=4.4 Hz, 1H); ESIMS found C$_{16}$H$_{12}$F$_3$NO$_2$ m/z 307.9 (M+H).

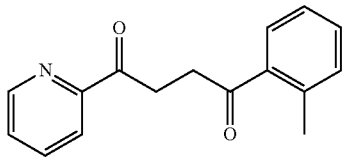

1-(Pyridin-2-yl)-4-(o-tolyl)butane-1,4-dione 544

Oil (39 mg, 0.15 mmol). $^1$H NMR (CDCl$_3$, 400 MHz) δ ppm 2.51 (s, 3H), 3.37 (t, J=6.4 Hz, 2H), 3.69 (t, J=6.4 Hz, 2H), 7.21-7.34 (m, 2H), 7.38 (dt, J=1 Hz, J=7.2 Hz, 1H), 7.49 (dd, 1H), 7.76-7.90 (m, 2H), 8.05 (d, J=7.6 Hz, 1H), 8.72 (d, J=4.4 Hz, 1H); ESIMS found C$_{16}$H$_{15}$NO$_2$ m/z 254.0 (M+H).

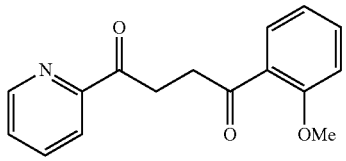

1-(2-Methoxyphenyl)-4-(pyridin-2-yl)butane-1,4-dione 547

White solid (40 mg, 0.15 mmol). $^1$H NMR (CDCl$_3$, 400 MHz) δ ppm 3.47 (t, J=6.8 Hz, 2H), 3.64 (t, J=6.8 Hz, 2H), 3.93 (s, 3H), 6.94-7.07 (m, 2H), 7.41-7.53 (m, 2H), 7.77 (dd, 1H), 7.84 (dt, J=1.2 Hz, J=8 Hz, 1H), 8.05 (d, J=8 Hz, 1H), 8.71 (d, J=4.4 Hz, 1H); ESIMS found C$_{16}$H$_{15}$NO$_3$ m/z 270.1 (M+H).

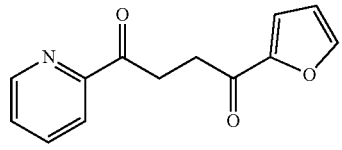

1-(Furan-2-yl)-4-(pyridin-2-yl)butane-1,4-dione 554

White solid (11 mg, 0.05 mmol). $^1$H NMR (CDCl$_3$, 400 MHz) δ ppm 3.32 (t, J=6.8 Hz, 2H), 3.69 (t, J=6.8 Hz, 2H), 6.56 (dd, J=1.6 Hz, J=3.2 Hz, 1H), 7.23-7.30 (m, 1H), 7.50 (t, J=6.4 Hz, 1H), 7.61 (s, 1H), 7.85 (dt, J=1.6 Hz, J=7.6 Hz, 1H), 8.05 (d, J=8.4 Hz, 1H), 8.71 (d, J=4.4 Hz, 1H); ESIMS found C$_{13}$H$_{11}$NO$_3$ m/z 230.1 (M+H).

1-(2-Fluorophenyl)-4-(thiophen-2-yl)butane-1,4-dione 557

White solid (15 mg, 0.06 mmol). $^1$H NMR (CDCl$_3$, 400 MHz) δ ppm 3.35-3.42 (m, 2H), 3.42-3.50 (m, 2H), 7.12-7.20 (m, 2H), 7.24 (td, J=7.80 Hz, J=1.00 Hz, 1H), 7.49-7.57 (m, 1H), 7.65 (dd, J=4.89 Hz, J=1.13 Hz, 1H), 7.83 (dd, J=3.89 Hz, J=1.13 Hz, 1H), 7.90 (td, J=7.59 Hz, J=1.88 Hz, 1H); ESIMS found C$_{14}$H$_{11}$FO$_2$S m/z 262.9 (M+H).

1-(Thiophen-2-yl)-4-(2-(trifluoromethyl)phenyl)butane-1,4-dione 559

White solid (69 mg, 0.22 mmol). $^1$H NMR (DMSO-d$_6$, 400 MHz) δ ppm 3.25-3.31 (m, 2H), 3.35-3.40 (m, 2H), 7.27 (dd, J=4.89, 3.89 Hz, 1H), 7.73 (t, J=7.80 Hz, 1H), 7.80-7.88 (m, 2H), 7.92 (d, J=7.56 Hz, 1H), 8.03 (dd, J=5.04, 1.00 Hz, 1H), 8.06 (dd, J=3.76, 1.00 Hz, 1H); ESIMS found C$_{15}$H$_{11}$F$_3$O$_2$S m/z 312.9 (M+H).

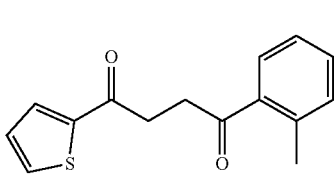

1-(Thiophen-2-yl)-4-(o-tolyl)butane-1,4-dione 560

White solid (38 mg, 0.15 mmol). $^1$H NMR (CDCl$_3$, 400 MHz) δ ppm 2.53 (s, 3H), 3.34-3.47 (m, 4H), 7.18 (t, J=4.4 Hz, 1H), 7.24-7.35 (m, 2H), 7.41 (t, J=7.6 Hz, 1H), 7.67 (d, J=4.8 Hz, 1H), 7.82 (d, J=7.6 Hz, 1H), 7.85 (d, J=2.8 Hz, 1H); ESIMS found C$_{15}$H$_{14}$O$_2$S m/z 259.0 (M+H).

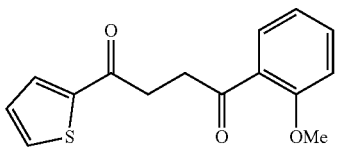

1-(2-Methoxyphenyl)-4-(thiophen-2-yl)butane-1,4-dione 562

White solid (60 mg, 0.22 mmol). $^1$H NMR (CDCl$_3$, 400 MHz) δ ppm 3.36 (t, J=6.8 Hz, 2H), 3.47 (t, J=6.8 Hz, 2H), 3.94 (s, 3H), 6.95-7.07 (m, 2H), 7.16 (dt, J=5.2 Hz, 1H), 7.48 (dt, 1H), 7.64 (d, J=4 Hz, 1H), 7.78 (dd, J=5.6, J=7.6 Hz, 1H), 7.83 (dd, 1H); ESIMS found C$_{15}$H$_{14}$O$_3$S m/z 275.0 (M+H).

Example 2

Preparation of 1-(1H-indol-5-yl)-4-phenylbutane-1,4-dione (261) is depicted below in Scheme 16

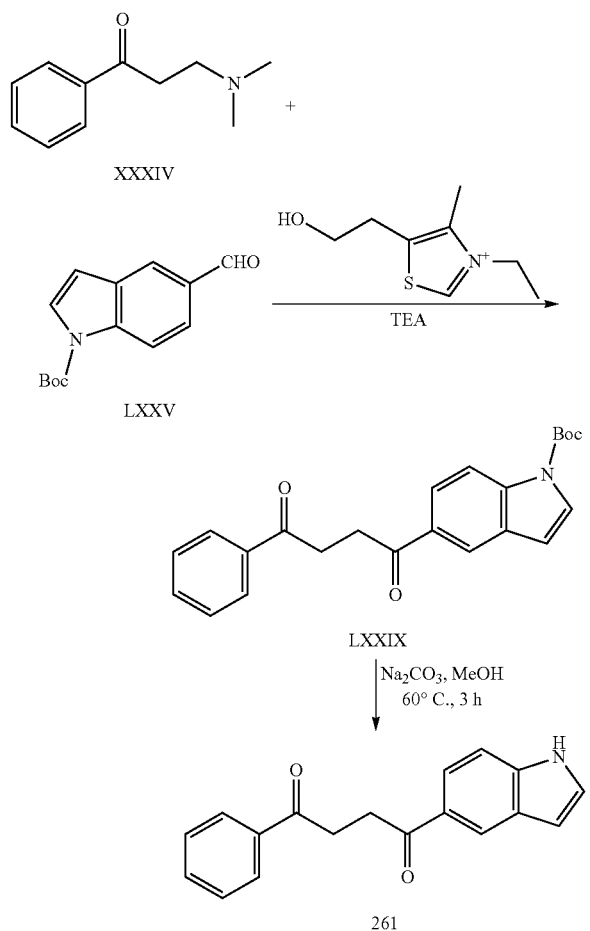

Scheme 16

Step 1-2

To a well stirred solution of 3-(dimethylamino)-1-phenylpropan-1-one (XXXIV) (120 mg, 0.678 mmol, 1.0 eq) in 1,4-dioxane (3 mL) was added tert-butyl 5-formyl-1H-indole-1-carboxylate (LXXV) (166 mg, 0.678 mmol, 1.0 eq), 3-ethyl-5-(2-hydroxyeth-yl)-4-methylthiazolium brominde (51 mg, 0.203 mmol, 0.3 eq) and TEA (0.5 mL). The reaction mixture was refluxed for 16 h. TLC analysis (PE:EtOAc, 3:1) showed the reaction was complete. The solution was cooled to room temperature and diluted with water (20 mL). The product was extracted with EtOAc (3×30 mL). The combined organic layers was dried over anhydrous Na$_2$SO$_4$, filtered and concentrated under reduced pressure to give crude tert-butyl 5-(4-oxo-4-phenylbutanoyl)-1H-indole-1-carboxylate (LXXIX) (52 mg) as a white solid. The crude product was dissolved in methanol (2 mL). Anhydrous sodium carbonate (144 mg, 1.36 mmol, 2.0 eq) was added. Then the mixture was stirred at 60° C. for 3 h. The solid was filtered off and the residue was concentrated in vacuum to give 1-(1H-indol-5-yl)-4-phenylbutane-1,4-dione (261) as a white solid. (42 mg, 0.15 mmol, 22.3%) $^1$H NMR (DMSO-d$_6$, 400 MHz) δ ppm 3.41 (t, J=6.4 Hz, 2H), 3.47 (t, J=6.4 Hz, 2H), 6.62 (s, 1H), 7.41-7.52 (m, 2H), 7.56 (t, J=7.6 Hz, 2H), 7.66 (t, 1H), 7.77 (d, J=8.4 Hz, 1H), 8.03 (d, J=7.2 Hz, 2H), 8.37 (s, 1H), 11.46 (s, 1H); ESIMS found C$_{18}$H$_{15}$NO$_2$ m/z 278.0 (M+H).

The following compounds were prepared in accordance with the procedure described in the above Example 2.

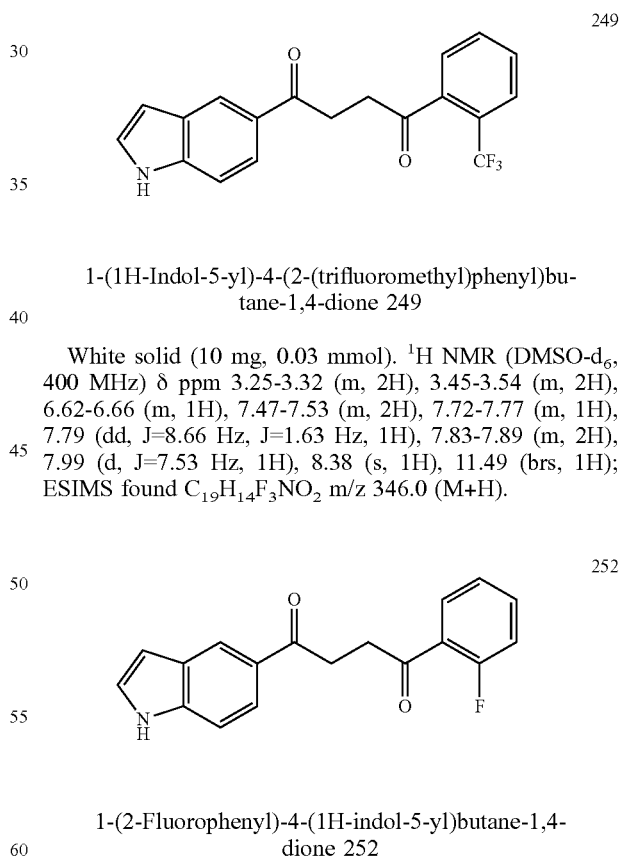

1-(1H-Indol-5-yl)-4-(2-(trifluoromethyl)phenyl)butane-1,4-dione 249

White solid (10 mg, 0.03 mmol). $^1$H NMR (DMSO-d$_6$, 400 MHz) δ ppm 3.25-3.32 (m, 2H), 3.45-3.54 (m, 2H), 6.62-6.66 (m, 1H), 7.47-7.53 (m, 2H), 7.72-7.77 (m, 1H), 7.79 (dd, J=8.66 Hz, J=1.63 Hz, 1H), 7.83-7.89 (m, 2H), 7.99 (d, J=7.53 Hz, 1H), 8.38 (s, 1H), 11.49 (brs, 1H); ESIMS found C$_{19}$H$_{14}$F$_3$NO$_2$ m/z 346.0 (M+H).

1-(2-Fluorophenyl)-4-(1H-indol-5-yl)butane-1,4-dione 252

White solid (10 mg, 0.03 mmol). $^1$H NMR (CDCl$_3$, 400 MHz) δ ppm 3.41-3.51 (m, 2H), 3.51-3.60 (m, 2H), 6.66 (s, 1H), 7.10-7.19 (m, 1H), 7.19-7.30 (m, 2H), 7.41 (d, J=8.8 Hz, 1H), 7.47-7.58 (m, 1H), 7.83-7.96 (m, 2H), 8.40 (s, 1H), 8.59 (brs, 1H); ESIMS found C$_{18}$H$_{14}$FNO$_2$ m/z 296.0 (M+H).

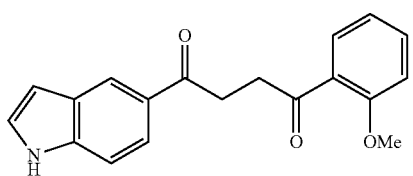

1-(1H-Indol-5-yl)-4-(2-methoxyphenyl)butane-1,4-dione 255

White solid (36 mg, 0.12 mmol). $^1$H NMR (CDCl$_3$, 400 MHz) δ ppm 3.44-3.57 (m, 4H), 3.94 (s, 3H), 6.69 (ddd, J=3.14, 2.01, 0.88 Hz, 1H), 6.97-7.01 (m, 1H), 7.01-7.06 (m, 1H), 7.29 (dd, J=3.26, 2.51 Hz, 1H), 7.43 (d, J=8.30 Hz, 1H), 7.45-7.51 (m, 1H), 7.79 (dd, J=7.78, 1.76 Hz, 1H), 7.94 (dd, J=8.66, 1.63 Hz, 1H), 8.38-8.46 (m, 2H); ESIMS found C$_{19}$H$_{17}$NO$_3$ m/z 308.2 (M+H).

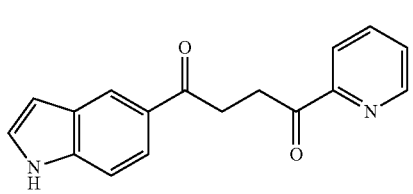

1-(1H-Indol-5-yl)-4-(pyridin-2-yl)butane-1,4-dione 258

White solid (10 mg, 0.04 mmol). $^1$H NMR (CDCl$_3$, 400 MHz) δ ppm 3.56-3.65 (m, 2H), 3.69-3.78 (m, 2H), 6.70 (ddd, J=3.20 Hz, J=2.07 Hz, J=1.00 Hz, 1H), 7.31 (dd, J=3.14 Hz, J=2.38 Hz, 1H), 7.45 (d, J=8.53 Hz, 1H), 7.51 (ddd, J=7.53 Hz, J=4.77 Hz, J=1.25 Hz, 1H), 7.87 (td, J=7.78 Hz, J=1.76 Hz, 1H), 7.95 (dd, J=8.66 Hz, J=1.63 Hz, 1H), 8.09 (dt, J=7.84 Hz, J=1.10 Hz, 1H), 8.42-8.45 (m, 1H), 8.42-8.50 (brs, 1H), 8.71-8.78 (m, 1H); ESIMS found C$_{17}$H$_{14}$N$_2$O$_2$ m/z 279.1 (M+H).

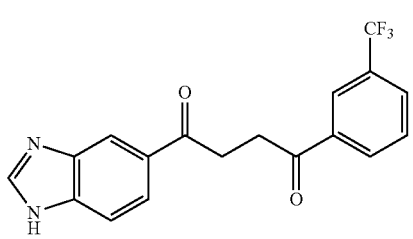

1-(1H-Benzo[d]imidazol-5-yl)-4-(3-(trifluoromethyl)phenyl)butane-1,4-dione 263

White solid (27 mg, 0.08 mmol). $^1$H NMR (DMSO-d$_6$, 400 MHz) δ ppm 3.46-3.62 (m, 4H), 7.78 (d, J=8.53 Hz, 1H), 7.83 (t, J=7.78 Hz, 1H), 7.99 (dd, J=8.53 Hz, J=1.51 Hz, 1H), 8.05 (d, J=7.78 Hz, 1H), 8.27 (s, 1H), 8.35 (d, J=7.78 Hz, 1H), 8.38 (d, J=1.00 Hz, 1H), 8.79 (s, 1H); ESIMS found C$_{18}$H$_{13}$F$_3$N$_2$O$_2$ m/z 346.9 (M+H).

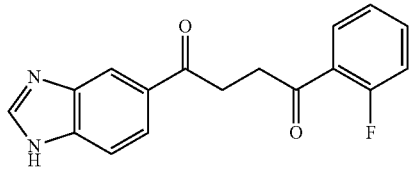

1-(1H-Benzo[d]imidazol-5-yl)-4-(2-fluorophenyl)butane-1,4-dione 265

White solid (15 mg, 0.05 mmol). $^1$H NMR (DMSO-d$_6$, 400 MHz) δ ppm 3.33-3.43 (m, 2H), 3.47-3.52 (m, 2H), 7.30-7.39 (m, 2H), 7.62-7.73 (m, 2H), 7.85 (td, J=7.72 Hz, J=1.88 Hz, 1H), 7.89 (dd, J=8.53 Hz, J=1.51 Hz, 1H), 8.30 (brd, J=1.51 Hz, 1H), 8.33 (s, 1H), 12.50 (brs, H); ESIMS found C$_{17}$H$_{13}$FN$_2$O$_2$ m/z 297.1 M+H).

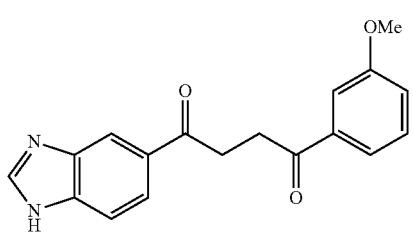

1-(1H-Benzo[d]imidazol-5-yl)-4-(3-methoxyphenyl)butane-1,4-dione 269

White solid (15 mg, 0.05 mmol). $^1$H NMR (CDCl$_3$, 400 MHz) δ ppm 3.47 (s, 4H), 3.84 (s, 3H), 7.12 (dd, J=2.4 Hz, J=8.4 Hz, 1H), 7.38 (t, J=8 Hz, 1H), 7.49 (s, 1H), 7.60 (d, J=7.6 Hz, 1H), 7.81 (d, J=8.4 Hz, 1H), 8.14 (d, J=8.8 Hz, 1H), 8.45 (s, 1H), 9.28 (brs, 1H); ESIMS found C$_{18}$H$_{16}$N$_2$O$_3$ m/z 309.0 (M+H).

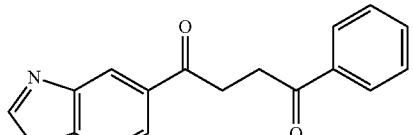

1-(1H-Benzo[d]imidazol-5-yl)-4-phenylbutane-1,4-dione 274

White solid (20 mg, 0.07 mmol). $^1$H NMR (DMSO-d$_6$, 400 MHz) δ ppm 3.40-3.46 (m, 2H), 3.47-3.55 (m, 2H), 7.53-7.60 (m, 2H), 7.62-7.71 (m, 2H), 7.90 (d, J=8.78 Hz, 1H), 8.01-8.09 (m, 2H), 8.35-8.49 (m, 2H), 12.80 (brs, 1H); ESIMS found C$_{17}$H$_{14}$N$_2$O$^2$ m/z 279.1 (M+H).

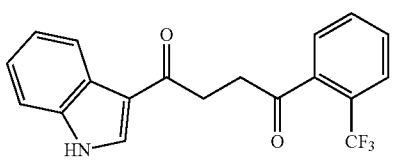

1-(1H-Indol-3-yl)-4-(2-(trifluoromethyl)phenyl)butane-1,4-dione 314

White solid (27 mg, 0.08 mmol). $^1$H NMR (DMSO-d$_6$, 400 MHz) δ ppm 3.23-3.29 (m, 2H), 3.30-3.36 (m, 2H), 7.13-7.25 (m, 2H), 7.48 (dd, J=7.42, 0.76 Hz, 1H), 7.73 (t, J=7.52 Hz, 1H), 7.84 (t, J=7.02 Hz, 2H), 7.98 (dd, J=7.53, 1.24 Hz, 1H), 8.17 (d, J=7.26 Hz, 1H), 8.43 (s, 1H), 11.97 (br. s., 1H); ESIMS found C$_{19}$H$_{14}$F$_3$NO$_2$ m/z 346.0 (M+H).

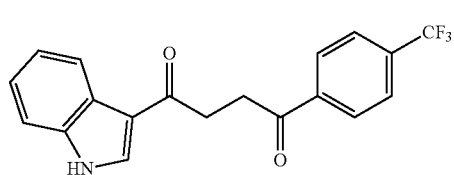

1-(1H-Indol-3-yl)-4-(4-(trifluoromethyl)phenyl)butane-1,4-dione 316

White solid (11 mg, 0.03 mmol). $^1$H NMR (DMSO-d$_6$, 400 MHz) δ ppm 3.18 (t, J=6.4 Hz, 2H), 3.44 (t, J=6.4 Hz, 2H), 7.11-7.27 (m, 2H), 7.49 (d, J=8 Hz, 1H), 7.94 (d, J=8 Hz, 2H), 8.14 (d, J=7.6 Hz, 1H), 8.23 (d, J=8 Hz, 2H), 8.43 (s, 1H), 11.97 (brs, 1H); ESIMS found C$_{19}$H$_{14}$F$_3$NO$_2$ m/z 345.9 (M+H).

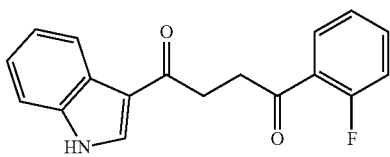

1-(2-Fluorophenyl)-4-(1H-indol-3-yl)butane-1,4-dione 317

White solid (10 mg, 0.03 mmol). $^1$H NMR (CDCl$_3$, 400 MHz) δ ppm 3.33-3.42 (m, 2H), 3.46-3.56 (m, 2H), 7.17 (dd, J=11.17 Hz, J=8.41 Hz, 1H), 7.214 (dt, J=0.76 Hz, J=7.52 Hz, 1H), 7.26 (s, 1H), 7.26-7.34 (m, 3H), 7.38-7.46 (m, 1H), 7.48-7.59 (m, H), 7.92 (td, J=7.53 Hz, J=1.76H, 1H), 7.98 (d, J=3.0 Hz, 1H), 8.34-8.42 (m, 1H), 8.74 (brs, 1H); ESIMS found C$_{18}$H$_{14}$FNO$_2$ m/z 296.0 (M+H).

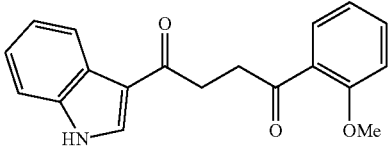

1-(1H-Indol-3-yl)-4-(2-methoxyphenyl)butane-1,4-dione 319

White solid (60 mg, 0.20 mmol). $^1$H NMR (CDCl$_3$, 400 MHz) δ ppm 3.33 (t, J=6.78 Hz, 2H), 3.52 (t, J=6.50 Hz, 2H), 3.93 (s, 3H), 6.94-7.06 (m, 2H), 7.25-7.32 (m, 1H), 7.38-7.45 (m, 1H), 7.48 (ddd, J=8.34, 7.34, 1.88 Hz, 1H), 7.79 (dd, J=7.65, 1.88 Hz, 1H), 7.96 (d, J=3.01 Hz, 1H), 8.36-8.44 (m, 1H), 8.84 (brs, 1H); ESIMS found C$_{19}$H$_{17}$NO$_3$ m/z 308.0 (M+H).

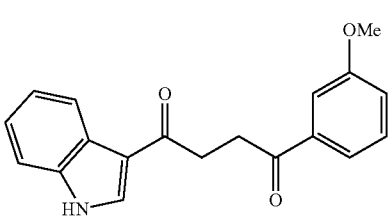

1-(1H-Indol-3-yl)-4-(3-methoxyphenyl)butane-1,4-dione 320

White solid (30 mg, 0.10 mmol). $^1$H NMR (CDCl$_3$, 400 MHz) δ ppm 3.38 (t, J=6.8 Hz, 2H), 3.51 (t, J=6.8 Hz, 2H), 3.87 (s, 3H), 7.13 (dd, J=2.4 Hz, J=8 Hz, 1H), 7.24-7.35 (m, 2H), 7.36-7.47 (m, 2H), 7.56 (s, 1H), 7.67 (d, J=8 Hz, 1H), 7.99 (s, 1H), 8.39 (dd, J=3.6 Hz, J=5.2 Hz, 1H), 8.74 (brs, 1H); ESIMS found C$_{19}$H$_{17}$NO$_3$ m/z 308.0 (M+H).

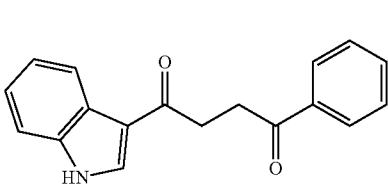

1-(1H-Indol-3-yl)-4-phenylbutane-1,4-dione 325

White solid (16 mg, 0.06 mmol). $^1$H NMR (DMSO-d$_6$, 400 MHz) δ ppm 3.23-3.50 (m, 4H), 7.08-7.26 (m, 2H), 7.47 (d, J=8 Hz, 1H), 7.55 (t, J=7.6 Hz, 2H), 7.66 (t, J=7.6 Hz, 1H), 8.03 (d, J=7.2 Hz, 2H), 8.14 (d, J=7.6 Hz, 1H), 8.42 (s, 1H), 11.94 (brs, 1H); ESIMS found C$_{18}$H$_{15}$NO$_2$ m/z 278.0 (M+H).

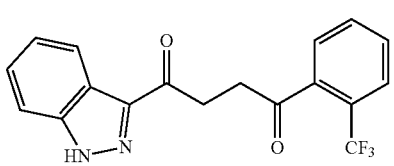

1-(1H-Indazol-3-yl)-4-(2-(trifluoromethyl)phenyl)butane-1,4-dione 326

White solid (20 mg, 0.06 mmol). $^1$H NMR (CDCl$_3$, 400 MHz) δ ppm 3.36 (t, J=6.27 Hz, 2H) 3.71 (dd, J=6.90, 5.65 Hz, 2H) 7.33 (ddd, J=8.09, 6.96, 0.75 Hz, 1H) 7.45 (ddd, J=8.52 Hz, J=7.78 Hz, J=1.00 Hz, 1H) 7.53-7.62 (m, 2H) 7.67 (t, J=7.64 Hz, 1H) 7.76 (dd, J=17.82, 7.53 Hz, 2H) 8.35 (td, J=1.00 Hz, J=8.14 Hz, 1H), 10.57 (brs, 1H); ESIMS found C$_{18}$H$_{13}$F$_3$N$_2$O$_2$ m/z 346.9 (M+H).

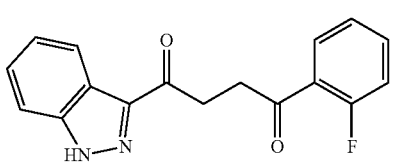

1-(2-Fluorophenyl)-4-(1H-indazol-3-yl)butane-1,4-dione 329

White solid (11 mg, 0.04 mmol). $^1$H NMR (CDCl$_3$, 400 MHz) δ ppm 3.38-3.45 (m, 2H), 3.47-3.63 (m, 2H), 7.28-7.50 (m, 4H), 7.65-7.73 (m, 2H), 7.86 (td, J=7.65, 1.76 Hz, 1H), 8.15 (d, J=8.28 Hz, 1H); ESIMS found C$_{17}$H$_{13}$FN$_2$O$_2$ m/z 297.0 (M+H).

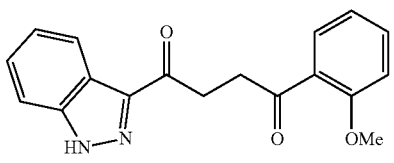

1-(1H-Indazol-3-yl)-4-(2-methoxyphenyl)butane-1,4-dione 332

Yellow solid (30 mg, 0.10 mmol). $^1$H NMR (CDCl$_3$, 400 MHz) δ ppm 3.51-3.59 (m, 2H), 3.60-3.70 (m, 2H), 3.94 (s, 3H), 6.95-7.07 (m, 2H), 7.30 (ddd, J=8.09, 7.09, 0.88 Hz, 1H), 7.39-7.45 (m, 1H), 7.45-7.51 (m, 1H), 7.53 (d, J=8.53 Hz, 1H), 7.82 (dd, J=7.65, 1.88 Hz, 1H), 8.34 (d, J=8.05 Hz, 1H); ESIMS found C$_{18}$H$_{16}$N$_2$O$_3$ m/z 309.0 (M+H).

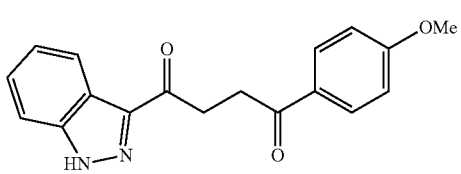

1-(1H-Indazol-3-yl)-4-(4-methoxyphenyl)butane-1,4-dione 334

White solid (50 mg, 0.16 mmol). $^1$H NMR (CDCl$_3$, 400 MHz) δ ppm 3.50 (t, J=6.4 Hz, 2H), 3.69 (t, J=6.4 Hz, 2H), 3.89 (s, 3H), 6.97 (d, J=8.8 Hz, 2H), 7.30 (t, J=7.6 Hz, 1H), 7.43 (t, J=7.6 Hz, 1H), 7.53 (d, J=8.4 Hz, 1H), 8.06 (d, J=8.8 Hz, 2H), 8.32 (d, J=8 Hz, 1H); ESIMS found C$_{18}$H$_{16}$N$_2$O$_3$ m/z 309.2 (M+H).

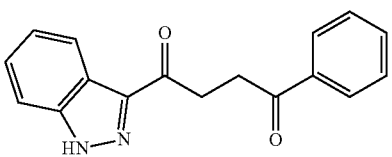

1-(1H-Indazol-3-yl)-4-phenylbutane-1,4-dione 338

White solid (25 mg, 0.09 mmol). $^1$H NMR (DMSO-d$_6$, 400 MHz) δ ppm 3.44-3.50 (m, 2H), 3.50-3.58 (m, 2H), 7.31 (ddd, J=8.04 Hz, J=7.50 Hz, J=1.00 Hz, 1H), 7.46 (ddd, J=8.28 Hz, J=7.64 Hz, J=1.28 Hz, 1H), 7.53-7.60 (m, 2H), 7.67 (tt, J=7.28 Hz, J=1.24 Hz, 1H), 7.69 (td, J=8.28 Hz, J=1.00 Hz, 1H), 8.01-807 (m, 2H), 8.15 (td, J=9.00, 1.00 Hz, 1H), 13.87 (s, 1H); ESIMS found C$_{17}$H$_{14}$N$_2$O$_2$ m/z 279.1 (M+H).

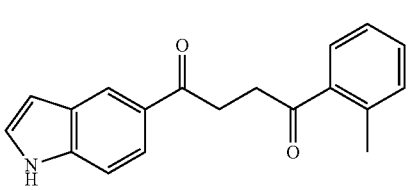

1-(1H-indol-5-yl)-4-(o-tolyl)butane-1,4-dione 445

White solid (14 mg, 0.05 mmol). $^1$H NMR (CDCl$_3$, 400 MHz) δ ppm 2.53 (s, 3H), 3.32-3.45 (m, 2H), 3.52-3.61 (m, 2H), 6.68 (ddd, J=3.07, 2.07, 0.88 Hz, 1H), 7.24-7.34 (m, 3H), 7.38 (dd, J=7.40, 1.38 Hz, 1H), 7.42 (d, J=8.53 Hz, 1H), 7.85 (dd, J=7.45, 0.60 Hz, 1H), 7.92 (dd, J=8.69, 1.52 Hz, 1H), 8.42 (s, 1H), 8.53 (brs, 1H); ESIMS found C$_{19}$H$_{17}$NO$_2$ m/z 292.2 (M+H).

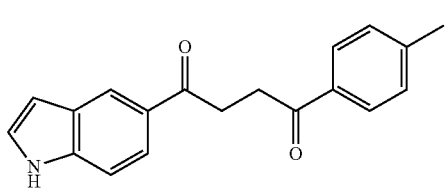

1-(1H-Indol-5-yl)-4-(p-tolyl)butane-1,4-dione 447

White solid (11 mg, 0.04 mmol). $^1$H NMR (CDCl$_3$, 400 MHz) δ ppm 2.43 (s, 3H), 3.48 (t, J=6 Hz, 2H), 3.56 (t, J=6 Hz, 2H), 6.69 (s, 1H), 7.27 (s, 1H), 7.29 (d, J=8.4 Hz, 2H), 7.44 (d, J=8.4 Hz, 1H), 7.96 (dt, J=1.6 Hz, J=8.4 Hz, 1H), 7.97 (d, J=8.4 Hz, 2H), 8.44 (s, 1H); ESIMS found C$_{19}$H$_{17}$NO$_2$ m/z 292.0 (M+H).

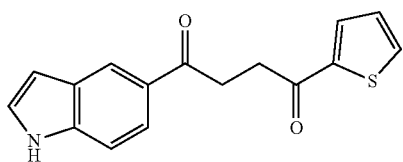

1-(1H-Indol-5-yl)-4-(thiophen-2-yl)butane-1,4-dione 451

Yellow solid (17 mg, 0.06 mmol). $^1$H NMR (DMSO-d$_6$, 400 MHz) δ ppm 3.29-3.40 (m, 2H), 3.40-3.54 (m, 2H), 6.62 (d, J=2.76 Hz, 1H), 7.28 (dd, J=4.89, 3.89 Hz, 1H), 7.45-7.50 (m, 2H), 7.75 (dd, J=8.53, 1.51 Hz, 1H), 8.01 (d, J=5.27 Hz, 1H), 8.06 (d, J=4.47 Hz, 1H), 8.35 (s, 1H), 11.49 (brs, 1H); ESIMS found C$_{16}$H$_{13}$NO$_2$S m/z 284.0 (M+H).

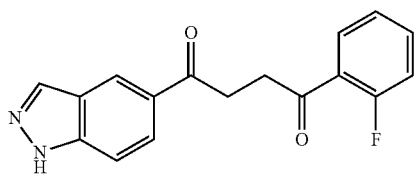

1-(2-Fluorophenyl)-4-(1H-indazol-5-yl)butane-1,4-dione 495

Yellow solid (7 mg, 0.02 mmol). $^1$H NMR (CD$_3$OD, 400 MHz) δ ppm 3.41-3.49 (m, 2H), 3.52-3.60 (m, 2H), 7.22-7.35 (m, 2H), 7.61 (d, J=8.78 Hz, 2H), 7.89 (td, J=7.65, 1.76 Hz, 1H), 8.07 (dd, J=8.78, 1.51 Hz, 1H), 8.24 (s, 1H), 8.65 (s, 1H); ESIMS found C$_{17}$H$_{13}$FN$_2$O$_2$ m/z 297.0 (M+H).

1-(4-Fluorophenyl)-4-(1H-indazol-5-yl)butane-1,4-dione 497

White solid (10 mg, 0.03 mmol). $^1$H NMR (CDCl$_3$, 400 MHz) δ ppm 3.44-3.51 (m, 2H), 3.52-3.59 (m, 2H), 7.12-7.22 (m, 2H), 7.56 (d, J=9.03 Hz, 1H), 8.04-8.15 (m, 3H), 8.23 (d, J=1.00 Hz, 1H), 8.53-8.59 (m, 1H), 10.28 (brs, 1H); ESIMS found C$_{17}$H$_{13}$FN$_2$O$_2$ m/z 297.0 (M+H).

1-(1H-Indazol-5-yl)-4-(2-(trifluoromethyl)phenyl)butane-1,4-dione 498

White solid (21 mg, 0.06 mmol). $^1$H NMR (DMSO-d$_6$, 400 MHz) δ ppm 3.26-3.37 (m, 2H), 3.45-3.57 (m, 2H), 7.63 (d, J=9.03 Hz, 1H), 7.74 (t, J=7.39 Hz, 1H), 7.85 (t, J=7.76 Hz, 2H), 7.98 (d, J=8.53 Hz, 2H), 8.29 (s, 1H), 8.64 (s, 1H), 13.42 (brs, 1H); ESIMS found C$_{18}$H$_{13}$F$_3$N$_2$O$_2$ m/z 347.0 (M+H).

1-(1H-Indazol-5-yl)-4-(p-tolyl)butane-1,4-dione 503

White solid (15 mg, 0.05 mmol). $^1$H NMR (DMSO-d$_6$, 400 MHz) δ ppm 2.40 (s, 3H), 3.40 (t, J=4 Hz, 2H), 3.46 (t, J=3.6 Hz, 2H), 7.36 (d, J=8 Hz, 2H), 7.63 (d, J=8.8 Hz, 1H), 7.93 (d, J=8 Hz, 2H), 7.95 (d, J=8.8 Hz, 1H), 8.29 (s, 1H), 8.62 (s, 1H); ESIMS found C$_{18}$H$_{16}$N$_2$O$_2$ m/z 293.0 (M+H).

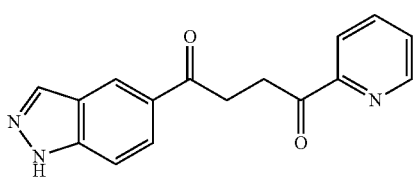

1-(1H-Indazol-5-yl)-4-(pyridin-2-yl)butane-1,4-dione 507

White solid (20 mg, 0.07 mmol). $^1$H NMR (DMSO-d$_6$, 400 MHz) δ ppm 3.49-3.54 (m, 2H), 3.54-3.59 (m, 2H), 7.62 (d, J=8.78 Hz, 1H), 7.69 (ddd, J=7.40 Hz, J=4.77 Hz, J=1.38 Hz, 1H), 7.93-7.99 (m, 2H), 8.03 (dt, J=1.76 Hz, J=7.52 Hz, 1H), 8.29 (s, 1H), 8.62 (s, 1H), 8.78 (td, J=1.00 Hz, J=4.85 Hz, 1H), 13.40 (brs, 1H); ESIMS found C$_{16}$H$_{13}$N$_3$O$_2$ m/z 280.1 (M+H).

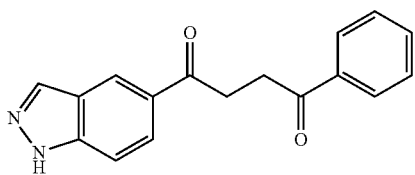

1-(1H-Indazol-5-yl)-4-phenylbutane-1,4-dione 513

White solid (18 mg, 0.06 mmol). $^1$H NMR (DMSO-d$_6$, 400 MHz) δ ppm 3.40-3.46 (m, 2H), 3.46-3.53 (m, 2H), 7.56 (t, J=7.28, 2H), 7.60-7.70 (m, 2H), 7.96 (dd, J=8.78 Hz, J=1.51 Hz, 1H), 8.01-8.07 (m, 2H), 8.29 (s, 1H), 8.62 (s, 1H), 13.39 (brs, 1H); ESIMS found C$_{17}$H$_{14}$N$_2$O$_2$ m/z 279.0 (M+H).

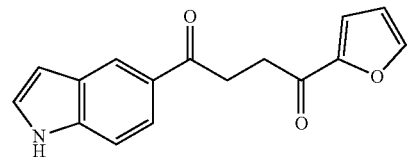

1-(Furan-2-yl)-4-(1H-indazol-5-yl)butane-1,4-dione 515

White solid (12 mg, 0.05 mmol). $^1$H NMR (DMSO-d$_6$, 400 MHz) δ ppm 3.23 (dd, J=6.78 Hz, J=5.27 Hz, 2H), 3.47 (dd, J=6.90 Hz, J=5.14 Hz, 2H), 6.74 (dd, J=3.51 Hz, J=1.76 Hz, 1H), 7.51 (dd, J=3.51 Hz, J=0.75 Hz, 1H), 7.62 (d, J=8.78 Hz, 1H), 7.95 (dd, J=1.76 Hz, J=8.74 Hz, 1H), 8.01 (dd, J=0.76 Hz, J=1.52 Hz, 1H), 8.28 (s, 1H), 8.60 (s, 1H), 13.40 (brs, 1H); ESIMS found C$_{15}$H$_{12}$N$_2$O$_3$ m/z 269.1 (M+H).

1-(1H-Indol-3-yl)-4-(o-tolyl)butane-1,4-dione 518

Yellow solid (14 mg, 0.05 mmol). $^1$H NMR (DMSO-d$_6$, 400 MHz) δ ppm 2.39 (s, 3H), 3.22-3.33 (m, 4H), 7.14-7.25 (m, 2H), 7.26-7.39 (m, 2H), 7.40-7.55 (m, 2H), 7.87 (d, J=7.53 Hz, 1H), 8.15 (d, J=7.03 Hz, 1H), 8.41 (s, 1H), 11.97 (brs, 1H); ESIMS found C$_{19}$H$_{17}$NO$_2$ m/z 292.2 (M+H).

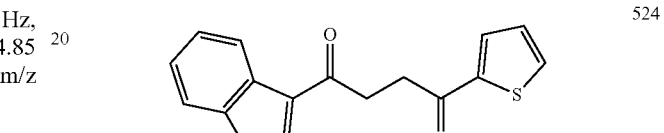

1-(1H-Indol-3-yl)-4-(thiophen-2-yl)butane-1,4-dione 524

White solid (28 mg, 0.10 mmol). $^1$H NMR (DMSO-d$_6$, 400 MHz) δ ppm 3.26-3.37 (m, 4H), 7.13-7.23 (m, 2H), 7.27 (dd, J=4.77 Hz, J=3.76 Hz, 1H), 7.47 (d, J=7.43 Hz, 1H), 8.00 (d, J=5.02 Hz, 1H), 8.04 (dd, J=3.76 Hz, J=1.00 Hz, 1H), 8.13 (d, J=7.54 Hz, 1H), 8.40 (s, 1H), 11.96 (brs, 1H); ESIMS found C$_{16}$H$_{13}$NO$_2$S m/z 283.9 (M+H).

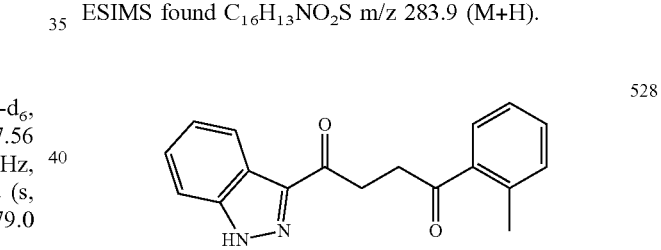

1-(1H-Indazol-3-yl)-4-(o-tolyl)butane-1,4-dione 528

Yellow solid (30 mg, 0.10 mmol). $^1$H NMR (DMSO-d$_6$, 400 MHz) δ ppm 2.38 (s, 3H), 3.33-3.43 (m, 2H), 3.48-3.60 (m, 2H), 7.25-7.40 (m, 3H), 7.40-7.53 (m, 2H), 7.69 (d, J=8.04 Hz, 1H), 7.88 (d, J=7.52 Hz, 1H), 8.15 (d, J=7.80 Hz, 1H); ESIMS found C$_{18}$H$_{16}$N$_2$O$_2$ m/z 293 (M+H).

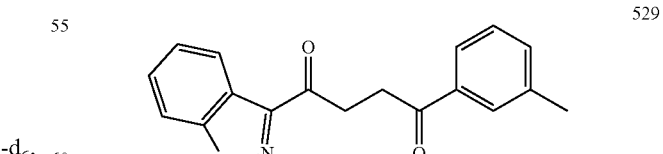

1-(1H-Indazol-3-yl)-4-(m-tolyl)butane-1,4-dione 529

White solid (85 mg, 0.29 mmol). $^1$H NMR (DMSO-d$_6$, 400 MHz) δ ppm 2.40 (s, 3H), 3.42-3.49 (m, 2H), 3.50-3.56

(m, 2H), 7.31 (ddd, J=8.03 Hz, J=7.03 Hz, J=1.00 Hz, 1H), 7.41-7.51 (m, 3H), 7.69 (d, J=8.53 Hz, 1H), 7.80-7.86 (m, 2H), 8.15 (dt, J=8.09 Hz, J=0.97 Hz, 1H), 13.87 (brs, 1H); ESIMS found $C_{18}H_{16}N_2O_2$ m/z 293.1 (M+H).

Example 3

Preparation of 1-(5,8-dihydroxy-2,3-dihydrobenzo[b][1,4]dioxin-6-yl)-3-phenylpropane-1,3-dione (3) and 1-(5,8-dimethoxy-2,3-dihydrobenzo[b][1,4]dioxin-6-yl)-3-phenyl-propane-1,3-dione (6) is depicted below in Scheme 17.

Scheme 17

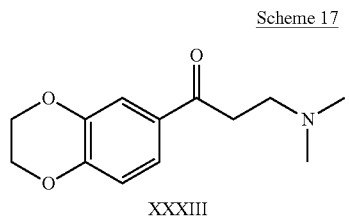

XXXIII

+

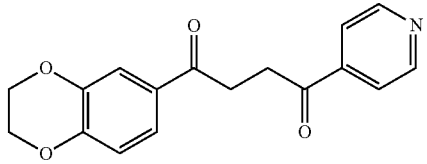

→ TEA, dioxane

LXXX

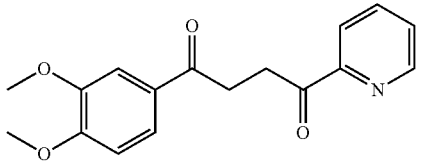

14

Step 1

To a well stirred solution of 1-(2,3-dihydrobenzo[b][1,4]dioxin-6-yl)-3-(dimethylamino)propan-1-one (XXXIII) (100 mg, 0.425 mmol, 1.0 eq) in 1,4-dioxane (3 mL) was added nicotinaldehyde (LXXX) (55 mg, 0.511 mmol, 1.2 eq), 3-ethyl-5-(2-hydroxyethyl)-4-methylthiazolium bromide (32 mg, 0.128 mmol, 0.3 eq) and TEA (0.5 mL). The reaction mixture was refluxed for 16 h. TLC analysis (PE:EtOAc 3:1) showed the reaction was complete. The solution was cooled to room temperature and diluted with water (20 mL). The product was extracted with EtOAc (3×30 mL). The combined organic layers was dried over anhydrous $Na_2SO_4$, filtered and concentrated under reduced pressure. The residue was purified by HPLC to give 1-(2,3-dihydrobenzo[b][1,4]dioxin-6-yl)-4-(pyridin-3-yl)butane-1,4-dione (14) as a white solid. (13 mg, 0.04 mmol, 10.3% yield). $^1$H NMR (CDCl$_3$, 400 MHz) δ ppm 3.43 (s, 4H), 4.27-4.31 (m, 2H), 4.31-4.38 (m, 2H), 6.94 (AA'BB' quartet, 1H), 7.42-7.49 (m, 1H), 7.55-7.61 (m, 2H), 8.31 (d, J=8.4 Hz, 1H), 8.81 (brs, 1H), 9.28 (brs, 1H); ESIMS found $C_{17}H_{15}NO_4$ m/z 298.0 (M+H).

The following compound was prepared in accordance with the procedure described in the above Example 3.

1-(2,3-Dihydrobenzo[b][1,4]dioxin-6-yl)-4-(pyridin-4-yl)butane-1,4-dione 15

White solid (30 mg, 0.10 mmol). $^1$H NMR (CDCl$_3$, 400 MHz) δ ppm 3.32-3.50 (m, 4H), 4.24-4.45 (m, 4H), 6.94 (AA'BB' quartet, 1H), 7.52-7.64 (m, 2H), 7.82 (d, J=6 Hz, 2H), 8.84 (d, J=5.6 Hz, 2H); ESIMS found $C_{17}H_{15}NO_4$ m/z 298.0 (M+H).

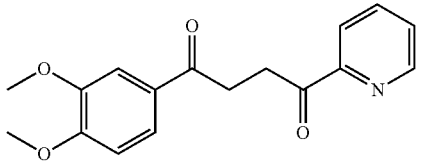

1-(3,4-Dimethoxyphenyl)-4-(pyridin-2-yl)butane-1,4-dione 207

White solid (12 mg, 0.04 mmol). $^1$H NMR (CDCl$_3$, 400 MHz) δ ppm 3.46 (t, J=6.4 Hz, 2H), 3.69 (t, J=6.4 Hz, 2H), 3.93 (s, 3H), 3.97 (s, 3H), 6.93 (d, J=8.4 Hz, 1H), 7.51 (dd, J=4.8 Hz, J=7.6 Hz, 1H), 7.58 (s, 1H), 7.71 (dd, J=2 Hz, J=8.4 Hz, 1H), 7.87 (t, 1H), 8.07 (d, J=7.6 Hz, 1H), 8.74 (d, J=4.4 Hz, 1H); ESIMS found $C_{17}H_{17}NO_4$ m/z 300.0 (M+H).

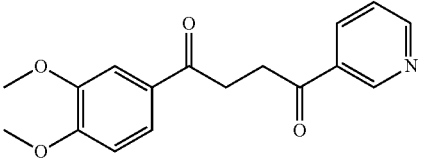

1-(3,4-Dimethoxyphenyl)-4-(pyridin-3-yl)butane-1,4-dione 208

White solid (10 mg, 0.03 mmol). $^1$H NMR (CDCl$_3$, 400 MHz) δ ppm 3.41-3.53 (m, 4H), 3.94 (s, 3H), 3.97 (s, 3H), 6.94 (d, J=8.4 Hz, 1H), 7.48 (dd, J=4.8 Hz, J=7.6 Hz, 1H), 7.56 (d, J=1.6 Hz, 1H), 7.71 (dd, J=1.6 Hz, J=8 Hz, 1H), 8.34 (d, J=8 Hz, 1H), 8.82 (d, J=3.2 Hz, 1H), 9.29 (s, 1H); ESIMS found $C_{17}H_{17}NO_4$ m/z 300.0 (M+H).

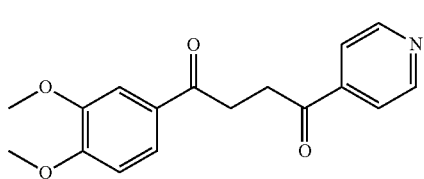

209

1-(3,4-Dimethoxyphenyl)-4-(pyridin-4-yl)butane-1,4-dione 209

White solid (40 mg, 0.13 mmol). $^1$H NMR (CDCl$_3$, 400 MHz) δ ppm 3.42 (t, J=6 Hz, 2H), 3.48 (t, J=6.4 Hz, 2H), 3.94 (s, 3H), 3.97 (s, 3H), 6.93 (d, J=8 Hz, 1H), 7.56 (d, J=2 Hz, 1H), 7.70 (dd, J=2 Hz, J=8.4 Hz, 1H), 7.83 (dd, J=1.2 Hz, J=8.4 Hz, 2H), 8.85 (dd, J=1.6 Hz, J=6 Hz, 2H); ESIMS found C$_{17}$H$_{17}$NO$_4$ m/z 300.0 (M+H).

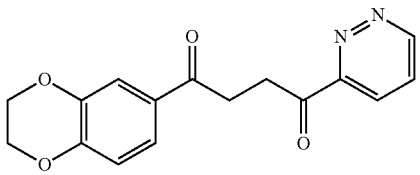

341

1-(2,3-Dihydrobenzo[b][1,4]dioxin-6-yl)-4-(pyridazin-3-yl)butane-1,4-dione 341

White solid (30 mg, 0.10 mmol). $^1$H NMR (CDCl$_3$, 400 MHz) δ ppm 3.41-3.48 (m, 2H), 3.75-3.84 (m, 2H), 4.24-4.34 (m, 4H), 6.87-6.94 (m, 1H), 7.50-7.58 (m, 2H), 7.64 (dd, J=8.53 Hz, J=5.02 Hz, 1H), 8.11 (dd, J=8.53 Hz, J=1.76 Hz, 1H), 9.33 (dd, J=5.02 Hz, J=1.76 Hz, 1H); ESIMS found C$_{16}$H$_{14}$N$_2$O$_4$ m/z 299.0 (M+H).

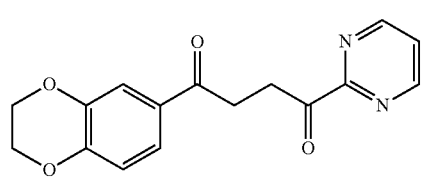

339

1-(2,3-Dihydrobenzo[b][1,4]dioxin-6-yl)-4-(pyrimidin-2-yl)butane-1,4-dione 339

White solid (20 mg, 0.07 mmol). $^1$H NMR (CDCl$_3$, 400 MHz) δ ppm 3.46 (t, J=6.40 Hz, 2H), 3.65 (t, J=6.30 Hz, 2H), 4.24-4.36 (m, 4H), 6.86-6.95 (m, 1H), 7.46 (t, J=4.77 Hz, 1H), 7.51-7.61 (m, 2H), 8.95 (d, J=4.90 Hz, 2H); ESIMS found C$_{16}$H$_{14}$N$_2$O$_4$ m/z 299.0 (M+H).

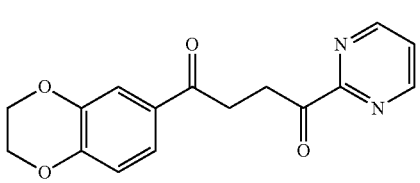

362

1-(Chroman-6-yl)-4-(pyrimidin-2-yl)butane-1,4-dione 362

Brown oil (175.7 mg, 0.59 mmol). $^1$H NMR (DMSO-d$_6$, 500 MHz) δ ppm 1.95 (quin, J=5.50 Hz, 2H), 2.81 (t, J=6.31 Hz, 2H), 3.36 (t, J=5.50 Hz, 2H), 3.50 (t, J=6.00 Hz, 2H), 4.22 (t, J=5.20 Hz, 2H), 6.84 (d, J=8.78 Hz, 1H), 7.72-7.76 (m, 2H), 7.77 (s, 1H), 9.04 (d, J=4.94 Hz, 2H); ESIMS found C$_{17}$H$_{16}$N$_2$O$_3$ m/z 296.9 (M+H).

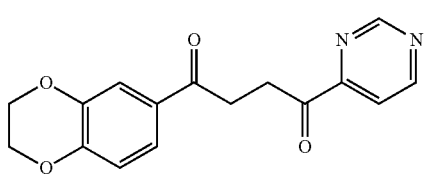

340

1-(2,3-Dihydrobenzo[b][1,4]dioxin-6-yl)-4-(pyrimidin-4-yl)butane-1,4-dione 340

White solid (30 mg, 0.10 mmol). $^1$H NMR (CDCl$_3$, 400 MHz) δ ppm 3.39-3.46 (m, 2H), 3.57-3.64 (m, 2H), 4.26-4.37 (m, 4H), 6.89-6.96 (m, 1H), 7.52-7.60 (m, 2H), 7.91 (dd, J=5.02 Hz, J=1.51 Hz, 1H), 8.99 (d, J=5.02 Hz, 1H), 9.40 (d, J=1.26 Hz, 1H); ESIMS found C$_{16}$H$_{14}$N$_2$O$_4$ m/z 299.1 (M+H).

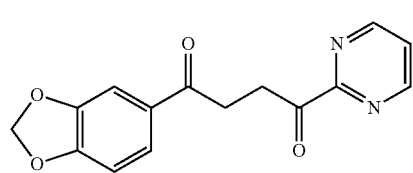 [SMILES: O=C(CCC(=O)c1ncccn1)c1ccc2c(c1)OCO2]

372

1-(Benzo[d][1,3]dioxol-5-yl)-4-(pyrimidin-2-yl)butane-1,4-dione 372

Light brown solid (55.2 mg, 0.19 mmol). $^1$H NMR (DMSO-d$_6$, 500 MHz) δ ppm 3.38 (t, J=6.10 Hz, 2H), 3.51 (t, J=6.10 Hz, 2H), 6.15 (s, 2H), 7.06 (d, J=8.23 Hz, 1H), 7.47 (d, J=1.65 Hz, 1H), 7.68 (dd, J=8.23, 1.65 Hz, 1H), 7.74 (t, J=4.81 Hz, 1H), 9.04 (d, J=4.39 Hz, 2H); ESIMS found C$_{15}$H$_{12}$N$_2$O$_4$ m/z 385.1 (M+H).

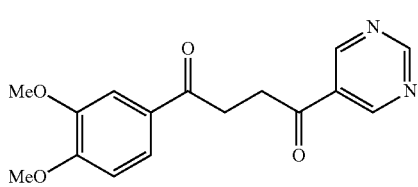 [SMILES: COc1ccc(C(=O)CCC(=O)c2cncnc2)cc1OC]

1-(3,4-Dimethoxyphenyl)-4-(pyrimidin-5-yl)butane-1,4-dione 430

White solid (10 mg, 0.03 mmol). $^1$H NMR (CDCl$_3$, 400 MHz) δ ppm 3.40 (t, J=5.6 Hz, 2H), 3.51 (t, J=6 Hz, 2H), 3.93 (s, 3H), 3.97 (s, 3H), 6.93 (d, J=8.4 Hz, 1H), 7.53 (d, J=2 Hz, 1H), 7.69 (dd, J=2 Hz, J=8.4 Hz, 1H), 9.33 (s, 2H), 9.39 (s, 1H); ESIMS found C$_{16}$H$_{16}$N$_2$O$_4$ m/z 301.0 (M+H).

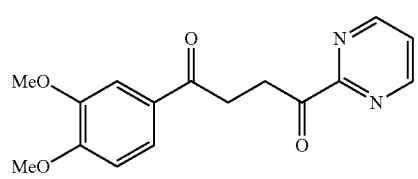 [SMILES: COc1ccc(C(=O)CCC(=O)c2ncccn2)cc1OC]

1-(3,4-Dimethoxyphenyl)-4-(pyrimidin-2-yl)butane-1,4-dione 431

White solid (70 mg, 0.23 mmol). $^1$H NMR (CDCl$_3$, 400 MHz) δ ppm 3.51 (t, J=6.4 Hz, 2H), 3.68 (t, J=6.4 Hz, 2H), 3.93 (s, 3H), 3.96 (s, 3H), 6.92 (d, J=8.4 Hz, 1H), 7.48 (t, J=4.8 Hz, 1H), 7.55 (d, J=1.6 Hz, 1H), 7.70 (dd, J=2 Hz, J=8.4 Hz, 1H), 8.96 (d, J=4.4 Hz, 2H); ESIMS found C$_{16}$H$_{16}$N$_2$O$_4$ m/z 301.1 (M+H).

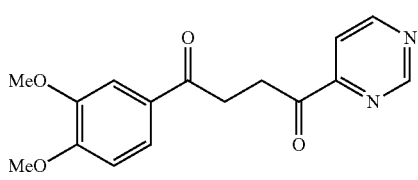 [SMILES: COc1ccc(C(=O)CCC(=O)c2ccncn2)cc1OC]

1-(3,4-Dimethoxyphenyl)-4-(pyrimidin-4-yl)butane-1,4-dione 432

White solid (40 mg, 0.13 mmol). $^1$H NMR (CDCl$_3$, 400 MHz) δ ppm 3.48 (t, J=6 Hz, 2H), 3.62 (t, J=6 Hz, 2H), 3.93 (s, 3H), 3.96 (s, 3H), 6.92 (d, J=8 Hz, 1H), 7.54 (d, J=1.2 Hz, 1H), 7.68 (d, J=8 Hz, 1H), 7.92 (d, J=4.8 Hz, 1H), 9.00 (d, J=5.4 Hz, 1H), 9.41 (s, 1H); ESIMS found C$_{16}$H$_{16}$N$_2$O$_4$ m/z 301.0 (M+H).

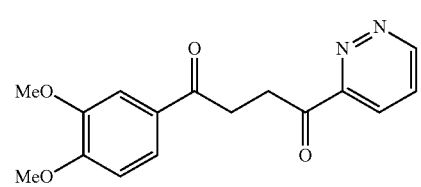 [SMILES: COc1ccc(C(=O)CCC(=O)c2cccnn2)cc1OC]

1-(3,4-Dimethoxyphenyl)-4-(pyridazin-3-yl)butane-1,4-dione 433

White solid (70 mg, 0.23 mmol). $^1$H NMR (CDCl$_3$, 400 MHz) δ ppm 3.52 (t, J=6 Hz, 2H), 3.84 (t, J=6 Hz, 2H), 3.93 (s, 3H), 3.97 (s, 3H), 6.94 (d, J=8.4 Hz, 1H), 7.56 (d, J=1.6 Hz, 1H), 7.62-7.74 (m, 2H), 8.15 (dd, J=2 Hz, J=8.4 Hz, 1H), 9.36 (dd, J=2 Hz, J=4.8 Hz, 1H); ESIMS found C$_{16}$H$_{16}$N$_2$O$_4$ m/z 301.1 (M+H).

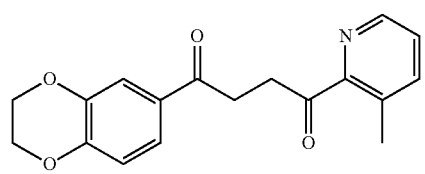 [SMILES: Cc1cccnc1C(=O)CCC(=O)c1ccc2c(c1)OCCO2]

1-(2,3-Dihydrobenzo[b][1,4]dioxin-6-yl)-4-(3-methylpyridin-2-yl) butane-1,4-dione 568

White solid (207.8 mg, 0.30 mmol, 7.9% yield). $^1$H NMR (DMSO-d$_6$, 500 MHz) δ ppm 2.45 (s, 3H), 3.29-3.32 (m, 2H), 3.42-3.45 (m, 2H), 4.28-4.30 (m, 2H), 4.32-4.34 (m, 2H), 6.98 (d, J=8.4 Hz, 1H), 7.47 (d, J=2.1 Hz, 1H), 7.51-7.55 (m, 2H), 7.78 (dd, J=0.7 Hz, 7.7 Hz, 1H), 8.59 (dd, J=1.0 Hz, J=4.6 Hz, 1H); ESIMS found C$_{18}$H$_{17}$NO$_4$ m/z 312.0 (M+H).

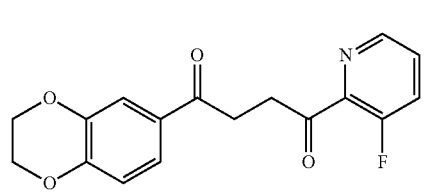 [SMILES: O=C(CCC(=O)c1ncccc1F)c1ccc2c(c1)OCCO2]

1-(2,3-Dihydrobenzo[b][1,4]dioxin-6-yl)-4-(3-fluoropyridin-2-yl) butane-1,4-dione 569

White solid (94.8 mg, 0.30 mmol, 3.8% yield). $^1$H NMR (DMSO-d$_6$, 500 MHz) δ ppm 3.32-3.34 (m, 2H), 3.43-3.46 (m, 2H), 4.29-4.30 (m, 2H), 4.33-4.34 (m, 2H), 6.99 (d, J=8.4 Hz, 1H), 7.48 (d, J=2.1 Hz, 1H), 7.54 (dd, J=2.1 Hz, J=8.4 Hz, 1H), 7.76-7.78 (m, 1H), 7.88-7.92 (m, 1H), 8.59 (dt, J=1.4 Hz, J=4.5 Hz, 1H); ESIMS found C$_{17}$H$_{14}$FNO$_4$ m/z 315.9 (M+H).

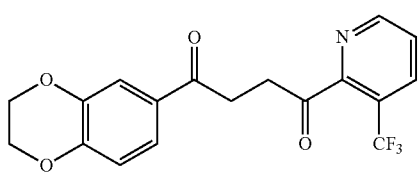

1-(2,3-Dihydrobenzo[b][1,4]dioxin-6-yl)-4-(3-(trifluoromethyl) pyridin-2-yl)butane-1,4-dione 570

Tan solid (449 mg, 1.23 mmol, 22.0% yield). $^1$H NMR (DMSO-$d_6$, 500 MHz) δ ppm 3.32-3.35 (m, 2H), 3.45-3.48 (m, 2H), 4.29-4.30 (m, 2H), 4.33-4.34 (m, 2H), 6.99 (d, J=8.4 Hz, 1H), 7.48 (d, J=2.1 Hz, 1H), 7.55 (dd, J=2.1 Hz, J=8.5 Hz, 1H), 7.84 (dd, J=4.9 Hz, J=7.9 Hz, 1H), 8.37 (d, J=8.0 Hz, 1H), 8.96 (d, J=4.6 Hz, 1H); ESIMS found $C_{18}H_{14}F_3NO_4$ m/z 366.3 (M+H).

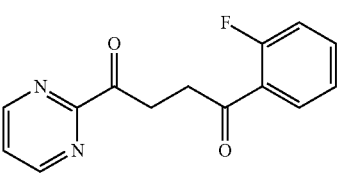 [SMILES: O=C(CCC(=O)c1ccccc1F)c1ncccn1]

1-(2-Fluorophenyl)-4-(pyrimidin-2-yl)butane-1,4-dione 712

Off-white solid (167.2 mg, 0.65 mmol). $^1$H NMR (DMSO-$d_6$, 500 MHz) δ ppm 3.39 (m, 2H), 3.56 (t, J=6.10 Hz, 2H), 7.34-7.41 (m, 2H), 7.66-7.71 (m, 1H), 7.74 (t, J=4.94 Hz, 1H), 7.85 (td, J=7.68, 1.65 Hz, 1H), 9.04 (d, J=4.94 Hz, 2H); ESIMS found $C_{14}H_{11}FN_2O_2$ m/z 259.0 (M+H).

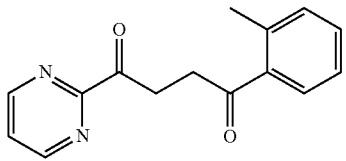 [SMILES: Cc1ccccc1C(=O)CCC(=O)c1ncccn1]

1-(Pyrimidin-2-yl)-4-(o-tolyl)butane-1,4-dione 715

Brown solid (17.9 mg, 0.07 mmol). $^1$H NMR (DMSO-$d_6$, 500 MHz) δ ppm 2.38 (s, 3H), 3.33 (t, J=6.10 Hz, 2H), 3.54 (t, J=6.10 Hz, 2H), 7.30 (d, J=7.43 Hz, 1H), 7.35 (t, J=7.67 Hz, 1H), 7.44 (td, J=7.60, 1.10 Hz, 1H), 7.74 (t, J=4.90 Hz, 1H), 7.86 (d, J=7.68 Hz, 1H), 9.04 (d, J=4.94 Hz, 2H); ESIMS found $C_{15}H_{14}N_2O_2$ m/z 255.0 (M+H).

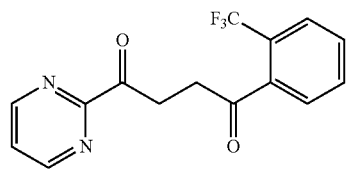 [SMILES: O=C(CCC(=O)c1ccccc1C(F)(F)F)c1ncccn1]

1-(Pyrimidin-2-yl)-4-(2-(trifluoromethyl)phenyl) butane-1,4-dione 716

Light brown solid (85.8 mg, 0.28 mmol). $^1$H NMR (DMSO-$d_6$, 500 MHz) δ ppm 3.34 (t, J=6.30 Hz, 2H), 3.56 (t, J=6.10 Hz, 2H), 7.72-7.77 (m, 2H), 7.81-7.88 (m, 2H), 7.92 (d, J=7.14 Hz, 1H), 9.05 (d, J=4.94 Hz, 2H); ESIMS found $C_{15}H_{11}F_3N_2O_2$ m/z 309.0 (M+H).

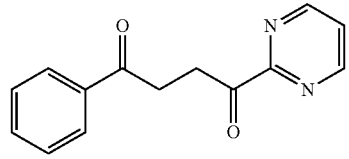

1-Phenyl-4-(pyrimidin-2-yl)butane-1,4-dione 718

Off-white solid (186.5 mg, 0.78 mmol). $^1$H NMR (DMSO-$d_6$, 500 MHz) δ ppm 3.46 (t, J=6.10 Hz, 2H), 3.56 (t, J=6.10 Hz, 2H), 7.56 (t, J=7.70 Hz, 2H), 7.67 (t, J=7.40 Hz, 1H), 7.75 (t, J=4.94 Hz, 1H), 8.02 (d, J=7.36 Hz, 2H), 9.05 (d, J=4.94 Hz, 2H); ESIMS found $C_{14}H_{12}N_2O_2$ m/z 241.1 (M+H).

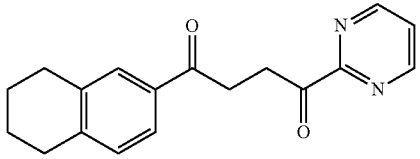 [SMILES: O=C(CCC(=O)c1ncccn1)c1ccc2c(c1)CCCC2]

1-(Pyrimidin-2-yl)-4-(5,6,7,8-tetrahydronaphthalen-2-yl)butane-1,4-dione 737

Off-white solid (480 mg, 1.63 mmol, 24.2% yield). $^1$H NMR (DMSO-$d_6$, 500 MHz) δ ppm 1.75-1.77 (m, 4H), 2.78-2.80 (m, 4H), 3.38-3.41 (m, 2H), 3.51-3.53 (m, 2H), 7.21 (d, J=7.8 Hz, 1H), 7.61-7.71 (m, 2H), 7.74 (t, J=4.9 Hz, 1H), 9.04 (d, J=4.9 Hz, 1H); ESIMS found $C_{18}H_{18}N_2O_2$ m/z 295.0 (M+H).

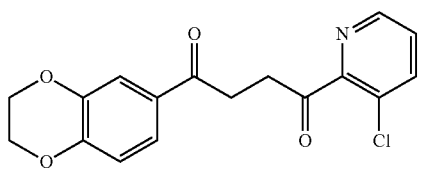 [SMILES: O=C(CCC(=O)c1ncccc1Cl)c1ccc2c(c1)OCCO2]

1-(3-Chloropyridin-2-yl)-4-(2,3-dihydrobenzo[b][1,4]dioxin-6-yl) butane-1,4-dione 767

White solid (311 mg, 0.94 mmol, 12.6% yield). $^1$H NMR (DMSO-$d_6$, 500 MHz) δ ppm 3.30-3.34 (m, 2H), 3.40-3.43 (m, 2H), 4.28-4.30 (m, 2H), 4.33-4.34 (m, 2H), 6.99 (d, J=8.4 Hz, 1H), 7.48 (d, J=2.1 Hz, 1H), 7.54 (dd, J=2.1 Hz, J=8.4 Hz, 1H), 7.65 (dd, J=4.6 Hz, J=8.2 Hz, 1H), 8.08 (dd, J=1.3 Hz, J=8.2 Hz, 1H), 8.67 (dd, J=1.3 Hz, J=4.5 Hz, 1H); ESIMS found $C_{17}H_{14}C_1NO_4$ m/z 331.9 (M+H).

Example 4

Preparation of 1-(5,8-dihydroxy-2,3-dihydrobenzo[b][1,4]dioxin-6-yl)-3-phenylpropane-1,3-dione (3) and 1-(5,8-dimethoxy-2,3-dihydrobenzo[b][1,4]dioxin-6-yl)-3-phenylpropane-1,3-dione (6) is depicted below in Scheme 18

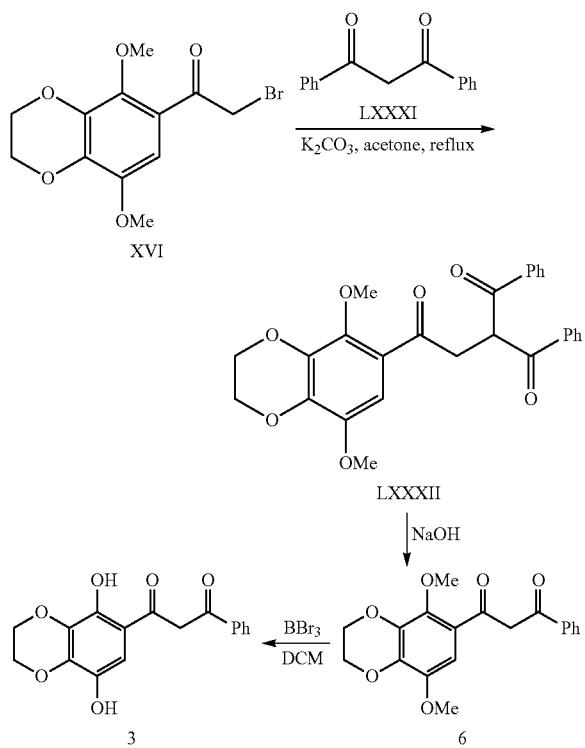

Step 1

A solution of crude 2-bromo-1-(5,8-dimethoxy-2,3-dihydrobenzo[b][1,4]dioxin-6-yl)ethanone (XVI) (1.1 g, 3.36 mmol), 1,3-diphenylpropane-1,3-dione (LXXXI) (778 mg, 3.47 mmol), $K_2CO_3$ (480 mg, 3.47 mmol), and KI (10 mg) in acetone was heated to reflux for 2 h. The reaction mixture was cooled, filtered and concentrated under vacuum. The residue was purified by column chromatography on silica gel (20% EtOAc/PE) to give 2-benzoyl-4-(5,8-dimethoxy-2,3-dihydrobenzo[b][1,4]dioxin-6-yl)-1-phenylbutane-1,4-dione (LXXXII) (1.1 g, 2.39 mmol, 70% yield for two steps) as a yellow solid. $^1$H NMR (CDCl$_3$, 500 MHz) δ ppm 3.79-3.88 (m, 5H), 3.90 (s, 3H), 4.36 (dd, J=19.32 Hz, 4.52 Hz, 4H), 6.08 (t, J=6.40 Hz, 1H), 6.98 (s, 1H) 7.43-7.52 (m, 4H), 7.54-7.63 (m, 2H), 8.02 (d, J=7.53 Hz, 4H).

Step 2

A solution of 2-benzoyl-4-(5,8-dimethoxy-2,3-dihydrobenzo[b][1,4]dioxin-6-yl)-1-phenylbutane-1,4-dione (LXXXII) (1.1 g, 2.4 mmol) in EtOH (20 mL) was added 2% aqueous NaOH (20 mL, 10 mmol) dropwise at 10° C. and then stirred at room temperature for 18 h. The reaction mixture was filtered, and the solid was washed with water (20 mL), 10% EtOAc/PE (50 mL) and dissolved in DCM (60 mL). The DCM layer was washed with 0.5 N HCl (20 mL), brine (20 mL), dried over anhydrous $Na_2SO_4$ and concentrated under vacuum to produce 1-(5,8-dimethoxy-2,3-dihydrobenzo[b][1,4]dioxin-6-yl)-3-phenylpropane-1,3-dione (6) (750 mg, 2.19 mmol, 88% yield) as a yellow solid. $^1$H NMR (CDCl$_3$, 500 MHz) δ ppm 3.42 (d, J=6.02 Hz, 2H), 3.49 (d, J=6.02 Hz, 2H), 3.87 (s, 3H), 3.96 (s, 3H), 4.37 (dd, J=14.18 Hz, 4.89 Hz, 4H), 6.97 (s, 1H), 7.42-7.52 (m, 2H), 7.56 (d, J=7.28 Hz, 1H), 8.04 (d, J=7.28 Hz, 2H).

Step 3

To a solution of 1-(5,8-dimethoxy-2,3-dihydrobenzo[b][1,4]dioxin-6-yl)-3-phenylpropane-1,3-dione (6) (750 mg, 2.1 mmol) in anhydrous DCM (100 mL) was added a solution of BBr$_3$ (0.56 mL, 6.3 mmol) in anhydrous DCM (1 mL) at −10° C. dropwise. This reaction solution was stirred at −10° C. for 3 h and then quenched with ice water (40 mL). The DCM layer was dried over anhydrous $Na_2SO_4$, and concentrated under vacuum. The residue was purified by the silica gel column (10% MeOH/DCM), and recrystallized with (MeOH:DCM:EtOAc=1:2:2) (20 mL) to yield 1-(5,8-dihydroxy-2,3-dihydrobenzo[b][1,4]dioxin-6-yl)-3-phenylpropane-1,3-dione (3) as a light yellow solid (200 mg, 0.64 mmol, 29.0% yield). $^1$H NMR (DMSO-$d_6$, 500 MHz) δ ppm 3.23-3.49 (m, 4H), 4.26 (d, J=4 Hz, 2H), 4.33 (d, J=2.4 Hz, 2H), 6.96 (s, 1H), 7.55 (t, J=7.2 Hz, 2H), 7.66 (t, J=7.2 Hz, 1H), 8.01 (d, J=7.6 Hz, 2H), 9.06 (s, 1H), 11.81 (s, 1H); ESIMS found $C_{17}H_{14}O_6$ m/z 315.1 (M+H).

The following compound was prepared in accordance with the procedure described in the above Example 4.

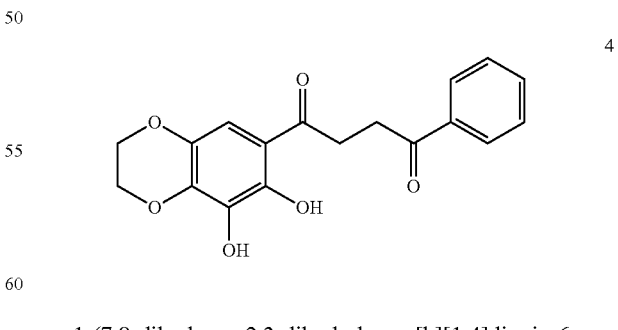

1-(7,8-dihydroxy-2,3-dihydrobenzo[b][1,4]dioxin-6-yl)-4-phenylbutane-1,4-dione 4

Light yellow solid (160 mg, 0.51 mmol, 69.7% yield). $^1$H NMR (CDCl$_3$, 500 MHz): δ ppm 3.37-3.45 (m, 4H), 4.27 (t, J=4 Hz, 2H), 4.41 (t, J=4 Hz, 2H), 5.49 (s, 1H), 7.03 (s, 1H), 7.49 (t, J=7.6 Hz, 2H), 7.59 (t, J=7.6 Hz, 1H), 8.03 (d, J=7.6 Hz, 1H), 12.08 (s, 1H); ESIMS found $C_{18}H_{16}O_6$ m/z 329.1 (M+H).

Evaluation of Biological Activity

The biological activity of the compounds described herein can be tested using any suitable assay known to those of skill in the art, e.g., those assays described in WO 2001/053268 or WO 2005/009997, both of which are incorporated by reference in their entireties. For example, the activity of a compound may be tested using one or more of the test methods described below.

Example 5

Compounds that enhance the Wnt activity, or Activators, were assayed as follows. Reporter cell lines were generated by stably transducing cells of colon cancer cell lines (with a lentiviral construct that included a Wnt-responsive promoter driving expression of the firefly luciferase gene).

Lentiviral constructs were made in which the SP5 promoter, a promoter having eight TCF/LEF binding sites derived from the SP5 promoter, was linked upstream of the firefly luciferase gene. The lentiviral constructs also included a hygromycin resistance gene as a selectable marker. The SP5 promoter construct was used to transduce SW480 cells, a colon cancer cell line having a mutated APC gene that generates a truncated APC protein, leading to de-regulated accumulation of β-catenin.

Cultured SW480 cells bearing a reporter construct were distributed at approximately 10,000 cells per well into 384- or 96-well multiwell plates. Compounds from a small molecule compound library were then added to the wells in half-log dilutions using a maximum concentration of three or ten micromolar. A series of control wells for each cell type received only buffer and compound solvent DMSO. Twenty-four hours after the addition of compound, reporter activity for luciferase was assayed, for example, by addition of the BrightGlo luminescence reagent (Promega) and the Victor3 plate reader (Perkin Elmer). Readings were normalized to DMSO only treated cells, and any activities above DMSO were considered activation. Compounds were considered activators if reporter activities were 2× fold or greater than DMSO. $EC_{50}$ is the concentration at half maximal activation. Table 2 shows the activity of selected activators.

TABLE 2

| Compound | Wnt activation, $EC_{50}$ (μM) |
|---|---|
| 1 | 0.005 |
| 2 | 0.001-0.003 |
| 3 | >10 |
| 4 | >10 |
| 9 | 0.1 |
| 10 | >10 |
| 11 | 0.013 |
| 12 | 0.005 |
| 13 | 0.192 |
| 14 | 0.306 |
| 15 | 0.09 |
| 16 | 0.007 |
| 18 | >10 |
| 19 | 0.003 |
| 21 | 0.031 |
| 28 | 0.009 |
| 61 | 0.025 |
| 68 | 0.006 |
| 69 | >10 |
| 71 | 0.0025 |

TABLE 2-continued

| Compound | Wnt activation, $EC_{50}$ (μM) |
|---|---|
| 76 | >10 |
| 80 | 0.01 |
| 207 | >10 |
| 208 | >10 |
| 209 | >10 |
| 210 | 0.002 |
| 213 | 0.018 |
| 214 | 0.01 |
| 216 | 0.011 |
| 217 | 0.343 |
| 222 | 0.003 |
| 232 | 0.134 |
| 235 | 0.494 |
| 238 | >10 |
| 240 | 0.669 |
| 242 | 0.789 |
| 248 | >10 |
| 249 | 0.004 |
| 252 | 0.001 |
| 255 | 0.017 |
| 258 | 0.016 |
| 261 | 0.042 |
| 263 | >10 |
| 265 | 0.201 |
| 269 | >10 |
| 274 | 6.8 |
| 275 | 0.009 |
| 278 | 0.018 |
| 281 | 0.061 |
| 287 | 0.087 |
| 288 | >10 |
| 291 | 0.125 |
| 292 | 0.595 |
| 294 | 1.721 |
| 300 | 0.018 |
| 301 | 0.039 |
| 307 | 0.055 |
| 310 | 0.068 |
| 313 | 0.044 |
| 314 | 0.016 |
| 316 | >10 |
| 317 | >10 |
| 319 | 0.279 |
| 320 | >10 |
| 325 | 0.063 |
| 326 | 0.117 |
| 329 | 0.089 |
| 332 | 0.680 |
| 334 | >10 |
| 338 | 0.064 |
| 339 | 0.009 |
| 340 | 0.209 |
| 341 | 0.095 |
| 342 | 0.009 |
| 343 | 0.351 |
| 344 | 0.307 |
| 345 | >10 |
| 346 | 0.024 |
| 358 | 0.014 |
| 362 | 0.188 |
| 364 | 0.013 |
| 365 | 0.033 |
| 368 | 0.016 |
| 372 | 0.097 |
| 374 | 0.013 |
| 375 | 0.071 |
| 379 | >10 |
| 385 | 0.165 |
| 425 | 5.95 |
| 426 | 8.80 |
| 430 | >10 |
| 431 | >10 |
| 432 | 4.8 |
| 433 | >10 |
| 442 | 2.15 |
| 445 | 0.010 |

TABLE 2-continued

| Compound | Wnt activation, $EC_{50}$ (µM) |
|---|---|
| 447 | >10 |
| 451 | 0.037 |
| 455 | 0.032 |
| 456 | 0.673 |
| 457 | 2.89 |
| 462 | 0.424 |
| 485 | >10 |
| 495 | 0.008 |
| 497 | 0.048 |
| 498 | 0.012 |
| 503 | 0.487 |
| 507 | 0.036 |
| 513 | 0.039 |
| 515 | 0.127 |
| 518 | 0.646 |
| 524 | 0.088 |
| 528 | 0.148 |
| 529 | 0.695 |
| 538 | 0.063 |
| 541 | 2.81 |
| 544 | 0.9 |
| 547 | >10 |
| 554 | >10 |
| 557 | 0.026 |
| 559 | 0.340 |
| 560 | 0.055 |
| 562 | 0.106 |
| 569 | 0.00196 |
| 570 | 0.026 |
| 718 | 0.681 |
| 737 | 0.022 |
| 767 | 0.002164 |

The term "comprising" as used herein is synonymous with "including," "containing," or "characterized by," and is inclusive or open-ended and does not exclude additional, unrecited elements or method steps.

What is claimed is:

1. A compound of Formula IV:

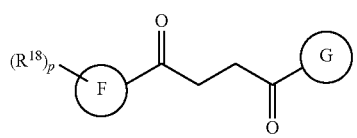

or a pharmaceutically acceptable salt thereof, wherein:

Ring F is

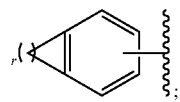

Ring G is selected from the group consisting of

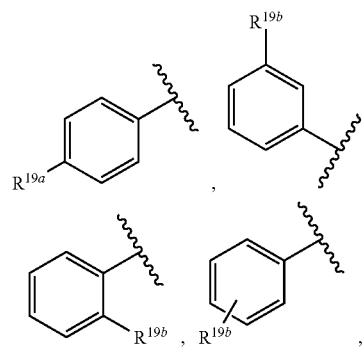

and a 5-6 membered heteroaryl $R^{19d}$, wherein a carbon atom on the ring is attached to the carbonyl carbon;

each $R^{18}$ is independently selected at each occurrence from the group consisting of H, —$C_{1-3}$ haloalkyl, halide, —$OR^{20}$, $CF_3$, and CN;

$R^{19a}$ is selected from the group consisting of H, unsubstituted $C_{2-6}$ alkyl, —$CH_2OH$, —$CH_2N(R^{21})_2$, —$C_{1-3}$ haloalkyl, F, Br, I, —$OR^{20}$, $CF_3$, and CN;

each $R^{19b}$ is independently selected at each occurrence from the group consisting of H, unsubstituted $C_{2-6}$ alkyl, —$CH_2OH$, —$CH_2N(R^{21})_2$, —$C_{1-3}$ haloalkyl, halide, —$OR^{20}$, $CF_3$, and CN;

$R^{19c}$ is 2-5 substituents, each independently selected at each occurrence from the group consisting of H, —$CH_2OH$, —$CH_2N(R^{21})_2$, —$C_{1-3}$ haloalkyl, halide, —$OR^{20}$, $CF_3$, and CN;

$R^{19d}$ is 1-4 substituents, each independently selected at each occurrence from the group consisting of H, —$CH_2OH$, —$CH_2N(R^{21})_2$, —$C_{1-3}$ haloalkyl, halide, —$OR^{20}$, $CF_3$, and CN;

each $R^N$ is independently selected from the group consisting of H, unsubstituted —$C_{3-6}$ alkyl, —$C_{1-3}$ haloalkyl, and $CF_3$;

each $R^{21}$ is independently selected from the group consisting of H and unsubstituted —$C_{1-3}$ alkyl;

p is an integer of 1 to 13; and r is an integer of 1 to 5.

2. The compound of claim 1, wherein r is an integer of 2 to 4.

3. The compound of claim 2, wherein $R^{18}$ is F and p is 1-2.

4. The compound of claim 2, wherein $R^{18}$ is H.

5. The compound of claim 2, wherein

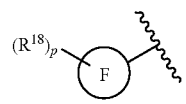

is selected from the group consisting of:

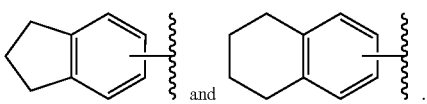

6. The compound of claim 1, wherein $R^{19b}$, $R^{19c}$, and $R^{19d}$ are selected from the group consisting of H, F, Cl, Me, OMe, $CF_3$, and CN.

7. The compound of claim 1, is
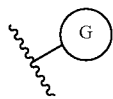
selected from the group consisting of:
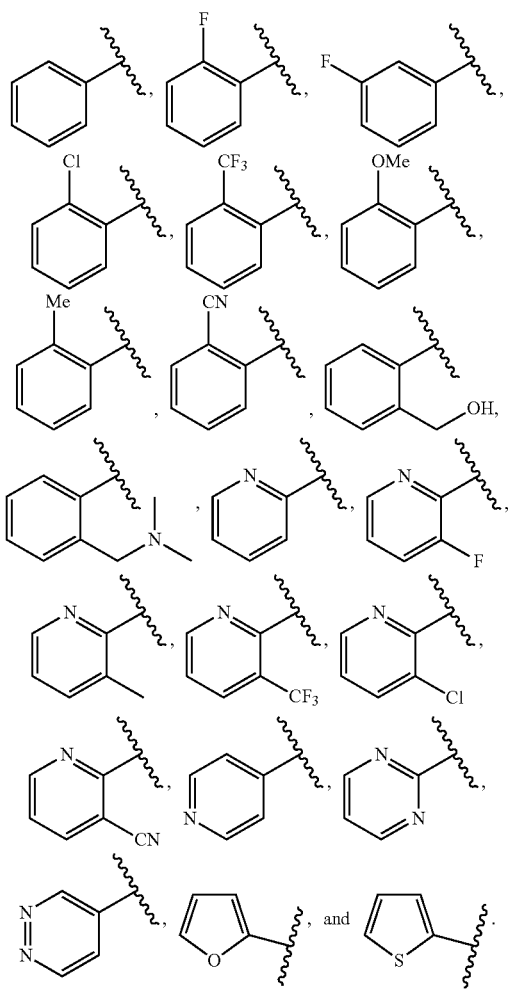
8. The compound of claim 7,
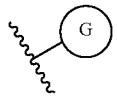
is selected from the group consisting of:
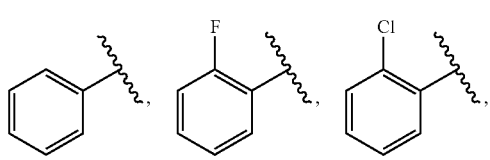
-continued
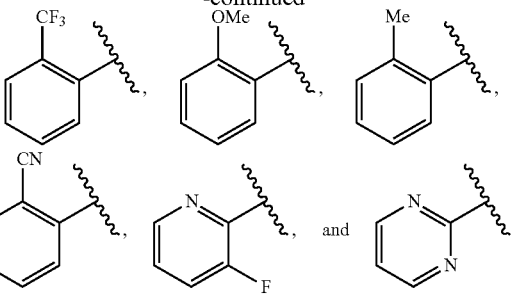
9. The compound of claim 8,
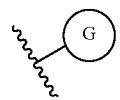
is selected from the group consisting of:
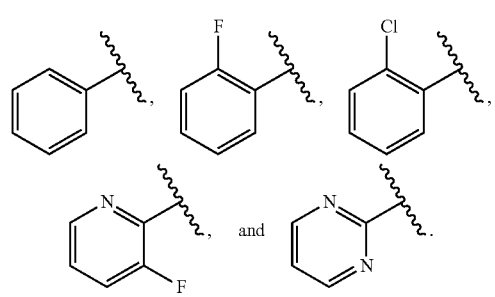
10. The compound of claim 1, wherein the compound of Formula Ma is selected from the group consisting of: Formula IV is selected from the group consisting of:
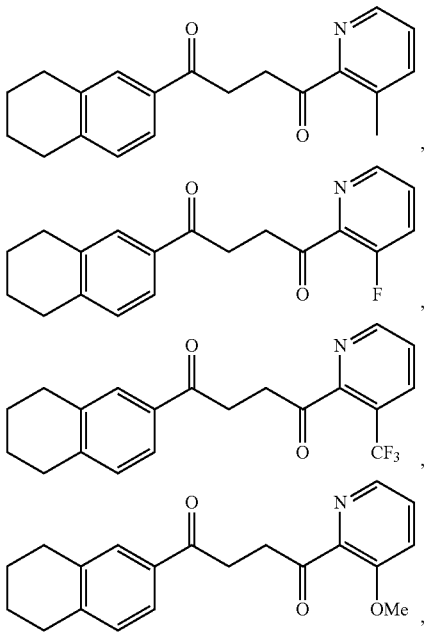

291
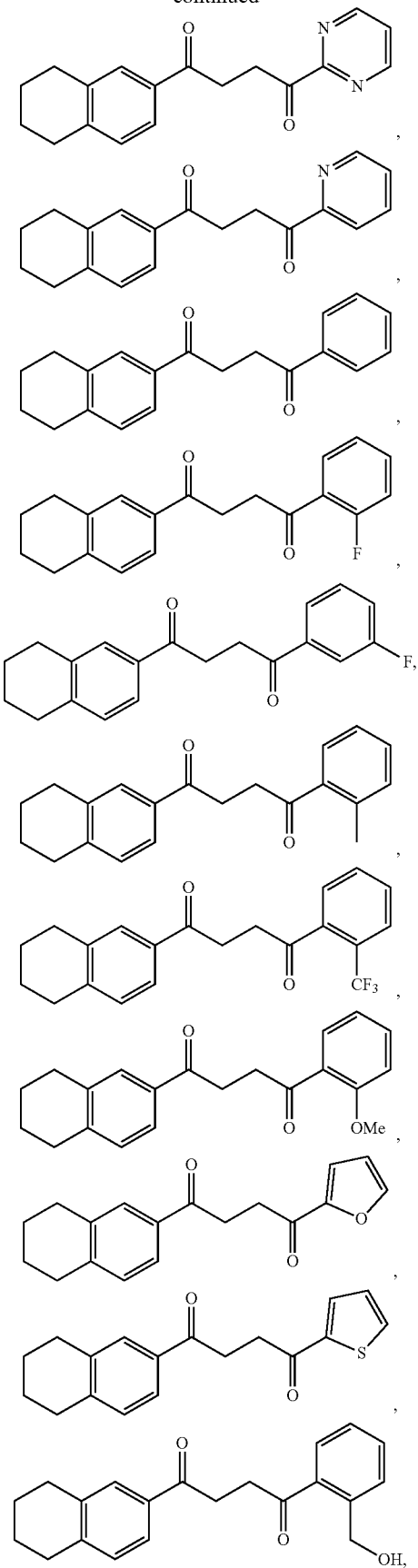
292
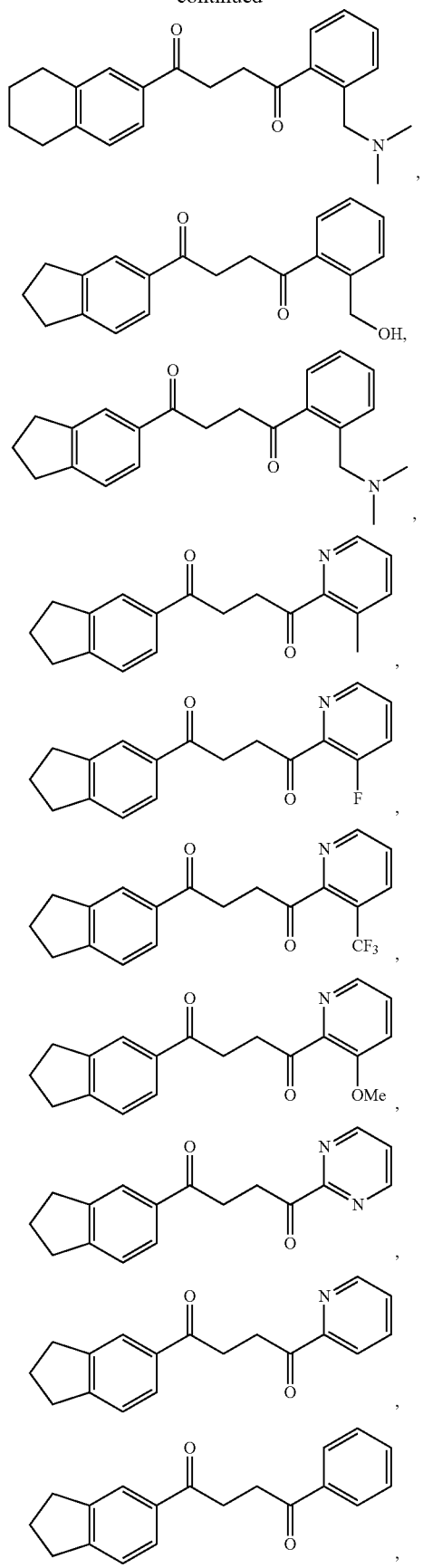

-continued
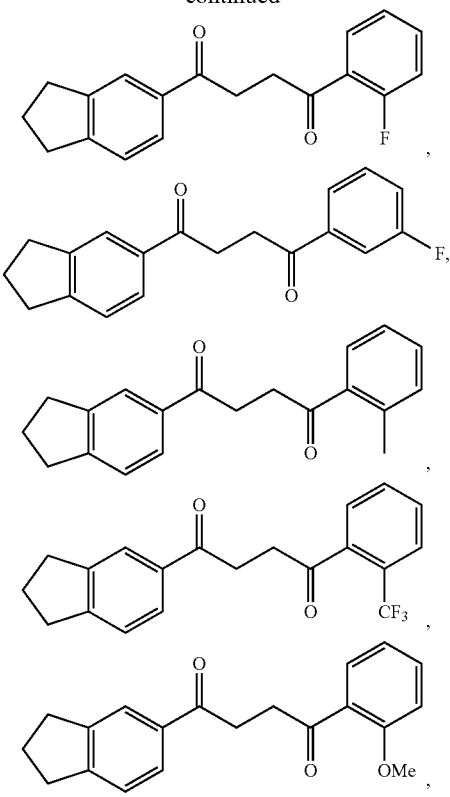
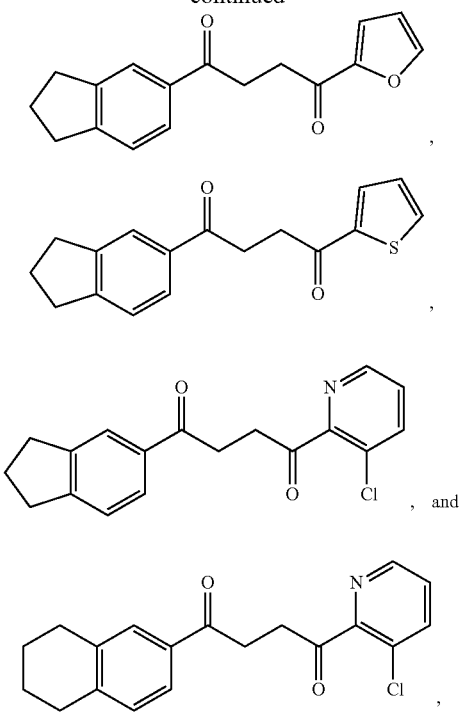
or a pharmaceutically acceptable salt thereof.
* * * * *